(12) United States Patent
Grunden et al.

(10) Patent No.: US 10,752,911 B2
(45) Date of Patent: Aug. 25, 2020

(54) SYNTHETIC PATHWAY FOR BIOLOGICAL CARBON DIOXIDE SEQUESTRATION

(71) Applicant: NORTH CAROLINA STATE UNIVERSITY, Raleigh, NC (US)

(72) Inventors: Amy Michele Grunden, Holly Springs, NC (US); Heike Sederoff, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 0 days.

(21) Appl. No.: 15/875,313

(22) Filed: Jan. 19, 2018

(65) Prior Publication Data

US 2018/0163220 A1     Jun. 14, 2018

Related U.S. Application Data

(63) Continuation-in-part of application No. PCT/US2016/043054, filed on Jul. 20, 2016.

(60) Provisional application No. 62/194,446, filed on Jul. 20, 2015.

(51) Int. Cl.

| | |
|---|---|
| *C12N 15/82* | (2006.01) |
| *C12N 9/00* | (2006.01) |
| *C12N 9/04* | (2006.01) |
| *C12N 9/02* | (2006.01) |
| *C12N 9/88* | (2006.01) |
| *C12N 5/04* | (2006.01) |
| *A23L 7/00* | (2016.01) |
| *C12N 15/52* | (2006.01) |

(52) U.S. Cl.
CPC ............ *C12N 15/8259* (2013.01); *A23L 7/00* (2016.08); *C12N 5/04* (2013.01); *C12N 9/0006* (2013.01); *C12N 9/0008* (2013.01); *C12N 9/88* (2013.01); *C12N 9/93* (2013.01); *C12N 15/52* (2013.01); *C12N 15/8243* (2013.01); *C12N 15/8261* (2013.01); *C12N 15/8269* (2013.01); *C12Y 101/01042* (2013.01); *C12Y 102/07003* (2013.01); *C12Y 401/03001* (2013.01); *C12Y 602/01004* (2013.01); *C12Y 602/01005* (2013.01); *C12Y 604/01007* (2013.01); *C12N 2810/40* (2013.01); *Y02A 40/146* (2018.01); *Y02P 60/247* (2015.11)

(58) Field of Classification Search
None
See application file for complete search history.

(56) References Cited

U.S. PATENT DOCUMENTS

2014/0150135 A1* 5/2014 Grunden ............ C12N 15/8261
800/290

FOREIGN PATENT DOCUMENTS

| CA | 2892551 | 6/2014 |
|---|---|---|
| WO | WO 2010/012796 | 2/2010 |
| WO | WO 2011/095528 | 8/2011 |

OTHER PUBLICATIONS

International Preliminary Report on Patentability and International Search Report corresponding to International Application No. PCT/US2016/043054, dated Jan. 23, 2018, 13 pages.

* cited by examiner

*Primary Examiner* — Bratislav Stankovic
(74) *Attorney, Agent, or Firm* — Myers Bigel, P.A.

(57) ABSTRACT

This invention relates to methods for increasing carbon fixation and/or increasing biomass production in a plant, comprising: introducing into a plant, plant part, and/or plant cell heterologous polynucleotides encoding (1) a succinyl CoA synthetase, (2) a 2-oxoglutarate:ferredoxin oxidoreductase, (3) a 2-oxoglutarate carboxylase, (4) an oxalosuccinate reductase, or (5) an isocitrate lyase, or (6) a succinyl CoA synthetase and a 2-oxoglutarate:ferredoxin oxidoreductase, (7) a 2-oxoglutarate carboxylase and an oxalosuccinate reductase polypeptide, and/or (8) a 2-oxoglutarate carboxylase polypeptide, an oxalosuccinate reductase polypeptide and an isocitrate lyase polypeptide to produce a stably transformed plant, plant part, and/or plant cell, wherein said heterologous polynucleotides are from a bacterial and/or an archaeal species. Additionally, transformed plants, plant parts, and/or plant cells are provided as well as products produced from the transformed plants, plant parts, and/or plant cells.

18 Claims, 28 Drawing Sheets

Specification includes a Sequence Listing.

Fig. 14
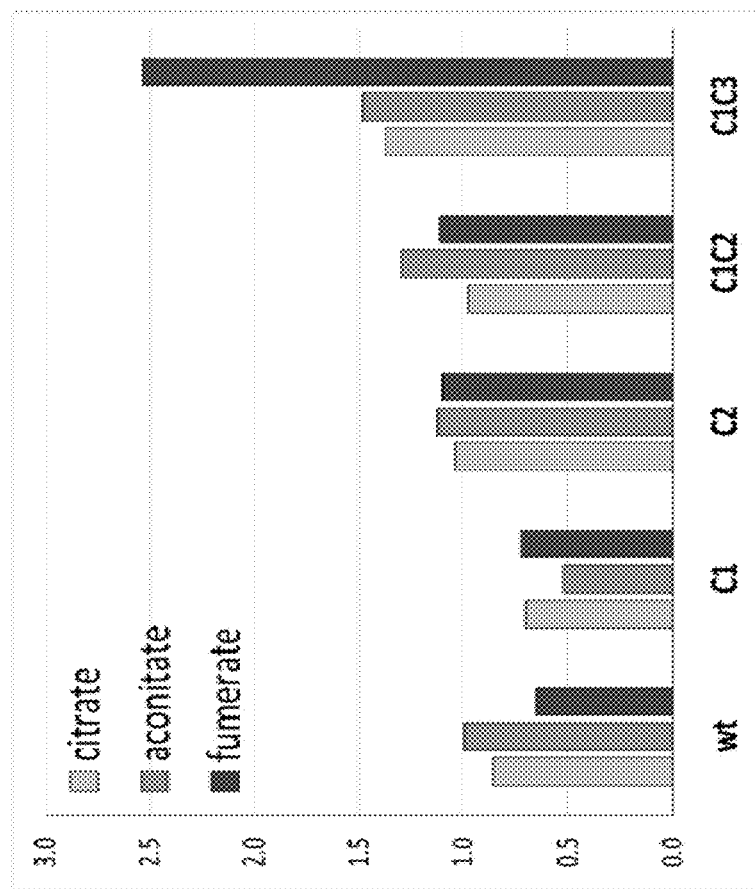
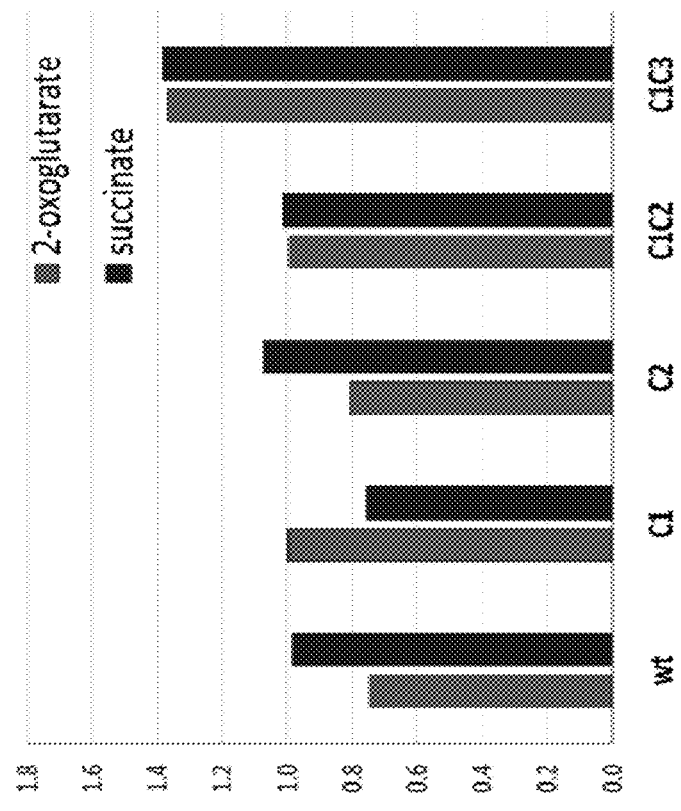

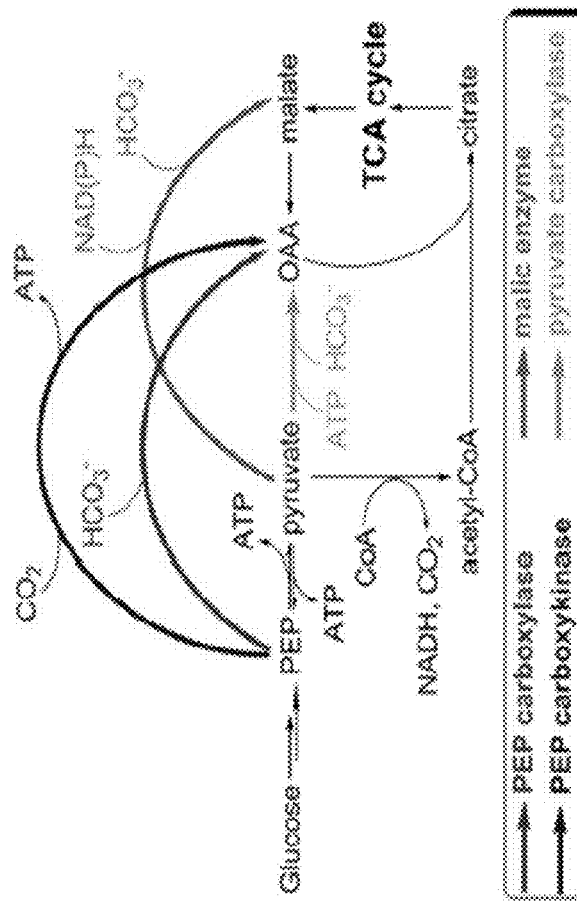
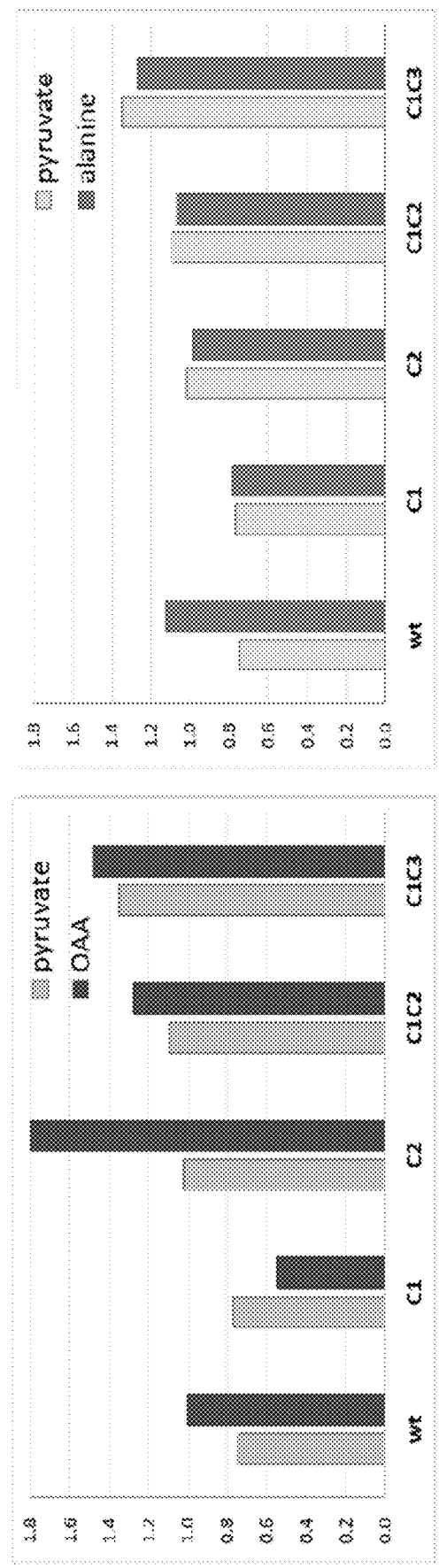
Fig. 18

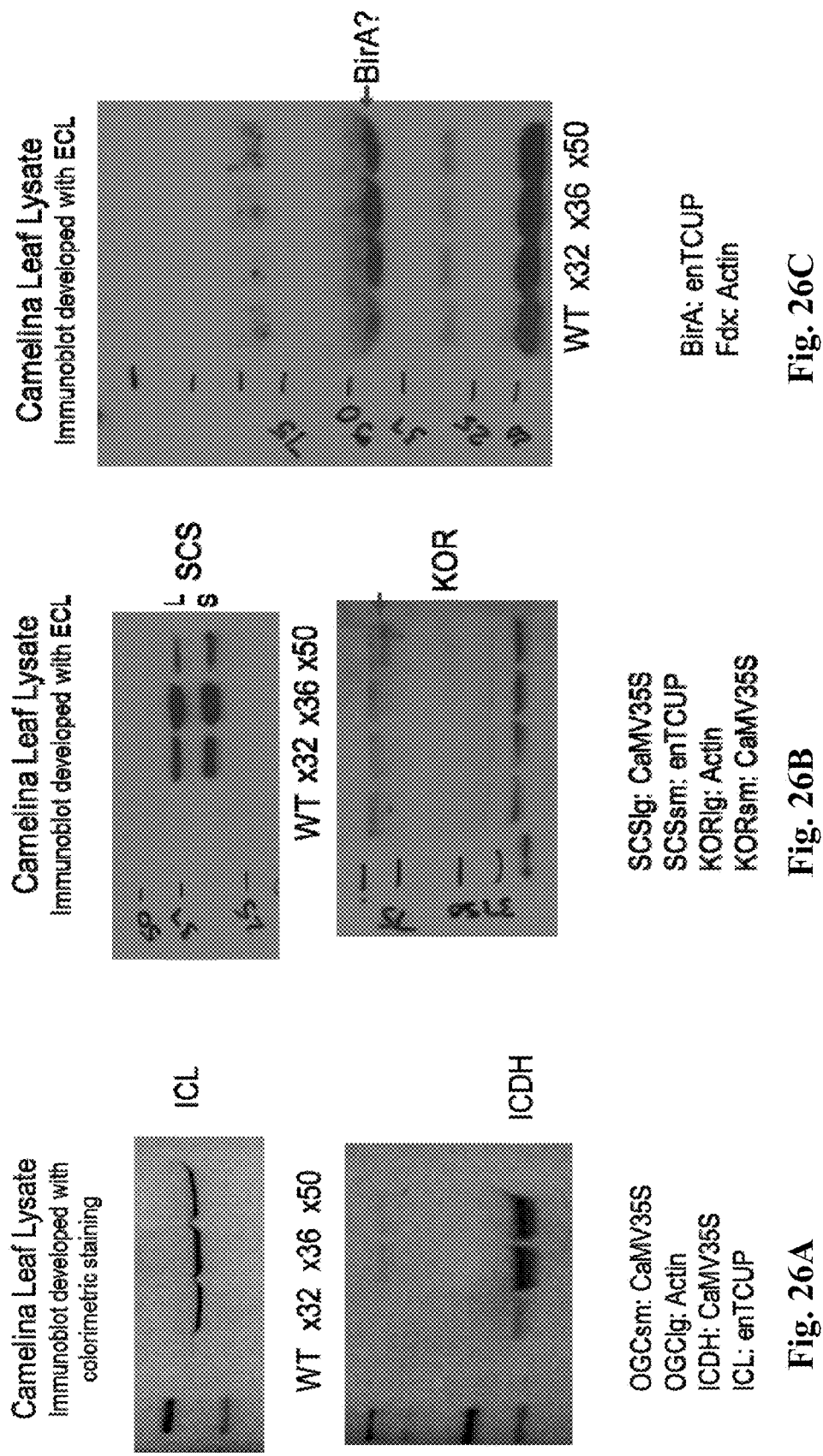

SEQUENCE LISTING

```
<160> NUMBER OF SEQ ID NOS: 85

<210> SEQ ID NO 1
<211> LENGTH: 289
<212> TYPE: PRT
<213> ORGANISM: Escherichia coli K12

<400> SEQUENCE: 1

Met Ser Ile Leu Ile Asp Lys Asn Thr Lys Val Ile Cys Gln Gly Phe
1               5                   10                  15

Thr Gly Ser Gln Gly Thr Phe His Ser Glu Gln Ala Ile Ala Tyr Gly
            20                  25                  30

Thr Lys Met Val Gly Gly Val Thr Pro Gly Lys Gly Gly Thr Thr His
        35                  40                  45

Leu Gly Leu Pro Val Phe Asn Thr Val Arg Glu Ala Val Ala Ala Thr
    50                  55                  60

Gly Ala Thr Ala Ser Val Ile Tyr Val Pro Ala Pro Phe Cys Lys Asp
65                  70                  75                  80

Ser Ile Leu Glu Ala Ile Asp Ala Gly Ile Lys Leu Ile Ile Thr Ile
                85                  90                  95

Thr Glu Gly Ile Pro Thr Leu Asp Met Leu Thr Val Lys Val Lys Leu
            100                 105                 110

Asp Glu Ala Gly Val Arg Met Ile Gly Pro Asn Cys Pro Gly Val Ile
        115                 120                 125

Thr Pro Gly Glu Cys Lys Ile Gly Ile Gln Pro Gly His Ile His Lys
    130                 135                 140
```

```
Pro Gly Lys Val Gly Ile Val Ser Arg Ser Gly Thr Leu Thr Tyr Glu
145                 150                 155                 160

Ala Val Lys Gln Thr Thr Asp Tyr Gly Phe Gly Gln Ser Thr Cys Val
                165                 170                 175

Gly Ile Gly Gly Asp Pro Ile Pro Gly Ser Asn Phe Ile Asp Ile Leu
            180                 185                 190

Glu Met Phe Glu Lys Asp Pro Gln Thr Glu Ala Ile Val Met Ile Gly
            195                 200                 205

Glu Ile Gly Gly Ser Ala Glu Glu Ala Ala Tyr Ile Lys Glu
        210                 215                 220

His Val Thr Lys Pro Val Val Gly Tyr Ile Ala Gly Val Thr Ala Pro
225                 230                 235                 240

Lys Gly Lys Arg Met Gly His Ala Gly Ala Ile Ile Ala Gly Gly Lys
                245                 250                 255

Gly Thr Ala Asp Glu Lys Phe Ala Ala Leu Glu Ala Ala Gly Val Lys
            260                 265                 270

Thr Val Arg Ser Leu Ala Asp Ile Gly Glu Ala Leu Lys Thr Val Leu
            275                 280                 285

Lys

<210> SEQ ID NO 2
<211> LENGTH: 388
<212> TYPE: PRT
<213> ORGANISM: Escherichia coli K12

<400> SEQUENCE: 2

Met Asn Leu His Glu Tyr Gln Ala Lys Gln Leu Phe Ala Arg Tyr Gly
1               5                   10                  15

Leu Pro Ala Pro Val Gly Tyr Ala Cys Thr Thr Pro Arg Glu Ala Glu
            20                  25                  30

Glu Ala Ala Ser Lys Ile Gly Ala Gly Pro Trp Val Val Lys Cys Gln
        35                  40                  45

Val His Ala Gly Gly Arg Gly Lys Ala Gly Gly Val Lys Val Val Asn
    50                  55                  60

Ser Lys Glu Asp Ile Arg Ala Phe Ala Glu Asn Trp Leu Gly Lys Arg
65                  70                  75                  80

Leu Val Thr Tyr Gln Thr Asp Ala Asn Gly Gln Pro Val Asn Gln Ile
                85                  90                  95

Leu Val Glu Ala Ala Thr Asp Ile Ala Lys Glu Leu Tyr Leu Gly Ala
            100                 105                 110

Val Val Asp Arg Ser Ser Arg Arg Val Val Phe Met Ala Ser Thr Glu
        115                 120                 125

Gly Gly Val Glu Ile Glu Lys Val Ala Glu Glu Thr Pro His Leu Ile
    130                 135                 140

His Lys Val Ala Leu Asp Pro Leu Thr Gly Pro Met Pro Tyr Gln Gly
145                 150                 155                 160

Arg Glu Leu Ala Phe Lys Leu Gly Leu Glu Gly Lys Leu Val Gln Gln
                165                 170                 175

Phe Thr Lys Ile Phe Met Gly Leu Ala Thr Ile Phe Leu Glu Arg Asp
            180                 185                 190

Leu Ala Leu Ile Glu Ile Asn Pro Leu Val Ile Thr Lys Gln Gly Asp
        195                 200                 205

Leu Ile Cys Leu Asp Gly Lys Leu Gly Ala Asp Gly Asn Ala Leu Phe
    210                 215                 220
```

```
Arg Gln Pro Asp Leu Arg Glu Met Arg Asp Gln Ser Gln Glu Asp Pro
225                 230                 235                 240

Arg Glu Ala Gln Ala Ala Gln Trp Glu Leu Asn Tyr Val Ala Leu Asp
            245                 250                 255

Gly Asn Ile Gly Cys Met Val Asn Gly Ala Gly Leu Ala Met Gly Thr
        260                 265                 270

Met Asp Ile Val Lys Leu His Gly Gly Glu Pro Ala Asn Phe Leu Asp
    275                 280                 285

Val Gly Gly Gly Ala Thr Lys Glu Arg Val Thr Glu Ala Phe Lys Ile
290                 295                 300

Ile Leu Ser Asp Asp Lys Val Lys Ala Val Leu Val Asn Ile Phe Gly
305                 310                 315                 320

Gly Ile Val Arg Cys Asp Leu Ile Ala Asp Gly Ile Ile Gly Ala Val
                325                 330                 335

Ala Glu Val Gly Val Asn Val Pro Val Val Val Arg Leu Glu Gly Asn
            340                 345                 350

Asn Ala Glu Leu Gly Ala Lys Lys Leu Ala Asp Ser Gly Leu Asn Ile
        355                 360                 365

Ile Ala Ala Lys Gly Leu Thr Asp Ala Ala Gln Gln Val Val Ala Ala
370                 375                 380

Val Glu Gly Lys
385

<210> SEQ ID NO 3
<211> LENGTH: 2036
<212> TYPE: DNA
<213> ORGANISM: Escherichia coli K12

<400> SEQUENCE: 3
atgaacttac atgaatatca ggcaaaacaa cttttttgccc gctatggctt accagcaccg      60
gtgggttatg cctgtactac tccgcgcgaa gcagaagaag ccgcttcaaa atcggtgcc     120 ggtccgtggg tagtgaaatg tcaggttcac gctggtggcc gcggtaaagc gggcggtgtg     180
aaagttgtaa acagcaaaga agacatccgt gcttttgcag aaaactggct gggcaagcgt     240
ctggtaacgt atcaaacaga tgccaatggc caaccggtta accagattct ggttgaagca     300
gcgaccgata tcgctaaaga gctgtatctc ggtgccgttg ttgaccgtag ttcccgtcgt     360
gtggtcttta tggcctccac cgaaggcggc gtggaaatcg aaaaagtggc ggaagaaact     420
ccgcacctga tccataaagt tgcgcttgat ccgctgactg gcccgatgcc gtatcaggga     480
cgcgagctgg cgttcaaact gggtctggaa ggtaaactgg ttcagcagtt caccaaaatc     540
ttcatgggcc tggcgaccat tttcctggag cgcgacctgg cgttgatcga atcaacccg     600 ctggtcatca ccaaacaggg cgatctgatt tgcctcgacg caaactggg cgctgacggc     660 aacgcactgt ccgccagcc tgatctgcgc gaaatgcgtg accagtcgca ggaagatccg     720
cgtgaagcac aggctgcaca gtgggaactg aactacgttg cgctggacgg taacatcggt     780
tgtatggtta acggcgcagg tctggcgatg ggtacgatgg acatcgttaa actgcacggc     840
ggcgaaccgg ctaacttcct tgacgttggc ggcggcgcaa ccaagaacg tgtaaccgaa     900 gcgttcaaaa tcatcctctc tgacgacaaa gtgaaagccg ttctggttaa catcttcggc     960
ggtatcgttc gttgcgacct gatcgctgac ggtatcatcg gcgcggtagc agaagtgggt    1020
gttaacgtac cggtcgtggt acgtctggaa ggtaacaacg ccgaactcgg cgcgaagaaa    1080
ctggctgaca gcggcctgaa tattattgca gcaaaaggtc tgacggatgc agctcagcag    1140
```

-continued

```
gttgttgccg cagtggaggg gaaataatgt ccattttaat cgataaaaac accaaggtta    1200
tctgccaggg ctttaccggt agccagggga ctttccactc agaacaggcc attgcatacg    1260
gcactaaaat ggttggcggc gtaaccccag gtaaaggcgg caccacccac ctcggcctgc    1320
cggtgttcaa caccgtgcgt gaagccgttg ctgccactgg cgctaccgct tctgttatct    1380
acgtaccagc accgttctgc aaagactcca ttctggaagc catcgacgca ggcatcaaac    1440
tgattatcac catcactgaa ggcatcccga cgctggatat gctgaccgtg aaagtgaagc    1500
tggatgaagc aggcgttcgt atgatcggcc cgaactgccc aggcgttatc actccgggtg    1560
aatgcaaaat cggtatccag cctggtcaca ttcacaaacc gggtaaagtg ggtatcgttt    1620
cccgttccgg tacactgacc tatgaagcgg ttaaacagac cacggattac ggtttcggtc    1680
agtcgacctg tgtcggtatc ggcggtgacc cgatcccggg ctctaacttt atcgacattc    1740
tcgaaatgtt cgaaaaagat ccgcagaccg aagcgatcgt gatgatcggt gagatcggcg    1800
gtagcgctga agaagaagca gctgcgtaca tcaaagagca cgttaccaag ccagttgtgg    1860
gttacatcgc tggtgtgact cgcgccgaaag gcaaacgtat gggccacgcg ggtgccatca    1920
ttgccggtgg gaaagggact gcggatgaga aattcgctgc tctggaagcc gcaggcgtga    1980
aaaccgttcg cagcctggcg gatatcggtg aagcactgaa aactgttctg aaataa        2036
```

<210> SEQ ID NO 4
<211> LENGTH: 295
<212> TYPE: PRT
<213> ORGANISM: Azotobacter vinelandii DJ

<400> SEQUENCE: 4

```
Met Ser Ile Leu Val Asn Lys Asp Thr Lys Val Ile Cys Gln Gly Phe
1               5                   10                  15

Thr Gly Ser Gln Gly Thr Phe His Ser Glu Gln Ala Ile Ala Tyr Gly
                20                  25                  30

Thr Arg Met Val Gly Gly Val Thr Pro Gly Lys Gly Gly Leu Val His
            35                  40                  45

Leu Asp Leu Pro Val Phe Asp Thr Val Arg Glu Ala Val Glu Ala Thr
        50                  55                  60

Gly Ala Asp Ala Ser Val Ile Tyr Val Pro Ala Pro Phe Cys Lys Asp
65                  70                  75                  80

Ser Ile Leu Glu Ala Ala Phe Ala Gly Val Arg Leu Ile Val Cys Ile
                85                  90                  95

Thr Glu Gly Val Pro Thr Leu Asp Met Leu Gln Val Lys Leu Lys Cys
            100                 105                 110

Asp Glu Leu Gly Val Arg Leu Ile Gly Pro Asn Cys Pro Gly Val Ile
        115                 120                 125

Thr Pro Gly Glu Cys Lys Ile Gly Ile Gln Pro Gly Asn Ile His Met
130                 135                 140

Pro Gly Arg Val Gly Ile Val Ser Arg Ser Gly Thr Leu Thr Tyr Glu
145                 150                 155                 160

Ala Val Lys Gln Thr Thr Asp Ala Gly Phe Gly Gln Ser Thr Cys Val
                165                 170                 175

Gly Ile Gly Gly Asp Pro Ile Pro Gly Ser Ser Phe Ile Asp Ile Leu
            180                 185                 190

Gly Leu Phe Gln Asp Asp Pro Gln Thr Glu Ala Ile Val Met Ile Gly
        195                 200                 205

Glu Ile Gly Gly Ser Ala Glu Glu Glu Ala Ala Ala Tyr Ile Lys Ala
```

```
            210                 215                 220
Lys Val Asp Lys Pro Val Val Ser Tyr Ile Ala Gly Val Thr Ala Pro
225                 230                 235                 240

Ser Gly Lys Arg Met Gly His Ala Gly Ala Ile Ile Ser Gly Gly Lys
            245                 250                 255

Gly Thr Ala Asp Glu Lys Phe Ala Ala Leu Gln Asp Ala Gly Val Gln
            260                 265                 270

Thr Val Arg Ser Leu Ala Asp Ile Gly Lys Ala Leu Ala Glu Leu Thr
            275                 280                 285

Gly Trp Glu Arg Lys Gln Ser
            290                 295

<210> SEQ ID NO 5
<211> LENGTH: 389
<212> TYPE: PRT
<213> ORGANISM: Azotobacter vinelandii DJ

<400> SEQUENCE: 5

Met Asn Leu His Glu Tyr Gln Gly Lys Gln Leu Phe Ala Glu Tyr Gly
1               5                   10                  15

Leu Pro Val Ser Arg Gly Val Ala Ile Asp Thr Pro Glu Ala Ala Ala
            20                  25                  30

Glu Ala Cys Asp Arg Ile Gly Gly Asp Cys Trp Val Ala Lys Val Gln
        35                  40                  45

Val His Ala Gly Gly Arg Gly Lys Ala Gly Gly Val Lys Leu Val Lys
    50                  55                  60

Ser Arg Glu Glu Ala Lys Val Phe Ala Val Asn Trp Leu Gly Lys Arg
65                  70                  75                  80

Leu Val Thr Tyr Gln Thr Asp Ala Ser Gly Gln Pro Val Gly Lys Ile
                85                  90                  95

Leu Val Glu Ala Cys Thr Glu Ile Glu Arg Glu Leu Tyr Leu Gly Ala
            100                 105                 110

Val Val Asp Arg Ser Ser Arg Arg Ile Val Phe Met Ala Ser Thr Glu
        115                 120                 125

Gly Gly Val Asn Ile Glu Gln Val Ala His Glu Thr Pro Glu Lys Ile
    130                 135                 140

Leu Lys Ala Ser Ile Asp Pro Leu Val Gly Ala Gln Pro Phe Gln Ala
145                 150                 155                 160

Arg Asp Leu Ala Phe Arg Leu Gly Leu Glu Gly Asp Gln Leu Lys Gln
                165                 170                 175

Phe Thr His Ile Phe Ile Gly Leu Ala Lys Leu Phe Gln Glu His Asp
            180                 185                 190

Leu Ala Leu Val Glu Val Asn Pro Leu Val Val Gln Lys Asp Gly Asn
        195                 200                 205

Leu Leu Cys Leu Asp Ala Lys Ile Asn Leu Asp Thr Asn Ala Leu Phe
    210                 215                 220

Arg Gln Pro Arg Leu Arg Ala Met His Asp Pro Ser Gln Asp Asp Pro
225                 230                 235                 240

Arg Glu Val His Ala Ala Lys Trp Glu Leu Asn Tyr Val Ala Leu Glu
                245                 250                 255

Gly Asn Ile Gly Cys Met Val Asn Gly Ala Gly Leu Ala Met Gly Thr
            260                 265                 270

Met Asp Ile Val Asn Leu His Gly Gly Arg Pro Ala Asn Phe Leu Asp
        275                 280                 285
```

Val Gly Gly Gly Ala Thr Lys Glu Arg Val Thr Glu Ala Phe Lys Ile
    290                 295                 300

Ile Leu Ser Asp Ala Lys Val Lys Ala Val Leu Val Asn Ile Phe Gly
305                 310                 315                 320

Gly Ile Val Arg Cys Asp Met Ile Ala Glu Gly Ile Ile Gly Ala Val
                325                 330                 335

Arg Glu Val Gly Val Lys Val Pro Val Val Arg Leu Glu Gly Asn
            340                 345                 350

Asn Ala Glu Leu Gly Ala Glu Met Leu Ala Arg Ser Gly Leu Asn Ile
        355                 360                 365

Ile Pro Ala Ser Thr Leu Thr Asp Ala Ala Val Gln Val Val Lys Ala
    370                 375                 380

Ala Glu Asp Asn Pro
385

<210> SEQ ID NO 6
<211> LENGTH: 2054
<212> TYPE: DNA
<213> ORGANISM: Azotobacter vinelandii DJ

<400> SEQUENCE: 6

| | | | | | |
|---|---|---|---|---|---|
| atgaatctcc | atgaatatca | gggcaagcag | cttttcgccg | aatatggttt | acccgtgtcc | 60 |
| cgaggcgttg | ccatcgatac | cccggaggcc | gcggcggagg | cctgcgacag | gattggcggc | 120 |
| gactgctggg | tcgcgaaggt | ccaggtgcat | gccggcggtc | gtggcaaggc | cggtggcgtc | 180 |
| aagctggtca | agagccggga | ggaggcgaag | gtcttcgccg | tcaactggct | gggcaagcga | 240 |
| ctggtgaccct | accagaccga | cgcttcgggg | cagccggtcg | gcaagatcct | ggtcgaggcc | 300 |
| tgcaccgaga | tcgagcggga | gctttacctg | ggagcggtgg | tcgatcgctc | gagccgccgc | 360 |
| atcgtcttca | tggcctcgac | cgaggcgggg | gtgaacatcg | agcaggtcgc | ccatgaaacg | 420 |
| cccgagaaga | tcctcaaggc | cagcatcgac | ccctggtcg | cgcccagcc | gttccaggcc | 480 |
| cgcgacctgg | ccttccggct | gggtctcgaa | ggcgatcagc | tcaagcagtt | cacccatatc | 540 |
| ttcatcggtc | tggccaagct | gttccaggag | cacgatctgg | ccctggtgga | ggtgaatccg | 600 |
| ctggtggtcc | agaaggacgg | caatctgctc | tgcctggacg | ccaagatcaa | tctcgatacc | 660 |
| aacgccctgt | tccgccaacc | cagactgcgc | gccatgcacg | acccttccca | ggacgatccc | 720 |
| cgcgaagtgc | atgcggcgaa | gtgggagctg | aactacgtgg | ccctcgaggg | caacatcggc | 780 |
| tgcatggtca | acggcgccgg | actggccatg | gcaccatgg | acatcgtcaa | tctccatggg | 840 |
| ggccggccgg | ccaacttcct | cgacgtcggc | ggcggcgcga | ccaaggagcg | ggtgaccgag | 900 |
| gccttcaaga | tcattctctc | cgatgccaag | gtaaaagccg | tgctggtcaa | catcttcggc | 960 |
| ggcatcgtgc | gctgcgacat | gatcgccgaa | ggcatcatcg | gcgcggtccg | ggaggtaggc | 1020 |
| gtcaaggttc | cggtggtggt | ccgcctggag | ggcaacaacg | cggaactggg | cgccgagatg | 1080 |
| ctggcccgga | gcggcctgaa | catcattccg | gccagcaccc | tgaccgatgc | ggcggtgcag | 1140 |
| gtggtcaagg | cagcggagga | caacccatga | gtattttggt | caacaaggac | accaaggtca | 1200 |
| tctgccaggg | attcaccggt | agccagggga | ccttccacag | cgaacaggcc | attgcctatg | 1260 |
| gcaccccggat | ggtcggaggc | gtgacgccgg | gcaaggagg | actcgtccat | ctcgacctgc | 1320 |
| cggtattcga | cacggtccgc | gaggccgtgg | aggccaccgg | cgccgacgcc | tcggtcatct | 1380 |
| acgtaccgc | gcccttctgc | aaggattcca | ttctcgaggc | ggctttcgcc | ggtgtccggc | 1440 |
| tgatcgtctg | catcaccgag | ggcgtaccga | ccctcgacat | gctgcaggtc | aagctcaagt | 1500 |

-continued

```
gcgacgagct gggcgtgcgc ctgatcggcc ccaactgtcc gggcgtgatc actcccggcg   1560
agtgcaagat cggcatccag ccgggcaata tccacatgcc gggcagggtc ggcatcgttt   1620
cccggtcggg caccctgact tacgaggcgg tgaagcagac caccgacgcg ggcttcggcc   1680
agtccacctg cgtgggtatc ggtggcgacc cgattccggg gtccagtttc atcgatatcc   1740
tcggtctgtt ccaggacgat ccgcagaccg aagccatcgt gatgatcggc gaaatcggcg   1800
gcagtgccga ggaggaggcg gcggcctaca tcaaggccaa ggtcgacaag ccggtggttt   1860
cctacatcgc cggcgtcacc cgcccctcgg caagcgcat ggggcatgcc ggtgcgatca   1920
tctccggcgg caagggcact gcggacgaga agttcgccgc cctgcaggat gccggcgtgc   1980
agaccgtgcg ttccctggcg gatatcggca aggccctggc cgaactgacc ggctgggaga   2040
ggaagcagtc ctga                                                    2054
```

<210> SEQ ID NO 7
<211> LENGTH: 294
<212> TYPE: PRT
<213> ORGANISM: Bradyrhizobium sp.BTAi1

<400> SEQUENCE: 7

```
Met Ser Ile Leu Ile Asp Lys Asn Thr Lys Val Ile Cys Gln Gly Phe
1               5                  10                  15

Thr Gly Lys Asn Gly Thr Phe His Ser Glu Ala Ala Ile Ala Tyr Gly
            20                  25                  30

Thr Lys Met Val Gly Gly Thr Ser Pro Gly Lys Gly Gly Ser Thr His
        35                  40                  45

Leu Gly Leu Pro Val Phe Asp Thr Val Lys Glu Ala Arg Glu Ala Thr
    50                  55                  60

Gly Ala Asp Ala Ser Val Ile Tyr Val Pro Pro Pro Gly Ala Ala Asp
65                  70                  75                  80

Ala Ile Cys Glu Ala Ile Asp Ala Glu Val Pro Leu Ile Val Cys Ile
                85                  90                  95

Thr Glu Gly Ile Pro Val Leu Asp Met Val Arg Val Lys Arg Ser Leu
            100                 105                 110

Gln Gly Ser Lys Ser Arg Leu Ile Gly Pro Asn Cys Pro Gly Val Met
        115                 120                 125

Thr Ala Gly Glu Cys Lys Ile Gly Ile Met Pro Ala Asn Ile Phe Lys
    130                 135                 140

Pro Gly Ser Val Gly Ile Val Ser Arg Ser Gly Thr Leu Thr Tyr Glu
145                 150                 155                 160

Ala Val Phe Gln Thr Thr Ser Glu Gly Leu Gly Gln Thr Thr Ala Val
                165                 170                 175

Gly Ile Gly Gly Asp Pro Val Lys Gly Thr Glu Phe Ile Asp Met Leu
            180                 185                 190

Glu Met Phe Leu Ala Asp Pro Lys Thr Glu Ser Ile Ile Met Ile Gly
        195                 200                 205

Glu Ile Gly Gly Ser Ala Glu Glu Asp Ala Ala Gln Phe Ile Lys Asp
    210                 215                 220

Glu Ala Lys Arg Gly Arg Lys Lys Pro Met Val Gly Phe Ile Ala Gly
225                 230                 235                 240

Val Thr Ala Pro Pro Gly Arg Arg Met Gly His Ala Gly Ala Ile Ile
                245                 250                 255

Ser Gly Gly Lys Gly Asp Ala Gly Ser Lys Thr Ala Ala Met Glu Ala
            260                 265                 270
```

```
Ala Gly Ile Thr Val Ser Pro Ser Pro Ala Arg Leu Gly Lys Thr Leu
        275                 280                 285

Val Glu Lys Leu Lys Ser
    290

<210> SEQ ID NO 8
<211> LENGTH: 398
<212> TYPE: PRT
<213> ORGANISM: Bradyrhizobium sp.BTAi1

<400> SEQUENCE: 8

Met Asn Ile His Glu Tyr Gln Ala Lys Ala Leu Leu His Glu Phe Gly
1               5                   10                  15

Val Pro Ile Ser Lys Gly Val Pro Val Leu Arg Pro Glu Asp Ser Asp
            20                  25                  30

Ala Ala Ala Lys Ala Leu Gly Gly Pro Val Trp Val Val Lys Ser Gln
        35                  40                  45

Ile His Ala Gly Gly Arg Gly Lys Gly Lys Phe Lys Glu Ala Ser Ala
    50                  55                  60

Gly Asp Lys Gly Gly Val Arg Leu Ala Lys Ser Ile Asp Glu Val Asn
65                  70                  75                  80

Ala Phe Ala Lys Gln Met Leu Gly Ala Thr Leu Val Thr Val Gln Thr
                85                  90                  95

Gly Pro Asp Gly Lys Gln Val Asn Arg Leu Tyr Ile Glu Asp Gly Ser
            100                 105                 110

Asp Ile Asp Lys Glu Phe Tyr Leu Ser Leu Leu Val Asp Arg Glu Thr
        115                 120                 125

Ser Lys Val Ala Phe Val Val Ser Thr Glu Gly Gly Val Asn Ile Glu
    130                 135                 140

Asp Val Ala His Ser Thr Pro Glu Lys Ile Ile Thr Phe Ser Val Asp
145                 150                 155                 160

Pro Ala Thr Gly Val Met Pro His His Gly Arg Ala Val Ala Lys Ala
                165                 170                 175

Leu Lys Leu Ser Gly Asp Leu Ala Lys Gln Ala Glu Lys Leu Thr Ile
            180                 185                 190

Gln Leu Tyr Thr Ala Phe Val Ala Lys Asp Met Ala Met Leu Glu Ile
        195                 200                 205

Asn Pro Leu Val Val Thr Lys Gln Gly Gln Leu Arg Val Leu Asp Ala
    210                 215                 220

Lys Val Ser Phe Asp Ser Asn Ala Leu Phe Lys His Pro Glu Val Val
225                 230                 235                 240

Ala Leu Arg Asp Glu Thr Glu Asp Ala Lys Glu Ile Glu Ala Ser
                245                 250                 255

Lys Tyr Asp Leu Asn Tyr Val Ala Leu Asp Gly Thr Ile Gly Cys Met
            260                 265                 270

Val Asn Gly Ala Gly Leu Ala Met Ala Thr Met Asp Ile Ile Lys Leu
        275                 280                 285

Tyr Gly Met Glu Pro Ala Asn Phe Leu Asp Val Gly Gly Gly Ala Ser
    290                 295                 300

Lys Glu Lys Val Ala Ala Ala Phe Lys Ile Ile Thr Ala Asp Pro Asn
305                 310                 315                 320

Val Lys Gly Ile Leu Val Asn Ile Phe Gly Gly Ile Met Lys Cys Asp
                325                 330                 335

Val Ile Ala Glu Gly Val Ala Ala Val Lys Glu Val Gly Leu Lys
            340                 345                 350
```

Val Pro Leu Val Val Arg Leu Glu Gly Thr Asn Val Asp Leu Gly Lys
        355                 360                 365

Lys Ile Ile Ser Glu Ser Gly Leu Asn Val Leu Pro Ala Asp Asn Leu
    370                 375                 380

Asp Asp Ala Ala Gln Lys Ile Val Lys Ala Val Lys Gly Gly
385                 390                 395

<210> SEQ ID NO 9
<211> LENGTH: 2138
<212> TYPE: DNA
<213> ORGANISM: Bradyrhizobium sp.BTAi1

<400> SEQUENCE: 9

```
atgaacattc acgaatatca ggccaaggca ctgctgcacg agttcggcgt gccgatttcc      60
aagggcgtgc cggtgctccg tccggaggac tcggatgcgg cggcgaaggc gctcggcggt     120
ccggtctggg tcgtgaagag ccagatccac gccggcggcc gtggcaaggg caagttcaag     180
gaggcctcgg ccggcgacaa gggcggcgtc cgcctcgcca gtcgattga cgaggtcaat     240
gcgttcgcca agcagatgct cggcgcaacc ctcgtcaccg tgcagaccgg ccccgatggc     300
aagcaggtca accgcctcta catcgaggac ggctcggata tcgacaagga attctacctg     360
tcgctgctgg tcgatcgcga gacctcgaag gtcgctttcg tggtgtcgac cgaaggcggc     420
gtcaacatcg aggacgttgc tcacagcacg cctgagaaga tcatcacctt ctcagtcgat     480
ccggccaccg gcgtgatgcc gcatcacggt cgcgccgtcg ccaaggcgct gaagctctcg     540
ggcgatctcg ccaagcaggc cgagaagctg accatccagc tctataccgc cttcgtcgcc     600
aaggacatgg cgatgctcga gatcaacccg ctggtcgtca ccaagcaggg ccagctgcgt     660
gtgctcgacg ccaaggtgtc gttcgactcc aacgcgctgt tcaagcaccc cgaggtcgtg     720
gcgctgcgtg acgagaccga ggaagacgcc aaggagatcg aggcctccaa atacgatctc     780
aactatgtcg cgctcgacgg caccatcggc tgcatggtca acgcgccgg cctcgcgatg     840
gcgacgatgg acatcatcaa gctctacggc atggagccgg ccaacttcct cgacgtcggc     900
ggcggcgcca gcaaggagaa ggtcgcgcg gcgttcaaga tcatcaccgc cgacccgaac     960
gtgaagggca tcctggtcaa catcttcggc ggcatcatga agtgcgatgt catcgccgag    1020
ggcgtcgtgg ccgcggtcaa ggaagtcggc ctgaaggtgc cgctggtggt cgcgcctcgaa    1080
ggcaccaatg tcgatctcgg caagaagatc atcagcgagt ccggtctgaa cgtgctgccc    1140
gccgacaatc tcgacgacgc cgcgcagaag atcgtcaagg ccgtcaaggg aggctgagcg    1200
ccgtttcagg cgctcgctta gctcctcacc gcaacgcttt tagagaaagc acgatgtcca    1260
ttctcatcga caagaacacc aaggtcatct gtcagggctt cactggcaag aacggcaccct    1320
tccactccga ggcggcgatc gcctacggca ccaagatggt cggcggcacc tcgccgggca    1380
aaggcggctc gacccatctc ggcctgccgg tgttcgacac cgtcaaggag gctcgcgagg    1440
ccactggcgc tgacgcgtcg gtgatctacg tgccgccgcc gggtgcggcc gacgccattt    1500
gcgaggcgat cgacgccgag gtcccgctga tcgtctgcat caccgagggc atcccggtgc    1560
tcgacatggt cagggtcaag cgctcgctgc agggctccaa gtcgcgcctg atcggcccga    1620
actgcccggg cgtcatgacc gccggagagt gcaagatcgg catcatgccg ccaatatct    1680
tcaagcccgg ctcggtcggc atcgtgtcac gctccggcac gctgacctat gaagcggtgt    1740
tccagaccac ctcggaaggc ctcggtcaga ccaccgcggt cggtatcggc ggcgacccgg    1800
tcaagggcac cgagttcatc gacatgctgg agatgttcct tgccgacccc aagaccgagt    1860
```

```
cgatcatcat gatcggcgag atcggcggct cggccgagga agacgcggcc cagttcatca    1920
aggacgaggc caagcgcggc cgcaagaagc cgatggtcgg attcatcgcc ggcgtcacgg    1980
cgcctccggg ccgtcgcatg ggccatgccg gcgcgatcat ctcgggcggc aagggtgatg    2040
ccggttcgaa gacggccgcg atggaagcgg ctggtatcac ggtgtcgccg tcgccggcgc    2100
ggctcggcaa aacgcttgtc gaaaagttga atcctga                             2138
```

```
<210> SEQ ID NO 10
<211> LENGTH: 291
<212> TYPE: PRT
<213> ORGANISM: Azospirillum sp. B510

<400> SEQUENCE: 10

Met Ala Val Leu Val Asp Lys Asn Thr Lys Val Ile Cys Gln Gly Phe
1               5                   10                  15

Thr Gly Ala Gln Gly Thr Phe His Ser Glu Gln Ala Ile Ala Tyr Gly
                20                  25                  30

Thr Lys Met Val Gly Val Thr Pro Gly Lys Gly Gly Ala Lys His
            35                  40                  45

Leu Asp Leu Pro Ile Phe Asp Thr Val Ala Glu Ala Val Glu Lys Thr
    50                  55                  60

Gly Ala Asn Ala Ser Val Ile Tyr Val Pro Pro Pro Phe Ala Ala Asp
65                  70                  75                  80

Ala Ile Leu Glu Ala Ile Asp Ala Glu Ile Pro Leu Val Val Cys Ile
                85                  90                  95

Thr Glu Gly Ile Pro Val Leu Asp Met Val Arg Val Lys Arg Ala Leu
            100                 105                 110

Asn Gly Ser Ala Thr Arg Leu Ile Gly Pro Asn Cys Pro Gly Val Ile
        115                 120                 125

Thr Pro Asp Glu Cys Lys Ile Gly Ile Met Pro Gly His Ile His Lys
    130                 135                 140

Arg Gly Lys Ile Gly Ile Val Ser Arg Ser Gly Thr Leu Thr Tyr Glu
145                 150                 155                 160

Ala Val Ala Gln Thr Thr Ala Ala Gly Leu Gly Gln Thr Thr Cys Ile
                165                 170                 175

Gly Ile Gly Gly Asp Pro Val Asn Gly Thr Asn Phe Val Asp Ser Leu
            180                 185                 190

Glu Leu Phe Val Lys Asp Pro Glu Thr Glu Gly Ile Ile Met Ile Gly
        195                 200                 205

Glu Ile Gly Gly Asp Ala Glu Val Lys Gly Ala Glu Phe Ile Lys Ala
    210                 215                 220

Ser Gly Thr Arg Lys Pro Val Val Gly Phe Ile Ala Gly Arg Thr Ala
225                 230                 235                 240

Pro Pro Gly Arg Arg Met Gly His Ala Gly Ala Val Ile Ser Gly Gly
                245                 250                 255

Asn Asp Thr Ala Asp Phe Lys Ile Asp Phe Met Lys Ser Val Gly Ile
            260                 265                 270

Ala Val Ala Asp Ser Pro Ala Ser Leu Gly Ser Thr Met Leu Lys Val
        275                 280                 285

Phe Lys Gly
    290

<210> SEQ ID NO 11
<211> LENGTH: 389
```

<212> TYPE: PRT
<213> ORGANISM: Azospirillum sp. B510

<400> SEQUENCE: 11

```
Met Asn Leu His Glu Tyr Gln Gly Lys Gln Leu Phe Ala Glu Tyr Gly
1               5                   10                  15

Leu Pro Val Ser Arg Gly Val Ala Ile Asp Thr Pro Glu Ala Ala Ala
            20                  25                  30

Glu Ala Cys Asp Arg Ile Gly Gly Asp Cys Trp Val Ala Lys Val Gln
        35                  40                  45

Val His Ala Gly Gly Arg Gly Lys Ala Gly Gly Val Lys Leu Val Lys
    50                  55                  60

Ser Arg Glu Glu Ala Lys Val Phe Ala Val Asn Trp Leu Gly Lys Arg
65                  70                  75                  80

Leu Val Thr Tyr Gln Thr Asp Ala Ser Gly Gln Pro Val Gly Lys Ile
                85                  90                  95

Leu Val Glu Ala Cys Thr Glu Ile Glu Arg Glu Leu Tyr Leu Gly Ala
            100                 105                 110

Val Val Asp Arg Ser Ser Arg Arg Ile Val Phe Met Ala Ser Thr Glu
        115                 120                 125

Gly Gly Val Asn Ile Glu Gln Val Ala His Glu Thr Pro Glu Lys Ile
    130                 135                 140

Leu Lys Ala Ser Ile Asp Pro Leu Val Gly Ala Gln Pro Phe Gln Ala
145                 150                 155                 160

Arg Asp Leu Ala Phe Arg Leu Gly Leu Glu Gly Asp Gln Leu Lys Gln
                165                 170                 175

Phe Thr His Ile Phe Ile Gly Leu Ala Lys Leu Phe Gln Glu His Asp
            180                 185                 190

Leu Ala Leu Val Glu Val Asn Pro Leu Val Val Gln Lys Asp Gly Asn
        195                 200                 205

Leu Leu Cys Leu Asp Ala Lys Ile Asn Leu Asp Thr Asn Ala Leu Phe
210                 215                 220

Arg Gln Pro Arg Leu Arg Ala Met His Asp Pro Ser Gln Asp Asp Pro
225                 230                 235                 240

Arg Glu Val His Ala Ala Lys Trp Glu Leu Asn Tyr Val Ala Leu Glu
                245                 250                 255

Gly Asn Ile Gly Cys Met Val Asn Gly Ala Gly Leu Ala Met Gly Thr
            260                 265                 270

Met Asp Ile Val Asn Leu His Gly Gly Arg Pro Ala Asn Phe Leu Asp
        275                 280                 285

Val Gly Gly Gly Ala Thr Lys Glu Arg Val Thr Glu Ala Phe Lys Ile
    290                 295                 300

Ile Leu Ser Asp Ala Lys Val Lys Ala Val Leu Val Asn Ile Phe Gly
305                 310                 315                 320

Gly Ile Val Arg Cys Asp Met Ile Ala Glu Gly Ile Ile Gly Ala Val
                325                 330                 335

Arg Glu Val Gly Val Lys Val Pro Val Val Arg Leu Glu Gly Asn
            340                 345                 350

Asn Ala Glu Leu Gly Ala Glu Met Leu Ala Arg Ser Gly Leu Asn Ile
        355                 360                 365

Ile Pro Ala Ser Thr Leu Thr Asp Ala Ala Val Gln Val Val Lys Ala
    370                 375                 380

Ala Glu Asp Asn Pro
385
```

<210> SEQ ID NO 12
<211> LENGTH: 2074
<212> TYPE: DNA
<213> ORGANISM: Azospirillum sp. B510

<400> SEQUENCE: 12

| | | | | | |
|---|---|---|---|---|---|
| atgaacatcc | atgagtacca | ggcgaaaagc | ctgctgaaga | agtacggcgt | cgcggttccc | 60 |
| cgcggcggcg | tcgcctacac | cccgcaggag | gccgagacgg | tcgcccgcga | gctgggcggt | 120 |
| ccggtctggg | tggtgaagtc | ccagatccac | gccggcggcc | gcggcgccgg | ccgcttcaag | 180 |
| gacaaccccg | aaggcaaggg | cggcgtccgc | gtcgtcaagt | cgatcgagga | tgtcggcaag | 240 |
| aacgccgccg | agatgctgaa | ccacgttctc | gtgaccaagc | agaccggcgc | cgaaggccgc | 300 |
| gaggtcaagc | gcctctatgt | cgaggaaggc | gccgacatca | agcgcgagct | gtatctcggc | 360 |
| atgctgatcg | accgcgccac | cggccgcgtg | acgatcatgg | cctcgaccga | aggcggcatg | 420 |
| gagatcgagg | aggtcgccca | caacacgccg | gagaagatca | tcaaggtcgc | ggtcgacccg | 480 |
| gccaccggca | tccagggcta | ccacacccgc | aaggtcgcct | tcgcgctcgg | cctggaaggc | 540 |
| aagcaggtcg | gtgcggccgc | caagttcatc | caggccgcct | atcaggcctt | catcgacctc | 600 |
| gactgcgcca | tcgtcgagat | caacccgctg | atcgtcaccg | ggtcgggcga | catcctggcg | 660 |
| ctcgacgcca | agatgaactt | cgacgacaac | gcgctgttcc | gtcacaagga | cgttgaagag | 720 |
| ctgcgcgacg | aggccgaaga | ggacccggcg | agatcgagg | cggccaagca | cagcctcaac | 780 |
| tacgtcaagc | tcgatggcaa | catcggctgc | atggtcaacg | cgccggcct | ggcgatggcc | 840 |
| accatggaca | tcatcaagct | ctatggcggc | gagccggcca | acttcctcga | cgtcggcggc | 900 |
| ggcgccacca | aggagcgcgt | caccgcggcc | ttcaagctga | tcctgtccga | cagcaacgtc | 960 |
| gaaggcatcc | tggtcaacat | cttcggcggc | atcatgcgct | gcgacgtgat | cgccgagggc | 1020 |
| gtggtcgccg | cggcgcgcga | agtgcatctg | catgttccgc | tggtggtgcg | cctggaaggc | 1080 |
| accaacgtcg | atctgggcaa | gaagatcctg | gccgaatccg | gcctgccgat | cctctcggcc | 1140 |
| gacaacctcg | ccgacgccgc | cgagaaggtg | gtcaaggccg | tgaaggaggc | cgcgtgaaat | 1200 |
| ggctgttctc | gtcgataaga | acacgaaggt | gatctgccag | ggcttcaccg | gagcccaggg | 1260 |
| caccttccac | tccgagcagg | ccatcgccta | cggcaccaag | atggtcggcg | gcgtgacccc | 1320 |
| cggcaagggc | ggcgccaagc | atcttgacct | gccgatcttc | gacaccgtcg | ccgaggcggt | 1380 |
| cgagaagacc | ggggccaacg | cctcggtgat | ctatgtgccg | ccgcccttcg | cggccgacgc | 1440 |
| gatcctggag | gcgatcgacg | ccgagatccc | gctggtggtc | tgcatcaccg | aaggcatccc | 1500 |
| ggtgctcgac | atggtccgcg | tcaagcgcgc | cctcaacggc | tccgccacgc | gcctgatcgg | 1560 |
| cccgaactgc | cccggcgtca | tcacgccgga | cgagtgcaag | atcggcatca | tgccgggcca | 1620 |
| catccacaag | cgtggcaaga | tcggcatcgt | ctcgcgctcc | ggcacgctga | cctatgaggc | 1680 |
| cgtcgcgcag | accacggcgg | ccggtctcgg | ccagaccacc | tgcatcggca | tcggcggcga | 1740 |
| cccggtcaac | ggcaccaact | tcgtcgacag | cctggagctg | ttcgtgaagg | acccggagac | 1800 |
| cgagggcatc | atcatgatcg | gcgagatcgg | cggtgacgcc | gaggtcaagg | gcgcggagtt | 1860 |
| catcaaggcg | tcgggcacga | ggaagccggt | cgtcggcttc | atcgccggcc | gcacggcgcc | 1920 |
| tccgggccgc | cgcatgggcc | atgccggtgc | cgtcatctcc | ggcggcaacg | acaccgccga | 1980 |
| cttcaagatc | gacttcatga | agtcggtcgg | catcgccgtc | gccgacagcc | ccgccagcct | 2040 |
| gggctccacc | atgctgaagg | tgttcaaggg | ctga | | | 2074 |

<210> SEQ ID NO 13
<211> LENGTH: 640
<212> TYPE: PRT
<213> ORGANISM: Halobacterium sp. NRC-1

<400> SEQUENCE: 13

Met Pro Tyr Trp Ser Thr Ala Gly Pro Asp Gln Ile Met Thr Asp Asp
1               5                   10                  15

Glu Leu Ile Trp Arg Ile Ala Gly Gly Ser Gly Asp Gly Ile Asp Ser
            20                  25                  30

Thr Ser Gln Asn Phe Ala Lys Ala Leu Met Arg Ser Gly Leu Asp Val
        35                  40                  45

Phe Thr His Arg His Tyr Pro Ser Arg Ile Arg Gly Gly His Thr Tyr
    50                  55                  60

Val Glu Ile Arg Ala Arg Asp Gly Thr Val Thr Ser Arg Gly Asp Gly
65                  70                  75                  80

Tyr Asn Phe Leu Leu Ala Leu Gly Asp Ser Phe Ala Arg Asn Pro Ser
                85                  90                  95

Glu Glu Ala Val Tyr Gly Asp Glu Glu Val Lys Pro Leu Thr Glu Asn
            100                 105                 110

Leu Asp Asp Leu Arg Ala Gly Gly Val Ile Ile Tyr Asp Glu Gly Leu
        115                 120                 125

Leu Asp Asp Glu Asp Val Gly Asp Leu Glu Gln Gln Ala Asp Ala Asn
130                 135                 140

Asp Trp His Leu Tyr Pro Leu Asp Leu Arg Gly Leu Ala Lys Glu His
145                 150                 155                 160

Gly Arg Glu Val Met Arg Asn Thr Ala Gly Val Ala Thr Ala Ala
            165                 170                 175

Leu Ile Asp Met Asp Leu Asp His Ile Glu Asp Leu Met Ser Asp Ala
        180                 185                 190

Met Gly Gly Asp Ile Leu Glu Gln Asn Leu Thr Val Leu Arg Asp Ala
    195                 200                 205

Tyr Glu Gln Val Ser Glu Met Glu His Thr His Asp Leu Ser Val Pro
    210                 215                 220

Thr Gly Ser His Asp Glu Pro Gln Val Leu Met Ser Gly Ser His Ala
225                 230                 235                 240

Ile Ala Tyr Gly Ala Ile Asp Ala Gly Cys Arg Phe Ile Ser Gly Tyr
                245                 250                 255

Pro Met Thr Pro Trp Thr Asp Ala Phe Thr Ile Met Thr Gln Leu Leu
            260                 265                 270

Pro Asp Met Gly Gly Val Ser Glu Gln Val Glu Asp Glu Ile Ala Ala
        275                 280                 285

Ala Ala Met Ala Val Gly Ala Ser His Ala Gly Ala Lys Ala Met Ser
    290                 295                 300

Gly Ser Ser Gly Gly Gly Phe Ala Leu Met Ser Glu Pro Leu Gly Leu
305                 310                 315                 320

Ala Glu Met Thr Glu Thr Pro Leu Val Leu Leu Glu Ala Gln Arg Ala
                325                 330                 335

Gly Pro Ser Thr Gly Met Pro Thr Lys Pro Glu Gln Ala Asp Leu Glu
            340                 345                 350

His Val Leu Tyr Thr Ser Gln Gly Asp Ser His Arg Val Ala Phe Gly
        355                 360                 365

Pro Lys Asp Pro Lys Glu Cys Tyr Glu Gln Thr Arg Thr Ala Phe Glu
    370                 375                 380

```
Ile Ala Tyr Asp Tyr Gln Ile Pro Val Ile Leu Leu Tyr Asp Gln Lys
385                 390                 395                 400

Leu Ser Gly Glu Tyr Arg Asn Val Asp Ala Ser Phe Phe Asp Arg Glu
            405                 410                 415

Pro Ala Ala Asp Leu Gly Thr Thr Leu Ser Glu Asp Gln Ile Pro Asp
        420                 425                 430

Ala Pro His Asp Pro Thr Gly Lys Tyr His Arg Tyr Gln His Asp Val
    435                 440                 445

Glu Asp Gly Val Ser Pro Arg Thr Ile Pro Gly Gln Ser Gly Gly Arg
450                 455                 460

Tyr Leu Ala Ser Gly Asn Glu His Trp Pro Asn Gly His Ile Ser Glu
465                 470                 475                 480

Asp Thr Asp Asn Arg Val Ala Gln Val Glu Arg Arg Leu Gln Lys Leu
                485                 490                 495

Ala Ala Ile Arg Asp Asp Leu Asp Glu Arg Asp Gln Gln Thr His Tyr
            500                 505                 510

Gly Asp Glu Asp Ala Asp Ile Gly Leu Ile Ala Trp Gly Ser Gln Glu
        515                 520                 525

Gly Thr Val Glu Glu Ala Val His Arg Leu Asn Asp Asp Gly Asn Ser
530                 535                 540

Val Lys Ala Leu Gly Ile Ser Asp Leu Ala Pro Phe Pro Val Ala Glu
545                 550                 555                 560

Thr Arg Ala Phe Val Asp Ser Val Asp Glu Ala Ile Val Val Glu Met
                565                 570                 575

Ser Ser Thr Lys Gln Phe Arg Gly Leu Ile Gln Lys Glu Val Gly Asp
            580                 585                 590

Ile Gly Gly Lys Leu Ser Ser Leu Leu Lys Tyr Asn Gly Asn Pro Phe
        595                 600                 605

Glu Pro Ala Glu Ile Val Glu Ala Val Glu Ile Glu Gln Ala Gly Asp
    610                 615                 620

Gly Ala Glu Pro Ala Ala Gln Thr Thr Leu Glu Pro Ala Ala Gly Asp
625                 630                 635                 640

<210> SEQ ID NO 14
<211> LENGTH: 312
<212> TYPE: PRT
<213> ORGANISM: Halobacterium sp. NRC-1

<400> SEQUENCE: 14

Met Ser Lys Ala Phe Ser Ala Ile Asp Glu Asp Arg Glu Val Asp Arg
1               5                   10                  15

Asp Ala Phe Thr Pro Gly Val Glu Pro Gln Pro Thr Trp Cys Pro Gly
            20                  25                  30

Cys Gly Asp Phe Gly Val Leu Lys Ala Leu Lys Gly Ala Met Ala Glu
        35                  40                  45

Leu Gly Lys Asp Pro Glu Glu Ile Leu Leu Ala Thr Gly Ile Gly Cys
    50                  55                  60

Ser Gly Lys Leu Asn Ser Tyr Phe Asp Ser Tyr Gly Phe His Thr Ile
65                  70                  75                  80

His Gly Arg Ser Leu Pro Val Ala Arg Ala Ala Lys Leu Ala Asn His
                85                  90                  95

Asp Leu Glu Val Val Ala Ala Gly Gly Asp Gly Asp Gly Tyr Gly Ile
            100                 105                 110

Gly Gly Asn His Phe Met His Thr Ala Arg Glu Asn His Asp Ile Thr
```

```
            115                 120                 125
Tyr Ile Val Phe Asn Asn Glu Val Phe Gly Leu Thr Lys Gly Gln Thr
130                 135                 140

Ser Pro Thr Ser Pro Lys Gly His Lys Ser Lys Thr Gln Pro His Gly
145                 150                 155                 160

Ser Ala Lys Ser Pro Ile Arg Pro Leu Ser Leu Ser Met Thr Ser Gly
                165                 170                 175

Ala Ser Tyr Val Ala Arg Thr Ala Ala Val Asn Pro Asn Gln Ala Lys
            180                 185                 190

Asp Ile Leu Val Glu Ala Ile Gln His Asp Gly Phe Ala His Val Asp
            195                 200                 205

Phe Leu Thr Gln Cys Pro Thr Trp Asn Lys Asp Ala Lys Gln Tyr Val
210                 215                 220

Pro Tyr Val Asp Val Gln Glu Ser Asp Glu Tyr Asp Phe Asp Val Thr
225                 230                 235                 240

Asp Arg Arg Glu Ala Gln Glu Leu Met Thr Glu Thr Glu Ala Leu
                245                 250                 255

Tyr Asp Gly Thr Val Leu Thr Gly Arg Tyr Tyr Gln Asp Glu Gln Arg
                260                 265                 270

Pro Ser Tyr Gln Ala Glu Lys Gln Ser Arg Gly Asp Met Pro Glu Glu
            275                 280                 285

Pro Val Ala Lys Arg Tyr Phe Asp Asp Asp Tyr Glu Trp Glu Arg Ser
290                 295                 300

Phe Asp Val Ile Asp Arg His Lys
305                 310
```

<210> SEQ ID NO 15
<211> LENGTH: 2864
<212> TYPE: DNA
<213> ORGANISM: Halobacterium sp. NRC-1

<400> SEQUENCE: 15

```
atgccatatt ggtccacggc tgggccagac cagattatga ctgacgacga actcatctgg    60
cgaatcgcag ggggttccgg agacgggatc gactcgacaa gccagaattt cgccaaagcg   120
ctgatgcgct cgggcctcga cgtcttcacg caccgccact acccgtcgcg gatccgcggc   180
ggccacacgt acgtggagat ccgggcgcgg acggtaccg taacctcccg cggtgacggc   240
tacaacttcc tgctcgcgct cggcgactcg ttcgcccgca acccgagcga ggaggccgtc   300
tacggcgacg aggaagtgaa gccgctcact gagaacctcg acgacctgcg cgcgggcggc   360
gtcatcatct cgacgagggg gctgctcgac gacgaggacg tcggcgacct cgaacagcag   420
gccgacgcca cgactggca tctctacccg cttgacctgc gcgggctcgc caaggaacac   480
ggccgcgagg tcatgcgcaa caccgcgggc gtcggcgcca ccgcggcgct catcgacatg   540
gacctcgacc acatcgagga cctgatgagc gacgccatgg gcggcgacat cctcgaacag   600
aacctcacgg tgctccgcga cgcctacgag caggtgtcgg aaatggagca cacccacgac   660
ctatcggtgc cgaccgggag ccacgacgag ccacaagtgc tcatgtccgg gagccacgcg   720
atcgcgtacg gcgcgatcga cgccggctgc cggttcatct ccgggtatcc gatgacgccg   780
tggacggacg cgttcacgat catgacccag ctgttgcccg acatgggcgg ggtctccgag   840
caggtcgaag acgagatcgc ggcgcgggcg atggcggtgg gtgcaagcca cgccggcgcg   900
aaggcgatgt ccgctcctc cggcggcggg ttcgcgttga tgagcgagcc cctgggcctc   960
gcggagatga ccgagacgcc cctggtgttg ctggaagccc agcgcgccgg gccgtccacg   1020
```

-continued

```
ggcatgccga cgaagcccga gcaggccgac ctggagcacg tgctgtacac cagccagggg    1080
gacagccacc gcgttgcgtt cggccccaaa gaccccaagg agtgttacga gcagacccgc    1140
acggcgttcg agatcgcgta cgactaccag atccccgtga tcctgctgta cgatcagaag    1200
ctctccgggg agtaccggaa cgtcgacgcg tcgttcttcg accgcgagcc ggcggcggac    1260
ctcgggacga cgctctccga ggaccagatc cccgacgcgc acacgaccc  gacggggaag    1320 taccaccgct accagcacga cgtcgaggac ggcgtcagcc ccggacgat  ccggggcag    1380 tccggcggtc ggtatctcgc ctccggcaac gagcactggc cgaacggcca tcagcgag    1440 gacaccgaca accgcgtggc gcaggtcgag cgccgcctcc agaagctggc ggcgatccgc    1500
gacgacctcg acgagcgcga ccagcagacc cactacggcg acgaggacgc cgacatcggc    1560
ctcatcgcgt ggggcagcca ggagggcacc gtcgaggaag cggtccaccg gctgaacgac    1620
gacggcaaca gcgtgaaggc gttggggatc agcgacctcg cgccgttccc cgtcgcggag    1680
acgcgggcgt tcgtcgacag cgtcgacgaa gccatcgtcg tggagatgtc ctccaccaag    1740
cagttccgtg gcctcatcca agaggaggtc ggagacatcg gcggaagct  gtcgagtctc    1800 ctgaaataca acggcaaccc gttcgagccc gcggagatcg tcgaggccgt tgagatcgaa    1860
caggccggcg acggcgcgga gccggccgcc cagaccacac tcgaacccgc agcaggtgac    1920
tgataatgag taaggcattc agcgcgattg atgaggaccg cgaggtcgac cgggacgcgt    1980
tcacgcccgg cgtcgaaccg cagccgacgt ggtgtcctgg ctgtggtgac ttcggtgtcc    2040
tgaaggccct gaaaggggcg atggcggagc tcggcaagga ccccgaggag atactgcttg    2100
cgaccgggat cggctgttcc gggaagctca acagctactt cgacagctac ggcttccaca    2160
cgatccacgg cgctcccctg cccgtggccc gcgccgcgaa gctggccaac cacgacctgg    2220
aggtcgtggc cgccggcggt gacggcgacg gctacgggat cggcggcaac cacttcatgc    2280
acaccgcccg ggagaaccac gacatcacgt acatcgtgtt caacaacgaa gtgttcggcc    2340
tgacgaaggg ccagacatcg ccgacgagcc ccaagggg ca caagtccaag acccagcccc    2400
acggctccgc gaagtccccg atccgaccgc tctcgctgag catgacctcg ggggcgtcgt    2460
acgtggcgcg aaccgcggcc gtgaacccca accaggcaaa ggacatcctc gtggaagcca    2520
tccagcacga cggcttcgcg cacgtggact tcctgacgca gtgtccgacc tggaacaagg    2580
acgccaagca gtacgtcccg tacgtggacg tccaggagtc cgacgagtac gacttcgacg    2640
tcacggaccg gcgggaggca caggagctga tgaccgagac cgaggaagcc ctctacgacg    2700
ggaccgtgct gaccggccgg tactaccagg acgagcagcc ggtcgtat  caggccgaaa    2760 agcagtcccg cggggacatg cccgaggaac cggttgcaaa gcggtacttc gacgacgact    2820
acgagtggga gcgctcgttc gacgtcatcg accgccacaa gtaa              2864
```

<210> SEQ ID NO 16
<211> LENGTH: 607
<212> TYPE: PRT
<213> ORGANISM: Hydrogenobacter thermophilus TK-6

<400> SEQUENCE: 16

```
Met Ala Phe Asp Leu Thr Ile Lys Ile Gly Gly Glu Gly Gly Glu Gly
1               5                  10                  15

Val Ile Ser Ala Gly Asp Phe Leu Thr Glu Ser Ala Ala Arg Ala Gly
            20                  25                  30

Tyr Tyr Val Val Asn Phe Lys Ser Phe Pro Ala Glu Ile Lys Gly Gly
        35                  40                  45
```

```
Tyr Ala Gln Ser Thr Ile Arg Val Ser Asn Lys Lys Leu Tyr Thr Thr
     50                  55                  60
Gly Asp Gly Phe Asp Ile Leu Cys Cys Phe Asn Gly Glu Ala Tyr Glu
 65                  70                  75                  80
Phe Asn Arg Lys His Leu Arg Pro Gly Thr Val Leu Val Tyr Asp Ser
                 85                  90                  95
Ser Asp Phe Glu Pro Glu His Gly Val Val Met Tyr Pro Val
            100                 105                 110
Pro Leu Ser His Leu Ala Lys Asp Ile Met Lys Ala Tyr Ile Thr Lys
            115                 120                 125
Asn Val Ile Ala Leu Gly Val Leu Cys Gly Leu Phe Asp Ile Pro Val
            130                 135                 140
Gln Ser Ile Lys Asp Ser Ile Lys Ala Lys Phe Leu Arg Lys Gly Gln
145                 150                 155                 160
Glu Ile Ile Glu Leu Asn Tyr Lys Ala Leu Glu Thr Gly Ile Asn Tyr
                165                 170                 175
Val Arg Glu Asn Ile Lys Lys Leu Asp Gly Tyr Leu Phe Pro Pro Ala
                180                 185                 190
Lys Glu Pro Lys Asp Val Val Ile Met Glu Gly Asn Gln Ala Ile Ala
            195                 200                 205
Lys Gly Ala Val Val Ala Gly Cys Lys Phe Tyr Ala Ala Tyr Pro Ile
            210                 215                 220
Thr Pro Ala Thr Thr Val Gly Asn Tyr Ile Val Glu Asp Leu Ile Arg
225                 230                 235                 240
Val Gly Gly Trp Leu Tyr Gln Ala Glu Asp Glu Ile Ala Ser Leu Gly
                245                 250                 255
Met Ala Leu Gly Ala Ser Phe Ala Gly Val Lys Ala Met Thr Ala Thr
                260                 265                 270
Ser Gly Pro Gly Leu Cys Leu Met Thr Glu Phe Ile Ser Tyr Ala Gly
            275                 280                 285
Met Thr Glu Leu Pro Ile Val Ile Val Asp Val Gln Arg Val Gly Pro
290                 295                 300
Ala Thr Gly Met Pro Thr Lys His Glu Gln Gly Asp Leu Tyr His Ala
305                 310                 315                 320
Ile Tyr Ser Gly His Gly Glu Ile Pro Arg Ala Val Leu Ala Pro Thr
                325                 330                 335
Asn Val Glu Glu Ser Phe Tyr Leu Thr Val Glu Ala Phe Asn Leu Ala
            340                 345                 350
Glu Lys Tyr Gln Ile Pro Val Ile Val Leu Thr Asp Ala Ser Leu Ser
            355                 360                 365
Leu Arg Ala Glu Ala Phe Pro Thr Pro Lys Val Lys Asp Ile Lys Val
370                 375                 380
Ile Asn Arg Trp Val Tyr Asn Ala Glu Asp Pro Glu Gly Lys Phe
385                 390                 395                 400
Arg Arg Ala Gly Arg Phe Leu Arg Tyr Ala Leu Phe Thr Glu Asp Gly
                405                 410                 415
Ile Thr Pro Met Gly Val Pro Gly Asp Pro Asn Ala Ile His Ala Ile
            420                 425                 430
Thr Gly Leu Glu Arg Gln Glu Asn Ser Asp Pro Arg Asn Arg Pro Asp
            435                 440                 445
Ile Arg Thr Trp Gln Met Asp Lys Arg Phe Lys Lys Met Glu Lys Leu
            450                 455                 460
```

Leu Arg Glu Asp Ala Glu Lys Phe Tyr Glu Met Asp Ala Pro Phe Glu
465                 470                 475                 480

Lys Ala Asp Ile Gly Ile Ile Ser Trp Gly Leu Thr Ala Ser Ala Thr
            485                 490                 495

Lys Glu Ala Val Glu Arg Leu Arg Ser Lys Gly Arg Lys Ile Asn Ala
        500                 505                 510

Leu Tyr Pro Lys Leu Leu Trp Pro Leu Arg Val Asp Ile Leu Glu Asn
    515                 520                 525

Phe Ala Lys Ser Cys Arg Arg Ile Ile Met Pro Glu Ser Asn Tyr Ser
530                 535                 540

Gly Gln Leu Ala Thr Val Leu Arg Ala Glu Thr Arg Ile Arg Pro Ile
545                 550                 555                 560

Ser Tyr Cys Ile Tyr Arg Gly Glu Pro Phe Ile Pro Arg Glu Ile Glu
            565                 570                 575

Glu Phe Ile Glu Tyr Val Leu Glu Asn Ser Tyr Ile Glu Glu Gly Lys
        580                 585                 590

Phe Thr Pro Ala Asn Leu Tyr Gly Glu Lys Ala Tyr Gly Leu Ile
    595                 600                 605

<210> SEQ ID NO 17
<211> LENGTH: 295
<212> TYPE: PRT
<213> ORGANISM: Hydrogenobacter thermophilus TK-6

<400> SEQUENCE: 17

Met Leu Glu Val His Leu Lys Pro Ala Asp Tyr Lys Ser Asp Val Glu
1               5                   10                  15

Pro Thr Trp Cys Ser Gly Cys Gly Asp Phe Gly Val Val Ala Ala Leu
            20                  25                  30

Thr Arg Ala Tyr Ser Glu Leu Gly Leu Lys Pro Glu Asn Ile Val Ser
        35                  40                  45

Val Ser Gly Ile Gly Cys Ser Ser Arg Leu Pro Leu Phe Val Lys Asn
    50                  55                  60

Tyr Ser Val His Ser Leu His Gly Arg Ala Ile Pro Val Ala Val Gly
65                  70                  75                  80

Ile Lys Leu Ala Arg Pro Asp Leu Thr Val Ile Val Glu Thr Gly Asp
                85                  90                  95

Gly Asp Leu Phe Ser Ile Gly Ala Gly His Asn Pro His Ala Ala Arg
            100                 105                 110

Arg Asn Ile Asp Ile Thr Val Ile Cys Met Asp Asn Gln Val Tyr Gly
        115                 120                 125

Leu Thr Lys Asn Gln Val Ser Pro Thr Ser Arg Glu Gly Leu Tyr Gly
    130                 135                 140

Ser Leu Thr Pro Tyr Gly Ser Ile Asp Arg Pro Val Asn Pro Ile Ala
145                 150                 155                 160

Thr Met Leu Ser Tyr Gly Ala Thr Phe Val Ala Gln Thr Tyr Ala Gly
                165                 170                 175

Asn Leu Lys His Met Thr Glu Val Ile Lys Gln Ala Ile Gln His Lys
            180                 185                 190

Gly Phe Ser Phe Val Asn Val Ile Ser Pro Cys Pro Thr Phe Asn Lys
        195                 200                 205

Val Asp Thr Phe Gln Tyr Tyr Lys Gly Lys Val Lys Asp Ile Asn Glu
    210                 215                 220

Gln Gly His Asp Pro Ser Asp Tyr Arg Lys Ala Leu Glu Leu Ala Phe
225                 230                 235                 240

```
His Asp Leu Asp His Tyr His Asp Pro Asn Ala Pro Val Pro Ile Gly
            245                 250                 255

Val Phe Tyr Lys Ala Glu Leu Glu Thr Tyr Glu Asp Arg Met Gln Ser
        260                 265                 270

Val Lys Arg Arg Tyr Lys Gln Val Glu Asp Val Gln Glu Leu Ile Asp
        275                 280                 285

Met Cys Lys Pro Lys Ala Leu
        290             295

<210> SEQ ID NO 18
<211> LENGTH: 2725
<212> TYPE: DNA
<213> ORGANISM: Hydrogenobacter thermophilus TK-6

<400> SEQUENCE: 18
atggcgtttg atttgaccat caaaataggt ggtgaaggtg gtgaaggtgt tatatccgcc      60
ggggattttt tgacggaatc tgcagcacgg gctggttatt atgtggttaa ctttaagagc     120
ttccccgcgg agataaaggg tgggtatgcc cagtccacca tcagagtctc caacaaaaag     180
ctttacacaa caggagatgg cttttgacatt ctgtgctgtt ttaatggtga ggcttacgaa     240
tttaacagga agcatttaag gccgggtacg gtgctcgttt atgactcttc ggattttgag     300
ccggaggagc acgagggtgt ggtcatgtat ccggttcccc tctcccatct ggcaaaggac     360
ataatgaagg cttacataac aaagaatgta atagctctgg gtgttctctg tgggctgttt     420 gatataccctg tgcagtctat aaaagactca ataaaagcaa agttttaag aaagggacag     480 gagataatag aactaaacta taaggctctg agacgggta taaactatgt cagggagaat     540
ataaagaaat tggatggata cctttttccct cctgcaaagg aaccaaaaga tgtggtaatc     600
atggagggca atcaggcaat agccaagggt gcggtggtgg caggctgtaa gttttatgca     660
gcttatccca taacgccggc aacgacggta ggaaactaca tagtagaaga cctcataagg     720
gtgggaggtt ggctctatca agctgaggat gaaatagcct ccctcggtat ggctttaggg     780 gcttctttg caggcgtaaa agctatgacc gccacctccg gaccgggatt atgccttatg     840
acggagttta tctcttacgc aggtatgacg gagcttccca tagtgatagt ggatgtgcag     900
agggtaggac ctgcaacggg tatgcctacc aagcacgaac agggagacct ctaccacgcc     960
atatactcag gcacggtga ataccaagg gcagtgcttg ctcccaccaa tgtggaagag    1020
agcttttacc ttactgtgga ggcttttcaat ctggcggaaa agtatcagat acccgttata    1080
gttctgacgg atgcatccct ttctctgaga gcggaagcct tccctactcc aaaggtaaag    1140
gacattaagg tgataaacag atgggtctat aatgcagaag atgaccccga gggtaagttc    1200
agaagagctg gaagatttct taggtatgcc cttttttaccg aggacggcat aacgcctatg    1260
ggtgtacccg gagaccccaa cgccatacac gccataacgg gcttgagcg tcaagaaaac    1320 tcagacccaa gaaacagacc tgacataaga acatggcaga tggacaaaag gtttaagaag    1380
atggaaaagc tcctgaggga agatgcggaa aagttttacg atatggatgc accctttgag    1440
aaggctgaca taggtatcat atcctggggt cttaccgcat ccgctacaaa ggaggctgtt    1500
gagagactaa ggagcaaagg tagaaaaata acgccttgt atcccaagct cctctggcca    1560
ctcagggtgg atatactgga aaactttgca aaaagctgta ggagaataat catgcctgag    1620
agtaactaca gcggtcagct tgcaactgtg cttaggggctg aaacgcgtat aagacctata    1680
agctactgca tatacagggg agaacccttt ataccgaggg agatagagga gtttatagag    1740
```

```
tatgtactgg agaactctta cattgaggag ggcaaattta cacctgcaaa cctttacggc    1800
gaaaaggctt acggactaat ttaaaggagg tgtaagtatg ttagaagttc acttaaaacc    1860
tgcagactac aagagcgatg tagaacccac ctggtgttcg ggatgcggtg attttggtgt    1920
ggtggcggct ctaactagag cttattcgga gcttggatta aagcctgaaa acatagtttc    1980
cgtatccggt ataggttgtt cctcaaggct tcccctcttt gttaaaaact actcggtgca    2040
ttcactgcac ggaagagcta tcccagtagc tgtaggcata aagctggcaa ggccggacct    2100
taccgtcata gtggaaacgg gcgacggaga cctcttctcc ataggcgcgg acacaaccc     2160 acacgcagca cgcagaaaca tagacataac cgtcatatgt atggacaatc aggtttatgg    2220
tcttaccaaa aatcaagttt ctccaacttc aagggaagga ctttacggct ccctaacacc    2280
ttacggctcc atagacagac ctgtaaaccc catagccacc atgctctcct acggtgccac    2340
ctttgttgca cagacttatg cgggcaatct caagcacatg acagaggtga taaagcaagc    2400
tatacagcat aaaggctttt cctttgtaaa tgtgatatct ccctgcccca cctttaacaa    2460
agtggacacc ttccagtact ataagggtaa ggtgaaggac ataaacgagc agggacacga    2520
cccatccgat tacagaaagg ctcttgaact tgctttccat gaccttgacc actatcacga    2580
tccgaacgct ccagtaccta taggcgtatt ttacaaagct gagctggaaa cctacgaaga    2640
caggatgcag tccgtgaaga gaaggtacaa acaggtggaa gatgtgcaag aactcataga    2700
tatgtgtaag ccaaaagctt tatga                                          2725
```

<210> SEQ ID NO 19
<211> LENGTH: 578
<212> TYPE: PRT
<213> ORGANISM: Bacillus sp. M3-13

<400> SEQUENCE: 19

```
Met Ile Asn Gln Leu Ser Trp Lys Val Gly Gln Gln Gly Glu Gly
1               5                   10                  15

Ile Glu Ser Thr Gly Glu Ile Phe Ser Ile Ala Leu Asn Arg Leu Gly
            20                  25                  30

Tyr Tyr Leu Tyr Gly Tyr Arg His Phe Ser Ser Arg Ile Lys Gly Gly
        35                  40                  45

His Thr Asn Asn Lys Ile Arg Val Ser Thr Gln Val Arg Ser Ile
    50                  55                  60

Ser Asp Asp Leu Asp Ile Leu Val Ala Phe Asp Gln Glu Thr Ile Asp
65                  70                  75                  80

Val Asn Tyr His Glu Leu Arg Glu Gly Gly Val Val Ile Ala Asp Ala
                85                  90                  95

Lys Phe Lys Pro Ser Ile Pro Glu Asp Gly Lys Ala Thr Leu Tyr Ala
            100                 105                 110

Val Pro Phe Thr Glu Ile Ala Thr Glu Leu Gly Thr Ser Leu Met Lys
        115                 120                 125

Asn Met Val Ala Val Gly Ala Ser Ser Ala Ile Leu Asp Leu Asp Ala
    130                 135                 140

Glu Ser Phe Arg Glu Val Val Gln Glu Ile Phe Gly Arg Lys Gly Glu
145                 150                 155                 160

Ser Ile Val Glu Lys Asn Met Glu Ala Ile Arg Ala Gly Val Gln Phe
                165                 170                 175

Ile Lys Asp Gln Ala Glu Asn Leu Glu Thr Met Gln Leu Ala Lys Ala
            180                 185                 190

Asp Gly Asn Lys Arg Leu Phe Met Ile Gly Asn Asp Ala Ile Ala Leu
```

```
            195                 200                 205
Gly Ala Val Ala Ala Gly Ser Arg Phe Met Pro Ala Tyr Pro Ile Thr
210                 215                 220

Pro Ala Ser Glu Ile Met Glu Tyr Leu Ile Lys Lys Leu Pro Lys Phe
225                 230                 235                 240

Gly Gly Thr Val Ile Gln Thr Glu Asp Glu Ile Ala Ala Cys Thr Met
                    245                 250                 255

Ala Ile Gly Ala Asn Tyr Ala Gly Val Arg Thr Leu Thr Ala Ser Ala
                260                 265                 270

Gly Pro Gly Leu Ser Leu Met Met Glu Ala Ile Gly Leu Ser Gly Met
                275                 280                 285

Thr Glu Thr Pro Leu Val Val Asp Thr Gln Arg Gly Gly Pro Ser
290                 295                 300

Thr Gly Leu Pro Thr Lys Ile Glu Gln Ser Asp Leu Met Ala Met Ile
305                 310                 315                 320

Tyr Gly Thr His Gly Glu Ile Pro Lys Val Val Met Ala Pro Ser Thr
                    325                 330                 335

Val Gln Glu Ala Phe Tyr Asp Thr Ile Glu Ala Phe Asn Ile Ala Glu
                340                 345                 350

Glu Tyr Gln Val Pro Val Ile Leu Leu Thr Asp Leu Gln Leu Ser Leu
                355                 360                 365

Gly Lys Gln Ser Val Glu Ala Leu Asp Tyr Lys Asn Ile Glu Ile Arg
370                 375                 380

Arg Gly Lys Leu Asp Ile Asn Gln Glu Leu Pro Ala Ala Asp Asp Lys
385                 390                 395                 400

Ala Tyr Phe Lys Arg Tyr Glu Val Thr Glu Asp Gly Val Ser Pro Arg
                    405                 410                 415

Val Ile Pro Gly Met Lys His Gly Ile His Val Thr Gly Val Glu
                420                 425                 430

His Glu Glu Thr Gly Lys Pro Ser Glu Val Ala Ala Asn Arg Gln Ala
                435                 440                 445

Gln Met Asp Lys Arg Leu Arg Lys Leu Asn Asn Leu Lys Phe Asn Thr
450                 455                 460

Pro Val His Val Asn Ala Lys His Glu Glu Ala Asp Val Leu Leu Val
465                 470                 475                 480

Gly Phe Asn Ser Thr Arg Gly Thr Ile Glu Glu Ala Met Glu Arg Leu
                    485                 490                 495

Glu Leu Glu Gly Val Lys Ala Asn His Ala Gln Val Arg Leu Ile His
                500                 505                 510

Pro Phe Pro Thr Glu Glu Ile Ala Pro Leu Val Lys Ala Ala Lys Lys
                515                 520                 525

Val Ile Val Val Glu Tyr Asn Ala Thr Gly Gln Leu Ala Asn Ile Leu
530                 535                 540

Lys Met Asn Val Gly Glu His Glu Lys Ile Arg Ser Leu Leu Lys Tyr
545                 550                 555                 560

Asp Gly Asp Pro Phe Leu Pro Lys Glu Ile His Thr Lys Cys Lys Glu
                    565                 570                 575

Leu Leu

<210> SEQ ID NO 20
<211> LENGTH: 288
<212> TYPE: PRT
<213> ORGANISM: Bacillus sp. M3-13
```

<400> SEQUENCE: 20

```
Met Ala Thr Phe Lys Asp Phe Arg Asn Asn Val Lys Pro Asn Trp Cys
1               5                   10                  15
Pro Gly Cys Gly Asp Phe Ser Val Gln Ala Ala Ile Gln Arg Ala Ala
            20                  25                  30
Ala Asn Val Gly Leu Glu Pro Glu Asn Leu Ala Val Val Ser Gly Ile
        35                  40                  45
Gly Cys Ser Gly Arg Ile Ser Gly Tyr Ile Asn Ser Tyr Gly Phe His
    50                  55                  60
Gly Ile His Gly Arg Ser Leu Pro Ile Ala Gln Gly Val Lys Met Ala
65                  70                  75                  80
Asn Lys Asp Leu Thr Val Ile Ala Ser Gly Asp Gly Asp Gly Phe
                85                  90                  95
Ala Ile Gly Leu Gly His Thr Ile His Ala Ile Arg Arg Asn Ile Asp
            100                 105                 110
Val Thr Tyr Ile Val Met Asp Asn Gln Ile Tyr Gly Leu Thr Lys Gly
        115                 120                 125
Gln Thr Ser Pro Arg Ser Glu Val Gly Phe Lys Thr Lys Ser Thr Pro
    130                 135                 140
Gln Gly Ser Ile Glu Ser Ser Leu Ser Val Met Glu Met Ala Leu Thr
145                 150                 155                 160
Ala Gly Ala Thr Phe Val Ala Gln Ser Phe Ser Thr Asp Leu Lys Asp
                165                 170                 175
Leu Thr Ser Leu Ile Glu Gln Gly Ile Lys His Lys Gly Phe Ser Leu
            180                 185                 190
Ile Asn Val Phe Ser Pro Cys Val Thr Tyr Asn Lys Val Asn Thr Tyr
        195                 200                 205
Asp Trp Phe Lys Glu Asn Leu Thr Lys Leu Ala Asp Ile Glu Gly Tyr
    210                 215                 220
Asp Ala His Asn Lys Val Ser Ala Met Gln Thr Leu Met Glu His Asn
225                 230                 235                 240
Gly Leu Val Thr Gly Leu Ile Tyr Gln Asn Lys Asp Gln Gln Ser Tyr
                245                 250                 255
Gln Asp Leu Val Pro Asn Tyr Ser Glu Glu Pro Leu Ala Lys Ala Asp
            260                 265                 270
Leu Gln Leu Asp Glu Glu Gln Phe Asn Ala Leu Val Lys Glu Phe Met
        275                 280                 285
```

<210> SEQ ID NO 21
<211> LENGTH: 2604
<212> TYPE: DNA
<213> ORGANISM: Bacillus sp. M3-13

<400> SEQUENCE: 21

```
atgatcaatc aactttcatg gaaagttgga gggcaacaag gggaaggtat cgaaagtacc      60
ggtgagattt tctccattgc attaaatcgt ttaggctatt atttatatgg ttatcgccat     120
ttttcttctc gtattaaagg tggacatacg aacaacaaaa ttcgtgtgag tacgactcag     180
gtccgttcca tttcggacga ccttgatata ttagtagcgt ttgatcaaga aacaatcgac     240
gtaaactatc atgaactccg cgaaggtgga gtggtaattg cagatgcaaa gtttaaacca     300
agcatacctg aagacgggaa agctacattg tacgctgtac cattcactga aattgctact     360
gagcttggaa catcattgat gaagaacatg gttgctgtcg gagcttcaag tgccatcctt     420
gatttagatg cggaatcatt ccgtgaagtg gtgcaagaaa ttttcggacg caaaggcgaa     480
```

```
tccattgttg agaaaaacat ggaagcgatc cgagcaggtg ttcaattcat taaagatcaa    540
gctgaaaatt tagaaacaat gcagcttgca aaagcagacg gcaataaacg actattcatg    600
atcggtaatg atgcgattgc attgggtgca gttgctgcag gatctcgttt tatgccggct    660
tacccaatta ctccagcatc tgaaattatg gaatacttaa tcaaaaagct tccaaaattc    720
ggcggtactg tgattcaaac ggaagatgag attgctgctt gtaccatggc aattggtgcc    780
aactatgcag gtgtacgtac tttgactgct tcagcaggcc cgggactatc cttaatgatg    840
gaagcaattg gactttctgg tatgacagaa acaccgcttg tagttgtgga cacgcaacgt    900
ggaggaccaa gtacagggtt accgacaaag attgagcagt ctgaccttat ggcgatgatc    960
tatggtactc acggagagat cccgaaagtg gtaatggctc ctagtactgt acaagaggct   1020
ttctacgata caatcgaggc atttaacatt gcagaagaat atcaagtacc tgtcattctt   1080
ttaactgatc ttcaattgtc tctagggaag caatcggtag aagcattaga ttacaaaaac   1140
attgaaatta gacgcggaaa gctggatatc aatcaagagc ttccggctgc tgacgataaa   1200
gcatatttca aacgatatga agtaacagaa gatggcgtat ctccccgtgt gattcctggc   1260
atgaaacacg gtatccatca cgttactggt gtagagcacg aagagacagg taagccttct   1320
gaagttgctg cgaaccgtca agcacagatg gacaagcgtc ttcgtaaatt gaataacctt   1380
aaattcaata cgcctgttca tgttaatgca agcatgaag aagcggatgt actacttgtt    1440
ggatttaact cgacgcgcgg aacgatcgaa gaggcaatgg aaagattgga attggaaggt   1500
gttaaagcta accatgcaca agtccgcctg atccacccat tcccgacaga agaaatcgcg   1560
ccactggtaa agcggctaa aaaagttatt gttgtggagt ataacgctac tggacaactt    1620
gcaaacatcc ttaaaatgaa tgttggcgag catgagaaaa tccgtagtct cttaaagtat   1680 gatgggatc cattcttacc gaaagaaatc cacacaaaat gcaaggagtt gttataaatg    1740
gcaacgttta aagactttcg aaataatgta aaacctaact ggtgccctgg tgtggagac    1800 ttctcggtac aagctgccat tcaacgtgct gccgcaaatg ttggtttaga gcctgaaaat   1860
cttgcagtag tatctggaat agggtgttct ggacgtattt ccgggtacat caattcctac   1920
ggtttccatg gtattcatgg tcgctctcta ccaatcgcac aaggtgtgaa atggcgaat    1980 aaagatctta cggttatcgc ttcaggtgga gatggagatg gatttgccat cggtttaggt   2040
cataccatcc atgcaattcg tcgaaatatt gatgttacat acatcgttat ggataatcag   2100
atttatggac taacaaaagg ccaaacatca ccacgtagtg aagtaggatt caaaacaaaa   2160
tctacaccac aaggttccat tgaatcctca ctgtctgtaa tggaaatggc tttaacagca   2220
ggagcgacat ttgtagcgca aagcttctct actgatttga agacctaac ttccttgatc    2280 gaacaaggaa tcaagcataa agggttctct ctaattaacg tgtttagccc gtgtgttaca   2340
tataataaag tgaacacata tgactggttt aaagaaaatt tgacaaaatt ggctgacatt   2400
gaaggttatg acgctcacaa caaagtttct gcgatgcaga cactaatgga gcataatggc   2460
ctagtaactg gtttgatcta tcagaataag gaccaacagt cttatcaaga tttggttcct   2520
aattatagcg aagagcctct tgcaaaagca gatcttcaat tagacgaaga acaattcaac   2580
gcactagtaa aagaattcat gtaa                                          2604
```

<210> SEQ ID NO 22
<211> LENGTH: 582
<212> TYPE: PRT
<213> ORGANISM: Paenibacillus lar

```
<400> SEQUENCE: 22

Met Ile Ser Gln Leu Ser Trp Lys Ile Gly Gly Gln Gln Gly Glu Gly
1               5                   10                  15

Val Glu Ser Thr Asp Arg Ile Phe Ser Thr Ala Leu Asn Arg Leu Gly
            20                  25                  30

Tyr Tyr Leu Tyr Gly Tyr Arg His Phe Ser Ser Arg Ile Lys Gly Gly
        35                  40                  45

His Thr Asn Asn Lys Ile Arg Ile Ser Thr Lys Pro Ile Arg Ser Ile
    50                  55                  60

Ser Asp Asp Leu Asp Ile Leu Val Ala Phe Asp Gln Glu Ser Ile Asp
65                  70                  75                  80

Leu Asn Ala His Glu Leu Arg Glu Asn Ala Val Val Ala Asp Ala
                85                  90                  95

Lys Phe Asn Pro Thr Leu Pro Glu Gly Ile Asn Ala Arg Leu Phe Pro
                100                 105                 110

Val Pro Ile Thr Ala Ile Ala Glu Glu Leu Gly Thr Ser Leu Phe Lys
            115                 120                 125

Asn Met Ala Ala Ser Gly Ala Ser Trp Ala Leu Leu Gly Leu Pro Leu
130                 135                 140

Glu Val Phe Asn Lys Ala Val Glu Glu Glu Tyr Gly Arg Lys Cys Ala
145                 150                 155                 160

Ala Val Val Glu Lys Asn Ile Glu Ala Val Lys Arg Gly Ala Glu Tyr
                165                 170                 175

Val Leu Asp Leu Ala Gly Gly Pro Leu Glu Glu Phe Arg Leu Glu Pro
            180                 185                 190

Ala Asp Gly Lys Gln Lys Leu Phe Ile Ile Gly Asn Asp Ala Ile Gly
        195                 200                 205

Leu Gly Ala Val Ala Ala Gly Cys Arg Phe Met Pro Ala Tyr Pro Ile
210                 215                 220

Thr Pro Ala Ser Glu Ile Met Glu Tyr Leu Ile Lys Val Leu Pro Lys
225                 230                 235                 240

Tyr Gly Gly Thr Val Ile Gln Thr Glu Asp Glu Ile Ala Ala Cys Thr
                245                 250                 255

Met Ala Ile Gly Ala Asn Tyr Gly Gly Val Arg Ala Met Thr Thr Ser
            260                 265                 270

Ala Gly Pro Gly Leu Ser Leu Met Met Glu Ala Ile Gly Leu Ala Gly
        275                 280                 285

Met Thr Glu Ile Pro Val Val Ile Val Asp Thr Gln Arg Gly Gly Pro
290                 295                 300

Ser Thr Gly Leu Pro Thr Lys Gln Glu Gln Ser Asp Ile Asn Ala Met
305                 310                 315                 320

Ile Tyr Gly Thr His Gly Glu Ile Pro Lys Ile Val Ile Ala Pro Ser
                325                 330                 335

Thr Ile Glu Glu Cys Phe Tyr Asp Thr Val Glu Ala Phe Asn Leu Ala
            340                 345                 350

Glu Glu Tyr Gln Cys Pro Val Ile Val Leu Thr Asp Leu Gln Leu Ser
        355                 360                 365

Leu Gly Lys Gln Ser Ser Glu Leu Leu Asp Tyr Asn Lys Ile Ser Ile
370                 375                 380

Asn Arg Gly Lys Leu Val His Glu Leu Glu Pro Ala Glu Pro Asn Thr
385                 390                 395                 400

Met Phe Lys Arg Tyr Glu Phe Thr Glu Asp Gly Ile Ser Leu Arg Val
            405                 410                 415
```

-continued

```
Leu Pro Gly Thr Lys Tyr Gly Ile His His Val Thr Gly Val Glu His
            420                 425                 430

Asp Gln Thr Gly Arg Pro Asn Glu Gly Thr Asp Asn Arg Lys Lys Met
        435                 440                 445

Met Asp Lys Arg Leu Arg Lys Leu Thr Asn Val Lys Val Thr Asn Pro
    450                 455                 460

Ile His Val Asp Ala Pro His Glu Glu Pro Asp Val Leu Ile Ile Gly
465                 470                 475                 480

Ile Gly Ser Thr Gly Gly Thr Ile Asp Glu Ala Arg Gly Arg Leu Asp
                485                 490                 495

Lys Asp Gly Leu Lys Thr Asn His Ile Thr Val Arg Leu Leu Asn Pro
            500                 505                 510

Phe Pro Ala Glu Glu Leu Arg Pro Tyr Met Glu Lys Ala Lys Thr Val
        515                 520                 525

Val Val Val Glu Asn Asn Ala Thr Ala Gln Leu Ala Asn Leu Ile Lys
    530                 535                 540

Leu His Val Gly Phe Ala Asp Lys Ile Lys Asn Leu Leu Lys Tyr Asn
545                 550                 555                 560

Gly Asn Pro Phe Leu Pro Ser Glu Ile Tyr Gln Glu Val Lys Glu Leu
                565                 570                 575

Asn Val Thr Trp Gln His
            580

<210> SEQ ID NO 23
<211> LENGTH: 288
<212> TYPE: PRT
<213> ORGANISM: Paenibacillus larvae subsp. larvae B-3650

<400> SEQUENCE: 23

Met Ala Thr Leu Lys Asp Phe Arg Asn Asn Val Lys Pro Asn Trp Cys
1               5                   10                  15

Pro Gly Cys Gly Asp Phe Ser Val Gln Ala Ser Ile Gln Arg Ala Ala
            20                  25                  30

Ala Asn Val Gly Leu Glu Pro Glu Gln Leu Ala Ile Ile Ser Gly Ile
        35                  40                  45

Gly Cys Ser Gly Arg Ile Ser Gly Tyr Val Asn Ala Tyr Gly Leu His
    50                  55                  60

Gly Val His Gly Arg Ala Leu Pro Ile Ala Gln Gly Val Lys Met Ala
65                  70                  75                  80

Asn Arg Glu Leu Thr Val Val Ala Ala Gly Gly Asp Gly Asp Gly Phe
                85                  90                  95

Ala Ile Gly Met Gly His Thr Val His Ala Ile Arg Arg Asn Ile Asp
            100                 105                 110

Ile Thr Tyr Ile Val Met Asp Asn Gln Ile Tyr Gly Leu Thr Lys Gly
        115                 120                 125

Gln Thr Ser Pro Arg Ser Gly Glu Gly Phe Lys Thr Lys Ser Thr Pro
    130                 135                 140

Gln Gly Ser Ile Glu Thr Pro Leu Ala Pro Leu Glu Met Ala Leu Ala
145                 150                 155                 160

Ala Gly Ala Thr Phe Val Ala Gln Ser Phe Ser Ser Asn Leu Lys Gln
                165                 170                 175

Leu Thr His Val Ile Glu Glu Gly Ile Lys His Lys Gly Phe Ser Ile
            180                 185                 190

Ile Asn Val Phe Ser Pro Cys Val Thr Phe Asn Lys Val Asn Thr Tyr
```

195                 200                 205
Asp Trp Phe Lys Glu His Val Val Asn Leu Asp Asp Leu Pro Asp Tyr
    210                 215                 220

Asp Pro Ser Asn Arg Ile Gln Val Met Thr Lys Leu Met Glu Thr Glu
225                 230                 235                 240

Gly Met Leu Thr Gly Ile Ile Tyr Gln Asp Thr Ser Lys Pro Ser Tyr
                245                 250                 255

Glu Gln Leu Val Pro Gly Phe Lys Glu Glu Ala Leu Ala Lys Gln Asp
            260                 265                 270

Ile His Leu Ser Glu Glu Glu Phe Asp Lys Leu Val Ala Glu Phe Lys
        275                 280                 285

<210> SEQ ID NO 24
<211> LENGTH: 2603
<212> TYPE: DNA
<213> ORGANISM: Paenibacillus larvae subsp. larvae B-3650

<400> SEQUENCE: 24

| | |
|---|---|
| atgattagtc agctatcgtg aagatcggg ggacaacaag gtgaagggt ggaaagcacc | 60 |
| gatcgtattt tttccacagc attgaaccgc cttgggtatt atttgtatgg gtatcgtcat | 120 |
| ttctcttctc ggattaaagg gggacatacg aacaacaaaa ttcggatcag tacaaagccg | 180 |
| attcgatcga tctcggatga tctggatatc cttgtagcgt ttgaccaaga atccattgat | 240 |
| ttaaatgcac atgagcttcg ggagaatgca gttgttgtgg ctgatgccaa atttaacccg | 300 |
| acattgcctg aagggatcaa tgcgcgcttg tttccagtac cgattacagc gattgcagaa | 360 |
| gaacttggaa cgtctctttt caaaaacatg ccgcttcag gcgcatcatg ggctttgctt | 420 |
| ggtcttccat tggaagtatt caacaaagcg gtagaagaag agtatggccg taagtgtgca | 480 |
| gcagtagttg agaaaaacat tgaagcagtt aaacgcggag ctgagtatgt gcttgatctt | 540 |
| gctggaggtc ctcttgaaga atttagactt gagccggctg acggtaaaca aaaactgttt | 600 |
| attatcggaa atgatgctat cgggcttggc gcagttgcgg cgggttgccg tttcatgcct | 660 |
| gcatatccga tcaccccagc ttccgaaata atggaatatt tgattaaagt gcttcctaaa | 720 |
| tatgcggaa ctgttatcca aacggaggat gaaattgccg cctgtacgat ggcgatcggg | 780 |
| gcgaactacg ggggagtacg tgcaatgacc acttctgcgg gaccgggttt gtcactgatg | 840 |
| atggaagcga ttggtcttgc cggaatgaca gaaataccgg tcgtgattgt ggatacccaa | 900 |
| cgcggaggcc caagtacagg attgccgaca agcaggaac aaagtgatat taatgcgatg | 960 |
| atttacggaa ctcatggaga aattcctaaa attgtcatcg cacctagtac gattgaagaa | 1020 |
| tgtttctatg atacggtaga ggcatttaac ttggccgaag aatatcaatg cccggttatc | 1080 |
| gttttaacag atttgcaact ttctcttggc aaacaatcat ccgaactgct ggattataac | 1140 |
| aagatctcca ttaaccgggg gaaattggta catgaattag agcctgccga gcctaataca | 1200 |
| atgttcaaac gttatgaatt tacgaagat ggaatatctc tgcgtgttct tcccggaacg | 1260 |
| aagtatggta ttcatcatgt aacaggtgtt gagcatgatc aaaccggacg tccgaatgag | 1320 |
| ggaacggata accggaaaaa aatgatggat aaacgcctta gaaaattaac aaatgtcaag | 1380 |
| gtgactaatc cgattcatgt ggatgcgccg catgaagaac cggatgtgct aattattgga | 1440 |
| atcgggtcca caggcggtac gatagatgaa gccagaggac gtcttgacaa agacgggcta | 1500 |
| aaaactaatc acattactgt tcgcctgctg aacccattcc cggcggaaga gctccgccct | 1560 |
| tatatggaaa aagccaaaac tgtagtagtt gtagaaaaca acgcaactgc acagctggct | 1620 |

-continued

```
aatctgatca agcttcatgt aggatttgcg gataaaatta aaaacctgct gaaatataac    1680
gggaatccgt tcttaccgtc tgaaatctac caagaagtca aggagctgaa tgtaacatgg    1740
caacattgaa agattttcgt aacaacgtaa agccgaactg gtgtccagga tgcggggact    1800
tttccgtaca ggcgtccatc cagcgtgctg cggccaatgt tggattggaa ccggaacagc    1860
ttgctattat ttccggaatc ggttgttcag gccggatatc cggttatgta aatgcatacg    1920
gtctccacgg tgttcatggt agagctcttc caatcgctca gggagttaaa atggcaaacc    1980
gagaattgac tgttgtagcc gcaggcggtg acggggacgg atttgccatc ggcatgggtc    2040
atacagtaca tgccatccgc cgtaatattg atataactta cattgtcatg gataatcaaa    2100
tctatggatt gacgaaaggc cagacctctc cgcgaagcgg tgagggcttc aaaacaaaaa    2160
gtacacccca gggtccattg agactccat tggcaccact tgagatggct cttgcggcag    2220
gagcgacttt cgtagcccag tctttctcca gcaatctgaa gcagctgacg cacgtgattg    2280
aagaaggtat caaacataaa ggattttcta ttattaatgt attcagtcct tgtgtaaacct    2340 tcaacaaggt aaatacgtac gactggttca agaacatgt ggtgaattta gatgatttac    2400
ctgattatga tccttcaaac cgtattcagg tcatgacaaa gctcatggaa acagaaggga    2460
tgctaaccgg aattatttat caggatacaa gtaaaccttc ctatgagcag ctcgttcctg    2520
gatttaagga agaagctctc gcaaaacaag atattcatct gagtgaggaa gagtttgaca    2580
aattggtagc agagttttaaa taa                                            2603
```

<210> SEQ ID NO 25
<211> LENGTH: 584
<212> TYPE: PRT
<213> ORGANISM: Haladaptatus paucihalophilus DX253

<400> SEQUENCE: 25

```
Met Gln Asp Leu Asn Trp Ala Ile Gly Gly Glu Ala Gly Asp Gly Ile
1               5                   10                  15

Asp Ser Thr Gly Lys Ile Phe Ala Gln Ala Leu Ser Arg Ala Gly Arg
            20                  25                  30

His Val Phe Thr Ser Lys Asp Phe Ala Ser Arg Ile Arg Gly Gly Tyr
        35                  40                  45

Thr Ala Tyr Lys Ile Arg Ser Ser Thr Asp Arg Val Glu Ser Val Val
    50                  55                  60

Asp Arg Leu Asp Ile Leu Val Ala Leu Thr Gln Arg Thr Ile Asp Glu
65                  70                  75                  80

Asn Leu Asp Glu Leu His Glu Asp Ser Val Ile Ile Tyr Asp Gly Glu
                85                  90                  95

Arg Thr Glu Met Glu Asp Val Asp Ile Pro Glu Glu Met Ile Gly Leu
            100                 105                 110

Ala Val Pro Leu Arg Ser Leu Ala Lys Asp Ala Gly Gly Thr Ile Met
        115                 120                 125

Gln Asn Thr Val Ala Leu Gly Ala Ala Cys Glu Val Ala Asn Phe Pro
    130                 135                 140

Ile Glu Asn Leu Asp Ser Ala Leu Asp Lys Lys Phe Gly Ala Lys Gly
145                 150                 155                 160

Glu Ala Ile Val Glu Asn Asn Lys Glu Ala Ala Arg Leu Gly Gln Glu
                165                 170                 175

Tyr Val Gln Glu Glu Tyr Asp Tyr Asp Phe Glu Tyr Asp Val Glu Thr
            180                 185                 190

Thr Asp Asn Asp Tyr Val Leu Leu Asn Gly Asp Glu Ala Ile Gly Met
```

```
                195                 200                 205
Gly Ala Ile Ala Ala Gly Cys Arg Phe Tyr Ser Gly Tyr Pro Ile Thr
210                 215                 220

Pro Ala Thr Asn Val Met Glu Tyr Leu Thr Gly Arg Ile Glu His Phe
225                 230                 235                 240

Gly Gly Thr Val Met Gln Ala Glu Asp Glu Leu Ser Ala Ile Asn Met
            245                 250                 255

Ala Leu Gly Ala Ala Arg Ala Gly Ala Arg Ser Met Thr Ala Thr Ser
            260                 265                 270

Gly Pro Gly Ile Asp Leu Met Thr Glu Thr Phe Gly Leu Ile Ala Gln
            275                 280                 285

Ser Glu Thr Pro Leu Val Ile Cys Asp Val Met Arg Ser Gly Pro Ser
            290                 295                 300

Thr Gly Met Pro Thr Lys Gln Glu Gln Gly Asp Leu Asn Met Thr Leu
305                 310                 315                 320

Tyr Gly Gly His Gly Glu Ile Pro Arg Phe Val Val Ala Pro Thr Asn
                325                 330                 335

Val Ala Glu Cys Phe His Lys Thr Val Glu Ala Phe Asn Phe Ala Glu
            340                 345                 350

Lys Tyr Gln Thr Pro Val Phe Leu Leu Ala Asp Leu Ala Met Ala Val
            355                 360                 365

Thr Glu Gln Thr Phe Ser Pro Glu Glu Phe Asp Met Asp Ser Val Glu
            370                 375                 380

Ile Glu Arg Gly Asn Ile Val Asp Glu Asp Ile Glu Ala Trp Thr
385                 390                 395                 400

Asp Glu Lys Asp Arg Phe Gln Pro His Phe Pro Thr Ala Asp Gly Ile
                405                 410                 415

Ser Pro Arg Ala Phe Pro Gly Thr Lys Gly Gly Ala His Met Ser Thr
            420                 425                 430

Gly Leu Glu His Asn Ala Leu Gly Arg Arg Thr Glu Asp Thr Glu Ile
            435                 440                 445

Arg Val Glu Gln Val Asp Lys Arg Asn Arg Lys Val Glu Thr Ala Gln
450                 455                 460

Glu Glu Glu Asp Trp Ser Pro Arg Glu Phe Gly Asp Glu Asp Ala Asp
465                 470                 475                 480

Thr Leu Val Ile Ser Trp Gly Ser Asn Glu Gly Pro Met Arg Glu Ala
                485                 490                 495

Leu Asp Phe Leu Glu Glu Asp Val Ser Val Arg Phe Leu Ser Val
            500                 505                 510

Pro Tyr Ile Phe Pro Arg Pro Asp Leu Thr Glu Asp Ile Glu Ser Ala
            515                 520                 525

Asp Thr Val Ile Val Glu Cys Asn Glu Thr Gly Gln Phe Ala Asn
            530                 535                 540

Val Leu Glu His Asp Ala Leu Thr Arg Val Glu Arg Ile Asn Lys Tyr
545                 550                 555                 560

Asn Gly Ile Arg Phe Lys Ala Asp Glu Leu Ala Asp Ile Lys Ala
                565                 570                 575

Lys Leu Gly Gln Glu Val Glu Ala
            580

<210> SEQ ID NO 26
<211> LENGTH: 287
<212> TYPE: PRT
<213> ORGANISM: Haladaptatus paucihalophilus DX253
```

<400> SEQUENCE: 26

```
Met Ser Ser Glu Val Arg Phe Thr Asp Phe Lys Ser Asp Lys Gln Pro
1               5                   10                  15
Thr Trp Cys Pro Gly Cys Gly Asp Phe Gly Thr Met Asn Gly Met Met
            20                  25                  30
Lys Ala Leu Ala Glu Thr Gly Asn Ser Pro Asp Asp Thr Phe Val Val
        35                  40                  45
Ala Gly Ile Gly Cys Ser Lys Ile Gly Thr Phe Met His Ser Tyr
    50                  55                  60
Ala Ile His Gly Val His Gly Arg Ala Leu Pro Val Gly Thr Gly Val
65                  70                  75                  80
Lys Leu Ala Asn Pro Asp Leu Glu Val Met Val Ala Gly Gly Asp Gly
                85                  90                  95
Asp Gly Tyr Ser Ile Gly Val Gly His Phe Ile His Ala Val Arg Arg
            100                 105                 110
Asn Val Asp Met Ser Tyr Val Val Met Asp Asn Arg Ile Tyr Gly Leu
        115                 120                 125
Thr Lys Gly Gln Ala Ser Pro Thr Ser Arg Glu Asp Phe Glu Thr Ser
    130                 135                 140
Thr Thr Pro Glu Gly Pro Gln Gln Pro Val Asn Pro Leu Ala Leu
145                 150                 155                 160
Ala Leu Ser Ala Gly Ala Thr Phe Ile Ala Gln Ser Phe Ser Thr Asp
                165                 170                 175
Ala Gln Arg His Ala Glu Ile Val Gln Lys Ala Ile Glu His Asp Gly
            180                 185                 190
Phe Gly Phe Val Asn Val Phe Ser Pro Cys Val Thr Phe Asn Asp Val
        195                 200                 205
Asp Thr Tyr Asp Tyr Phe Arg Asp Ser Ile Val Asp Leu Ala Asp Glu
    210                 215                 220
Gly His Asp Pro His Asp Tyr Glu Ala Ala Lys Glu Lys Ile Leu Asp
225                 230                 235                 240
Ala Ser Lys Glu Tyr Gln Gly Val Ile Tyr Gln Asp Glu Asp Ser Val
                245                 250                 255
Pro Tyr Ser Glu Leu His Gly Ile Glu Gly Asn Met Ser Glu Ile Pro
            260                 265                 270
Asp Gly Ala Pro Glu Asp Ala Met Asp Leu Val Arg Glu Phe Tyr
        275                 280                 285
```

<210> SEQ ID NO 27
<211> LENGTH: 2615
<212> TYPE: DNA
<213> ORGANISM: Haladaptatus paucihalophilus DX253

<400> SEQUENCE: 27

```
atgcaagacc tgaactgggc catcggcggc gaagccggcg atggaatcga ttcgaccggg      60
aaaatctttg cgcaggcact ctcccgagcg ggccgacatg tcttcacgtc gaaggatttc     120
gcgtcccgta ttcgaggggg ctacaccgcg tacaagatcc ggtcgtctac cgaccgagtc     180
gagagcgtcg tcgaccgact ggacatcctc gtggcactga cccagcggac catcgacgag     240
aacctcgacg aacttcacga ggacagcgtg atcatctacg acggggaacg gacggagatg     300
gaggacgtcg acatccccga ggagatgatc ggattggccg ttccgctccg cagtctggcg     360
aaggacgcgg gtggaaccat catgcagaac accgtcgcgc tcggtgcggc gtgtgaagtg     420
```

```
gcgaacttcc ccatcgagaa cctcgacagc gcgctcgaca agaagttcgg cgcgaagggt     480
gaggccatcg tcgagaacaa caaggaagcc gcccgtctcg acaggagta cgtccaggag      540 gagtacgact acgacttcga gtacgacgtg aaacgacgg acaacgacta cgtcctgctc     600
aacggtgacg aggccatcgg catgggtgct atcgccgctg gctgtcgctt ctactccggc    660
taccccatca cgcccgcgac gaacgtcatg gagtatctca cgggccgaat cgagcacttc    720
ggcggcacgg tgatgcaggc cgaggacgaa ctgtcggcca tcaacatggc gctcggcgcg    780
gcgcgcgctg gcgcacgctc gatgacggcg acgtccggtc cgggtatcga cctgatgacc    840
gagacgttcg gtctcatcgc acagagcgag acgccgctcg tcatctgcga cgtgatgcgc    900
tccggtccct cgaccgggat gccgacgaaa caggaacagg gcgacctgaa catgacgctg    960 tacgcggcc acggcgagat ccgcggttc gtcgtcgcgc cgacgaacgt cgccgagtgt    1020
ttccacaaga ccgtcgaggc gttcaacttc gccgagaagt accagacccc cgtcttcctg   1080
ctcgccgacc tcgccatggc cgtcaccgag cagacgttct cgcccgagga gttcgacatg   1140
gattccgtcg aaatcgagcg cggaaacatc gtggacgagg acgacatcga ggcgtggacg   1200
gacgagaagg accggttcca gccccacttc ccgaccgctg acggcatcag cccgcgcgcg   1260
ttccccggaa cgaagggcgg tgcccacatg tccaccggtc tcgaacacaa tgcgctcggt   1320
cggcggaccg aggacaccga aatccgcgtc gagcaggtcg acaagcgaaa ccgcaaggtc   1380
gagacggcac aggaagaaga agactggagt ccgcgcgagt tcggcgacga agacgccgac   1440
acgctcgtca tctcgtgggg gtcgaacgaa gggccgatgc gcgaagccct cgacttcctc   1500
gaagaggacg acgtgagcgt tcggttcctc tcggttccgt acatcttccc ccgccccgac   1560
ctcaccgagg acatcgagtc cgcggacacc gtcatcgtgg tcgagtgtaa cgaaaccggg   1620
cagttcgcca acgttctcga acacgacgcg ctcactcgtg tcgagcggat aaacaagtac   1680
aacggtattc gattcaaggc cgacgagttg gccgacgaca tcaaagcgaa actcggacag   1740
gaggtagaag catgagttca gaggttcgat tcaccgactt caagtcggac aagcaaccga   1800
cgtggtgtcc cggatgcggc gacttcggga cgatgaacgg gatgatgaag gcactcgccg   1860
aaaccggcaa cagcccggac gacacgttcg tcgtcgcggg tatcggctgt tccggaaaaa   1920
tcgggacgtt catgcactcc tacgcgattc acggcgtgca cgggcgtgcg cttcccgtcg   1980
gcaccggcgt caaactcgcc aaccccgacc tcgaagtgat ggtcgcgggc ggcgacggtg   2040
acggctactc catcggtgtg ggtcacttta tccacgccgt gcgccggaac gtggacatgt   2100
cctacgtcgt catggacaac cgcatctacg ggctgacgaa gggacaggcc tcgccgacca   2160
gccgcgagga cttcgagacg agtacgacgc cggaaggccc gcaacagccc ccggtcaacc   2220
cgctcgccct cgccctctcg gcgggtgcga cgttcatcgc acagtccttc tcgaccgacg   2280
cacagcgaca cgccgaaatc gtccagaagg ccatcgagca cgacggcttc ggcttcgtga   2340
acgtcttctc gccctgcgtc acgttcaacg acgtggacac gtacgactac ttccgcgact   2400
ccatcgtcga cctcgcggac gagggtcacg acccgcacga ctacgaggcg ccaaagaga   2460 agattctcga cgccagcaag gagtatcagg gcgtcatcta ccaggacgaa gatagcgttc   2520
cgtacagcga actccacggc atcgagggca acatgtccga gattcccgac ggcgcacccg   2580
aggacgcgat ggacctcgtg cgcgagttct actga                              2615
```

<210> SEQ ID NO 28
<211> LENGTH: 573
<212> TYPE: PRT
<213> ORGANISM: Magnetococcus sp. MC-1

<400> SEQUENCE: 28

Met Glu Lys Lys Asp Leu Ile Ile Arg Val Ala Gly Glu Gly Glu
1               5                   10                  15

Gly Ile Ile Ser Ser Gly Asp Phe Ile Ala Ala Cys Ala Arg Ala
                20                  25                  30

Gly Leu Glu Val Tyr Thr Phe Lys Thr Phe Pro Ala Glu Ile Lys Gly
            35                  40                  45

Gly Tyr Ala Met Tyr Gln Val Arg Ala Ser Ser Glu Lys Leu Tyr Cys
    50                  55                  60

Gln Gly Asp Thr Phe Asp Val Phe Cys Ala Phe Asn Gly Glu Ala Tyr
65                  70                  75                  80

Glu Gln Asn Lys Asp Lys Ile Lys Pro Gly Thr Ala Phe Val Tyr Asp
                85                  90                  95

Tyr Pro Gly Gly Asp Phe Glu Pro Asp Glu Ile Pro Glu Gly Val Phe
            100                 105                 110

Ala Tyr Pro Ile Pro Met Ser Gln Thr Ala Lys Glu Met Lys Ser Tyr
        115                 120                 125

Arg Ser Lys Asn Met Val Ala Leu Gly Ala Leu Ser Glu Leu Phe Asn
130                 135                 140

Ile Ser Glu Asn Thr Leu Lys Glu Val Leu Ser Asp Lys Phe Gly Lys
145                 150                 155                 160

Lys Gly Glu Glu Val Leu Ala Phe Asn Leu Ala Phe Asp Lys Gly
                165                 170                 175

Lys Ala Leu Ala Lys Ala Leu Thr Lys Ala Asp Pro Phe Arg Val Ala
        180                 185                 190

Asp Pro Gln Glu Pro Lys Asp Val Ile Ile Met Ala Gly Asn Asp Ala
            195                 200                 205

Val Gly Leu Gly Gly Ile Leu Gly Gly Leu Glu Phe Phe Ser Ala Tyr
    210                 215                 220

Pro Ile Thr Pro Ala Thr Glu Val Ala Lys Tyr Val Ala Thr His Leu
225                 230                 235                 240

Pro Lys Cys Gly Gly Asp Leu Val Gln Ala Glu Asp Glu Ile Ala Ser
                245                 250                 255

Ile Ala Gln Val Leu Gly Ala Ser Tyr Ala Gly Lys Lys Ser Met Thr
        260                 265                 270

Ala Thr Ser Gly Pro Gly Leu Ala Leu Met Ser Glu Met Leu Gly Met
            275                 280                 285

Ala His Met Ser Glu Thr Pro Cys Leu Val Val Asp Val Gln Arg Gly
    290                 295                 300

Gly Pro Ser Thr Gly Leu Pro Thr Lys His Glu Gln Ser Asp Leu Phe
305                 310                 315                 320

Leu Ala Ile His Gly Gly His Gly Asp Ser Pro Arg Ile Val Leu Ser
                325                 330                 335

Val Glu Asp Val Lys Asp Cys Ile Ser Met Thr Val Asp Gly Leu Asn
        340                 345                 350

Leu Ala Glu Lys Tyr Gln Ala Pro Val Ile Val Leu Ser Asp Gly Ser
            355                 360                 365

Leu Ala Phe Ser Thr Gln Thr Ile Pro Arg Pro Lys Pro Glu Asp Phe
    370                 375                 380

Thr Ile Ile Asn Arg Lys Thr Trp Asp Gly Gln Gly Thr Tyr Lys Arg
385                 390                 395                 400

Tyr Glu Leu Thr Glu Asp Asn Ile Ser Pro Met Ala Ala Pro Gly Thr 405                 410                 415
Pro Asn Ala Lys His Ile Ala Thr Gly Leu Glu His Gly Glu Thr Gly
                420                 425                 430

Ala Pro Asn Tyr Ser Pro Ala Asn His Glu Leu Met His Arg Lys Arg
            435                 440                 445

Phe Asn Lys Gln Asn Ser Val Leu Asp Phe Tyr Lys Asn Met Glu Val
        450                 455                 460

Glu Gly Val Glu Gly Glu Ala Asp Val Gly Ile Ile Thr Trp Gly Ser
465                 470                 475                 480

Thr Ile Gly Val Val Arg Glu Ala Met Gln Arg Leu Thr Ala Glu Gly
                485                 490                 495

Leu Lys Val Lys Ala Met Tyr Pro Lys Leu Leu Trp Pro Met Pro Val
                500                 505                 510

Ala Asp Tyr Asp Ala Phe Gly Ala Thr Cys Lys Lys Val Ile Val Pro
            515                 520                 525

Glu Val Asn Phe Gln Gly Gln Leu Ser His Phe Ile Arg Ala Glu Thr
        530                 535                 540

Ser Ile Lys Pro Ile Pro Tyr Thr Ile Cys Gly Gly Leu Pro Phe Thr
545                 550                 555                 560

Pro Glu Met Ile Val Asn Arg Val Lys Glu Glu Ile Gln
                565                 570

<210> SEQ ID NO 29
<211> LENGTH: 292
<212> TYPE: PRT
<213> ORGANISM: Magnetococcus sp. MC-1

<400> SEQUENCE: 29

Met Thr Val Glu Ala Phe His Lys Met Glu Asn Met Lys Pro Lys Asp
1               5                   10                  15

Tyr Lys Ser Glu Val Pro Thr Thr Trp Cys Pro Gly Cys Gly His Phe
                20                  25                  30

Gly Ile Leu Asn Gly Val Tyr Arg Ala Met Ala Glu Leu Gly Ile Asp
            35                  40                  45

Ser Thr Lys Phe Ala Ala Ile Ser Gly Ile Gly Cys Ser Ser Arg Met
        50                  55                  60

Pro Tyr Phe Val Asp Ser Tyr Lys Met His Thr Leu His Gly Arg Ala
65                  70                  75                  80

Gly Ala Val Ala Thr Gly Thr Gln Val Ala Arg Pro Asp Leu Cys Val
                85                  90                  95

Val Val Ala Gly Gly Asp Gly Asp Gly Phe Ser Ile Gly Gly Gly His
            100                 105                 110

Met Pro His Met Ala Arg Lys Asn Val Asn Met Thr Tyr Val Leu Met
        115                 120                 125

Asp Asn Gly Ile Tyr Gly Leu Thr Lys Gly Gln Tyr Ser Pro Thr Ser
130                 135                 140

Arg Pro Glu Met Thr Ala Tyr Thr Thr Pro Tyr Gly Gly Pro Glu Asn
145                 150                 155                 160

Pro Met Asn Pro Leu Leu Tyr Met Leu Thr Tyr Gly Ala Thr Tyr Val
                165                 170                 175

Ala Gln Ala Phe Ala Gly Lys Pro Lys Asp Cys Ala Glu Leu Ile Lys
            180                 185                 190

Gly Ala Met Glu His Glu Gly Phe Ala Tyr Val Asn Ile Phe Ser Gln
        195                 200                 205

```
Cys Pro Thr Phe Asn Lys Ile Asp Thr Val Asp Phe Tyr Arg Asp Leu
    210                 215                 220

Val Glu Pro Ile Pro Glu Asp His Asp Thr Ser Asp Leu Gly Ala Ala
225                 230                 235                 240

Met Glu Leu Ala Arg Arg Pro Gly Gly Lys Ala Pro Thr Gly Leu Leu
                245                 250                 255

Tyr Lys Thr Ser Ala Pro Thr Leu Asp Gln Asn Leu Ala Lys Ile Arg
            260                 265                 270

Glu Arg Leu Gly Gly His Val Gly Tyr Asp Lys Asn Lys Ile Ile Ala
        275                 280                 285

Leu Ala Lys Pro
    290

<210> SEQ ID NO 30
<211> LENGTH: 2597
<212> TYPE: DNA
<213> ORGANISM: Magnetococcus sp. MC-1

<400> SEQUENCE: 30
atggagaaga aagatctgat tatccgcgtg gcaggtgagg gggggaagg tatcatctcc      60 tccggtgact tcattgctgc cgcatgtgcg cgggctggtt tggaggtcta cacctttaaa    120
accttcccgg cggaaatcaa gggcgggtac gcaatgtatc aagtccgtgc cagtagcgag    180
aagctctatt gtcagggtga caccttttgac gtgttctgcg cctttaatgg cgaagcttat   240
gagcagaaca agataagat taaacccggc accgcttttg tctatgacta tccaggcggt     300
gattttgaac tgacgagat ccctgagggt gtgtttgcat acccgatccc catgtcacaa     360
acagcgaagg aaatgaaatc ctaccgctcc aaaaacatgg tggctctggg tgctctgtcg    420
gagttgttta acatctcaga gaacacgctt aaagaggtgt gagcgacaa gtttggtaaa    480 aaaggcgaag aggttttggc gttcaaccta gaagcttttg ataagggtaa agcgctggca    540
aaggctctca ccaaagcgga tccttttccgt gtggcggatc cgcaagagcc taaagatgtg   600
atcatcatgg cgggtaacga tgccgtgggt ctgggtggca ttttgggtgg cttggagttt   660
ttctctgcct atcccattac ccccgcgacc gagtggcca agtatgtggc gactcacctg     720
cctaagtgtg gtggggattt ggtgcaggct gaggatgaga tcgcctctat cgcgcaggtg    780
ttgggtgcct cttatgcggg taaaaaatcc atgactgcca cctctggtcc tggtctggcg    840
ctcatgtccg agatgttggg catggcccac atgtctgaga ccccctgtct ggtggtggat    900
gtgcaacgtg gtggtccatc cacgggtctg cccactaagc atgagcagtc ggatctgttt    960
ttggccattc atggtggtca tggcgactcc ccgcgtattg tgctctcggt ggaagatgtg   1020
aaagattgca tcagcatgac tgtggacggt ctgaatttgg ctgagaaata tcaggccccc   1080
gtgattgtgc tctccgacgg ctctctggcc ttctctacgc agaccattcc ccgccctaaa   1140
cccgaagatt ttaccatcat caatcgtaaa acctgggatg ccaaggcac ctataagcgt    1200 tatgagttaa ccgaagataa catctccccg atggcggctc ccggtacccc taatgccaag   1260
cacattgcca cgggtctgga gcatggtgaa acgggtgcgc ccaactattc gcctgccaac   1320
catgagttga tgcatcgcaa cgcgcttcaac aagcaaaact ctgtgttaga tttttataaa   1380
aacatggaag ttgaggggt tgaggggcgaa gcggatgtgg gcattatcac ttgggggttcc   1440 accatcgggg tggtgcgtga ggcgatgcaa cgtttgaccg cagaggggct gaaggtcaag   1500
gcgatgtatc ccaaattgct gtggccaatg ccggttgcgg actatgatgc ctttggtgcc    1560
acctgtaaaa aggtgattgt ccctgaggtc aacttccagg ggcagctttc ccactttatc   1620
```

-continued

```
cgtgcggaaa cgtccattaa gcccattcct tacacgatct gtggcggttt gccgttcaca    1680
cctgagatga ttgtgaaccg ggttaaggag gagatccaat gactgtcgaa gccttccaca    1740
agatggaaaa tatgaagccc aaggactaca agtccgaggt tcccaccaca tggtgcccag    1800
gttgtggcca ctttggtatt ctgaacggtg tctaccgtgc gatggcagag ttgggcattg    1860
actcaaccaa atttgccgcc atttccggta ttggctgctc gtcacgtatg ccatacttcg    1920
ttgactccta caaaatgcac accctgcacg gtcgtgctgg tgcggtggca acgggtaccc    1980
aggttgcgcg tcctgatctg tgcgtggtgg tggcgggtgg tgatggcgat ggtttctcca    2040
tcggtggtgg tcacatgccc cacatggcgc gtaaaaatgt caacatgacc tacgtgctca    2100
tggataatgg gatctatggt ttgaccaagg gtcaatactc tccgacctcg cgtccagaga    2160
tgacggccta taccaccccct tatggtggtc ctgagaatcc catgaacccg ctgctctaca    2220
tgctcaccta tggtgcgacc tatgtggccc aggcttttgc cggcaagccc aaggattgtg    2280
cggagttgat caagggtgcc atggagcatg aagggtttgc ttatgtgaac atcttctctc    2340
agtgccccac ctttaacaaa attgacacgg tggatttcta tcgtgatctg gtagagccta    2400
tccctgagga tcatgatact tccgatcttg gggccgcgat ggagttggct cgtcgtccgg    2460
gtggtaaagc cccgactggc ctgttgtaca aacttcagc accaaccttg gaccagaact    2520
tggccaaaat tcgtgagcgc cttggtggtc acgtgggcta tgataagaac aagatcattg    2580
ccctggcaaa gccgtaa                                                   2597
```

<210> SEQ ID NO 31
<211> LENGTH: 472
<212> TYPE: PRT
<213> ORGANISM: Hydrogenobacter thermophilus TK-6

<400> SEQUENCE: 31

```
Met Phe Lys Lys Val Leu Val Ala Asn Arg Gly Glu Ile Ala Cys Arg
1               5                   10                  15

Val Ile Arg Ala Cys Lys Glu Leu Gly Ile Gln Thr Val Ala Ile Tyr
            20                  25                  30

Asn Glu Ile Glu Ser Thr Ala Arg His Val Lys Met Ala Asp Glu Ala
        35                  40                  45

Tyr Met Ile Gly Val Asn Pro Leu Asp Thr Tyr Leu Asn Ala Glu Arg
    50                  55                  60

Ile Val Asp Leu Ala Leu Glu Val Gly Ala Glu Ala Ile His Pro Gly
65                  70                  75                  80

Tyr Gly Phe Leu Ala Glu Asn Glu His Phe Ala Arg Leu Cys Glu Glu
                85                  90                  95

Lys Gly Ile Thr Phe Ile Gly Pro His Trp Lys Val Ile Glu Leu Met
            100                 105                 110

Gly Asp Lys Ala Arg Ser Lys Glu Val Met Lys Arg Ala Gly Val Pro
        115                 120                 125

Thr Val Pro Gly Ser Asp Gly Ile Leu Lys Asp Val Glu Glu Ala Lys
    130                 135                 140

Arg Ile Ala Lys Glu Ile Gly Tyr Pro Val Leu Leu Lys Ala Ser Ala
145                 150                 155                 160

Gly Gly Gly Gly Arg Gly Ile Arg Ile Cys Arg Asn Glu Glu Glu Leu
                165                 170                 175

Val Arg Asn Tyr Glu Asn Ala Tyr Asn Glu Ala Val Lys Ala Phe Gly
            180                 185                 190
```

```
Arg Gly Asp Leu Leu Leu Glu Lys Tyr Ile Glu Asn Pro Lys His Ile
            195                 200                 205

Glu Phe Gln Val Leu Gly Asp Lys Tyr Gly Asn Val Ile His Leu Gly
            210                 215                 220

Glu Arg Asp Cys Ser Ile Gln Arg Arg Asn Gln Lys Leu Val Glu Ile
225                 230                 235                 240

Ala Pro Ser Leu Leu Leu Thr Pro Glu Gln Arg Glu Tyr Tyr Gly Ser
            245                 250                 255

Leu Val Val Lys Ala Ala Lys Glu Ile Gly Tyr Tyr Ser Ala Gly Thr
            260                 265                 270

Met Glu Phe Ile Ala Asp Glu Lys Gly Asn Leu Tyr Phe Ile Glu Met
            275                 280                 285

Asn Thr Arg Ile Gln Val Glu His Pro Val Thr Glu Met Ile Thr Gly
            290                 295                 300

Val Asp Ile Val Lys Trp Gln Ile Arg Ile Ala Ala Gly Glu Arg Leu
305                 310                 315                 320

Arg Tyr Ser Gln Glu Asp Ile Arg Phe Asn Gly Tyr Ser Ile Glu Cys
            325                 330                 335

Arg Ile Asn Ala Glu Asp Pro Lys Lys Gly Phe Ala Pro Ser Ile Gly
            340                 345                 350

Thr Ile Glu Arg Tyr Tyr Val Pro Gly Gly Phe Gly Ile Arg Val Glu
            355                 360                 365

His Ala Ser Ser Lys Gly Tyr Glu Ile Thr Pro Tyr Tyr Asp Ser Leu
            370                 375                 380

Ile Ala Lys Leu Ile Val Trp Ala Pro Leu Trp Glu Val Ala Val Asp
385                 390                 395                 400

Arg Met Arg Ser Ala Leu Glu Thr Tyr Glu Ile Ser Gly Val Lys Thr
            405                 410                 415

Thr Ile Pro Leu Leu Ile Asn Ile Met Lys Asp Lys Asp Phe Arg Asp
            420                 425                 430

Gly Lys Phe Thr Thr Arg Tyr Leu Glu Glu His Pro His Val Phe Asp
            435                 440                 445

Tyr Ala Glu His Arg Asp Lys Glu Asp Phe Val Ala Phe Ile Ser Ala
450                 455                 460

Val Ile Ala Ser Tyr His Gly Leu
465                 470

<210> SEQ ID NO 32
<211> LENGTH: 652
<212> TYPE: PRT
<213> ORGANISM: Hydrogenobacter thermophilus TK-6

<400> SEQUENCE: 32

Met Gln Ala Val Glu Ile Met Glu Glu Ile Arg Glu Lys Phe Lys Glu
1               5                   10                  15

Phe Glu Lys Gly Gly Phe Arg Lys Lys Ile Leu Ile Thr Asp Leu Thr
            20                  25                  30

Pro Arg Asp Gly Gln Gln Cys Lys Leu Ala Thr Arg Val Arg Thr Asp
        35                  40                  45

Asp Leu Leu Pro Leu Cys Glu Ala Met Asp Lys Val Gly Phe Tyr Ala
    50                  55                  60

Val Glu Val Trp Gly Gly Ala Thr Tyr Asp Val Cys Leu Arg Tyr Leu
65                  70                  75                  80

Lys Glu Asp Pro Trp Glu Arg Leu Arg Arg Ile Lys Glu Val Met Pro
                85                  90                  95
```

-continued

```
Asn Thr Lys Leu Gln Met Leu Phe Arg Gly Gln Asn Ile Val Gly Tyr
            100                 105                 110

Arg Pro Lys Ser Asp Lys Leu Val Tyr Lys Phe Val Glu Arg Ala Ile
            115                 120                 125

Lys Asn Gly Ile Thr Val Phe Arg Val Phe Asp Ala Leu Asn Asp Asn
            130                 135                 140

Arg Asn Ile Lys Thr Ala Val Lys Ala Ile Lys Glu Leu Gly Gly Glu
145                 150                 155                 160

Ala His Ala Glu Ile Ser Tyr Thr Arg Ser Pro Ile His Thr Tyr Gln
                    165                 170                 175

Lys Trp Ile Glu Tyr Ala Leu Glu Ile Ala Glu Met Gly Ala Asp Trp
            180                 185                 190

Leu Ser Phe Lys Asp Ala Thr Gly Ile Ile Met Pro Phe Glu Thr Tyr
            195                 200                 205

Ala Ile Ile Lys Gly Ile Lys Glu Ala Thr Gly Gly Lys Leu Pro Val
            210                 215                 220

Leu Leu His Asn His Asp Met Ser Gly Thr Ala Ile Val Asn His Met
225                 230                 235                 240

Met Ala Val Leu Ala Gly Val Asp Met Leu Asp Thr Val Leu Ser Pro
                    245                 250                 255

Leu Ala Phe Gly Ser Ser His Pro Ala Thr Glu Ser Val Val Ala Met
                    260                 265                 270

Leu Glu Gly Thr Pro Phe Asp Thr Gly Ile Asp Met Lys Lys Leu Asp
            275                 280                 285

Glu Leu Ala Glu Ile Val Lys Gln Ile Arg Lys Lys Tyr Lys Lys Tyr
            290                 295                 300

Glu Thr Glu Tyr Ala Gly Val Asn Ala Lys Val Leu Ile His Lys Ile
305                 310                 315                 320

Pro Gly Gly Met Ile Ser Asn Met Val Ala Gln Leu Ile Glu Ala Asn
                    325                 330                 335

Ala Leu Asp Lys Ile Glu Glu Ala Leu Glu Val Pro Asn Val Glu
            340                 345                 350

Arg Asp Leu Gly His Pro Pro Leu Leu Thr Pro Ser Ser Gln Ile Val
            355                 360                 365

Gly Val Gln Ala Val Leu Asn Val Ile Ser Gly Glu Arg Tyr Lys Val
            370                 375                 380

Ile Thr Lys Glu Val Arg Asp Tyr Val Glu Gly Lys Tyr Gly Lys Pro
385                 390                 395                 400

Pro Gly Pro Ile Ser Lys Glu Leu Ala Glu Lys Ile Leu Gly Pro Gly
                    405                 410                 415

Lys Glu Pro Asp Phe Ser Ile Arg Ala Ala Asp Leu Ala Asp Pro Asn
            420                 425                 430

Asp Trp Asp Lys Ala Tyr Glu Glu Thr Lys Ala Ile Leu Gly Arg Glu
            435                 440                 445

Pro Thr Asp Glu Glu Val Leu Leu Tyr Ala Leu Phe Pro Met Gln Ala
            450                 455                 460

Lys Asp Phe Phe Val Ala Arg Glu Lys Gly Glu Leu His Pro Glu Pro
465                 470                 475                 480

Val Asp Glu Leu Val Glu Thr Thr Glu Val Lys Ala Gly Val Val Pro
                    485                 490                 495

Gly Ala Ala Pro Val Glu Phe Gly Ile Val Tyr His Gly Glu Lys Phe
            500                 505                 510
```

```
Lys Val Lys Val Glu Gly Val Ser Ala His Gln Glu Pro Gly Lys Pro
            515                 520                 525

Arg Lys Tyr Tyr Ile Arg Val Asp Gly Arg Leu Glu Glu Val Gln Ile
        530                 535                 540

Thr Pro His Val Glu Ala Ile Pro Lys Gly Gly Pro Thr Pro Thr Ala
545                 550                 555                 560

Val Gln Ala Glu Glu Lys Gly Ile Pro Lys Ala Thr Gln Pro Gly Asp
                565                 570                 575

Ala Thr Ala Pro Met Pro Gly Arg Val Arg Val Leu Val Lys Glu
            580                 585                 590

Gly Asp Lys Val Lys Glu Gly Gln Thr Val Ala Ile Val Glu Ala Met
        595                 600                 605

Lys Met Glu Asn Glu Ile His Ala Pro Ile Ser Gly Val Val Glu Lys
            610                 615                 620

Val Phe Val Lys Pro Gly Asp Asn Val Thr Pro Asp Asp Ala Leu Leu
625                 630                 635                 640

Arg Ile Lys His Ile Glu Glu Glu Val Ser Tyr Gly
                645                 650

<210> SEQ ID NO 33
<211> LENGTH: 3401
<212> TYPE: DNA
<213> ORGANISM: Hydrogenobacter thermophilus TK-6

<400> SEQUENCE: 33
atgtttaaga aggttttggt ggcaaataga ggtgagatag cttgcagggt tataagagcg      60
tgtaaagagc tgggtataca gacggttgcc atatacaacg agattgaatc caccgcaagg     120
catgtaaaga tggcggacga agcctacatg ataggtgtaa atcctctgga tacctacctg     180
aacgcagaaa ggatagtgga cctggctctt gaggtggggg ctgaggctat acatcccggt     240
tatggctttc tggcggagaa cgagcacttt gccagattgt gcgaagagaa gggcataacc     300
ttcataggtc cccactggaa ggtcatagag cttatgggag acaaagccag gtcaaaggag     360
gttatgaaaa gggcgggcgt cccaacagtc cctggaagcg acggcatact gaaagatgta     420
gaagaagcca acgcatagc caaagagata ggctatcctg tgcttttaaa ggcttctgcg     480
ggaggtggag aaggggtat aaggatatgc aggaacgagg aggagctggt aagaaactac     540
gagaacgctt acaacgaggc ggtcaaagcc ttcggcaggg gggacctgct tctgaaaaag     600
tacatagaaa accccaagca cattgagttt caggttttgg agataagta cggaaatgtt     660 atacacctgg gagaaagaga ctgttccata cagagaagaa accaaaaact tgtagagatt     720
gccccatcgc tccttcttac acctgagcaa agagagtatt acggctctct tgtggtaaaa     780
gcagcaaagg agataggtta ttacagcgct ggaactatgg agtttatagc cgacgaaaag     840
ggcaacctgt acttcataga gatgaacacc cgcattcagg tggagcatcc ggtaactgag     900
atgatcacag tgttgacat agtaaagtgg caaatcagga tagcggcagg agaaaggtta     960
aggtactctc aggaagacat aaggttcaac ggctactcca tagagtgcag gataaacgcg    1020
gaagatccca gaaaggctt tgcccccagc ataggcacca tagagagata ctatgtgccc    1080
ggaggatttg gcataaggt tgaacatgcc tcatcaaagg ttacgagat cactccctat    1140 tacgactccc tcatagccaa gctcatcgtg tgggctcctc tctgggaggt tgccgttgac    1200
agaatgaggt ccgctcttga aacctatgag atctccggtg tcaaaccac catacccgctc    1260 cttataaaca tcatgaagga caaagacttc agagatggta aatttaccac aaggtacctg    1320
```

| | |
|---|---|
| gaggagcatc cccatgtttt tgattacgct gaacacagag acaaagagga ctttgtagct | 1380 |
| tttatatccg cagtaatagc cagttatcat gggctttgat aaaaactctg gaggtgtagt | 1440 |
| acatgcaagc agttgagatt atggaagaga taagagaaaa gttcaaagag tttgaaaagg | 1500 |
| gaggctttag gaagaaaata ctcataacag accttacgcc cagggacgga cagcagtgca | 1560 |
| aactggcaac tcgggtcaga acagatgacc ttttgcccct ctgtgaggct atggacaagg | 1620 |
| tggggttcta tgcagttgag gtgtggggag gtgccaccta tgatgtgtgc ctcagatacc | 1680 |
| tcaaagaaga cccgtgggag agactgaggc gcataaagga agtgatgccc aacactaagc | 1740 |
| tccagatgct ctttagaggt caaaacatag tgggatacag acccaagtcc gataagctgg | 1800 |
| tttataagtt tgtggagaga gcaataaaaa acggtataac cgttttcaga gtgtttgacg | 1860 |
| ctctcaatga caacaggaac ataaagaccg ctgtaaaagc cataaaggag ctgggtggtg | 1920 |
| aggcacatgc cgagataagc tatacaagaa gtcctataca cacctaccaa aagtggatag | 1980 |
| agtacgctct tgaaatagcg gagatgggtg cggactggct gtcttttaag gatgccacgg | 2040 |
| gtataattat gcccttttgaa acttacgcca taataaaggg tataaggaa gccacaggtg | 2100 |
| gaaaacttcc ggtgctactt cacaaccacg acatgagcgg aaccgccata gtcaatcaca | 2160 |
| tgatggctgt gctggctggt gtggacatgc tggatactgt tctctcaccg cttgcctttg | 2220 |
| gctcttctca ccctgcgacg gaatccgtgg ttgccatgct tgaaggaaca ccctttgata | 2280 |
| caggcataga catgaagaag ttggacgaac ttgctgagat agtaaagcaa ataaggaaga | 2340 |
| agtacaaaaa gtatgagacg gagtatgctg gtgtaaatgc caaagtgctc atccacaaga | 2400 |
| tacccggcgg tatgatatcc aacatggtgg cacagctcat agaggcaaat gctttggata | 2460 |
| aaatagagga agctctcgaa gaggtaccaa atgtggaaag ggacctgggg catccaccac | 2520 |
| ttctgacacc ttcttcacag atagtgggtg ttcaggcggt tctcaatgtg atatccggtg | 2580 |
| agcgatacaa ggttataacc aaagaggtaa gagactatgt ggaaggcaag tatggaaagc | 2640 |
| cacccggtcc catatctaag gagctggctg agaagatcct cggtcctgga aaggaacccg | 2700 |
| acttctccat aagagctgca gacctggcag accccaacga ctgggataag gcttatgaag | 2760 |
| agacaaaagc tatacttgga agagagccta cagatgagga ggtgctcctt tatgctctct | 2820 |
| tcccccatgca ggcaaaggac ttttttgtag ccagagagaa gggagaactt catcctgagc | 2880 |
| cagttgatga gcttgttgaa caaactgaag taaaggcagg tgttgttcca ggtgcagcac | 2940 |
| ctgttgagtt tgaaatcgtc tatcacggtg agaagttcaa agtaaaagtg gaaggtgtga | 3000 |
| gcgctcatca ggagcccgga aagcccagaa agtactacat aagggtggac gggaggctgg | 3060 |
| aagaggtgca gataacgccc catgtggaag ctataccaaa aggaggaccc actccaacgg | 3120 |
| cagtacaagc cgaagagaaa ggcataccta aagctaccca gccaggtgat gctactgctc | 3180 |
| ctatgccggg aagggtcgtg agggttttgg taaaggaagg tgataaagta aagaaggtc | 3240 |
| aaacggtagc catagtggaa gccatgaaga tggagaacga gatccacgct cccataagcg | 3300 |
| gtgtagtaga aaaggtcttt gtcaaacccg gagataatgt aacacctgac gatgccctcc | 3360 |
| taagaataaa acacatagag gaagaggtca gttacggctg a | 3401 |

<210> SEQ ID NO 34
<211> LENGTH: 472
<212> TYPE: PRT
<213> ORGANISM: Candidatus Nitrospira defluvii

<400> SEQUENCE: 34

Met Phe Arg Lys Ile Leu Ile Ala Asn Arg Gly Glu Ile Ala Met Arg

-continued

```
1               5                   10                  15
Ile Ile Arg Gly Cys Arg Glu Leu Asn Ile Ala Thr Ala Ala Ile Tyr
                20                  25                  30

Ser Glu Ala Asp Ser Ser Gly Ile Tyr Val Lys Lys Ala Asp Glu Ser
                35                  40                  45

Tyr Leu Val Gly Pro Gly Pro Val Lys Gly Phe Leu Asp Gly Lys Gln
        50                  55                  60

Ile Val Glu Ile Ala Lys Arg Ile Gly Ala Asp Ala Ile His Pro Gly
65                  70                  75                  80

Tyr Gly Phe Leu Ser Glu Asn Thr Lys Phe Ala Arg Leu Cys Gln Thr
                85                  90                  95

Ser Gly Ile Thr Phe Ile Gly Pro Ser Pro Glu Thr Ile Asp Leu Met
                100                 105                 110

Gly Ser Lys Val Lys Ala Arg Gln Ile Ala Gln Ala Gly Val Pro
                115                 120                 125

Ile Val Pro Gly Thr Glu Gly Gly Val Thr Ser Val Asp Asp Ala Leu
        130                 135                 140

Ala Phe Ala His Gln Ile Asn Tyr Pro Val Met Ile Lys Ala Ser Ala
145                 150                 155                 160

Gly Gly Gly Gly Arg Gly Leu Arg Val Val Arg Ser Asp Gln Glu Leu
                165                 170                 175

Arg Glu Asn Ile Asp Val Ala Ser Arg Glu Ala Gln Ala Ala Phe Gly
                180                 185                 190

Asp Gly Ser Ile Phe Ile Glu Lys Tyr Ile Glu Arg Pro His His Ile
        195                 200                 205

Glu Phe Gln Ile Leu Gly Asp Lys His Gly Asn Ile Ile His Leu Gly
210                 215                 220

Glu Arg Asp Cys Ser Ile Gln Arg Arg His Gln Lys Leu Ile Glu Ile
225                 230                 235                 240

Ala Pro Ser Leu Ile Leu Thr Pro Lys Leu Arg Ala Gln Met Gly Glu
                245                 250                 255

Ala Ala Ile Ala Ile Ala Lys Ala Val His Tyr Asp Asn Ala Gly Thr
                260                 265                 270

Val Glu Phe Leu Leu Asp His Glu Gly His Phe Tyr Phe Met Glu Met
        275                 280                 285

Asn Pro Arg Leu Gln Val Glu His Thr Val Thr Glu Gln Ile Thr Ala
        290                 295                 300

Ile Asp Ile Val Arg Asn Gln Ile Ser Ile Ala Ala Gly Lys Pro Leu
305                 310                 315                 320

Glu Ile Arg Gln Lys Asp Val Thr Leu Gln Gly His Ala Ile Gln Cys
                325                 330                 335

Arg Ile Asn Ala Glu Asp Pro Arg Asn Asn Phe Met Pro Cys Thr Gly
                340                 345                 350

Thr Ile Thr Ala Tyr Leu Ser Pro Gly Gly Ile Gly Val Arg Ile Asp
                355                 360                 365

Gly Ala Val Tyr Arg Asp Tyr Thr Ile Pro Pro Tyr Tyr Asp Ala Leu
        370                 375                 380

Leu Ala Lys Leu Thr Val Arg Gly Arg Thr Trp Glu Glu Thr Val Ser
385                 390                 395                 400

Arg Met Arg Arg Ser Leu Glu Glu Tyr Val Leu Arg Gly Val Lys Thr
                405                 410                 415

Thr Ile Pro Phe Met Lys Asn Val Met Met Glu Gln Asp Phe Gln Ala
                420                 425                 430
```

```
Gly Arg Phe Asp Thr Ser Tyr Leu Glu Thr His Pro Asp Leu Tyr Gln
        435                 440                 445

Tyr Glu Ser Glu Glu Pro Glu Asp Leu Val Leu Ala Ile Ser Ala
    450                 455                 460

Ala Ile Ala Ala Tyr Glu Gly Leu
465                 470

<210> SEQ ID NO 35
<211> LENGTH: 643
<212> TYPE: PRT
<213> ORGANISM: Candidatus Nitrospira defluvii

<400> SEQUENCE: 35

Met Arg Val Lys Pro Ser Arg Pro Ser Ala Ser Arg Ala Val Gln Val
1               5                   10                  15

Met Gln Ala Ala Ser Pro Glu Phe Arg Val Thr Pro Ala Pro Gly Lys
            20                  25                  30

Lys Leu Leu Met Thr Glu Val Ala Leu Arg Asp Gly His Gln Cys Leu
        35                  40                  45

Leu Ala Thr Arg Met Arg Thr Glu Asp Met Leu Pro Ile Ala Gln Lys
50                  55                  60

Leu Asp Ala Val Gly Phe Trp Ser Leu Glu Val Trp Gly Gly Ala Thr
65                  70                  75                  80

Phe Asp Thr Cys Leu Arg Phe Leu Lys Glu Asp Pro Trp Glu Arg Leu
                85                  90                  95

Arg Ala Leu Arg Ala Ala Met Pro Lys Thr Lys Leu Gln Met Leu Leu
            100                 105                 110

Arg Gly Gln Asn Leu Val Gly Tyr Arg His Tyr Ala Asp Asp Val Leu
        115                 120                 125

Glu Lys Phe Ile Glu Arg Ser Ala Phe Asn Gly Ile Asp Val Phe Arg
130                 135                 140

Ile Phe Asp Ala Leu Asn Asp Val Arg Asn Leu Glu Arg Ala Ile Arg
145                 150                 155                 160

Glu Val Lys Ala Cys Glu Lys His Val Glu Ala Ala Ile Ser Tyr Thr
                165                 170                 175

Thr Ser Pro Val His Arg Leu Asp Gly Phe Val Thr Met Gly Lys Arg
            180                 185                 190

Leu Glu Asp Leu Gly Ala Asp Thr Ile Cys Ile Lys Asp Met Ala Gly
        195                 200                 205

Leu Leu Ala Pro Val Asp Ala Tyr Arg Leu Val Lys Ser Leu Lys Ala
    210                 215                 220

Ala Val Arg Val Pro Ile His Leu His Ser His Tyr Thr Ser Gly Met
225                 230                 235                 240

Gly Thr Met Ser Ala Leu Met Ala Val Met Ala Gly Leu Asp Leu Leu
                245                 250                 255

Asp Thr Ser Ile Ser Pro Leu Ala Gly Gly Ala Ser His Pro Pro Thr
            260                 265                 270

Glu Ser Met Val Ala Ala Leu Arg Gly Thr Pro Tyr Asp Ser Gly Leu
        275                 280                 285

Asp Leu Glu Asp Leu Gln Pro Ile Ala Glu His Phe Arg Asn Val Arg
290                 295                 300

Arg Lys Tyr Arg Gln Phe Glu Ser Asp Phe Thr Gly Val Asp Ala Glu
305                 310                 315                 320

Ile Leu Thr Ser Gln Ile Pro Gly Gly Met Leu Ser Asn Leu Ala Ala
```

```
                    325                 330                 335
Gln Leu Ala Glu Gln Asn Ala Leu Asp Arg Met Lys Glu Val Met Asp
                340                 345                 350
Glu Ile Pro Arg Val Arg Lys Asp Met Gly Tyr Pro Pro Leu Val Thr
            355                 360                 365
Pro Thr Ser Gln Ile Val Gly Thr Gln Ala Thr Leu Asn Val Leu Thr
370                 375                 380
Gly Glu Gln Gly Glu Arg Tyr Lys Val Ile Thr Thr Glu Thr Lys Asn
385                 390                 395                 400
Tyr Phe Leu Gly Leu Tyr Gly Arg Ala Pro Gly Pro Leu Asp Lys Glu
                405                 410                 415
Ile Met Ala Arg Ala Ile Gly Asp Glu Glu Pro Val Lys Gly Arg Pro
                420                 425                 430
Ala Asp Arg Leu Glu Ser Glu Phe Glu Lys Leu Lys Lys Asp Met Pro
            435                 440                 445
Glu Ser Ala Thr Thr Leu Glu Asp Gln Leu Ser Phe Ala Leu Phe Pro
        450                 455                 460
Ala Ile Ala Arg Asp Phe Phe Glu Ala Arg Glu Arg Gly Asp Leu Arg
465                 470                 475                 480
Ala Glu Pro Leu Glu Pro Thr Glu Thr Lys Gly Pro Ala Val Ala His
                485                 490                 495
Asp Leu His Leu Ala Pro Ala Glu Phe Asn Ile Thr Val His Gly Glu
                500                 505                 510
Asn Tyr His Val Val Ser Gly Ser Gly Arg Thr Thr Asp Gly Arg
            515                 520                 525
Lys Pro Tyr Tyr Ile Arg Val Asn Asp Arg Leu Gln Glu Val Ser Leu
        530                 535                 540
Glu Pro Leu Gln Glu Val Leu Ala Gly Val Pro Glu Ser Pro Glu Ala
545                 550                 555                 560
Gly Ser Thr Ser Lys Pro Lys Arg Pro Arg Pro Thr Lys Pro Gly Asp
                565                 570                 575
Val Ala Pro Pro Met Pro Gly Arg Val Val Lys Val Leu Val Thr Asp
            580                 585                 590
Gly Ala Gln Val Lys Thr Gly Asp Pro Leu Leu Ile Ile Glu Ala Met
        595                 600                 605
Lys Met Glu Ser Gln Val Pro Ala Pro Met Asp Gly Arg Val Ala Ala
            610                 615                 620
Ile Leu Val Val Glu Gly Asp Asn Val Lys Ile Asp Glu Thr Val Ile
625                 630                 635                 640
Gln Leu Glu

<210> SEQ ID NO 36
<211> LENGTH: 3374
<212> TYPE: DNA
<213> ORGANISM: Candidatus Nitrospira defluvii

<400> SEQUENCE: 36
atgtttcgga agatccttat tgccaaccgt ggcgaaatcg ccatgcgcat catccgtggc      60
tgtcgtgagc tcaatatcgc gacagcggcg atcgattctg aagccgactc ttcaggaatc     120
tacgtcaaaa aagccgacga gtcctacctc gtaggcccgg acccgtcaa ggggttcctg     180 gacggaaaac agatcgtgga gatcgccaag cgcatcggcg ccgacgcgat tcatcccgga     240
tacgggttcc tctctgaaaa cactaaattc gcccggctct gccaaacctc aggcattacc     300
```

-continued

| | |
|---|---|
| ttcatcggtc cgtcccccga gacgatcgac ctcatgggca gcaaagtgaa ggcgcgacag | 360 |
| atcgcccagc aggcgggggt cccgatcgtc cccggcaccg aaggcggagt caccagcgtc | 420 |
| gacgacgccc tggccttcgc ccatcagatc aactaccccg tcatgatcaa ggccagcgcc | 480 |
| ggcggcgggg gccgaggatt gcgggtcgtc cggtccgatc aggaattgcg agagaacatc | 540 |
| gatgtcgcgt cgcgagaagc acaggccgcg ttcggcgacg gcagcatctt catcgagaaa | 600 |
| tacatcgaac accgcacca tatcgaattt caaatcctgg cgacaaaca cggcaacatc | 660 |
| atccacctgg gtgagcggga ttgttccatt caacggcggc accagaaact gatcgaaatc | 720 |
| gccccctcat tgatcctgac gcccaaactg cgcgcccaaa tgggcgaggc cgccattgcc | 780 |
| atcgcgaaag cggtgcacta cgacaatgcc ggcaccgtcg agttcctcct cgaccacgag | 840 |
| ggccatttct acttcatgga aatgaatccc cgcctccagg tggaacatac cgtcacggaa | 900 |
| cagatcacgg ccatcgatat cgtccgcaat caaatttcca ttgcggcggg aaagcctctg | 960 |
| gagatccggc agaaggacgt aacgttgcag ggccatgcga ttcagtgccg catcaatgcc | 1020 |
| gaagacccgc gcaacaactt catgccctgc acaggcacca tcaccgccta tctgtcaccc | 1080 |
| ggcggaatcg gagtccgcat cgacggcgcg gtctatcgcg attacacgat tcctccctat | 1140 |
| tatgatcgcg tgttggcaaa actgaccgtc cgcgggcgca cctgggaaga gaccgtgagc | 1200 |
| cgcatgcggc gttcccttga agagtatgtg ctgcgcgggg tgaaaacgac cattccgttc | 1260 |
| atgaagaacg tgatgatgga acaggatttt caagccggac gattcgatac gtcctacctg | 1320 |
| gaaacccatc cggacctgta tcaatacgaa gaatccgagg agcctgagga cctggtgctg | 1380 |
| gccatctccg cagcgatcgc cgcgtacgaa ggactctgat aaaaactctg gaggtgtagt | 1440 |
| acatgcgtgt aaaacccagc cggccctctg cctcacgcgc cgtccaggtt atgcaggcgg | 1500 |
| cgagccctga gttccgcgtg acccggcgc cggggaaaaa gctttttaatg accgaggttg | 1560 |
| cgttgcgcga cgggcatcaa tgcctactcg cgaccaggat gcgcaccgag gacatgctac | 1620 |
| ccatcgccca aaaactggac gctgtgggat tctggtcgtt ggaagtctgg ggcggcgcca | 1680 |
| ccttcgatac ctgcctccgg ttcctcaagg aagacccctg ggagcgcctg cgcgcgctcc | 1740 |
| gcgcggcgat gccgaagacg aagctgcaaa tgttgttgcg cggccagaac ctggtcgggt | 1800 |
| atcgccacta cgccgacgac gtgctggaga gtttatcga gcgctcggcg tttaacggca | 1860 |
| tcgatgtctt ccgcatcttc gacgccctca cgatgttcg caatctggag cgggccatcc | 1920 |
| gtgaagtgaa agcctgcgaa aagcatgtgg aagcggccat ctcctacacc accagcccgg | 1980 |
| tccaccggct ggacgggttc gtcacgatgg gcaaacggtt ggaagacctg ggcgccgata | 2040 |
| ccatctgcat caaagacatg gccggcctgc tggcgcccgt cgatgcctac cgtctggtca | 2100 |
| agagcctcaa agcagcggtt cgcgtgccca tccacctgca ctcccactac acctcgggca | 2160 |
| tgggaaccat gtcggcgctg atggcggtca tggccgggct cgatctcctg gacacctcga | 2220 |
| tttctccgct tgccggaggc gcctcgcatc cccccaccga atctatggtg gctgcgttac | 2280 |
| ggggcacgcc ctatgacagc ggattggacc tggaagatct gcagcccatt gcagagcatt | 2340 |
| tccgaaacgt gcgccggaag taccggcaat ttgaaagcga cttcaccggt gtggacgctg | 2400 |
| aaattctgac gtcccagatt cccggcggca tgctctccaa tctcgccgcc caactggccg | 2460 |
| aacaaaacgc cttggaccga atgaaagaag tgatggacga aattcccgt gtccgcaaag | 2520 |
| acatgggcta tccgccgctt gtcacgccga ccagccagat cgtcggcacg caggccaccc | 2580 |
| tcaacgtgct cactggtgaa cagggcgagc gctacaaggt catcactacg gagaccaaga | 2640 |
| attatttcct cggcctctac ggccgggctc ccgggccgct tgataaagag atcatggcac | 2700 |

-continued

```
gggccatcgg ggacgaagag cccgtaaagg gccgaccggc cgaccggctt gaatcggaat   2760
ttgaaaaact caagaaggac atgcccgagt ccgccacgac gctggaagat caactgtcgt   2820
tcgccctctt ccccgcgatt gccagggatt tcttcgaagc acgcgagcgg ggcgacctgc   2880
gggcagagcc gctggagccg acggaaacga agggtcctgc cgtggcccac gatctccacc   2940
tcgcgccggc cgaattcaac atcaccgtgc acggcgagaa ttatcatgtc gtggtctcgg   3000
gctcaggccg caccaccgac ggccgcaagc cttactacat ccgggtcaac gaccggctgc   3060
aggaagtctc actggaaccg ctgcaggaag tgctggccgg cgtgcccgaa tcccagagg    3120 ccggcagcac gagcaagccg aaacggcccc gaccgaccaa accggcgat  gtcgccccgc   3180 ccatgcccgg tcgtgtcgtg aaagtcctgg taacggacgg cgcccaggta agaccggtg    3240 atccgctcct gatcattgag gccatgaaaa tggaaagcca agttcctgcg ccgatggacg    3300
ggcgggtcgc ggcgattctg gtcgtcgaag gcgacaacgt caagatcgac gaaaccgtca    3360
ttcaactgga gtag                                                      3374
```

<210> SEQ ID NO 37
<211> LENGTH: 472
<212> TYPE: PRT
<213> ORGANISM: Hydrogenobacter thermophilus TK-6

<400> SEQUENCE: 37

```
Met Phe Lys Lys Val Leu Val Ala Asn Arg Gly Glu Ile Ala Cys Arg
1               5                   10                  15

Val Ile Arg Ala Cys Lys Glu Leu Gly Ile Gln Thr Val Ala Ile Tyr
            20                  25                  30

Asn Glu Ile Glu Ser Thr Ala Arg His Val Lys Met Ala Asp Glu Ala
        35                  40                  45

Tyr Met Ile Gly Val Asn Pro Leu Asp Thr Tyr Leu Asn Ala Glu Arg
    50                  55                  60

Ile Val Asp Leu Ala Leu Glu Val Gly Ala Glu Ala Ile His Pro Gly
65                  70                  75                  80

Tyr Gly Phe Leu Ala Glu Asn Glu His Phe Ala Arg Leu Cys Glu Glu
                85                  90                  95

Lys Gly Ile Thr Phe Ile Gly Pro His Trp Lys Val Ile Glu Leu Met
            100                 105                 110

Gly Asp Lys Ala Arg Ser Lys Glu Val Met Lys Arg Ala Gly Val Pro
        115                 120                 125

Thr Val Pro Gly Ser Asp Gly Ile Leu Lys Asp Val Glu Glu Ala Lys
    130                 135                 140

Arg Ile Ala Lys Glu Ile Gly Tyr Pro Val Leu Leu Lys Ala Ser Ala
145                 150                 155                 160

Gly Gly Gly Gly Arg Gly Ile Arg Ile Cys Arg Asn Glu Glu Glu Leu
                165                 170                 175

Val Arg Asn Tyr Glu Asn Ala Tyr Asn Glu Ala Val Lys Ala Phe Gly
            180                 185                 190

Arg Gly Asp Leu Leu Leu Glu Lys Tyr Ile Glu Asn Pro Lys His Ile
        195                 200                 205

Glu Phe Gln Val Leu Gly Asp Lys Tyr Gly Asn Val Ile His Leu Gly
    210                 215                 220

Glu Arg Asp Cys Ser Ile Gln Arg Arg Asn Gln Lys Leu Val Glu Ile
225                 230                 235                 240

Ala Pro Ser Leu Leu Leu Thr Pro Glu Gln Arg Glu Tyr Tyr Gly Ser
```

245                 250                 255
Leu Val Val Lys Ala Ala Lys Glu Ile Gly Tyr Tyr Ser Ala Gly Thr
            260                 265                 270

Met Glu Phe Ile Ala Asp Glu Lys Gly Asn Leu Tyr Phe Ile Glu Met
            275                 280                 285

Asn Thr Arg Ile Gln Val Glu His Pro Val Thr Glu Met Ile Thr Gly
            290                 295                 300

Val Asp Ile Val Lys Trp Gln Ile Arg Ile Ala Ala Gly Glu Arg Leu
305                 310                 315                 320

Arg Tyr Ser Gln Glu Asp Ile Arg Phe Asn Gly Tyr Ser Ile Glu Cys
                325                 330                 335

Arg Ile Asn Ala Glu Asp Pro Lys Lys Gly Phe Ala Pro Ser Ile Gly
                340                 345                 350

Thr Ile Glu Arg Tyr Tyr Val Pro Gly Gly Phe Gly Ile Arg Val Glu
                355                 360                 365

His Ala Ser Ser Lys Gly Tyr Glu Ile Thr Pro Tyr Tyr Asp Ser Leu
                370                 375                 380

Ile Ala Lys Leu Ile Val Trp Ala Pro Leu Trp Glu Val Ala Val Asp
385                 390                 395                 400

Arg Met Arg Ser Ala Leu Glu Thr Tyr Glu Ile Ser Gly Val Lys Thr
                405                 410                 415

Thr Ile Pro Leu Leu Ile Asn Ile Met Lys Asp Lys Asp Phe Arg Asp
                420                 425                 430

Gly Lys Phe Thr Thr Arg Tyr Leu Glu Glu His Pro His Val Phe Asp
                435                 440                 445

Tyr Ala Glu His Arg Asp Lys Glu Asp Phe Val Ala Phe Ile Ser Ala
                450                 455                 460

Val Ile Ala Ser Tyr His Gly Leu
465                 470

<210> SEQ ID NO 38
<211> LENGTH: 652
<212> TYPE: PRT
<213> ORGANISM: Hydrogenobacter thermophilus TK-6

<400> SEQUENCE: 38

Met Gln Ala Val Glu Ile Met Glu Glu Ile Arg Glu Lys Phe Lys Glu
1               5                   10                  15

Phe Glu Lys Gly Gly Phe Arg Lys Lys Ile Leu Ile Thr Asp Leu Thr
            20                  25                  30

Pro Arg Asp Gly Gln Gln Cys Lys Leu Ala Thr Arg Val Arg Thr Asp
            35                  40                  45

Asp Leu Leu Pro Leu Cys Glu Ala Met Asp Lys Val Gly Phe Tyr Ala
        50                  55                  60

Val Glu Val Trp Gly Gly Ala Thr Tyr Asp Val Cys Leu Arg Tyr Leu
65                  70                  75                  80

Lys Glu Asp Pro Trp Glu Arg Leu Arg Arg Ile Lys Glu Val Met Pro
                85                  90                  95

Asn Thr Lys Leu Gln Met Leu Phe Arg Gly Gln Asn Ile Val Gly Tyr
            100                 105                 110

Arg Pro Lys Ser Asp Lys Leu Val Tyr Lys Phe Val Glu Arg Ala Ile
        115                 120                 125

Lys Asn Gly Ile Thr Val Phe Arg Val Phe Asp Ala Leu Asn Asp Asn
    130                 135                 140

```
Arg Asn Ile Lys Thr Ala Val Lys Ala Ile Lys Glu Leu Gly Gly Glu
145                 150                 155                 160

Ala His Ala Glu Ile Ser Tyr Thr Arg Ser Pro Ile His Thr Tyr Gln
            165                 170                 175

Lys Trp Ile Glu Tyr Ala Leu Glu Ile Ala Glu Met Gly Ala Asp Trp
                180                 185                 190

Leu Ser Phe Lys Asp Ala Thr Gly Ile Ile Ala Pro Val Glu Thr Tyr
        195                 200                 205

Ala Ile Ile Lys Gly Ile Lys Glu Ala Thr Gly Gly Lys Leu Pro Val
    210                 215                 220

Leu Leu His Asn His Asp Met Ser Gly Met Ala Thr Val Asn His Leu
225                 230                 235                 240

Met Ala Val Leu Ala Gly Val Asp Met Leu Asp Thr Val Leu Ser Pro
                245                 250                 255

Leu Ala Phe Gly Ser Ser His Pro Ala Thr Glu Ser Val Val Ala Met
            260                 265                 270

Leu Arg Gly Thr Pro Phe Asp Thr Gly Ile Asp Met Lys Lys Leu Gln
        275                 280                 285

Glu Leu Ala Glu Ile Val Lys Gln Ile Arg Lys Lys Tyr Lys Lys Tyr
    290                 295                 300

Glu Thr Glu Tyr Ala Gly Val Asn Ala Lys Val Leu Ile His Lys Ile
305                 310                 315                 320

Pro Gly Gly Met Ile Ser Asn Met Val Ala Gln Leu Ile Glu Ala Asn
                325                 330                 335

Ala Leu Asp Lys Ile Glu Glu Ala Leu Glu Glu Val Pro Asn Val Glu
            340                 345                 350

Arg Asp Leu Gly His Pro Pro Leu Leu Thr Pro Ser Ser Gln Ile Val
        355                 360                 365

Gly Val Gln Ala Val Leu Asn Val Ile Ser Gly Glu Arg Tyr Lys Val
    370                 375                 380

Ile Thr Lys Glu Val Arg Asp Tyr Val Glu Gly Lys Tyr Gly Lys Pro
385                 390                 395                 400

Pro Gly Pro Ile Ser Lys Glu Leu Ala Glu Lys Ile Leu Gly Pro Gly
                405                 410                 415

Lys Glu Pro Asp Phe Ser Ile Arg Ala Ala Asp Leu Ala Asp Pro Asn
            420                 425                 430

Asp Trp Asp Lys Ala Tyr Glu Thr Lys Ala Ile Leu Gly Arg Glu
        435                 440                 445

Pro Thr Asp Glu Glu Val Leu Leu Tyr Ala Leu Phe Pro Met Gln Ala
450                 455                 460

Lys Asp Phe Phe Val Ala Arg Glu Lys Gly Glu Leu His Pro Glu Pro
465                 470                 475                 480

Val Asp Glu Leu Val Glu Thr Thr Glu Val Lys Ala Gly Val Val Pro
                485                 490                 495

Gly Ala Ala Pro Val Glu Phe Gly Ile Val Tyr His Gly Glu Lys Phe
            500                 505                 510

Lys Val Lys Val Glu Gly Val Ser Ala His Gln Glu Pro Gly Lys Pro
        515                 520                 525

Arg Lys Tyr Tyr Ile Arg Val Asp Gly Arg Leu Glu Val Gln Ile
    530                 535                 540

Thr Pro His Val Glu Ala Ile Pro Lys Gly Gly Pro Thr Pro Thr Ala
545                 550                 555                 560

Val Gln Ala Glu Glu Lys Gly Ile Pro Lys Ala Thr Gln Pro Gly Asp
```

565                 570                 575
Ala Thr Ala Pro Met Pro Gly Arg Val Val Arg Val Leu Val Lys Glu
                580                 585                 590

Gly Asp Lys Val Lys Glu Gly Gln Thr Val Ala Ile Val Glu Ala Met
            595                 600                 605

Lys Met Glu Asn Glu Ile His Ala Pro Ile Ser Gly Val Val Glu Lys
        610                 615                 620

Val Phe Val Lys Pro Gly Asp Asn Val Thr Pro Asp Asp Ala Leu Leu
625                 630                 635                 640

Arg Ile Lys His Ile Glu Glu Glu Val Ser Tyr Gly
                645                 650

<210> SEQ ID NO 39
<211> LENGTH: 3401
<212> TYPE: DNA
<213> ORGANISM: Hydrogenobacter thermophilus TK-6

<400> SEQUENCE: 39
atgtttaaga aggttttggt ggcaaataga ggtgagatag cttgcagggt tataagagcg      60
tgtaaagagc tgggtataca gacggttgcc atatacaacg agattgaatc caccgcaagg     120
catgtaaaga tggcggacga agcctacatg ataggtgtaa atcctctgga tacctacctg     180
aacgcagaaa ggatagtgga cctggctctt gaggtggggg ctgaggctat acatcccggt     240
tatggctttc tggcggagaa cgagcacttt gccagattgt gcgaagagaa gggcataacc     300
ttcataggtc cccactggaa ggtcatagag cttatgggag acaaagccag gtcaaaggag     360
gttatgaaaa gggcgggcgt cccaacagtc cctggaagcg acggcatact gaaagatgta     420
gaagaagcca aacgcatagc caaagagata ggctatcctg tgcttttaaa ggcttctgcg     480
ggaggtggag aagggtat aaggatatgc aggaacgagg aggagctggt aagaaactac     540
gagaacgctt acaacgaggc ggtcaaagcc ttcggcaggg gggacctgct tctggaaaag     600
tacatagaaa accccaagca cattgagttt caggttttgg gagataagta cggaaatgtt     660
atacacctgg gagaaagaga ctgttccata cagagaagaa accaaaaact tgtagagatt     720
gccccatcgc tccttcttac acctgagcaa agagagtatt acggctctct tgtggtaaaa     780
gcagcaaagg ataggtta ttacagcgct ggaactatgg agtttatagc cgacgaaaag     840
ggcaacctgt acttcataga gatgaacacc cgcattcagg tggagcatcc ggtaactgag     900
atgatcacag tgttgacat agtaaagtgg caaatcagga tagcggcagg agaaaggtta     960
aggtactctc aggaagacat aaggttcaac ggctactcca tagagtgcag gataaacgcg    1020
gaagatccca gaaaggctt gccccagc ataggcacca tagagagata ctatgtgccc    1080
ggaggatttg gcataaggt tgaacatgcc tcatcaaagg gttacgagat cactccctat    1140
tacgactccc tcatagccaa gctcatcgtg tgggctcctc tctgggaggt tgccgttgac    1200
agaatgaggt ccgctcttga aacctatgag atctccggtg tcaaaaccac catacccgctc    1260 cttataaaca tcatgaagga caaagacttc agagatggta aatttaccac aaggtacctg    1320
gaggagcatc cccatgtttt tgattacgct gaacacagag acaaagagga ctttgtagct    1380
tttatatccg cagtaatagc cagttatcat gggctttgat aaaaactctg gaggtgtagt    1440
acatgcaagc agttgagatt atggaagaga taagagaaaa gttcaaagag tttgaaaagg    1500
gaggctttag gaagaaaata ctcataacag accttacgcc cagggacgga cagcagtgca    1560
aactggcaac tcgggtcaga acagatgacc ttttgcccct ctgtgaggct atggacaagg    1620

```
tggggttcta tgcagttgag gtgtggggag gtgccaccta tgatgtgtgc ctcagatacc   1680
tcaaagaaga cccgtgggag agactgaggc gcataaagga agtgatgccc aacactaagc   1740
tccagatgct ctttagaggt caaaacatag tgggatacag acccaagtcc gataagctgg   1800
tttataagtt tgtggagaga gcaataaaaa acggtataac cgttttcaga gtgtttgacg   1860
ctctcaatga caacaggaac ataaagaccg ctgtaaaagc cataaaggag ctgggtggtg   1920
aggcacatgc cgagataagc tatacaagaa gtcctataca cacctaccaa agtggatag   1980 agtacgctct tgaaatagcg gagatgggtg cggactggct gtcttttaag gatgccacgg   2040
gtataattgc gcccgtcgaa acttacgcca ataaagggt ataaaggaa gccacaggtg    2100 gaaaacttcc ggtgctactt cacaaccacg acatgagcgg aatggccacc gtcaatcacc   2160
tgatggctgt gctggctggt gtggacatgc tggatactgt tctctcaccg cttgccttg    2220 gctcttctca ccctgcgacg gaatccgtgg ttgccatgct tcggggaaca cccttgata   2280 caggcataga catgaagaag ttgcaggaac ttgctgagat agtaaagcaa ataaggaaga   2340
agtacaaaaa gtatgagacg gagtatgctg gtgtaaatgc caaagtgctc atccacaaga   2400
tacccggcgg tatgatatcc aacatggtgg cacagctcat agaggcaaat gctttggata   2460
aaatagagga agctctcgaa gaggtaccaa atgtggaaag ggacctgggg catccaccac   2520
ttctgacacc ttcttcacag atagtgggtg ttcaggcggt tctcaatgtg atatccggtg   2580
agcgatacaa ggttataacc aaagaggtaa gagactatgt ggaaggcaag tatggaaagc   2640
cacccggtcc catatctaag gagctggctg agaagatcct cggtcctgga aggaacccg   2700 acttctccat aagagctgca gacctggcag accccaacga ctgggataag gcttatgaag   2760
agacaaaagc tatacttgga agagagccta cagatgagga ggtgctcctt tatgctctct   2820
tccccatgca ggcaaaggac ttttttgtag ccagagagaa gggagaactt catcctgagc   2880
cagttgatga gcttgttgaa acaactgaag taaaggcagg tgttgttcca ggtgcagcac   2940
ctgttgagtt tgaaatcgtc tatcacggtg agaagttcaa agtaaaagtg gaaggtgtga   3000
gcgctcatca ggagcccgga aagcccagaa agtactacat aagggtggac gggaggctgg   3060
aagaggtgca gataacgccc catgtggaag ctataccaaa aggaggaccc actccaacgg   3120
cagtacaagc cgaagagaaa ggcataccta agctaccca gccaggtgat gctactgctc   3180
ctatgccggg aagggtcgtg agggttttgg taaggaagg tgataaagta aaagaaggtc   3240
aaacggtagc catagtggaa gccatgaaga tggagaacga gatccacgct cccataagcg   3300
gtgtagtaga aaaggtcttt gtcaaacccg gagataatgt aacacctgac gatgccctcc   3360
taagaataaa acacatagag gaagaggtca gttacggcta a                     3401
```

<210> SEQ ID NO 40
<211> LENGTH: 472
<212> TYPE: PRT
<213> ORGANISM: Hydrogenobacter thermophilus TK-6

<400> SEQUENCE: 40

Met Phe Lys Lys Val Leu Val Ala Asn Arg Gly Glu Ile Ala Cys Arg
1               5                   10                  15

Val Ile Arg Ala Cys Lys Glu Leu Gly Ile Gln Thr Val Ala Ile Tyr
            20                  25                  30

Asn Glu Ile Glu Ser Thr Ala Arg His Val Lys Met Ala Asp Glu Ala
        35                  40                  45

Tyr Met Ile Gly Val Asn Pro Leu Asp Thr Tyr Leu Asn Ala Glu Arg
    50                  55                  60

```
Ile Val Asp Leu Ala Leu Glu Val Gly Ala Glu Ala Ile His Pro Gly
 65                  70                  75                  80

Tyr Gly Phe Leu Ala Glu Asn Glu His Phe Ala Arg Leu Cys Glu Glu
                 85                  90                  95

Lys Gly Ile Thr Phe Ile Gly Pro His Trp Lys Val Ile Glu Leu Met
            100                 105                 110

Gly Asp Lys Ala Arg Ser Lys Glu Val Met Lys Arg Ala Gly Val Pro
        115                 120                 125

Thr Val Pro Gly Ser Asp Gly Ile Leu Lys Asp Val Glu Glu Ala Lys
    130                 135                 140

Arg Ile Ala Lys Glu Ile Gly Tyr Pro Val Leu Leu Lys Ala Ser Ala
145                 150                 155                 160

Gly Gly Gly Gly Arg Gly Ile Arg Ile Cys Arg Asn Glu Glu Glu Leu
                165                 170                 175

Val Arg Asn Tyr Glu Asn Ala Tyr Asn Glu Ala Val Lys Ala Phe Gly
            180                 185                 190

Arg Gly Asp Leu Leu Leu Glu Lys Tyr Ile Glu Asn Pro Lys His Ile
        195                 200                 205

Glu Phe Gln Val Leu Gly Asp Lys Tyr Gly Asn Val Ile His Leu Gly
210                 215                 220

Glu Arg Asp Cys Ser Ile Gln Arg Arg Asn Gln Lys Leu Val Glu Ile
225                 230                 235                 240

Ala Pro Ser Leu Leu Leu Thr Pro Glu Gln Arg Glu Tyr Tyr Gly Ser
                245                 250                 255

Leu Val Val Lys Ala Ala Lys Glu Ile Gly Tyr Tyr Ser Ala Gly Thr
            260                 265                 270

Met Glu Phe Ile Ala Asp Glu Lys Gly Asn Leu Tyr Phe Ile Glu Met
        275                 280                 285

Asn Thr Arg Ile Gln Val Glu His Pro Val Thr Glu Met Ile Thr Gly
290                 295                 300

Val Asp Ile Val Lys Trp Gln Ile Arg Ile Ala Ala Gly Glu Arg Leu
305                 310                 315                 320

Arg Tyr Ser Gln Glu Asp Ile Arg Phe Asn Gly Tyr Ser Ile Glu Cys
                325                 330                 335

Arg Ile Asn Ala Glu Asp Pro Lys Lys Gly Phe Ala Pro Ser Ile Gly
            340                 345                 350

Thr Ile Glu Arg Tyr Tyr Val Pro Gly Gly Phe Gly Ile Arg Val Glu
        355                 360                 365

His Ala Ser Ser Lys Gly Tyr Glu Ile Thr Pro Tyr Tyr Asp Ser Leu
370                 375                 380

Ile Ala Lys Leu Ile Val Trp Ala Pro Leu Trp Glu Val Ala Val Asp
385                 390                 395                 400

Arg Met Arg Ser Ala Leu Glu Thr Tyr Glu Ile Ser Gly Val Lys Thr
                405                 410                 415

Thr Ile Pro Leu Leu Ile Asn Ile Met Lys Asp Lys Asp Phe Arg Asp
            420                 425                 430

Gly Lys Phe Thr Thr Arg Tyr Leu Glu Glu His Pro His Val Phe Asp
        435                 440                 445

Tyr Ala Glu His Arg Asp Lys Glu Asp Phe Val Ala Phe Ile Ser Ala
    450                 455                 460

Val Ile Ala Ser Tyr His Gly Leu
465                 470
```

<210> SEQ ID NO 41
<211> LENGTH: 652
<212> TYPE: PRT
<213> ORGANISM: Hydrogenobacter thermophilus TK-6

<400> SEQUENCE: 41

Met Gln Ala Val Glu Ile Met Glu Glu Ile Arg Glu Lys Phe Lys Glu
1               5                   10                  15

Phe Glu Lys Gly Gly Phe Arg Lys Lys Ile Leu Ile Thr Asp Leu Thr
            20                  25                  30

Pro Arg Asp Gly Gln Gln Cys Lys Leu Ala Thr Arg Val Arg Thr Asp
        35                  40                  45

Asp Leu Leu Pro Leu Cys Glu Ala Met Asp Lys Val Gly Phe Tyr Ala
    50                  55                  60

Val Glu Val Trp Gly Gly Ala Thr Tyr Asp Val Cys Leu Arg Tyr Leu
65                  70                  75                  80

Lys Glu Asp Pro Trp Glu Arg Leu Arg Arg Ile Lys Glu Val Met Pro
                85                  90                  95

Asn Thr Lys Leu Gln Met Leu Phe Arg Gly Gln Asn Ile Val Gly Tyr
            100                 105                 110

Arg Pro Lys Ser Asp Lys Leu Val Tyr Lys Phe Val Glu Arg Ala Ile
        115                 120                 125

Lys Asn Gly Ile Thr Val Phe Arg Val Phe Asp Ala Leu Asn Asp Asn
    130                 135                 140

Arg Asn Ile Lys Thr Ala Val Lys Ala Ile Lys Glu Leu Gly Gly Glu
145                 150                 155                 160

Ala His Ala Glu Ile Ser Tyr Thr Arg Ser Pro Ile His Thr Tyr Gln
                165                 170                 175

Lys Trp Ile Glu Tyr Ala Leu Glu Ile Ala Glu Met Gly Ala Asp Trp
            180                 185                 190

Leu Ser Phe Lys Asp Ala Thr Gly Ile Ile Ala Pro Val Glu Thr Tyr
        195                 200                 205

Ala Ile Ile Lys Gly Ile Lys Glu Ala Thr Gly Gly Lys Leu Pro Val
    210                 215                 220

Leu Leu His Asn His Asp Met Ser Gly Met Ala Ile Val Asn His Leu
225                 230                 235                 240

Met Ala Val Leu Ala Gly Val Asp Met Leu Asp Thr Val Leu Ser Pro
                245                 250                 255

Leu Ala Phe Gly Ser Ser His Pro Ala Thr Glu Ser Val Val Ala Met
            260                 265                 270

Leu Glu Gly Thr Pro Phe Asp Thr Gly Ile Asp Met Lys Lys Leu Asp
        275                 280                 285

Glu Leu Ala Glu Ile Val Lys Gln Ile Arg Lys Lys Tyr Lys Lys Tyr
    290                 295                 300

Glu Thr Glu Tyr Ala Gly Val Asn Ala Lys Val Leu Ile His Lys Ile
305                 310                 315                 320

Pro Gly Gly Met Ile Ser Asn Met Val Ala Gln Leu Ile Glu Ala Asn
                325                 330                 335

Ala Leu Asp Lys Ile Glu Glu Ala Leu Glu Glu Val Pro Asn Val Glu
            340                 345                 350

Arg Asp Leu Gly His Pro Pro Leu Leu Thr Pro Ser Ser Gln Ile Val
        355                 360                 365

Gly Val Gln Ala Val Leu Asn Val Ile Ser Gly Glu Arg Tyr Lys Val
    370                 375                 380

```
Ile Thr Lys Glu Val Arg Asp Tyr Val Glu Gly Lys Tyr Gly Lys Pro
385                 390                 395                 400

Pro Gly Pro Ile Ser Lys Glu Leu Ala Glu Lys Ile Leu Gly Pro Gly
            405                 410                 415

Lys Glu Pro Asp Phe Ser Ile Arg Ala Ala Asp Leu Ala Asp Pro Asn
        420                 425                 430

Asp Trp Asp Lys Ala Tyr Glu Glu Thr Lys Ala Ile Leu Gly Arg Glu
    435                 440                 445

Pro Thr Asp Glu Glu Val Leu Leu Tyr Ala Leu Phe Pro Met Gln Ala
450                 455                 460

Lys Asp Phe Phe Val Ala Arg Glu Lys Gly Leu His Pro Glu Pro
465                 470                 475                 480

Val Asp Glu Leu Val Glu Thr Thr Glu Val Lys Ala Gly Val Val Pro
            485                 490                 495

Gly Ala Ala Pro Val Glu Phe Glu Ile Val Tyr His Gly Glu Lys Phe
        500                 505                 510

Lys Val Lys Val Glu Gly Val Ser Ala His Gln Glu Pro Gly Lys Pro
    515                 520                 525

Arg Lys Tyr Tyr Ile Arg Val Asp Gly Arg Leu Glu Glu Val Gln Ile
530                 535                 540

Thr Pro His Val Glu Ala Ile Pro Lys Gly Gly Pro Thr Pro Thr Ala
545                 550                 555                 560

Val Gln Ala Glu Glu Lys Gly Ile Pro Lys Ala Thr Gln Pro Gly Asp
            565                 570                 575

Ala Thr Ala Pro Met Pro Gly Arg Val Val Arg Val Leu Val Lys Glu
        580                 585                 590

Gly Asp Lys Val Lys Glu Gly Gln Thr Val Ala Ile Val Glu Ala Met
    595                 600                 605

Lys Met Glu Asn Glu Ile His Ala Pro Ile Ser Gly Val Val Glu Lys
610                 615                 620

Val Phe Val Lys Pro Gly Asp Asn Val Thr Pro Asp Asp Ala Leu Leu
625                 630                 635                 640

Arg Ile Lys His Ile Glu Glu Val Ser Tyr Gly
            645                 650

<210> SEQ ID NO 42
<211> LENGTH: 3401
<212> TYPE: DNA
<213> ORGANISM: Hydrogenobacter thermophilus TK-6

<400> SEQUENCE: 42
atgtttaaga aggttttggt ggcaaataga ggtgagatag cttgcagggt tataagagcg      60
tgtaaagagc tgggtataca gacggttgcc atatacaacg agattgaatc caccgcaagg    120
catgtaaaga tggcggacga agcctacatg ataggtgtaa atcctctgga tacctacctg    180
aacgcagaaa ggatagtgga cctggctctt gaggtggggg ctgaggctat acatcccggt    240
tatggctttc tggcggagaa cgagcacttt gccagattgt gcgaagagaa gggcataacc    300
ttcataggtc cccactggaa ggtcatagag cttatgggag acaaagccag gtcaaaggag    360
gttatgaaaa gggcgggcgt cccaacagtc cctggaagcg acggcatact gaaagatgta    420
gaagaagcca aacgcatagc caaagagata ggctatcctg tgcttttaaa ggcttctgcg    480
ggaggtggag gaagggggtat aaggatatgc aggaacgagg aggagctggt aagaaactac    540
gagaacgctt acaacgaggc ggtcaaagcc ttcggcaggg gggacctgct tctggaaaag    600
```

| | |
|---|---|
| tacatagaaa accccaagca cattgagttt caggttttgg gagataagta cggaaatgtt | 660 |
| atacacctgg gagaaagaga ctgttccata cagagaagaa accaaaaact tgtagagatt | 720 |
| gccccatcgc tccttcttac acctgagcaa agagagtatt acggctctct tgtggtaaaa | 780 |
| gcagcaaagg agataggtta ttacagcgct ggaactatgg agtttatagc cgacgaaaag | 840 |
| ggcaacctgt acttcatcga gatgaacacc cgcattcagg tggagcatcc ggtaactgag | 900 |
| atgatcacag gtgttgacat agtaaagtgg caaatcagga tagcggcagg agaaaggtta | 960 |
| aggtactctc aggaagacat aaggttcaac ggctactcca tagagtgcag gataaacgcg | 1020 |
| gaagatccca agaaaggctt tgccccagc ataggcacca tagagagata ctatgtgccc | 1080 |
| ggaggatttg gcataagggt tgaacatgcc tcatcaaagg gttacgagat cactccctat | 1140 |
| tacgactccc tcatagccaa gctcatcgtg tgggctcctc tctgggaggt tgccgttgac | 1200 |
| agaatgaggt ccgctcttga aacctatgag atctccggtg tcaaaaccac cataccgctc | 1260 |
| cttataaaca tcatgaagga caaagacttc agagatggta aatttaccac aaggtacctg | 1320 |
| gaggagcatc cccatgtttt tgattacgct gaacacagag acaaagagga ctttgtagct | 1380 |
| tttatatccg cagtaatagc cagttatcat gggctttgat aaaaactctg gaggtgtagt | 1440 |
| acatgcaagc agttgagatt atggaagaga taagagaaaa gttcaaagag tttgaaaagg | 1500 |
| gaggctttag gaagaaaata ctcataacag accttacgcc cagggacgga cagcagtgca | 1560 |
| aactggcaac tcgggtcaga acagatgacc ttttgcccct ctgtgaggct atggacaagg | 1620 |
| tggggttcta tgcagttgag gtgtggggag gtgccaccta tgatgtgtgc ctcagatacc | 1680 |
| tcaaagaaga cccgtgggag agactgaggc gcataaagga agtgatgccc aacactaagc | 1740 |
| tccagatgct ctttagaggt caaaacatag tgggatacag acccaagtcc gataagctgg | 1800 |
| tttataagtt tgtggagaga gcaataaaaa acggtataac cgttttcaga gtgtttgacg | 1860 |
| ctctcaatga caacaggaac ataaagaccg ctgtaaaagc cataaaggag ctgggtggtg | 1920 |
| aggcacatgc cgagataagc tatacaagaa gtcctataca cacctaccaa aagtggatag | 1980 |
| agtacgctct tgaaatagcg gagatggggtg cggactggct gtcttttaag gatgccacgg | 2040 |
| gtataattgc gcccgtcgaa acttacgcca taataaaggg tataaaggaa gccacaggtg | 2100 |
| gaaaacttcc ggtgctactt cacaaccacg acatgagcgg aatggccata gtcaatcacc | 2160 |
| tgatggctgt gctggctggt gtggacatgc tggatactgt tctctcaccg cttgcctttg | 2220 |
| gctcttctca ccctgcgacg gaatccgtgg ttgccatgct tgaaggaaca ccctttgata | 2280 |
| caggcataga catgaagaag ttggacgaac ttgctgagat agtaaagcaa ataaggaaga | 2340 |
| agtacaaaaa gtatgagacg gagtatgctg gtgtaaatgc caaagtgctc atccacaaga | 2400 |
| tacccggcgg tatgatatcc aacatggtgg cacagctcat agaggcaaat gctttggata | 2460 |
| aaatagagga agctctcgaa gaggtaccaa atgtggaaag ggacctgggg catccaccac | 2520 |
| ttctgacacc ttcttcacag atagtgggtg ttcaggcggt tctcaatgtg atatccggtg | 2580 |
| agcgatacaa ggttataacc aaagaggtaa gagactatgt ggaaggcaag tatggaaagc | 2640 |
| cacccggtcc catatctaag gagctggctg agaagatcct cggtcctgga aaggaacccg | 2700 |
| acttctccat aagagctgca gacctggcag accccaacga ctgggataag gcttatgaag | 2760 |
| agacaaaagc tatacttgga agagagccta cagatgagga ggtgctcctt tatgctctct | 2820 |
| tccccatgca ggcaaaggac ttttttgtag ccagagagaa gggagaactt catcctgagc | 2880 |
| cagttgatga gcttgttgaa acaactgaag taaaggcagg tgttgttcca ggtgcagcac | 2940 |

```
ctgttgagtt tgaaatcgtc tatcacggtg agaagttcaa agtaaaagtg aaggtgtga      3000 gcgctcatca ggagcccgga aagcccagaa agtactacat aagggtggac gggaggctgg      3060
aagaggtgca gataacgccc catgtggaag ctataccaaa aggaggaccc actccaacgg      3120
cagtacaagc cgaagagaaa ggcataccta aagctaccca gccaggtgat gctactgctc      3180
ctatgccggg aagggtcgtg agggttttgg taaaggaagg tgataaagta aagaaggtc       3240 aaacggtagc catagtggaa gccatgaaga tggagaacga gatccacgct cccataagcg      3300
gtgtagtaga aaggtctttt gtcaaacccg gagataatgt aacacctgac gatgccctcc      3360
taagaataaa acacatagag gaagaggtca gttacggctg a                          3401
```

<210> SEQ ID NO 43
<211> LENGTH: 472
<212> TYPE: PRT
<213> ORGANISM: Thiocystis violascens DSM198

<400> SEQUENCE: 43

```
Met Leu Arg Lys Ile Leu Ile Ala Asn Arg Gly Glu Ile Ala Val Arg
1               5                   10                  15

Val Ile Arg Ala Cys Ala Glu Met Gly Ile Arg Ser Ala Ala Ile Tyr
            20                  25                  30

Ala Glu Ala Asp Arg His Ser Leu His Val Lys Lys Ala Asp Glu Ala
        35                  40                  45

Tyr Ser Leu Gly Ser Asp Pro Leu Ala Gly Tyr Leu Asn Val His Asn
    50                  55                  60

Ile Val Asn Leu Ala Leu Ser Thr Gly Cys Asp Ala Val His Pro Gly
65                  70                  75                  80

Tyr Gly Phe Leu Ser Glu Asn Pro Glu Leu Ala Arg Ala Cys Ala Arg
                85                  90                  95

Arg Gly Leu Thr Phe Ile Gly Pro Thr Ala Glu Val Ile Ala Arg Met
            100                 105                 110

Gly Asp Lys Thr Glu Ala Arg Leu Ala Met Gln Lys Ala Gly Val Pro
        115                 120                 125

Val Thr Pro Gly Ser Pro Gly Asn Leu Glu Ser Leu Asp Ala Ala Leu
    130                 135                 140

Arg Phe Ala Asp Glu Ile Gly Tyr Pro Ile Met Leu Lys Ala Thr Ser
145                 150                 155                 160

Gly Gly Gly Gly Arg Gly Ile Arg Arg Cys Asp Ala His Ala Leu
                165                 170                 175

Arg Asn Asn Tyr Glu Arg Val Ile Ser Glu Ala Thr Lys Ala Phe Gly
            180                 185                 190

Arg Ala Glu Val Phe Leu Glu Lys Cys Val Val Asn Pro Lys His Ile
        195                 200                 205

Glu Val Gln Ile Leu Gly Asp His His Gly Asn Cys Val His Leu Tyr
    210                 215                 220

Glu Arg Asp Cys Ser Ile Gln Arg Arg Asn Gln Lys Leu Ile Glu Ile
225                 230                 235                 240

Ala Pro Ser Pro Gln Leu Asp Glu Ala Glu Arg Gln Tyr Val Gly Gly
                245                 250                 255

Leu Ala Val Leu Ala Ala Arg Ala Val Gly Tyr Thr Asn Ala Gly Thr
            260                 265                 270

Ile Glu Phe Leu Arg Asp Ser Asp Gly Arg Phe Tyr Phe Met Glu Met
        275                 280                 285

Asn Thr Arg Ile Gln Val Glu His Thr Ile Thr Glu Thr Ile Thr Gly
```

-continued

```
    290                 295                 300

Val Asp Leu Val Glu Glu Gln Ile Arg Ile Ala Ala Gly Leu Pro Leu
305                 310                 315                 320

Arg Phe Lys Gln His Glu Ile Gln Arg Arg Gly Phe Ala Met Gln Phe
                325                 330                 335

Arg Val Asn Ala Glu Asp Pro Lys Asn Asn Phe Leu Pro Ser Phe Gly
            340                 345                 350

Arg Ile Ser Arg Tyr Tyr Ala Pro Gly Gly Pro Gly Val Arg Thr Asp
        355                 360                 365

Gly Ala Ile Tyr Thr Gly Tyr Thr Val Pro Pro His Tyr Asp Ser Met
    370                 375                 380

Leu Ala Lys Val Ile Val Trp Ala Leu Asn Trp Glu Asp Val Val Asn
385                 390                 395                 400

Arg Gly His Arg Ala Leu Arg Asp Ile Gly Val Tyr Gly Val Lys Thr
                405                 410                 415

Thr Ile Pro Phe Tyr Gln Glu Ile Leu Arg His Pro Asp Phe Arg Ser
            420                 425                 430

Gly Ser Phe Asp Thr Ser Phe Leu Glu Thr His Pro Glu Leu Leu Asp
        435                 440                 445

Tyr Ser Thr Lys Arg Arg Arg Glu Asp Val Ala Ala Val Leu Ala Ala
    450                 455                 460

Ala Ile Ala Ala His Ala Gly Leu
465                 470

<210> SEQ ID NO 44
<211> LENGTH: 609
<212> TYPE: PRT
<213> ORGANISM: Thiocystis violascens DSM198

<400> SEQUENCE: 44

Met Pro Lys Ile Asn Ile Thr Asp Val Val Leu Arg Asp Ala His Gln
1               5                   10                  15

Ser Leu Leu Ala Thr Arg Met Arg Thr Glu Asp Met Leu Pro Ile Cys
            20                  25                  30

Pro Lys Leu Asp Ala Ile Gly Tyr Trp Ser Leu Glu Cys Trp Gly Gly
        35                  40                  45

Ala Thr Phe Asp Ala Cys Val Arg Phe Leu Lys Glu Asp Pro Trp Glu
    50                  55                  60

Arg Leu Arg Lys Leu Arg Glu Ala Leu Pro Asn Thr Arg Leu Gln Met
65                  70                  75                  80

Leu Leu Arg Gly Gln Asn Leu Leu Gly Tyr Arg His Tyr Ser Asp Asp
                85                  90                  95

Val Val Arg Ala Phe Val Ala Arg Ala Ala Gln Asn Gly Met Asp Val
            100                 105                 110

Phe Arg Ile Phe Asp Ala Leu Asn Asp Pro Arg Asn Leu Lys Thr Ala
        115                 120                 125

Ile Glu Ala Thr Lys Ala Ala Gly Lys His Ala Gln Gly Thr Ile Cys
    130                 135                 140

Tyr Thr Val Ser Pro Val His Thr Val Ala Gly Phe Val Gln Leu Gly
145                 150                 155                 160

Lys Glu Leu Ala Ala Met Gly Cys Asp Ser Ile Ala Ile Lys Asp Met
                165                 170                 175

Ala Gly Leu Leu Thr Pro Tyr Val Thr Ala Glu Leu Val Lys Ala Leu
            180                 185                 190
```

```
Lys Asp Ser Val Asp Leu Pro Leu His Leu His Ser His Ala Thr Ser
    195                 200                 205

Gly Leu Ala Asp Met Cys His Leu Lys Ala Ile Glu Asn Gly Cys Asp
210                 215                 220

Thr Leu Asp Thr Ala Ile Ser Ser Met Ala Gly Gly Thr Ser His Pro
225                 230                 235                 240

Pro Thr Glu Ser Leu Val Ala Ala Leu Arg Gly Thr Asp Tyr Asp Thr
            245                 250                 255

Gly Leu Asp Leu Glu Ala Ile Gln Glu Val Gly Met Tyr Phe Tyr Gln
        260                 265                 270

Ile Arg Lys Lys Tyr His Gln Phe Glu Ser Asp Phe Thr Gly Val Asp
    275                 280                 285

Thr Arg Val Gln Val Asn Gln Val Pro Gly Gly Met Ile Ser Asn Leu
    290                 295                 300

Ala Asn Gln Leu Lys Glu Gln Asn Ser Leu Glu Arg Met Asn Ala Val
305                 310                 315                 320

Leu Glu Glu Ile Pro Arg Val Arg Met Asp Leu Gly Tyr Pro Pro Leu
                325                 330                 335

Val Thr Pro Thr Ser Gln Ile Val Gly Thr Gln Ala Val Leu Asn Val
            340                 345                 350

Leu Thr Asp Lys Arg Tyr Gln Thr Ile Thr Asn Glu Val Lys Leu Tyr
        355                 360                 365

Leu Gln Gly Arg Tyr Gly Arg Ala Pro Gly Ala Ile Asn Pro Thr Leu
    370                 375                 380

Gln Gln Gln Ala Ile Gly Asn Glu Asp Leu Ile Asp Cys Arg Pro Ala
385                 390                 395                 400

Asp Leu Leu Thr Pro Glu Met Glu Arg Leu Arg His Asp Ile Gly Glu
                405                 410                 415

Leu Ala Ile Ser Glu Glu Asp Ala Leu Thr Tyr Ala Met Phe Pro Glu
            420                 425                 430

Ile Gly Arg Ala Phe Leu Glu His Arg Ala Ala Gly Thr Leu His Pro
        435                 440                 445

Glu Pro Leu Glu Pro Leu Pro Ser Gly Ala Gly Pro Arg Thr Ala Pro
450                 455                 460

Thr Glu Phe Asn Ile Ala Val His Gly Glu Thr Tyr His Val Lys Val
465                 470                 475                 480

Thr Gly Thr Gly His Lys Ser Gln Asp Glu Arg His Phe Tyr Phe Ala
                485                 490                 495

Ile Asp Gly Ile Pro Glu Glu Val Val Glu Thr Leu Asp Glu Leu
            500                 505                 510

Val Leu Thr Gly Gly Ala Gln Gly Ala Val Lys Lys Ala Ile Ala Gly
        515                 520                 525

Lys Arg Pro Lys Pro Thr Gln Pro Gly His Val Ala Thr Ser Met Pro
530                 535                 540

Gly Asn Ile Val Asp Val Leu Lys Glu Gly Asp Thr Val Ala Ala
545                 550                 555                 560

Gly Gln Pro Val Leu Ile Thr Glu Ala Met Lys Met Glu Thr Glu Ile
                565                 570                 575

Gln Ala Pro Ile Ala Gly Thr Val Thr Ala Met Phe Val Ile Lys Gly
            580                 585                 590

Asp Ala Val Asn Pro Asp Glu Val Leu Leu Glu Ile Thr Pro Ala Glu
        595                 600                 605

Arg
```

<210> SEQ ID NO 45
<211> LENGTH: 3272
<212> TYPE: DNA
<213> ORGANISM: Thiocystis violascens DSM198

<400> SEQUENCE: 45

| | | | | | |
|---|---|---|---|---|---|
| atgcttcgaa | agattctgat | cgcgaaccgc | ggcgagattg | cggtccgtgt | catccgcgcc | 60 |
| tgtgccgaga | tggggatccg | ctcggcggcc | atctatgccg | aggccgaccg | tcattcgctc | 120 |
| catgtcaaaa | aggccgacga | agcctatagc | ctgggcagcg | atccgctggc | gggctatctc | 180 |
| aatgtccaca | acatcgtcaa | cctggccctg | tcgaccggtt | gcgatgccgt | gcatcccggc | 240 |
| tacggttttc | tgtccgaaaa | cccggaactg | gcgcgcgcct | gcgcgcgacg | cggactgacc | 300 |
| ttcatcggcc | cgaccgccga | ggtgatcgcc | cgcatgggcg | acaagaccga | ggcgcggctc | 360 |
| gcgatgcaga | aggccggtgt | tccggtgacg | cccggcagcc | ccggcaacct | ggagagcctg | 420 |
| gacgcggccc | tgcgcttcgc | cgacgagatc | ggctatccga | tcatgctcaa | ggcgacctcc | 480 |
| ggcggcggcg | ggcgcggcat | ccggcgctgt | gacgatgccc | atgcgctgcg | caataactac | 540 |
| gagcgcgtca | tctccgaagc | caccaaggcg | tttggtcgcg | ccgaggtctt | cctggaaaag | 600 |
| tgcgtggtca | atcccaaaca | catcgaagtt | cagatcttgg | gcgatcatca | tggcaactgc | 660 |
| gtgcatctct | acgagcgcga | ttgctcgatc | cagcgacgca | atcagaagct | gatcgagatc | 720 |
| gccccctcgc | cgcagctcga | cgaggccgaa | cgccagtatg | tcggcggcct | ggcggtgctg | 780 |
| gcggcgcgcg | ctgtcggtta | caccaatgcc | ggcaccatcg | agtttctgcg | cgattcggac | 840 |
| gggcgtttct | atttcatgga | tgaacacacc | cgcatccagg | tcgagcacac | catcaccgag | 900 |
| accatcaccg | gggtcgatct | ggtggaggaa | cagatccgca | ttgccgccgg | gctgccgctg | 960 |
| cgtttcaagc | agcacgagat | ccaacggcgc | ggcttcgcca | tgcagttccg | cgtcaatgcc | 1020 |
| gaggatccca | gaacaatttt | cctgccgagc | ttcgggcgca | tctcgcgcta | ttacgccccc | 1080 |
| ggcggtccgg | gcgtgcgtac | cgatggggcg | atctacaccg | gctacggt | tccgccgcat | 1140 |
| tatgattcca | tgctggccaa | ggtgatcgtc | tgggcgctga | actgggagga | tgtcgtcaat | 1200 |
| cgcggccatc | gcgcgctgcg | cgacatcggc | gtctatggcg | tcaagaccac | catcccccttc | 1260 |
| tatcaggaga | tcctgcgtca | ccccgatttt | cgctctggat | ccttcgatac | cagttttctg | 1320 |
| gagacgcatc | ccgagttgct | ggactattcc | accaaacgtc | gccgcgagga | tgtcgccgcc | 1380 |
| gtgctggcag | cggcgatcgc | ggcgcatgcc | ggtttgtaat | aaaaactctg | gaggtgtagt | 1440 |
| acatgccaaa | gatcaacatt | accgacgttg | tcctgcgcga | cgcccaccag | tcgctgctcg | 1500 |
| cgacgcgcat | gcgcaccgag | gacatgctgc | cgatctgtcc | caagctggac | gccatcggct | 1560 |
| actggtcgct | ggaatgctgg | ggcggcgcga | ccttcgatgc | ctgcgtgcgc | ttcctgaagg | 1620 |
| aagatccctg | ggagcgtctg | cgcaagctgc | gcgaggcgct | gccgaacact | cgcctgcaga | 1680 |
| tgctgctgcg | cggccagaat | ctgcttggct | accgtcatta | ttccgatgac | gtggtacgcg | 1740 |
| ccttcgtggc | ccgtgctgcc | cagaacggca | tggatgtgtt | ccgcatttttc | gatgcactca | 1800 |
| acgatccgcg | caatctcaag | acggcgatcg | aggccaccaa | ggccgccggc | aagcatgccc | 1860 |
| aaggcaccat | ctgctacacg | gtcagtccgg | ttcacaccgt | ggccggtttc | gtccagttgg | 1920 |
| ggaaggaact | ggcggccatg | ggctgcgact | ccatcgccat | caaggacatg | gcgggtctgc | 1980 |
| tgacgcccta | tgtcacggcc | gagctggtga | aggcgctgaa | ggatagcgtc | gacctgccgc | 2040 |
| tgcatctgca | ctcgcacgcc | acctcaggtc | tggccgatat | gtgccatctg | aaggccatcg | 2100 |

```
agaacggctg tgatacccctg ataccgcca tttcatcgat ggctggcggc acctcgcacc    2160
cgcccaccga gagtctggtc gccgcattgc gcggcaccga ctacgacacc ggcctggacc    2220
tggaggcgat ccaggaagtc gggatgtatt tctatcagat ccgcaagaag taccaccagt    2280
tcgagagcga cttcaccggc gtggacaccc gggtccaggt caatcaagtg cccggcggca    2340
tgatctccaa tctggccaac cagttgaagg aacagaattc gctggagcgc atgaacgcgg    2400
tgctcgaaga gattccgcga gtacgcatgg atctcggcta tccccgctg gtgacgccaa    2460 cctcgcagat cgtcggcacc caggcggtgc tcaacgtcct gaccgacaag cgctaccaga    2520
ccatcaccaa cgaggtgaag ctctatctgc aggggcgcta cggacgcgcg ccgggcgcga    2580
ttaacccgac ccttcagcag caggccatcg gcaacgagga cctgatcgac tgccgcccgg    2640
ccgacctgct gacaccggag atggagcgac tccgccacga tatcggcgaa ctcgcaatct    2700
ccgaggaaga cgccctcacg tatgccatgt cccggagat cgggcgcgct tcctggaac    2760 atcgcgccgc cggcaccctg catccggaac cgctggagcc gctacccagc ggcgctggcc    2820
cccgcaccgc gcccaccgag ttcaatatcg ccgtccatgg cgagacctat cacgtcaaag    2880
tgacaggcac gggacataag agtcaggacg aacgtcattt ctatttcgcc atcgatggca    2940 tccccggaaga ggtggtggtc gagacgctcg acgaactggt gctgacgggc ggcgcccagg    3000
gcgcggtcaa gaaagccatc gccggcaagc gtcccaagcc cactcagccc ggccatgtcg    3060
ccacctcgat gcccggcaac atcgtcgacg tgctggtgaa ggaaggcgat acggtggcgg    3120
ccggtcagcc ggtgctgatc accgaggcga tgaagatgga gaccgagatt caggcgccca    3180
tcgccgggac ggtcaccgcc atgttcgtca tcaaggcga tgcggtgaat ccggatgagg    3240
tgttgctgga gatcacgccg gctgagcgtt aa                                3272
```

<210> SEQ ID NO 46
<211> LENGTH: 472
<212> TYPE: PRT
<213> ORGANISM: Mariprofundus ferrooxydans PV-1

<400> SEQUENCE: 46

```
Met Phe Lys Arg Ile Leu Val Ala Asn Arg Gly Glu Cys Ala Ile Arg
1               5                   10                  15

Ile Ile Arg Ser Cys Arg Glu Leu Gly Ile Glu Ser Val Ala Ile Tyr
            20                  25                  30

Ser Glu Ala Asp Ala His Ala Leu His Val Lys Lys Ala Asp Arg Ala
        35                  40                  45

Val Met Ile Gly Pro Asp Pro Val Lys Ser Tyr Leu Asn Ile His Arg
    50                  55                  60

Ile Val Gly Val Ala Leu Asp Ser Gly Cys Asp Ala Val His Pro Gly
65                  70                  75                  80

Tyr Gly Phe Leu Ser Glu Asn Asp Glu Phe Ala Arg Ala Ile Ile Asp
                85                  90                  95

Ala Gly Leu Thr Tyr Ile Gly Pro Ser Pro Asp Ala Ile Arg Asp Met
            100                 105                 110

Gly Ser Lys Thr Lys Ala Arg Glu Ser Met Ile Ala Ala Gly Val Pro
        115                 120                 125

Val Ile Pro Gly Ser Asp Gly Ala Leu Asn Asn Val Asp Glu Ala Leu
    130                 135                 140

Glu Leu Ala His Lys Met Gly Tyr Pro Val Met Leu Lys Ala Ala Ala
145                 150                 155                 160

Gly Gly Gly Gly Arg Gly Ile Arg Arg Cys Asp Ser Asp Ala Gln Leu
```

```
                165                 170                 175
Arg Glu Asn Tyr Val Val Thr Gln Arg Glu Ala Met Ala Ala Phe Gly
            180                 185                 190

Ser Asp Ile Leu Phe Met Glu Lys Cys Ile Val Glu Pro His His Ile
        195                 200                 205

Glu Phe Gln Val Leu Ala Asp Ser His Gly Asn Thr Val His Leu Phe
    210                 215                 220

Glu Arg Asp Cys Ser Ile Gln Arg Arg Asn Gln Lys Leu Ile Glu Ile
225                 230                 235                 240

Ala Pro Ser Asn Phe Leu Thr Pro Lys Leu Arg Glu Ser Met Gly Ala
                245                 250                 255

Ile Ala Val Lys Ala Ala Gln Ala Val Gly Tyr Val Asn Ala Gly Thr
            260                 265                 270

Val Glu Phe Leu Val Asp Lys Asp Arg Asn Phe Trp Phe Met Glu Met
        275                 280                 285

Asn Thr Arg Leu Gln Val Glu His Thr Ile Thr Glu Thr Ile Thr Gly
    290                 295                 300

Val Asp Ile Val Ala Gln Gln Ile Ser Ile Ala Ala Gly Glu Ala Leu
305                 310                 315                 320

Pro Phe Thr Gln Ala Asp Leu Ser Phe Arg Gly Phe Ala Ile Glu Phe
                325                 330                 335

Arg Ile Asn Ala Glu Asp Pro Lys Asn Asn Phe Leu Pro Met Pro Gly
            340                 345                 350

Arg Ile Thr Arg Tyr Ile Ser Pro Gly Gly Met Gly Val Arg Val Asp
        355                 360                 365

Gly Cys Val Tyr Ala Gly Tyr Glu Ile Pro Pro Tyr Tyr Asp Ser Met
    370                 375                 380

Cys Ala Lys Leu Thr Val Ser Gly Leu Asn Trp His Asn Thr Val Met
385                 390                 395                 400

Arg Ala Gln Arg Ala Leu Gly Glu Tyr Asp Ile Arg Gly Met Lys Thr
                405                 410                 415

Thr Leu Pro Phe Tyr Arg Thr Ile Ala Ser Ser Glu Val Phe Met Gln
            420                 425                 430

Gly Glu Phe Asn Thr Gly Phe Met Asp Gln His Pro Glu Leu Leu Asp
        435                 440                 445

Tyr Asn Asp Asn Glu Arg Arg Glu Asp Ile Ala Ala Val Ala Met
    450                 455                 460

Ala Ile Ala Val His Ala Gly Leu
465                 470

<210> SEQ ID NO 47
<211> LENGTH: 617
<212> TYPE: PRT
<213> ORGANISM: Mariprofundus ferrooxydans PV-1

<400> SEQUENCE: 47

Met Thr Asp Thr Lys Lys Lys Leu Ala Ile Thr Glu Leu Ala Leu Arg
1               5                   10                  15

Asp Gly His Gln Ser Leu Leu Ala Thr Arg Met Arg Leu Asp Asp Met
            20                  25                  30

Leu Pro Ile Cys Glu Lys Leu Asp Thr Ile Gly Tyr Trp Ser Ile Glu
        35                  40                  45

Ala Trp Gly Gly Ala Thr Phe Asp Thr Cys Leu Arg Tyr Leu Lys Glu
    50                  55                  60
```

```
Gly Pro Trp Val Arg Leu Arg Glu Leu Asn Lys Ala Leu Pro Asn Thr
 65                  70                  75                  80

Pro Ile Gln Met Leu Leu Arg Gly Gln Asn Leu Leu Gly Tyr Arg His
                 85                  90                  95

Tyr Ala Asp Asp Val Val Lys Lys Phe Val Asp Met Ala Ala Ala Asn
            100                 105                 110

Gly Val Asp Val Phe Arg Val Phe Asp Ala Met Asn Asp Leu Arg Asn
        115                 120                 125

Val Arg Thr Ala Val Asn Gln Val Lys Ala Asn Asp Lys His Ala Glu
    130                 135                 140

Gly Thr Ile Cys Tyr Thr Thr Ser Pro Val His Thr Leu Glu Tyr Phe
145                 150                 155                 160

Ile Asp Leu Gly Lys Gly Phe Glu Asp Met Gly Cys Asp Thr Leu Ala
                165                 170                 175

Ile Lys Asp Met Ala Gly Leu Leu Thr Pro Thr Ala Thr Arg Glu Leu
            180                 185                 190

Ile Leu Ala Leu Lys Gln Ser Val Ser Ile Pro Leu His Leu His Ser
        195                 200                 205

His Ala Thr Ala Gly Val Ala Glu Met Val Gln Trp Glu Ala Val His
    210                 215                 220

Ala Gly Cys Asp Ile Ile Asp Thr Ala Ile Ser Pro Leu Ala Gly Gly
225                 230                 235                 240

Thr Ser His Pro Pro Thr Glu Ala Met Val Ala Ala Phe Ala Gly Thr
                245                 250                 255

Glu Tyr Asp Thr Gly Leu Asn Leu Val Ala Leu Gln Glu Ile Ala Ala
            260                 265                 270

Tyr Phe Lys Glu Val Arg Lys Lys Tyr Ala Arg Phe Glu Ser Asp Ser
        275                 280                 285

Thr Gly Val Asp Thr Arg Val Phe Val Asn Gln Ile Pro Gly Gly Met
    290                 295                 300

Ile Ser Asn Leu Ala Asn Gln Leu Arg Asp Gln Gly Ala Gln Asp Lys
305                 310                 315                 320

Met Asp Ala Val Leu Asp Glu Ile Pro Arg Val Arg Lys Asp Phe Gly
                325                 330                 335

Tyr Pro Pro Leu Val Thr Pro Thr Ser Gln Ile Val Gly Thr Gln Ala
            340                 345                 350

Val Leu Asn Val Met Ser Gly Lys Lys Tyr Lys Val Ile Thr Asn Glu
        355                 360                 365

Thr Arg Asp Tyr Leu Lys Gly Leu Tyr Gly Arg Ala Leu Gly Glu Ile
    370                 375                 380

Asn Glu Glu Val Arg Lys Leu Ala Ile Gly Asp Glu Glu Pro Ile Asp
385                 390                 395                 400

Ile Arg Pro Ala Asp Leu Leu Val Pro Glu Leu Asp Ala Leu Thr Arg
                405                 410                 415

Glu Val Gly Asp Arg Ala Thr Ser Val Glu Asp Val Leu Ser Tyr Ala
            420                 425                 430

Leu Phe Pro Thr Ile Ala Leu Glu Phe Phe Glu Glu Arg Ala Ser Gly
        435                 440                 445

Gln Phe Lys Pro Glu Ser Leu Asp Thr Pro Leu Glu Ala Ser Ser Thr
    450                 455                 460

Pro Glu Val Val Thr Ala Pro Ser Leu Ala Pro Thr Glu Phe Asn Ile
465                 470                 475                 480

Ile Ile His Gly Glu Glu Tyr His Ile Lys Ile Glu Gly Ser Gly His
```

```
                485                 490                 495
Lys Ser Asp Asp Val Arg Pro Phe Tyr Val Lys Val Asp Asn Val Leu
            500                 505                 510

Glu Glu Val Thr Val Glu Thr Leu Thr Glu Val Val Pro Thr His Asn
            515                 520                 525

Gly Asn Phe Asp Val Ser Lys Ala Ser Lys Gly Ser Arg Arg Pro Lys
            530                 535                 540

Ala Thr Ser Asp Ser Asp Val Thr Thr Ala Met Pro Gly Arg Ile Val
545                 550                 555                 560

Ala Ile Asn Val Ala Ile Gly Asp Gln Val Glu Ala Gly Thr Thr Val
                565                 570                 575

Leu Thr Val Glu Ala Met Lys Met Glu Asn Gln Val His Ala Pro Val
            580                 585                 590

Ser Gly Thr Val Thr Ala Ile Asn Val Ala Val Gly Asp Ser Val Asn
            595                 600                 605

Pro Asp Glu Cys Leu Met Gln Ile Asp
            610                 615

<210> SEQ ID NO 48
<211> LENGTH: 3362
<212> TYPE: DNA
<213> ORGANISM: Mariprofundus ferrooxydans PV-1

<400> SEQUENCE: 48
atgtttaaac gtattctggt agccaaccgt ggtgagtgtg ccattcgaat tatccgttca       60
tgtcgtgagc tgggtatcga atcggttgcc atctattctg aagctgatgc ccatgccctg      120
catgtgaaaa aagccgatcg cgctgtgatg atcggtcctg atccggtcaa gagctatctg      180
aacattcaca ggatagtcgg cgtcgcactg gactccggtt gcgatgctgt acatccgggc      240
tacggcttcc tctctgaaaa cgatgaattt gcgcgggcga ttatcgatgc aggactgacc      300
tatatcggcc cctcccccga cgcaatccgt gatatgggta gcaagaccaa ggcacgcgaa      360
tcgatgattg ccgccggcgt tccggtgatt cccggttcgg acggagctct caacaatgtc      420
gatgaggcgc tggagctggc gcataaaatg ggttacccgg tcatgctcaa ggcggcggcc      480
ggcggcggcg gacgcggcat tcgtcgctgc gacagcgatg ctcaactgcg cgaaaattat      540
gtcgtaaccc agcgcgaagc gatggctgca ttcggctccg atatcctgtt catgaaaaaa      600
tgcattgtcg aaccgcatca tattgaattc caggttctgg ccgacagtca tggcaatacc      660
gtgcacctgt ttgaacgcga ctgctcaatt cagcgacgta accagaagct gatcgaaatt      720
gccccgagca actttctcac ccccaagctg cgtgagagca tgggcgccat tgcggtcaag      780
gcagctcagg ctgtgggcta tgtcaatgcc ggtaccgtcg aatttctggt cgacaaggac      840
agaaacttct ggttcatgga gatgaacacc cgcctgcagg tggagcatac catcaccgaa      900
accattaccg cgtcgatat tgtcgcccag cagatctcga ttgcagcagg tgaagccctt      960
cccttcacgc aggcggatct gagcttccgt ggctttgcca tcgagtttcg catcaatgcc     1020
gaagatccga aaacaacttt cctgccgatg cccggtcgta ttacccgcta tatatctccc     1080
ggcggcatgg tgtgcgcgt ggatggctgc gtctatgccg gctacgaaat cccgccctac     1140
tacgattcga tgtgtgccaa actgacggta tccggtctga actggcataa caccgtcatg     1200
cgggcccagc gtgcactcgg cgaatacgat attcgcggca tgaaaaccac gctaccgttt     1260
taccgtacta tcgcctcatc ggaagtgttc atgcagggtg aattcaacac cggctttatg     1320
gatcagcatc cggagctgct ggattacaac gataatgagc ggcgtgaaga tatcgctgct     1380
```

```
gcggtggcga tggccatcgc cgtgcatgcc ggcctgtaat cgggtcggga aggttaacgt   1440
cgctggcacg cccgtgtgcc aacatgcgga taagcaaaca caacatcgcg taaaaaaggt   1500
atagagatat gactgacaca agaaaaaaac tggcaattac cgaactggct ctgcgtgacg   1560
gacatcagtc gctgctggct acgcgtatgc ggctcgacga catgctgccg atttgcgaga   1620
agctcgatac tatcggctac tggtcgattg aagcgtgggg cggcgcgacc ttcgatacct   1680
gcctgcgcta cctgaaagag ggtccgtggg tacgcttgcg tgagctgaac aaggcgctgc   1740
cgaacacacc catccagatg ctgctgcgcg ccagaacct  gcttggctac cgtcattatg   1800
ccgacgatgt ggtgaagaag tttgtcgata tggctgccgc caacggcgtt gacgtattcc   1860
gtgtattcga tgcaatgaat gacctgcgca atgtgcgtac ggccgtgaat caggtcaaag   1920
ccaacgacaa gcacgccgag ggcaccatct gctacaccac cagcccggta catacgctgg   1980
aatactttat cgatctgggt aagggcttcg aagatatggg ctgcgacacg ctggcgatca   2040
aggatatggc gggactgctt acgccgacgg ctacgcgtga actgatcctg ccctgaaac   2100 agtctgtctc catcccgctg catctgcact cccacgcaac agcggcgtg  ccgagatgg   2160 tacagtggga agcggtgcat gccggttgcg acatcatcga taccgccatc agcccgctgg   2220
ccggcggcac cagccatcca ccgacagaag ccatggtcgc ggccttgcc  ggtactgaat   2280 acgacacagg tctgaatctg gtagcgttgc aggaaatcgc cgcctacttc aaggaagtgc   2340
gtaaaaaata tgcccgtttt gaatccgatt caaccggcgt ggacacccgc gtattcgtca   2400
accagatccc tggcggcatg atctccaatc tggccaatca gctacgtgat cagggcgcac   2460
aggataagat ggacgccgtg ctcgatgaaa ttccacgcgt ccgcaaggat ttcggctacc   2520
cgccactggt cacaccaacc agccagattg tcggcaccca ggccgtgctc aatgtcatgt   2580
ccggcaagaa atacaaggtc attaccaacg agacgcgcga ctacctgaaa ggcttgtatg   2640
gccgtgcact cggcgaaatc aatgaagagg tgcgcaagct ggccatcggc gatgaagagc   2700
cgattgatat ccgtcctgcc gacctgctgg tgcctgagct cgatgccctg acccgtgaag   2760
tcggtgatcg ggctacttcg gtggaggatg tactctccta tgccctgttc cgaccattg   2820 ctctggagtt tttcgaagag cgggccagcg gtcagttcaa acctgaatca ctggacacgc   2880
ctctggaagc cagttccaca cctgaggttg ttaccgcacc gtccctggcg cctaccgaat   2940
tcaacatcat cattcatggt gaagaatacc atatcaagat cgaaggttcc ggtcacaaga   3000
gcgatgatgt gcgtccgttt tatgtcaagg tggataatgt actggaagag gtcaccgttg   3060
agacgctgac cgaggtcgta cctacccata acggcaattt tgatgtcagc aaggcatcca   3120
agggttcacg caggccgaaa gcaaccagcg acagcgatgt aacaacggcc atgccgggtc   3180
gtatcgtggc gatcaatgtc gccatcgcg  accaggtaga agccggcacc accgtcctga   3240
ccgtggaagc gatgaagatg gaaaatcagg tgcatgcacc ggtttccggt acggtcaccg   3300
ccatcaatgt cgcagtcggc gatagcgtca atcccgatga gtgcctgatg cagatcgact   3360
aa                                                                  3362
```

<210> SEQ ID NO 49
<211> LENGTH: 558
<212> TYPE: PRT
<213> ORGANISM: Pseudomonas stutzeri ATCC14405

<400> SEQUENCE: 49

Met Arg Ile Asn Asp Phe Arg Ile Val Leu Pro Val Val Arg Leu His
1               5                   10                  15

```
Phe Ala Glu Gln Ser Asn Leu Arg Arg Phe Cys Leu Thr Gly Gln Glu
             20                  25                  30

Thr Val Ile Pro Asp Thr His Ile Ser Lys Tyr Leu Ser Gln Arg Lys
         35                  40                  45

Gln Leu Phe Ile Phe Ser Asn Pro Pro His Gly Arg Arg Val Lys Arg
 50                  55                  60

Ile Ala Ser Lys Ala Ser Asp Pro Asp Pro Leu Ala Gly Arg Leu Leu
 65                  70                  75                  80

Asn Asp Pro Arg Glu Asp Ser Val Ile Lys Lys Leu Leu Ile Ala Asn
                 85                  90                  95

Arg Gly Glu Ile Ala Val Arg Ile Val Arg Ala Cys Ala Glu Met Gly
                100                 105                 110

Val Arg Ser Val Ala Val Phe Ser Glu Ala Asp Arg His Ala Leu His
            115                 120                 125

Val Lys Arg Ala Asp Glu Ala Tyr Phe Ile Gly Glu Asp Pro Leu Ala
130                 135                 140

Gly Tyr Leu Asn Pro Arg Lys Leu Val Asn Leu Ala Val Glu Thr Gly
145                 150                 155                 160

Cys Asp Ala Leu His Pro Gly Tyr Gly Phe Leu Ser Glu Asn Ala Glu
                165                 170                 175

Leu Ala Glu Ile Cys Ala Glu Arg Gly Ile Lys Phe Val Gly Pro Ser
            180                 185                 190

Ala Asp Val Ile Arg Arg Met Gly Asp Lys Thr Glu Ala Arg Arg Ser
        195                 200                 205

Met Ile Lys Ala Gly Val Pro Val Thr Pro Gly Thr Glu Gly Asn Val
210                 215                 220

Lys Asp Leu Ala Glu Ala Leu Arg Glu Ala Glu Arg Ile Gly Tyr Pro
225                 230                 235                 240

Val Met Leu Lys Ala Thr Ser Gly Gly Gly Gly Arg Gly Ile Arg Arg
                245                 250                 255

Cys Asn Ser Gln Ala Glu Leu Glu Ser Ala Tyr Pro Arg Val Ile Ser
            260                 265                 270

Glu Ala Thr Lys Ala Phe Gly Ser Ala Glu Val Phe Leu Glu Lys Cys
        275                 280                 285

Ile Val Glu Pro Lys His Ile Glu Ala Gln Val Leu Ala Asp Ser Phe
290                 295                 300

Gly Asn Thr Val His Leu Phe Glu Arg Asp Cys Ser Ile Gln Arg Arg
305                 310                 315                 320

Asn Gln Lys Leu Ile Glu Ile Ala Pro Ser Pro Gln Leu Thr Pro Glu
                325                 330                 335

Gln Arg Ala Tyr Ile Gly Asp Leu Ala Val Arg Ala Ala Lys Ala Val
            340                 345                 350

Gly Tyr Glu Asn Ala Gly Thr Val Glu Phe Leu Leu Ala Asp Gly Glu
        355                 360                 365

Val Tyr Phe Met Glu Met Asn Thr Arg Val Gln Val Glu His Thr Ile
370                 375                 380

Thr Glu Glu Ile Thr Gly Ile Asp Ile Val Arg Glu Gln Ile Arg Ile
385                 390                 395                 400

Ala Ser Gly Gln Pro Leu Ser Val Lys Gln Glu Asp Ile Gln His Arg
                405                 410                 415

Gly Phe Ser Leu Gln Phe Arg Ile Asn Ala Glu Asp Pro Arg Asn Asn
            420                 425                 430
```

```
Phe Leu Pro Cys Phe Gly Lys Ile Thr Arg Tyr Tyr Ala Pro Gly Gly
            435                 440                 445

Pro Gly Val Arg Thr Asp Thr Ala Ile Tyr Thr Gly Tyr Thr Ile Pro
    450                 455                 460

Pro Tyr Tyr Asp Ser Met Cys Leu Lys Leu Val Val Trp Ala Leu Thr
465                 470                 475                 480

Trp Glu Glu Ala Leu Ala Arg Gly Ser Arg Ala Leu Asp Asp Met Arg
                485                 490                 495

Val Gln Gly Val Lys Thr Thr Ala Thr Tyr Tyr Gln Gln Ile Leu Ala
                500                 505                 510

Asn Pro Asp Phe Arg Ser Gly Gln Phe Asn Thr Ser Phe Val Asp Asn
            515                 520                 525

His Pro Glu Leu Leu Asn Tyr Ser Ile Lys Lys Pro Gly Glu Leu
        530                 535                 540

Ala Leu Ala Ile Ala Ala Ala Ile Ala Ala His Ala Gly Leu
545                 550                 555
```

<210> SEQ ID NO 50
<211> LENGTH: 603
<212> TYPE: PRT
<213> ORGANISM: Pseudomonas stutzeri ATCC14405

<400> SEQUENCE: 50

```
Met Thr Ala Gln Lys Lys Ile Thr Val Thr Asp Thr Ile Leu Arg Asp
1               5                   10                  15

Ala His Gln Ser Leu Leu Ala Thr Arg Met Arg Thr Glu Asp Met Leu
                20                  25                  30

Pro Ile Cys Asp Lys Leu Asp Arg Val Gly Tyr Trp Ser Leu Glu Val
            35                  40                  45

Trp Gly Gly Ala Thr Phe Asp Ala Cys Val Arg Phe Leu Lys Glu Asp
    50                  55                  60

Pro Trp Glu Arg Leu Arg Gln Leu Lys Ala Ala Leu Pro Asn Thr Arg
65                  70                  75                  80

Leu Gln Met Leu Leu Arg Gly Gln Asn Leu Leu Gly Tyr Arg His Tyr
                85                  90                  95

Ser Asp Asp Val Val Glu Ala Phe Cys Ala Arg Ala Ala Glu Asn Gly
            100                 105                 110

Ile Asp Val Phe Arg Ile Phe Asp Ala Met Asn Asp Val Arg Asn Leu
        115                 120                 125

Glu Thr Ala Ile Arg Ala Val Lys Lys Ser Gly Lys His Ala Gln Gly
    130                 135                 140

Thr Ile Ala Tyr Thr Thr Ser Pro Val His Thr Val Glu Leu Phe Val
145                 150                 155                 160

Glu Gln Ala Arg Gln Met Ala Ala Met Gly Val Asp Ser Ile Ala Ile
                165                 170                 175

Lys Asp Met Ala Gly Leu Leu Thr Pro Phe Ala Thr Gly Asp Leu Val
            180                 185                 190

Arg Ala Leu Lys Ala Glu Ile Asp Leu Pro Val Phe Ile His Ser His
        195                 200                 205

Asp Thr Ala Gly Val Ala Ser Met Cys Gln Leu Lys Ala Ile Glu Asn
    210                 215                 220

Gly Ala Asp His Ile Asp Thr Ala Ile Ser Ser Met Ala Trp Gly Thr
225                 230                 235                 240

Ser His Pro Gly Thr Glu Ser Met Val Ala Ala Leu Lys Gly Thr Pro
                245                 250                 255
```

Tyr Asp Thr Gly Leu Asp Leu Glu Leu Leu Gln Glu Ile Gly Leu Tyr
            260                 265                 270

Phe Tyr Ala Val Arg Lys Lys Tyr His Gln Phe Glu Ser Glu Phe Thr
        275                 280                 285

Gly Val Asp Thr Arg Val Gln Val Asn Gln Val Pro Gly Gly Met Ile
    290                 295                 300

Ser Asn Leu Ala Asn Gln Leu Lys Glu Gln Gly Ala Leu His Arg Met
305                 310                 315                 320

Asp Glu Val Leu Ala Glu Ile Pro Lys Val Arg Lys Asp Leu Gly Tyr
                325                 330                 335

Pro Pro Leu Val Thr Pro Thr Ser Gln Ile Val Gly Thr Gln Ala Phe
                340                 345                 350

Phe Asn Val Leu Ala Gly Glu Arg Tyr Lys Thr Ile Thr Asn Glu Val
            355                 360                 365

Lys Leu Tyr Leu Gln Gly Arg Tyr Gly Gln Ala Pro Ala Pro Val Cys
    370                 375                 380

Glu Arg Leu Arg Phe Met Ala Ile Gly Ser Glu Val Ile Glu Cys
385                 390                 395                 400

Arg Pro Ala Asp Leu Leu Ala Pro Glu Leu Asp Lys Leu Arg Lys Asp
                405                 410                 415

Ile Gly Gly Leu Ala Lys Ser Glu Glu Asp Val Leu Thr Phe Ala Met
                420                 425                 430

Phe Pro Asp Ile Gly Arg Lys Phe Leu Glu Glu Arg Glu Ala Gly Thr
            435                 440                 445

Leu Gln Pro Glu Val Leu Leu Pro Ile Pro Asp Gly Asn Val Ala Ala
    450                 455                 460

Ala Ser Val Glu Gly Thr Pro Thr Glu Phe Val Ile Asp Val His Gly
465                 470                 475                 480

Glu Ser Tyr Arg Val Asp Ile Thr Gly Val Gly Val Lys Gly Glu Gly
                485                 490                 495

Lys Arg His Phe Tyr Leu Ser Ile Asp Gly Met Pro Glu Glu Val Val
                500                 505                 510

Phe Glu Pro Leu Asn Ala Phe Val Gly Gly Gly Ser Gly Arg Lys
            515                 520                 525

Gln Ala Ser Ala Pro Gly Asp Val Ser Thr Thr Met Pro Gly Asn Val
    530                 535                 540

Val Asp Val Leu Val Ala Val Gly Asp Val Val Lys Ala Gly Gln Thr
545                 550                 555                 560

Val Leu Val Ser Glu Ala Met Lys Met Glu Thr Glu Ile Gln Ala Pro
                565                 570                 575

Ile Ala Gly Thr Val Lys Ala Val His Val Ala Lys Gly Asp Arg Val
            580                 585                 590

Asn Pro Gly Glu Val Leu Ile Glu Ile Glu Gly
    595                 600

<210> SEQ ID NO 51
<211> LENGTH: 3499
<212> TYPE: DNA
<213> ORGANISM: Pseudomonas stutzeri ATCC14405

<400> SEQUENCE: 51
atgcgcatca atgattttcg catcgtttta ccagtagttc gcctgcattt cgcggaacag     60
tcaaacctgc ggcgtttctg tctgactggt caagaaacag tcattcctga cacacatata    120

```
agtaaatact tatcccaaag aaaacaatta ttcattttca gtaatccccc tcacgggcgt    180
agggtgaaac gaatcgccag caaggcgagt gatcctgacc cgctcgcggg tcgcctgctc    240
aacgatccga gggaagacag cgtgatcaag aagctgctga tcgccaaccg cggggaaatc    300
gcggtgcgca tcgtccgcgc ctgtgccgaa atgggcgtcc gctcggtggc ggtgttctcc    360
gaagccgacc gccatgcgct gcacgtcaag cgcgccgacg aggcctattt catcggcgag    420
gacccgctgg ccggctacct gaacccgcgc aagctggtaa acctggcggt agagaccggc    480
tgcgatgccc tgcatcccgg ctatggattc ctctccgaga cgccgaact ggcggaaatc    540 tgcgccgagc gcgggatcaa gttcgtcggg ccttcggcag acgtgattcg ccgcatgggc    600
gacaagaccg aagcccgtcg cagcatgatc aaggccggcg tgccggtcac gccgggcacc    660
gaaggcaacg tcaaggacct cgccgaggcg ctgcgcgaag ccgagcgcat cggttatccg    720
gtgatgctca aggccacctc cggtggtggc ggtcgtggca ttcgtcgctg caactcgcag    780
gcagagctcg agtcggcgta cccgcgggtg atctccgaag cgaccaaggc cttcggcagt    840
gccgaggtgt tcctggaaaa gtgcatcgtc gagcccaagc acatcgaggc gcaggtactg    900
gctgacagtt tcggcaacac cgtgcacctg ttcgagcgcg actgctcgat ccagcggcgc    960
aaccagaagc tcatcgagat cgcccccagc ccgcagctca cccccgagca gcgcgcctat   1020
atcggcgacc tggccgtgcg tgccgccaag gcggtgggtt acgagaacgc cggtaccgtg   1080
gagttcctgc tcgccgatgg cgaggtgtac ttcatggaga tgaacacccg ggtgcaggtg   1140
gagcacacca tcaccgagga aatcaccggc atcgacatcg tgcgcgagca gatccgcatc   1200
gcttcgggcc agccgctgtc ggtcaagcag gaagacatcc agcatcgcgg cttctccctg   1260
cagttccgca tcaacgccga ggacccgcgc aacaacttcc tgccctgctt cggcaagatc   1320
actcgctact acgctcccgg cgggccggcc gtgcgcaccg acacggcgat ctacaccggt   1380
tacaccattc caccgtatta cgactccatg tgcctgaagc tggtggtctg ggcgctgacc   1440
tgggaagagg cgctggcccg cggctcgcgc gcgctggatg acatgcgcgt gcagggtgtg   1500
aagaccactg ccacctacta ccagcagatt ctcgccaatc cggatttccg cagcggccag   1560
ttcaatacca gcttcgtcga caaccatccg gaactgctga actactcgat caaacgcaag   1620
ccgggcgagc tggccctggc cattgccgcc gccatcgccg cccacgcagg cctgtaagga   1680
acgcaccatg actgcccaga agaaaatcac cgtcaccgac accatcctgc gtgacgccca   1740
ccagtcgctg ctggccaccc gcatgcgcac cgaagacatg ctgccgatct gcgacaagct   1800
cgaccgcgtc ggctactggt cgctggaagt ctggggtggc gccaccttcg acgcctgcgt   1860
gcgcttcctc aaggaggacc catgggagcg cctgcgccag ctcaaggcag cgctgcccaa   1920
tacccgcctg cagatgctgc tgcgcgggca gaacctgctg ggctaccgtc actacagcga   1980
tgacgtggtg gaggcgttct gtgcccgtgc ggcggagaac ggcatcgacg tgttccgcat   2040
cttcgatgct atgaacgacg tacgaacct ggaaaccgcc atccgcgcgg tgaagaagag   2100
cggcaagcac gcccagggca ccatcgccta ccaccagc ccggtgcaca ccgtcgagct   2160
gttcgtcgag caggcgcggc agatggcggc catgggcgtc gactccatag ccatcaagga   2220
catggctggc ctgctgaccc cgttcgccac tggcgatctg gtccgcgcgc tgaaggccga   2280
gatcgacctt ccggtgttca tccattccca cgacaccgct ggtgtggcca gcatgtgcca   2340
gctcaaggcc atcgagaatg gcgccgacca catcgacacc gccatctcca gcatggcctg   2400
gggcaccagc catccgggca ccgagtccat ggtcgccgcg ctcaagggca cgccgtacga   2460
caccggcctc gacctcgagc tgctgcagga gatcggcctg tacttctacg ccgtgcgcaa   2520
```

```
gaagtatcac cagttcgaaa gcgagttcac cggcgtcgac acccgcgtgc aggtcaacca   2580
ggtgcccggc gggatgattt ccaacctcgc caaccagctc aaggagcagg gtgcgctgca   2640
ccgcatggac gaagtgctgg cggagattcc caaggtgcgc aaggacctcg gctacccgcc   2700
gctggtcacg ccgacctcgc agatcgtcgg cacccaggcg ttcttcaatg tgctcgccgg   2760
ggagcgctac aagaccatca ccaacgaggt gaagctctac ctgcagggcc gctacggtca   2820
ggcgccggca ccggtctgcg agcgcctgcg cttcatggcc atcggtagcg aggaggtcat   2880
cgagtgccgt ccggccgacc tgctggcacc ggagctggac aagctgcgca aggacatcgg   2940
cgggctggcc aagagcgaag aagacgtgct gaccttcgcc atgttcccgg acatcggccg   3000
caagttcctc gaggagcgcg aggcaggcac gttgcagccg gaagtgctgc tgccgattcc   3060
cgatggcaat gtcgcggcgg ccagcgtcga aggtacgccg accgagttcg tcatcgatgt   3120
ccacggcgag agctaccgtg tcgacatcac cggtgtcggc gtcaagggcg agggcaagcg   3180
gcacttctac ctgtccatcg acggcatgcc ggaggaagtg gtgttcgagc cgttgaacgc   3240
tttcgtcggc ggtggcggca gcgggcgcaa gcaggccagc gcgccgggcg acgtcagcac   3300
caccatgccg ggcaacgtgg tcgacgtgct ggtcgccgtc ggcgacgtgg tgaaggccgg   3360
gcagacggtg ctggtcagcg aggcgatgaa gatggagacc gagatccagg caccgatcgc   3420
cggcaccgtg aaggccgttc acgtcgccaa aggtgaccgg gtgaacccgg gagaagtctt   3480
gatagagatc gagggctaa                                                3499
```

<210> SEQ ID NO 52
<211> LENGTH: 741
<212> TYPE: PRT
<213> ORGANISM: Chlorobium limicola DSM 245

<400> SEQUENCE: 52

```
Met Ala Ser Lys Ser Thr Ile Ile Tyr Thr Lys Ile Asp Glu Ala Pro
1               5                   10                  15

Ala Leu Ala Thr Tyr Ser Leu Leu Pro Ile Ile Gln Ala Phe Thr Arg
            20                  25                  30

Gly Thr Gly Val Asp Val Glu Thr Arg Asp Ile Ser Leu Ala Gly Arg
        35                  40                  45

Ile Ile Ala Asn Phe Pro Glu Asn Leu Thr Glu Gln Arg Ile Pro
    50                  55                  60

Asp Tyr Leu Ala Gln Leu Gly Glu Leu Ala Leu Thr Pro Glu Ala Asn
65                  70                  75                  80

Ile Ile Lys Leu Pro Asn Ile Ser Ala Ser Ile Pro Gln Leu Lys Ala
                85                  90                  95

Ala Ile Lys Glu Leu Gln Glu His Gly Tyr Asn Val Pro Asn Tyr Pro
            100                 105                 110

Glu Ala Pro Ser Asn Asp Glu Lys Ala Ile Gln Ala Arg Tyr Ala
        115                 120                 125

Lys Val Leu Gly Ser Ala Val Asn Pro Val Leu Arg Glu Gly Asn Ser
    130                 135                 140

Asp Arg Arg Ala Pro Leu Ser Val Lys Ala Tyr Ala Gln Lys His Pro
145                 150                 155                 160

His Arg Met Ala Ala Trp Ser Lys Asp Ser Lys Ala His Val Ser His
                165                 170                 175

Met Asn Glu Gly Asp Phe Tyr Gly Ser Glu Gln Ser Val Thr Val Pro
            180                 185                 190
```

```
Ala Ala Thr Thr Val Arg Ile Glu Tyr Val Asn Gly Ala Asn Glu Val
            195                 200                 205
Thr Val Leu Lys Glu Lys Thr Ala Leu Leu Ala Gly Glu Val Ile Asp
210                 215                 220
Thr Ser Val Met Asn Val Arg Lys Leu Arg Asp Phe Tyr Ala Glu Gln
225                 230                 235                 240
Ile Glu Asp Ala Lys Ser Gln Gly Val Leu Leu Ser Leu His Leu Lys
            245                 250                 255
Ala Thr Met Met Lys Ile Ser Asp Pro Ile Met Phe Gly His Ala Val
            260                 265                 270
Ser Val Phe Tyr Lys Asp Val Phe Asp Lys His Gly Ala Leu Leu Ala
            275                 280                 285
Glu Leu Gly Val Asn Val Asn Asn Gly Leu Gly Asp Leu Tyr Ala Lys
290                 295                 300
Ile Gln Thr Leu Pro Glu Asp Lys Arg Ala Glu Ile Glu Ala Asp Ile
305                 310                 315                 320
Met Ala Val Tyr Lys Thr Arg Pro Glu Leu Ala Met Val Asp Ser Asp
            325                 330                 335
Lys Gly Ile Thr Asn Leu His Val Pro Asn Asp Ile Ile Ile Asp Ala
            340                 345                 350
Ser Met Pro Val Val Arg Asp Gly Gly Lys Met Trp Gly Pro Asp
            355                 360                 365
Gly Gln Leu His Asp Cys Lys Ala Val Ile Pro Asp Arg Cys Tyr Ala
            370                 375                 380
Thr Met Tyr Gly Glu Ile Val Asp Asp Cys Arg Lys Asn Gly Ala Phe
385                 390                 395                 400
Asp Pro Ser Thr Ile Gly Ser Val Pro Asn Val Gly Leu Met Ala Gln
            405                 410                 415
Lys Ala Glu Glu Tyr Gly Ser His Asp Lys Thr Phe Thr Ala Ala Gly
            420                 425                 430
Asp Gly Val Ile Arg Val Asp Ala Asp Gly Thr Val Leu Met Ser
            435                 440                 445
Gln Lys Val Glu Thr Gly Asp Ile Phe Arg Met Cys Gln Ala Lys Asp
450                 455                 460
Ala Pro Ile Arg Asp Trp Val Gly Leu Ala Val Arg Arg Ala Lys Ala
465                 470                 475                 480
Thr Gly Ala Pro Ala Val Phe Trp Leu Asp Ser Asn Arg Ala His Asp
            485                 490                 495
Ala Gln Ile Ile Ala Lys Val Asn Glu Tyr Leu Lys Asp Leu Asp Thr
            500                 505                 510
Asp Gly Val Glu Ile Lys Ile Met Pro Pro Val Glu Ala Met Arg Phe
            515                 520                 525
Thr Leu Gly Arg Phe Arg Ala Gly Gln Asp Thr Ile Ser Val Thr Gly
530                 535                 540
Asn Val Leu Arg Asp Tyr Leu Thr Asp Leu Phe Pro Ile Ile Glu Leu
545                 550                 555                 560
Gly Thr Ser Ala Lys Met Leu Ser Ile Val Pro Leu Leu Asn Gly Gly
            565                 570                 575
Gly Leu Phe Glu Thr Gly Ala Gly Gly Ser Ala Pro Lys His Val Gln
            580                 585                 590
Gln Phe Gln Lys Glu Gly Tyr Leu Arg Trp Asp Ser Leu Gly Glu Phe
            595                 600                 605
Ser Ala Leu Ala Ala Ser Leu Glu His Leu Ala Gln Thr Phe Gly Asn
```

| | | | | | | | | | | | |
|---|---|---|---|---|---|---|---|---|---|---|---|
| | 610 | | | | 615 | | | | 620 | | |
| Pro | Lys | Ala | Gln | Val | Leu | Ala | Asp | Thr | Leu | Asp | |
| 625 | | | | | 630 | | | | 635 | | |
| Gln | Ala | Ile | Gly | Lys | | | | | | | |
| | | | | 640 | | | | | | | |
| Phe | Leu | Asp | Asn | Gln | Lys | Ser | Pro | Ala | Arg | Lys | |
| | | | | 645 | | | | | 650 | | |
| Val | Gly | Gln | Ile | Asp | | | | | | | |
| | | | | 655 | | | | | | | |
| Asn | Arg | Gly | Ser | His | Phe | Tyr | Leu | Ala | Leu | Tyr | |
| | | | | 660 | | | | | 665 | | |
| Trp | Ala | Glu | Ala | Leu | | | | | | | |
| | | | 670 | | | | | | | | |
| Ala | Ala | Gln | Asp | Ser | Asp | Ala | Glu | Met | Lys | Ala | |
| | | | | 675 | | | | | 680 | | |
| Arg | Phe | Ala | Gly | Val | | | | | | | |
| | | | 685 | | | | | | | | |
| Ala | Ser | Ser | Leu | Ala | Ala | Lys | Glu | Glu | Leu | Ile | |
| | | | | 690 | | | | | 695 | | |
| Asn | Ala | Glu | Leu | Ile | | | | | | | |
| | | | 700 | | | | | | | | |
| Ala | Ala | Gln | Gly | Ser | Pro | Val | Asp | Met | Gly | Gly | |
| 705 | | | | | 710 | | | | | | |
| Tyr | Tyr | Gln | Pro | Asp | | | | | | | |
| | | | 715 | | | | | | | | |
| Asp | Glu | Lys | Thr | Ala | Ala | Ala | Met | Arg | Pro | Ser | |
| | | | | | | 725 | | | | | |
| Gly | Thr | Leu | Asn | Ala | | | | | | | |
| | | 730 | | | 735 | | | | | | |
| Ile | Ile | Asp | Ala | Met | | | | | | | |
| | | | 740 | | | | | | | | |

<210> SEQ ID NO 53
<211> LENGTH: 2226
<212> TYPE: DNA
<213> ORGANISM: Chlorobium limicola DSM 245

<400> SEQUENCE: 53

```
atggcaagca aatcgaccat catctacacc aagatcgacg aggcgccggc actggcgact      60
tactcgctgc ttccgatcat ccaggccttt acccgtggaa ccggcgttga tgtcgagacc     120
agggatatct cccttgccgg caggattatc gccaacttcc cggagaatct gaccgaagag     180
cagaggattc ccgactacct cgcccagctt ggcgagcttg cgctcacccc ggaagccaac     240
atcatcaaac tgccgaatat cagcgcttca attcctcagt gaaagccgc gatcaaagag      300
cttcaggagc atggttacaa tgttccgaac taccccgaag ccccgtcgaa tgacgaagag     360
aaagcaattc aggcccgtta tgccaaggta cttggcagtg ccgtgaaccc ggtgcttcgc     420
gaaggcaact ccgaccgccg cgcgccgctt tcggtcaagg catacgccca gaaacatccg     480
caccgtatgg ctgcatggag caaagactcc aaggctcacg tttcccacat gaacgagggc     540
gacttctacg cagcgagca gtccgtaacc gtgcctgccg ccaccaccgt tcgtatcgaa     600
tatgtcaacg gcgccaacga ggtgaccgtg ctgaaagaga aaccgcact gctcgccggt      660
gaagtgatcg acacgtcggt catgaacgtg cgcaagctcc gcgatttcta cgctgagcag     720
atcgaggatg ccaaatcgca gggcgtgctt ctttcgctgc acctgaaggc taccatgatg     780
aagatctccg atccgatcat gttcggccac gctgtttcgg tgttctacaa ggatgtgttt     840
gacaagcatg gcgcattgct cgccgagctt ggcgtgaacg tcaacaacgg cctcggcgat     900
ctctacgcta aaatccagac cctgccggaa gacaaacgcg ccgagatcga ggctgacatc     960
atggcggtct acaagacccg tcccgagctg gcgatggtcg attccgacaa gggcatcacc    1020
aacctgcacg tgccgaacga catcatcatc gacgcttcca tgccggtcgt tgtgcgcgac    1080
ggtggcaaga tgtggggccc cgacggtcag cttcacgact gcaaggccgt gattccggat    1140
cgctgctacg ccaccatgta cggcgaaatc gtggacgact gccgcaagaa cggcgcgttc    1200
gatccttcca ccatcggcag cgtgccgaat gtcggcctga tggcgcagaa ggctgaagag    1260
tatggttcgc acgacaagac cttcaccgcg ctggcgacg gcgtgattcg tgtggtcgat    1320
gccgacggta cggtactcat gtcgcagaag gtcgagaccg gcgacatttt ccgcatgtgc    1380
```

-continued

```
caggccaagg atgctccgat ccgcgactgg gtcggccttg ccgttcgccg cgccaaagcc    1440
accggtgctc cggctgtgtt ctggctcgac agcaaccgtg ctcacgatgc gcagatcatc    1500
gccaaggtga acgagtatct caaagacctc gacaccgacg cgtcgagat caagatcatg     1560 cctccggtcg aagccatgcg cttcacccct ggccgtttcc gtgccggaca ggacaccatt    1620
tcggtgaccg gcaacgtgct tcgtgactac ctcaccgacc tgttcccgat catcgagctc    1680
ggcaccagcg ccaagatgct ttcgatcgtt ccgctgctca acggtggtgg cctgtttgaa    1740
accggtgcag gtggttcggc tcccaagcac gtgcagcagt tccagaaaga gggctacctc    1800
cgctgggatt cgctcggcga gttctcggct ctggccgcgt cgcttgagca cctcgcacag    1860
accttcggca accccaaggc tcaggtgctg gccgacacgc tcgatcaggc gatcggtaag    1920
ttcctcgaca accagaagtc gcccgcccgc aaagtcggcc agatcgacaa ccgcggcagc    1980
cacttctacc tcgcgctcta ctgggcagag gctcttgccg cacaggattc cgatgccgag    2040
atgaaggcac gtttcgctgg cgttgcttct tcgctcgccg cgaaagagga gctcatcaac    2100
gccgagctga tcgccgcaca gggcagcccg gttgacatgg gtggctacta ccagcccgat    2160
gacgaaaaga ccgccgcagc catgcgtccg agcggtacgc tcaacgcgat catcgacgcc    2220
atgtga                                                               2226
```

<210> SEQ ID NO 54
<211> LENGTH: 400
<212> TYPE: PRT
<213> ORGANISM: Kosmotoga olearia TBF 19.5.1

<400> SEQUENCE: 54

```
Met Glu Gly Gln Lys Ile Lys Val Glu Asn Asn Ser Ile Leu Val Pro
1               5                   10                  15

Asn Asn Pro Ile Ile Pro Tyr Ile Ala Gly Asp Gly Ile Gly Pro Glu
            20                  25                  30

Ile Met Arg Ala Ala Met Leu Val Trp Asn Ser Ala Ile Ser Arg Val
        35                  40                  45

Tyr Ala Gly Lys Arg Lys Val Val Trp Lys Glu Ile Tyr Ala Gly Glu
    50                  55                  60

Lys Ala Ile Glu Ile Phe Gly Asp Pro Leu Pro Glu Glu Thr Ile Glu
65                  70                  75                  80

Ala Ile Lys Ser His Val Val Ser Ile Lys Ser Pro Leu Thr Thr Pro
                85                  90                  95

Val Gly Arg Gly Tyr Arg Ser Leu Asn Val Lys Leu Arg Gln Val Leu
            100                 105                 110

Asp Leu Tyr Ala Cys Ile Arg Pro Val Lys Trp Ile Lys Gly Val Pro
        115                 120                 125

Ala Pro Val Lys His Pro Glu Leu Leu Asp Val Ile Phe Arg Glu
    130                 135                 140

Asn Thr Glu Asp Val Tyr Ala Gly Ile Glu Trp Lys Lys Gly Ser Gln
145                 150                 155                 160

Glu Ala Lys Lys Val Ile Asp Phe Leu Arg Asp Thr Phe Asn Leu Glu
                165                 170                 175

Ile Arg Gly Asp Ser Gly Leu Gly Leu Lys Pro Ile Ser Glu Phe Ala
            180                 185                 190

Thr Lys Arg Ile Thr Arg Lys Ala Ile Gln Tyr Ala Leu Glu Asn Gly
        195                 200                 205

Arg Lys Ser Val Thr Ile Val His Lys Gly Asn Ile Met Lys Tyr Thr
```

```
                 210                215                220
Glu Gly Ala Phe Val Glu Trp Ala Tyr Glu Val Ala Leu Asn Glu Phe
225                 230                235                240

Glu Gly Lys Val Val Ser Glu Arg Glu Leu Asn Glu Pro Val Ser Glu
                245                250                255

Lys Leu Ile Val Lys Asp Arg Ile Ala Asp Asn Met Phe Gln Gln Ile
            260                265                270

Leu Leu Glu Pro Ser Glu Tyr Asp Ile Met Leu Leu Pro Asn Leu Asn
        275                280                285

Gly Asp Tyr Leu Ser Asp Ala Val Ala Ala Gln Val Gly Gly Ile Gly
    290                295                300

Leu Val Pro Gly Ala Asn Ile Gly Asp Phe Val Ala Leu Phe Glu Pro
305                 310                315                320

Thr His Gly Thr Ala Pro Gln Leu Ala Gly Lys Glu Ile Ala Asn Pro
                325                330                335

Thr Ser Leu Ile Leu Ser Gly Ala Met Met Phe Asp Tyr Ile Gly Trp
            340                345                350

Lys Glu Val Gly Ser Ile Ile Arg Lys Ala Val Glu Lys Thr Ile Met
        355                360                365

Asp Gly Lys Met Thr Ile Asp Leu Ala Arg Lys Lys Gly Val Glu Pro
    370                375                380

Leu Lys Thr Thr Glu Phe Ala Glu Glu Ile Ile Lys Asn Ile Glu Glu
385                 390                395                400

<210> SEQ ID NO 55
<211> LENGTH: 1203
<212> TYPE: DNA
<213> ORGANISM: Kosmotoga olearia TBF 19.5.1

<400> SEQUENCE: 55
atggaaggac agaaaataaa ggtagaaaac aacagtattt tggttccaaa taatcccata      60
atcccatata tagcaggtga tggaataggg cccgaaataa tgagggctgc gatgttggtg     120
tggaattcag caatttctcg tgtttatgca gggaaaagaa aagtcgtatg aaggaaata     180 tatgcaggtg aaaaggctat agaaatcttt ggtgatccac ttcctgaaga acaatagaa     240 gctattaaga gtcatgttgt ttctataaaa tcacctttga ccaccccggt cggaagggga     300
tacaggagcc ttaatgtgaa gctcaggcag gttctggatc tgtatgcatg tataaggcct     360
gtcaaatgga taaaggagt tccagctcca gttaagcacc cggaactttt agatgtggta     420
attttccgtg agaacacgga agacgtgtac gctggaatag aatggaaaaa aggctcacaa     480
gaagcgaaaa aggttatcga cttttttaaga gatacgttta atctggaaat tagaggcgat     540
tcaggacttg gattgaagcc cataagtgaa ttcgctacga agagaattac gagaaaagct     600
attcaatacg ccctggaaaa tggcagaaag agtgtcacca tagtccataa gggaaatata     660
atgaaataca cagagggcgc ttttgtagaa tgggcttatg aagtggcttt gaatgaattt     720
gaaggcaaag tggtttcgga gagagagtta atgagcccg tatctgaaaa attgatcgta     780
aaagatagaa tagcggataa catgttccag cagatactct tagaaccttc ggagtacgat     840
ataatgctcc tccctaacct gaatggagat tatctgtctg atgctgttgc agctcaggtt     900
ggtggtatag ggttagttcc tggtgcaaac ataggagatt ttgtggcttt gtttgaacca     960
acacacggta cagcaccgca acttgctgga aaggaaatag caaacccaac atccttgata    1020
ttatccggtg ctatgatgtt cgattatatt ggatggaaag aagttggaag tattataaga    1080
```

-continued

```
aaagctgttg agaaaactat aatggacggg aagatgacca tagatctcgc aagaaagaaa    1140
ggtgtagagc ctcttaaaac cacggaattt gcagaagaaa tcattaaaaa cattgaagaa    1200
tag                                                                  1203
```

<210> SEQ ID NO 56
<211> LENGTH: 418
<212> TYPE: PRT
<213> ORGANISM: Acinetobacter baumannii ACICU

<400> SEQUENCE: 56

```
Met Gly Tyr Gln Lys Ile Val Val Pro Ala Gly Asp Lys Ile Thr
 1               5                  10                  15

Val Lys Ala Asp Leu Ser Leu Asn Val Pro Asn His Pro Ile Ile Pro
                20                  25                  30

Phe Ile Glu Gly Asp Gly Ile Gly Val Asp Ile Thr Pro Ala Met Lys
                35                  40                  45

Lys Val Val Asp Ala Ala Ile Leu Lys Ala Tyr Gly Gly Lys Arg Ser
            50                  55                  60

Ile Glu Trp Met Glu Val Tyr Cys Gly Glu Lys Ala Asn Lys Ile Tyr
65                  70                  75                  80

Gly Thr Tyr Met Pro Glu Glu Thr Phe Glu Ala Leu Arg Glu Phe Val
                85                  90                  95

Val Ser Ile Lys Gly Pro Leu Thr Thr Pro Val Gly Gly Gly Ile Arg
                100                 105                 110

Ser Leu Asn Val Ala Leu Arg Gln Glu Leu Asp Leu Tyr Val Cys Val
                115                 120                 125

Arg Pro Val Arg Trp Phe Gln Gly Val Pro Ser Pro Val Gln His Pro
            130                 135                 140

Glu Leu Thr Asp Met Val Ile Phe Arg Glu Asn Ser Glu Asp Ile Tyr
145                 150                 155                 160

Ala Gly Ile Glu Trp Lys Ala Asp Ser Glu Glu Ala Lys Lys Val Ile
                165                 170                 175

Lys Phe Leu Gln Glu Glu Met Gly Val Thr Lys Ile Arg Phe Pro Glu
                180                 185                 190

Gly Cys Gly Ile Gly Ile Lys Pro Val Ser Lys Glu Gly Thr Gln Arg
            195                 200                 205

Leu Val Arg Lys Ala Ile Gln Phe Ala Ile Asp Asn Asp Lys Pro Ser
210                 215                 220

Val Thr Leu Val His Lys Gly Asn Ile Met Lys Tyr Thr Glu Gly Ala
225                 230                 235                 240

Phe Lys Glu Trp Gly Tyr Glu Leu Ala Leu Asp Arg Phe Gly Gly Glu
                245                 250                 255

Leu Ile Asp Gly Gly Pro Trp Val Lys Ile Lys Asn Pro Lys Asn Gly
            260                 265                 270

Lys Asp Ile Ile Lys Asp Val Ile Ala Asp Ala Phe Leu Gln Gln
            275                 280                 285

Ile Leu Met Arg Pro Ala Asp Tyr Ser Val Ile Ala Thr Leu Asn Leu
            290                 295                 300

Asn Gly Asp Tyr Ile Ser Asp Ala Leu Ala Ala Glu Val Gly Gly Ile
305                 310                 315                 320

Gly Ile Ala Pro Gly Ala Asn Ile Gly Gly Ala Ile Ala Val Tyr Glu
                325                 330                 335

Ala Thr His Gly Thr Ala Pro Lys Tyr Ala Gly Gln Asp Lys Val Asn
                340                 345                 350
```

```
Pro Gly Ser Ile Ile Leu Ser Ala Glu Met Met Leu Arg Asp Met Gly
        355                 360                 365

Trp Thr Glu Ala Ala Asp Leu Ile Ile Lys Gly Ile Ser Gly Ala Ile
    370                 375                 380

Ala Ala Lys Thr Val Thr Tyr Asp Phe Glu Arg Leu Met Pro Gly Ala
385                 390                 395                 400

Thr Leu Leu Arg Cys Ser Glu Phe Gly Asp Ala Ile Ile Gln His Met
                405                 410                 415

Glu Asp
```

```
<210> SEQ ID NO 57
<211> LENGTH: 1257
<212> TYPE: DNA
<213> ORGANISM: Acinetobacter baumannii ACICU

<400> SEQUENCE: 57
atgggttatc agaagatcgt ggttcctgcc gacggtgata aaattacagt aaaagcagac      60
ctgtcactga atgtaccaaa tcatccaatt attcctttca ttgagggtga cggtattggt     120
gtagatatta caccggcaat gaaaaaagtt gttgatgcgg caattttaaa agccatggc     180
ggcaaacgct ctattgaatg gatggaagtg tattgcggtg aaaaggccaa taaaatttac     240
ggtacttata tgccggaaga aaccttgaa gcgctgcgtg aatttgtagt ttcaattaaa      300
ggccctttaa ctacaccagt cggtggtggc attcgttcac ttaatgttgc actacgccaa     360
gaactggatt tgtatgtatg tgtgcgtcct gtgcgttggt tccaaggcgt cccttcacct     420
gttcaacatc ctgagttaac tgacatggtg attttccgtg aaaactcgga agatatttat     480
gcaggtattg aatggaaagc agattctgaa gaagctaaaa agttattaa attccttcaa     540
gaagaaatgg gggtcacaaa aattcgtttc cctgaaggat gtggtattgg tattaaaccc     600
gtttccaaag aaggaacaca gcgcttagtt cgtaaggcca ttcagtttgc aatcgataat     660
gacaaacctt cggtgactct tgttcataaa ggcaacatta tgaaatatac cgaaggtgcc     720
tttaagaat ggggtatga gttagcgcta gatcgtttcg gtggtgaatt aatcgatggt     780
ggcccatggg ttaaaattaa gaatcctaaa atggtaaag acatcattat taaagacgtg     840
attgcagatg ctttcttgca acaaatcttg atgcgtcctg ctgactactc tgtaattgca     900
acccttaatt taaatggtga ctatatttca gatgctttag cagcagaagt aggggaatc     960
gggattgcgc aggtgcgaa tattggtgga gctattgcag tgtatgaagc aacgcatggc    1020
actgcaccta aatatgctgg gcaagataaa gtcaacccgg ttcaattat tctctctgct    1080
gaaatgatgc tccgtgatat ggggtggaca gaagcagcgg acctgattat taaaggtatt    1140
tcaggagcga ttgcagctaa aaccgtaact tacgattttg agcgtttaat gccgggagcg    1200
accttgttac gttgctcaga atttggcgat gccataattc agcacatgga agattaa      1257
```

```
<210> SEQ ID NO 58
<211> LENGTH: 417
<212> TYPE: PRT
<213> ORGANISM: Marine gamma proteobacterium HTCC2080

<400> SEQUENCE: 58

Met Ser Tyr Lys His Ile Lys Val Pro Glu Ser Gly Asp Val Ile Thr
1               5                   10                  15

Val Asn Glu Asp Ser Ser Leu Ser Val Pro Asp Lys Pro Ile Ile Pro
            20                  25                  30
```

Tyr Ile Glu Gly Asp Gly Ile Gly Val Asp Ile Thr Pro Val Met Ile
                35                  40                  45

Asp Val Val Asn Ala Ala Val Asp Lys Ala Tyr Gly Gly Gln Lys Ala
 50                  55                  60

Ile Ser Trp Met Glu Ile Tyr Thr Gly Glu Lys Ala Ala Glu Leu Tyr
 65                  70                  75                  80

Glu Gly Asp Trp Phe Pro Glu Thr Leu Glu Ala Ile Lys Thr Tyr
                 85                  90                  95

Ala Val Ala Ile Lys Gly Pro Leu Thr Thr Pro Val Gly Gly Phe
                100                 105                 110

Arg Ser Leu Asn Val Ala Leu Arg Gln Glu Leu Asp Leu Tyr Thr Cys
                115                 120                 125

Leu Arg Pro Val Arg Trp Phe Glu Gly Val Pro Ser Pro Val Arg Arg
130                 135                 140

Pro Glu Asp Cys Asn Met Val Ile Phe Arg Glu Asn Ser Glu Asp Ile
145                 150                 155                 160

Tyr Ala Gly Ile Glu Tyr Gln Ala Gly Thr Pro Glu Ala Gln Lys Val
                165                 170                 175

Val Asp Phe Ile Ile Asn Glu Met Gly Ala Thr Lys Ile Arg Phe Pro
                180                 185                 190

Thr Asp Val Gly Ile Gly Ile Lys Pro Val Ser Ser Ala Gly Thr Lys
                195                 200                 205

Arg Leu Val Arg Lys Ala Ile Gln Tyr Ala Ile Asp Gln Asn Leu Pro
210                 215                 220

Ser Val Thr Leu Val His Lys Gly Asn Ile Met Lys Phe Thr Glu Gly
225                 230                 235                 240

Ala Phe Arg Asp Trp Gly Tyr Glu Leu Ala Gln Glu Phe Gly Gly
                245                 250                 255

Gln Leu Val Asp Gly Gly Pro Trp Val Glu Ile Lys Asn Pro Ile Thr
                260                 265                 270

Gly Asp Pro Ile Ile Lys Asp Val Ile Ala Asp Ala Met Leu Gln
                275                 280                 285

Gln Val Leu Thr Arg Pro Lys Glu Tyr Ser Val Val Ala Thr Leu Asn
                290                 295                 300

Leu Asn Gly Asp Tyr Leu Ser Asp Ala Leu Ala Ala Gln Val Gly Gly
305                 310                 315                 320

Ile Gly Ile Ala Pro Gly Ala Asn Leu Ser Asp Thr Val Ala Leu Phe
                325                 330                 335

Glu Ala Thr His Gly Thr Ala Pro Lys Tyr Ala Gly Gln Asp Lys Val
                340                 345                 350

Asn Pro Gly Ser Leu Ile Leu Ser Ala Glu Met Met Arg His Leu
                355                 360                 365

Gly Trp Asn Glu Ala Ala Asp Leu Ile Val Asp Gly Val Asn Gly Ala
                370                 375                 380

Ile Gln Ala Lys Thr Val Thr Tyr Asp Phe Glu Arg Leu Met Asp Gly
385                 390                 395                 400

Ala Thr Leu Val Ser Cys Ser Asp Phe Gly Lys Ala Ile Ile Lys Ala
                405                 410                 415

Met

<210> SEQ ID NO 59
<211> LENGTH: 1254
<212> TYPE: DNA
<213> ORGANISM: Marine gamma proteobacterium HTCC2080

<400> SEQUENCE: 59

```
atgtcataca agcacattaa ggttccggaa agcggagacg tgatcacagt caacgaggac       60
agcagcctgt ctgtgcctga caagcctatc atcccttaca tcgaaggtga cggaattggt      120
gtcgacatta cgccggtaat gattgatgtc gtcaatgccg cagtagacaa ggcctacggg      180
gggcaaaagg ccatatcttg atggagata tacaccggtg aaaaagcggc tgaattgtac       240
gaagggact ggtttcctga ggagacgctg gaggccataa aaacctatgc cgtcgctatc       300
aagggaccat tgacaacccc ggtaggtgga ggctttcgct cactcaacgt ggcgctgcgt      360
caagagctag atctttacac ctgcctgcgg ccggttcgct ggtttgaggg tgtcccttct      420
cctgtacgtc gccctgaaga ctgcaacatg gtgatctttc gagagaattc ggaagatata      480
tatgcgggca tcgaatatca ggctggaaca cctgaagcgc aaaaggttgt tgatttcatc      540
attaatgaaa tgggcgcgac aaagattcgt tttccaacgg acgtaggcat tggcataaag      600
cctgtctcct ctgcgggaac caagcgcttg gttcgtaaag ctattcagta tgccatcgat      660
caaaatctgc catctgtcac ccttgtacac aaaggcaaca tcatgaaatt taccgagggg      720
gcatttcggg attggggtta cgagcttgct caggaagagt ttggcgggca gttagtagac      780
ggtggtccgt gggtggaaat caaaaaccca ataaccggtg atccgatcat cattaaagat      840
gtgattgctg atgccatgct gcagcaggtt ttgacgcgtc caaggaata cagtgtagtc       900
gcaactttga atcttaatgg tgattatctt tccgatgctt tggccgctca ggtcggtgga      960
attggtatcg ctcctggcgc taacctttcc gataccgttg cattgtttga agccaccc ac    1020
ggaacagcac ctaaatacgc tggtcaggac aaggttaatc cgggctcgtt gattttgtcg     1080
gccgaaatga tgatgcgcca cctaggatgg aatgaggccg cagatcttat cgtcgatggt     1140
gtgaacggtg cgattcaagc caaaaccgtg acttatgact tgagcgatt gatggacggg      1200
gctactttgg tctcatgttc tgacttcgga aaagccataa taaaagccat gtaa           1254
```

<210> SEQ ID NO 60
<211> LENGTH: 422
<212> TYPE: PRT
<213> ORGANISM: Nitrosococcus halophilus Nc4

<400> SEQUENCE: 60

```
Met Ala Tyr Asp Lys Ile Ser Leu Pro Ser Asp Gly Glu Pro Ile Thr
1               5                   10                  15

Val Lys Glu Asp Tyr Ser Leu Glu Val Pro Ala Arg Pro Leu Ile Pro
            20                  25                  30

Phe Ile Glu Gly Asp Gly Ile Gly Val Asp Ile Thr Pro Val Met Arg
        35                  40                  45

Gln Val Val Asp Glu Ala Val Ala Lys Ala Tyr Gly Gly Glu Arg Ser
    50                  55                  60

Leu Ala Trp Ala Glu Val Tyr Ala Gly Glu Lys Ala Ala Gln Val Tyr
65                  70                  75                  80

Gly Ala Asp Gln Trp Leu Pro Ala Glu Thr Leu Asp Val Leu Arg Gln
                85                  90                  95

Phe Val Val Ser Ile Lys Gly Pro Leu Thr Thr Pro Val Gly Lys Gly
            100                 105                 110

Ile Arg Ser Leu Asn Val Ala Ile Arg Gln Thr Leu Asp Leu Tyr Ala
        115                 120                 125

Cys Ile Arg Pro Val Arg Tyr Phe Ser Gly Thr Pro Ser Pro Leu Ala
    130                 135                 140
```

```
Asp Pro Ser Arg Thr Asn Met Val Val Phe Arg Glu Asn Thr Glu Asp
145                 150                 155                 160

Ile Tyr Ala Gly Ile Glu Trp Ala Ala Arg Ser Pro Glu Ala Lys Gln
            165                 170                 175

Val Ile Glu Phe Leu Gln Gln Gln Met Gly Val Glu Lys Ile Arg Phe
            180                 185                 190

Pro Glu Ser Ser Gly Ile Gly Ile Lys Pro Val Ser Gln Glu Gly Ser
            195                 200                 205

Gln Arg Leu Ile Arg Lys Ala Leu Gln Tyr Ala Ile Asp Asn Asp Arg
210                 215                 220

Arg Ser Val Thr Leu Val His Lys Gly Asn Ile Met Lys Phe Thr Glu
225                 230                 235                 240

Gly Ala Phe Cys Asp Trp Gly Tyr Ala Leu Ala Gln Glu Glu Phe Gly
            245                 250                 255

Ala Arg Pro Ile Asp Gly Gly Pro Trp Cys Glu Phe Thr Asn Pro Lys
            260                 265                 270

Ser Gly Gly Lys Ile Ile Val Lys Asp Ala Ile Ala Asp Asn Phe Leu
            275                 280                 285

Gln Gln Ile Leu Leu Arg Pro Glu Glu Tyr Asp Val Ile Ala Thr Leu
290                 295                 300

Asn Leu Asn Gly Asp Tyr Ile Ser Asp Ala Leu Ala Ala Gln Val Gly
305                 310                 315                 320

Gly Ile Gly Met Ala Pro Gly Ala Asn Met Gly Asp Arg Val Ala Val
            325                 330                 335

Phe Glu Ala Thr His Gly Thr Ala Pro Lys Tyr Ala Gly Gln Asp Arg
            340                 345                 350

Val Asn Pro Ser Ser Ile Ile Leu Ser Gly Glu Met Met Leu Arg His
            355                 360                 365

Leu Gly Trp Asn Glu Ala Ala Asp Leu Ile Ile Gln Gly Ile Ser Gly
370                 375                 380

Ala Ile Ala Ala Lys Arg Val Thr Tyr Asp Leu Ala Arg Leu Met Glu
385                 390                 395                 400

Gly Ala Thr Gln Val Pro Cys Ser Gly Phe Gly Lys Ala Ile Ile Glu
            405                 410                 415

His Met Asp Val Ser Ser
            420

<210> SEQ ID NO 61
<211> LENGTH: 1269
<212> TYPE: DNA
<213> ORGANISM: Nitrosococcus halophilus Nc4

<400> SEQUENCE: 61
atggcctatg acaagatttc ccttccctcc gatggcgaac ccattaccgt caaggaggac      60
tacagccttg aagtccccgc ccgtcccctc attcccttta tagaagggga tggcattggg     120
gtggatatca ccccggtgat gcgccaggtg gtggatgagg cggtggcgaa ggcctatggg     180
ggagagcgtt ccctggcctg ggccgaggtg tatgcagggg agaaggccgc gcaagtgtat     240
ggcgccgatc aatggttgcc ggcggagact ttggatgtcc tgcggcaatt cgtggtgtct     300
atcaagggac gctaaccac gccggtcggc aaaggtatcc gttctcttaa tgtggcgatc     360
cgccaaacct tggatcttta tgcctgtatc cggccggtcc gttatttttc gggcacgccg     420
agccctctgg ctgatccctc ccgcaccaat atggtggtgt tcgggaaaaa taccgaggat     480
```

-continued

```
atctatgccg ggatcgagtg ggcggcccgt tcgccggagg cgaagcaggt cattgagttt    540
ttacaacagc agatgggggt ggaaaaaatc cgtttcccgg aaagctccgg cattggcatt    600
aaaccggtat cccaggaagg ttctcaacgc ctgatccgca aagccctgca atacgccatc    660
gataatgatc gccgttcggt gaccctagtg cataagggga acatcatgaa gtttaccgaa    720
ggcgccttct gtgactgggg ttatgccttg gcccaggagg agtttggcgc ccggcccatt    780
gatgggggc cctggtgtga attcacgaat cctaaaagcg gcggcaaaat tattgtcaaa     840
gacgcgattg ccgataattt tctccaacag atcctgctcc gccccgagga atatgatgtc    900
attgcgaccc tgaatcttaa tggagattac atttctgacg ctttagcggc ccaagtgggg    960
ggaattggca tggcgccggg agcgaacatg ggggatagg tcgccgtgtt tgaggccacc    1020
cacgggacgg cccccaagta tgccggtcag gatcgggtca atcccagcag cattatcctt    1080
tcagggaaa tgatgttgcg tcatctcggc tggaatgaag cggcggatct catcatccaa    1140
gggatttcgg gggctatcgc cgccaagagg gtgacttacg atctagcccg attgatggaa    1200
ggcgccaccc aagtaccctg ttctggattt ggaaaggcga ttatcgagca tatggacgtt    1260
tccagctag                                                             1269
```

<210> SEQ ID NO 62
<211> LENGTH: 432
<212> TYPE: PRT
<213> ORGANISM: Corynebacterium glutamicum ATCC 13032

<400> SEQUENCE: 62

```
Met Ser Asn Val Gly Lys Pro Arg Thr Ala Gln Glu Ile Gln Gln Asp
1               5                   10                  15

Trp Asp Thr Asn Pro Arg Trp Asn Gly Ile Thr Arg Asp Tyr Thr Ala
            20                  25                  30

Asp Gln Val Ala Asp Leu Gln Gly Ser Val Ile Glu Glu His Thr Leu
        35                  40                  45

Ala Arg Arg Gly Ser Glu Ile Leu Trp Asp Ala Val Thr Gln Glu Gly
    50                  55                  60

Asp Gly Tyr Ile Asn Ala Leu Gly Ala Leu Thr Gly Asn Gln Ala Val
65                  70                  75                  80

Gln Gln Val Arg Ala Gly Leu Lys Ala Val Tyr Leu Ser Gly Trp Gln
                85                  90                  95

Val Ala Gly Asp Ala Asn Leu Ser Gly His Thr Tyr Pro Asp Gln Ser
            100                 105                 110

Leu Tyr Pro Ala Asn Ser Val Pro Ser Val Val Arg Arg Ile Asn Asn
        115                 120                 125

Ala Leu Leu Arg Ser Asp Glu Ile Ala Arg Thr Glu Gly Asp Thr Ser
    130                 135                 140

Val Asp Asn Trp Val Val Pro Ile Val Ala Asp Gly Glu Ala Gly Phe
145                 150                 155                 160

Gly Gly Ala Leu Asn Val Tyr Glu Leu Gln Lys Ala Met Ile Ala Ala
                165                 170                 175

Gly Ala Ala Gly Thr His Trp Glu Asp Gln Leu Ala Ser Glu Lys Lys
            180                 185                 190

Cys Gly His Leu Gly Gly Lys Val Leu Ile Pro Thr Gln Gln His Ile
        195                 200                 205

Arg Thr Leu Asn Ser Ala Arg Leu Ala Ala Asp Val Ala Asn Thr Pro
    210                 215                 220

Thr Val Val Ile Ala Arg Thr Asp Ala Glu Ala Ala Thr Leu Ile Thr
```

```
                    225                 230                 235                 240
Ser Asp Val Asp Glu Arg Asp Gln Pro Phe Ile Thr Gly Glu Arg Thr
                245                 250                 255

Ala Glu Gly Tyr Tyr His Val Lys Asn Gly Leu Glu Pro Cys Ile Ala
            260                 265                 270

Arg Ala Lys Ser Tyr Ala Pro Tyr Ala Asp Met Ile Trp Met Glu Thr
        275                 280                 285

Gly Thr Pro Asp Leu Glu Leu Ala Lys Lys Phe Ala Glu Gly Val Arg
    290                 295                 300

Ser Glu Phe Pro Asp Gln Leu Leu Ser Tyr Asn Cys Ser Pro Ser Phe
305                 310                 315                 320

Asn Trp Ser Ala His Leu Glu Ala Asp Glu Ile Ala Lys Phe Gln Lys
                325                 330                 335

Glu Leu Gly Ala Met Gly Phe Lys Phe Gln Phe Ile Thr Leu Ala Gly
            340                 345                 350

Phe His Ser Leu Asn Tyr Gly Met Phe Asp Leu Ala Tyr Gly Tyr Ala
        355                 360                 365

Arg Glu Gly Met Thr Ser Phe Val Asp Leu Gln Asn Arg Glu Phe Lys
    370                 375                 380

Ala Ala Glu Glu Arg Gly Phe Thr Ala Val Lys His Gln Arg Glu Val
385                 390                 395                 400

Gly Ala Gly Tyr Phe Asp Gln Ile Ala Thr Thr Val Asp Pro Asn Ser
                405                 410                 415

Ser Thr Thr Ala Leu Lys Gly Ser Thr Glu Glu Gly Gln Phe His Asn
            420                 425                 430

<210> SEQ ID NO 63
<211> LENGTH: 1299
<212> TYPE: DNA
<213> ORGANISM: Corynebacterium glutamicum ATCC 13032

<400> SEQUENCE: 63
atgtcaaacg ttggaaagcc acgtaccgca caggaaatcc agcaggattg ggacaccaac     60
cctcgttgga acggcatcac ccgcgactac accgcagacc aggtagctga tctgcagggt    120
tccgtcatcg aggagcacac tcttgctcgc cgcggctcag agatcctctg ggacgcagtc    180
acccaggaag gtgacggata tcaacgcg cttggcgcac tcaccggtaa ccaggctgtt     240
cagcaggttc gtgcaggcct gaaggctgtc tacctgtccg gttggcaggt cgcaggtgac    300
gccaacctct ccggccacac ctaccctgac cagtccctct acccagcgaa ctccgttcca    360
agcgtcgttc gtcgcatcaa caacgcactg ctgcgttccg atgaaatcgc acgcaccgaa    420
ggcgacacct ccgttgacaa ctgggttgtc ccaatcgtcg cggacggcga agctggcttc    480
ggtggagcac tcaacgtcta cgaactccag aaggcaatga tcgcagctgg cgctgcaggc    540
acccactggg aagaccagct cgcttctgaa aagaagtgtg ccacctcgg cggcaaggtt     600 ctgatcccaa cccagcagca catccgcacc ctgaactctg cccgccttgc agcagacgtt    660
gcaaacaccc caactgttgt tatcgcacgt accgacgctg aggcagcaac cctgatcacc    720
tctgacgttg atgagcgcga ccaaccattc atcaccggtg agcgcaccgc agaaggctac    780
taccacgtca agaatggtct cgagccatgt atcgcacgtg caaagtccta cgcaccatac    840
gcagatatga tctggatgga gaccggcacc cctgacctgg agctcgctaa gaagttcgct    900
gaaggcgttc gctctgagtt cccagaccag ctgctgtcct acaactgctc cccatccttc    960
aactggtctg cacacctcga ggcagatgag atcgctaagt tccagaagga actcggcgca   1020
```

-continued

```
atgggcttca agttccagtt catcaccctc gcaggcttcc actccctcaa ctacggcatg    1080
ttcgacctgg cttacggata cgctcgcgaa ggcatgacct ccttcgttga cctgcagaac    1140
cgtgagttca aggcagctga agagcgtggc ttcaccgctg ttaagcacca gcgtgaggtt    1200
ggcgcaggct acttcgacca gatcgcaacc accgttgacc cgaactcttc taccaccgct    1260
ttgaagggtt ccactgaaga aggccagttc cacaactag                          1299
```

<210> SEQ ID NO 64
<211> LENGTH: 431
<212> TYPE: PRT
<213> ORGANISM: Gordonia alkanivorans NBRC 16433

<400> SEQUENCE: 64

```
Met Ser Asn Val Gly Lys Pro Arg Thr Ala Ala Glu Ile Gln Gln Asp
1               5                   10                  15

Trp Asp Thr Asn Pro Arg Trp Lys Gly Ile Lys Arg Asp Tyr Thr Ala
            20                  25                  30

Glu Gln Val Ala Gln Leu Gln Gly Ser Val Val Glu His Thr Leu
        35                  40                  45

Ala Arg Arg Gly Ala Glu Ile Leu Trp Asp Gly Val Thr Lys Gly Asp
50                  55                  60

Gly Ser Tyr Ile Asn Ala Leu Gly Ala Leu Thr Gly Asn Gln Ala Val
65                  70                  75                  80

Gln Gln Val Arg Ala Gly Leu Lys Ala Val Tyr Leu Ser Gly Trp Gln
                85                  90                  95

Val Ala Gly Asp Ala Asn Leu Ser Gly His Thr Tyr Pro Asp Gln Ser
            100                 105                 110

Leu Tyr Pro Ala Asn Ser Val Pro Asn Val Val Arg Arg Ile Asn Asn
        115                 120                 125

Ala Leu Leu Arg Ala Asp Glu Ile Ala Arg Val Glu Gly Asp Asp Ser
    130                 135                 140

Val Asp Asn Trp Val Val Pro Ile Val Ala Asp Gly Glu Ala Gly Phe
145                 150                 155                 160

Gly Gly Ala Leu Asn Val Tyr Glu Leu Gln Lys Ala Met Ile Ala Ala
                165                 170                 175

Gly Ala Ala Gly Thr His Trp Glu Asp Gln Leu Ala Ser Glu Lys Lys
            180                 185                 190

Cys Gly His Leu Gly Gly Lys Val Leu Ile Pro Thr Gln Gln His Ile
        195                 200                 205

Arg Thr Leu Asn Ser Ala Arg Leu Ala Ala Asp Val Ala Gly Val Pro
    210                 215                 220

Thr Val Val Ile Ala Arg Thr Asp Ala Glu Ala Thr Leu Ile Thr
225                 230                 235                 240

Ser Asp Val Asp Asp Arg Asp Lys Gln Phe Val Thr Gly Glu Arg Thr
                245                 250                 255

Ala Glu Gly Tyr Tyr His Val Lys Asn Gly Ile Glu Pro Cys Ile Glu
            260                 265                 270

Arg Ala Lys Ser Tyr Ala Pro Tyr Ala Asp Met Ile Trp Met Glu Thr
        275                 280                 285

Gly Thr Pro Asp Leu Glu Leu Ala Arg Lys Phe Ala Glu Ala Val Lys
    290                 295                 300

Ala Glu Tyr Pro Asp Gln Leu Leu Ser Tyr Asn Cys Ser Pro Ser Phe
305                 310                 315                 320
```

```
Asn Trp Ser Lys His Leu Asp Asp Ser Thr Ile Ala Lys Phe Gln Asn
            325                 330                 335

Glu Leu Gly Ala Met Gly Phe Thr Phe Gln Phe Ile Thr Leu Ala Gly
        340                 345                 350

Phe His Ser Leu Asn Tyr Gly Met Phe Asp Leu Ala Tyr Gly Tyr Ala
            355                 360                 365

Arg Glu Gln Met Thr Ala Phe Val Asp Leu Gln Asn Arg Glu Phe Lys
        370                 375                 380

Ala Ala Asp Glu Arg Gly Phe Thr Ala Val Lys His Gln Arg Glu Val
385                 390                 395                 400

Gly Ala Gly Tyr Phe Asp Ser Ile Ala Thr Thr Val Asp Pro Asn Thr
            405                 410                 415

Ser Thr Ala Ala Leu Lys Gly Ser Thr Glu Glu Gly Gln Phe His
        420                 425                 430
```

<210> SEQ ID NO 65
<211> LENGTH: 1296
<212> TYPE: DNA
<213> ORGANISM: Gordonia alkanivorans NBRC 16433

<400> SEQUENCE: 65

| | | |
|---|---|---|
| atgagcaacg tcggaaagcc ccgcaccgcc gcggagatcc agcaggactg ggacaccaac | 60 |
| ccccgctgga agggcatcaa gcgcgactac accgccgagc aggtcgctca gctccagggt | 120 |
| tcggtcgtcg aggagcacac cctcgcccgc cgtggcgccg agatcctgtg ggacggcgtg | 180 |
| accaagggtg acgttcctcta catcaacgct ctcggcgccc tcaccggcaa ccaggccgtg | 240 |
| cagcaggtcc gcgccggcct gaaggccgtg tacctgtcgg gttggcaggt cgccggtgac | 300 |
| gccaacctgt ccggccacac ctaccccgac cagtcgctgt acccggcgaa ctcggttccc | 360 |
| aacgttgttc gtcgcatcaa caacgcgctg ctccgcgccg acgagatcgc ccgcgtcgag | 420 |
| ggtgacgact cggtcgacaa ctgggtcgtg ccgatcgtcg ccgatggtga ggccggcttc | 480 |
| ggtggcgctc tcaacgtcta cgagctccag aaggccatga tcgccgcggg tgctgccggt | 540 |
| acccactggg aggatcagct cgcctcggag aagaagtgcg ccacctcgg tggcaaggtg | 600 |
| ctcatcccga cccagcagca catccgcacc ctgaactcgg cccgcctggc cgccgacgtc | 660 |
| gccggtgtcc ccaccgtcgt catcgcgcgt accgacgccg aggccgcgac cctcatcacc | 720 |
| tccgatgtgg acgaccgcga caagcagttc gtcaccggtg agcgcaccgc cgagggctac | 780 |
| taccacgtga gaacggcat cgagccgtgc atcgagcgtg cgaagtccta cgctccgtac | 840 |
| gccgacatga tctggatgga gaccggtacc ccggatctcg agctggctcg caagttcgcc | 900 |
| gaggccgtca aggccgagta cccccgaccag ctgctgtcct acaactgcag cccgtcgttc | 960 |
| aactggagca agcacctcga cgacagcacc atcgccaagt ccagaacga gctgggcgcc | 1020 |
| atgggcttca ccttccagtt catcaccctg gccggcttcc actcgctcaa ctacggcatg | 1080 |
| ttcgaccttg cctacggtta cgcccgcgag cagatgaccg ccttcgtcga cctgcagaac | 1140 |
| cgcgagttca aggcagccga cgagcgtggc ttcaccgccg tcaagcacca gcgtgaggtc | 1200 |
| ggcgccgggt acttcgacag catcgccacc accgtcgacc cgaacacctc gaccgcagct | 1260 |
| ctcaagggct cgaccgaaga gggccagttc cactag | 1296 |

<210> SEQ ID NO 66
<211> LENGTH: 429
<212> TYPE: PRT
<213> ORGANISM: Nocardia farcinica IFM 10152

```
<400> SEQUENCE: 66

Met Ser Thr Thr Gly Thr Pro Lys Thr Ala Glu Glu Ile Gln Lys Asp
1               5                   10                  15

Trp Asp Thr Asn Pro Arg Trp Lys Gly Val Thr Arg Asn Tyr Thr Ala
                20                  25                  30

Glu Gln Val Val Ala Leu Gln Gly Asn Val Val Glu His Thr Leu
            35                  40                  45

Ala Arg Arg Gly Ser Glu Ile Leu Trp Asp Leu Val Asn Asn Glu Asp
    50                  55                  60

Tyr Ile Asn Ser Leu Gly Ala Leu Thr Gly Asn Gln Ala Val Gln Gln
65                  70                  75                  80

Val Arg Ala Gly Leu Lys Ala Ile Tyr Leu Ser Gly Trp Gln Val Ala
                85                  90                  95

Gly Asp Ala Asn Leu Ser Gly His Thr Tyr Pro Asp Gln Ser Leu Tyr
            100                 105                 110

Pro Ala Asn Ser Val Pro Ala Val Val Arg Arg Ile Asn Asn Ala Leu
        115                 120                 125

Leu Arg Ala Asp Glu Ile Ala Lys Ile Glu Gly Asp Thr Ser Val Glu
130                 135                 140

Asn Trp Leu Ala Pro Ile Val Ala Asp Gly Glu Ala Gly Phe Gly Gly
145                 150                 155                 160

Ala Leu Asn Val Tyr Glu Leu Gln Lys Ala Met Ile Ala Ala Gly Val
                165                 170                 175

Ala Gly Ser His Trp Glu Asp Gln Leu Ala Ser Glu Lys Lys Cys Gly
            180                 185                 190

His Leu Gly Gly Lys Val Leu Ile Pro Thr Gln Gln His Ile Arg Thr
        195                 200                 205

Leu Thr Ser Ala Arg Leu Ala Ala Asp Val Ala Gly Val Pro Thr Val
210                 215                 220

Val Ile Ala Arg Thr Asp Ala Glu Ala Ala Thr Leu Ile Thr Ser Asp
225                 230                 235                 240

Val Asp Glu Arg Asp Arg Pro Phe Ile Thr Gly Glu Arg Thr Ser Glu
                245                 250                 255

Gly Phe Tyr Gln Val Lys Asn Gly Ile Glu Pro Cys Ile Ala Arg Ala
            260                 265                 270

Lys Ala Tyr Ala Pro Tyr Ala Asp Leu Ile Trp Met Glu Thr Gly Thr
        275                 280                 285

Pro Asp Leu Glu Leu Ala Lys Lys Phe Ser Glu Ala Val Arg Ser Glu
290                 295                 300

Phe Pro Asp Gln Leu Leu Ala Tyr Asn Cys Ser Pro Ser Phe Asn Trp
305                 310                 315                 320

Ser Ala His Leu Asp Asp Ser Thr Ile Ala Lys Phe Gln Lys Glu Leu
                325                 330                 335

Gly Ala Met Gly Phe Lys Phe Gln Phe Ile Thr Leu Ala Gly Phe His
            340                 345                 350

Ser Leu Asn Tyr Gly Met Phe Asp Leu Ala Tyr Gly Tyr Ala Arg Glu
        355                 360                 365

Gly Met Thr Ala Phe Val Asp Leu Gln Asn Arg Glu Phe Lys Ala Ala
370                 375                 380

Glu Glu Arg Gly Phe Thr Ala Ile Lys His Gln Arg Glu Val Gly Ala
385                 390                 395                 400

Gly Tyr Phe Asp Ala Ile Ala Thr Thr Val Asp Pro Asn Thr Ser Thr
                405                 410                 415
```

Ala Ala Leu Lys Gly Ser Thr Glu Glu Gly Gln Phe His
            420                 425

<210> SEQ ID NO 67
<211> LENGTH: 1290
<212> TYPE: DNA
<213> ORGANISM: Nocardia farcinica IFM 10152

<400> SEQUENCE: 67

| | | | | | |
|---|---|---|---|---|---|
| atgtcgacca | ccggcacccc | gaagaccgct | gaggagatcc | agaaggattg | ggacaccaac | 60 |
| cctcgctgga | agggcgtcac | ccgtaactac | accgccgagc | aggtggttgc | gcttcagggc | 120 |
| aacgtcgtcg | aggagcacac | cctcgcccgt | cgcggctcgg | agatcctgtg | ggacctcgtc | 180 |
| aacaacgagg | actacatcaa | ctcgctgggc | gccctcaccg | gcaaccaggc | cgtgcagcag | 240 |
| gtccgcgccg | gcctgaaggc | catctacctg | tccggctggc | aggtcgccgg | tgacgcgaac | 300 |
| ctctcgggtc | acacctaccc | cgaccagtcg | ctgtacccgg | ccaactcggt | tccggccgtg | 360 |
| gtccgccgca | tcaacaacgc | gctgctgcgc | gccgacgaga | tcgccaagat | cgagggcgac | 420 |
| acctccgtcg | agaactggct | ggccccgatc | gtggccgacg | tgaggcgggc | cttcggtggc | 480 |
| gcgctcaacg | tctacgagct | gcagaaggcc | atgatcgccg | ccggtgtcgc | cggctcgcac | 540 |
| tgggaagacc | agctggcctc | ggagaagaag | tgcggccacc | tgggcggcaa | ggtgctcatc | 600 |
| cccacccagc | agcacatccg | caccctgacc | tccgcgcgtc | tggccgccga | cgtggccggt | 660 |
| gtgccgaccg | tcgtcatcgc | ccgcaccgat | gccgaggccg | ccaccctgat | cacctccgac | 720 |
| gtggacgagc | gcgaccgccc | gttcatcacc | ggtgagcgca | cctccgaggg | cttctaccag | 780 |
| gtcaagaacg | gcatcgagcc | ctgcatcgcc | cgcgccaagg | cctacgcgcc | ctacgcggac | 840 |
| ctgatctgga | tggagaccgg | caccccggac | ctcgagctgg | ccaagaagtt | ctccgaggcc | 900 |
| gtgcgcagcg | agttcccgga | ccagctgctg | gcctacaact | gctcgccgtc | gttcaactgg | 960 |
| tcggcgcacc | tggacgacag | caccatcgcc | aagttccaga | aggagctggg | cgcgatgggc | 1020 |
| ttcaagttcc | agttcatcac | cctggcgggc | ttccactcgc | tcaactacgg | catgttcgac | 1080 |
| ctggcctacg | gctacgcccg | cgagggcatg | accgccttcg | tcgacctgca | gaaccgcgag | 1140 |
| ttcaaggccg | ccgaggagcg | tggcttcacc | gccatcaagc | accagcgcga | ggtcggcgcg | 1200 |
| ggctacttcg | acgccatcgc | caccaccgtc | gacccgaaca | cctcgacggc | cgcgctgaag | 1260 |
| ggctccaccg | aagagggtca | gttccactga | | | | 1290 |

<210> SEQ ID NO 68
<211> LENGTH: 429
<212> TYPE: PRT
<213> ORGANISM: Rhodococcus pyridinivorans AK37

<400> SEQUENCE: 68

Met Ser Thr Thr Gly Thr Pro Arg Thr Ala Glu Glu Ile Gln Lys Asp
1               5                   10                  15

Trp Asp Thr Asn Pro Arg Trp Lys Gly Ile Thr Arg Asn Tyr Thr Ala
            20                  25                  30

Glu Gln Val Ala Lys Leu Gln Gly Asn Val Val Glu Glu Ala Thr Leu
        35                  40                  45

Ala Arg Arg Gly Ser Glu Ile Leu Trp Asp Leu Val Asn Asn Glu Asp
    50                  55                  60

Tyr Ile Asn Ser Leu Gly Ala Leu Thr Gly Asn Gln Ala Val Gln Gln
65                  70                  75                  80

Val Arg Ala Gly Leu Lys Ala Ile Tyr Leu Ser Gly Trp Gln Val Ala
                85                  90                  95

Gly Asp Ala Asn Leu Ser Gly His Thr Tyr Pro Asp Gln Ser Leu Tyr
            100                 105                 110

Pro Ala Asn Ser Val Pro Gln Val Arg Arg Ile Asn Asn Ala Leu
            115                 120                 125

Leu Arg Ala Asp Glu Ile Ala Lys Val Glu Gly Asp Thr Ser Val Asp
            130                 135                 140

Asn Trp Leu Ala Pro Ile Val Ala Asp Gly Glu Ala Gly Phe Gly Gly
145                 150                 155                 160

Ala Leu Asn Val Tyr Glu Leu Gln Lys Ala Met Ile Ala Ala Gly Val
                165                 170                 175

Ala Gly Ser His Trp Glu Asp Gln Leu Ala Ser Glu Lys Lys Cys Gly
            180                 185                 190

His Leu Gly Gly Lys Val Leu Ile Pro Thr Gln Gln His Ile Arg Thr
            195                 200                 205

Leu Thr Ser Ala Arg Leu Ala Ala Asp Val Ala Asp Val Pro Thr Val
            210                 215                 220

Val Ile Ala Arg Thr Asp Ala Glu Ala Ala Thr Leu Ile Thr Ser Asp
225                 230                 235                 240

Val Asp Glu Arg Asp Arg Pro Phe Ile Thr Gly Glu Arg Thr Ala Glu
                245                 250                 255

Gly Phe Tyr His Val Lys Asn Gly Ile Glu Pro Cys Ile Ala Arg Ala
            260                 265                 270

Lys Ala Tyr Ala Pro Tyr Ser Asp Leu Ile Trp Met Glu Thr Gly Val
            275                 280                 285

Pro Asp Leu Glu Val Ala Lys Lys Phe Ala Glu Gly Val Arg Ser Glu
290                 295                 300

Phe Pro Asp Gln Leu Leu Ala Tyr Asn Cys Ser Pro Ser Phe Asn Trp
305                 310                 315                 320

Lys Ala His Leu Asp Asp Ala Thr Ile Ala Lys Phe Gln Lys Glu Leu
                325                 330                 335

Gly Ala Met Gly Phe Lys Phe Gln Phe Ile Thr Leu Ala Gly Phe His
            340                 345                 350

Ser Leu Asn Tyr Gly Met Phe Asp Leu Ala His Gly Tyr Ala Arg Glu
            355                 360                 365

Gly Met Thr Ala Phe Val Asp Leu Gln Glu Arg Glu Phe Lys Ala Ala
            370                 375                 380

Lys Glu Arg Gly Phe Thr Ala Ile Lys His Gln Arg Glu Val Gly Ala
385                 390                 395                 400

Gly Tyr Phe Asp Thr Ile Ala Thr Thr Val Asp Pro Asn Thr Ser Thr
                405                 410                 415

Ala Ala Leu Lys Gly Ser Thr Glu Glu Gly Gln Phe His
            420                 425

<210> SEQ ID NO 69
<211> LENGTH: 1290
<212> TYPE: DNA
<213> ORGANISM: Rhodococcus pyridinivorans AK37

<400> SEQUENCE: 69
atgtcgacca ccggcacccc gaggactgca gaagagatcc agaaggattg ggacaccaat      60
ccgcgctgga aggggatcac ccgcaactac accgccgagc aggtcgccaa gctgcagggc     120
aacgtcgtcg aggaagccac cctcgctcgc cgcggttccg agatcctgtg ggacctcgtc     180

```
aacaacgagg actacatcaa ctcgctcggc gccctcaccg gtaaccaggc ggtccagcag    240
gtccgcgccg gcctgaaggc catctacctc tccggttggc aggtcgccgg cgacgccaac    300
ctgtccggcc acacctaccc ggaccagtcg ctgtacccgg cgaactcggt tccgcaggtc    360
gtccgccgta tcaacaacgc gctgctgcgc gccgacgaga tcgccaaggt cgagggcgac    420
acttccgtcg acaactggct cgctccgatc gtcgccgacg gtgaggccgg cttcggtggc    480
gccctcaacg tctacgagct gcagaaggcc atgatcgcgg ccggcgtcgc cggttcccac    540
tgggaggacc agctcgcgtc ggagaagaag tgcggtcacc tcggtggcaa ggtgctcatc    600
cccacgcagc agcacatccg caccctgacc tcggctcgcc tcgcggccga cgtcgcggac    660
gtcccgaccg tggtcatcgc ccgcaccgac gccgaggccg cgaccctcat cacctccgat    720
gtcgacgagc gtgaccgccc gttcatcacc ggtgagcgca ccgccgaggg cttctaccac    780
gtcaagaacg gcatcgagcc ctgcatcgcc cgtgcgaagg cctacgctcc gtactccgac    840
ctcatctgga tggagaccgg tgttccggac ctcgaggtcg ccaagaagtt cgccgagggc    900
gtccgcagcg agttcccgga ccagctgctg gcctacaact gctcgccgtc cttcaactgg    960
aaggctcacc tggacgacgc gaccatcgcg aagttccaga aggagctcgg cgcgatgggc   1020
ttcaagttcc agttcatcac cctcgccggc ttccactcgc tcaactacgg catgttcgac   1080
ctggcgcacg gctacgcccg cgagggcatg acggccttcg tcgacctgca ggagcgcgag   1140
ttcaaggcgg ccaaggagcg cggcttcacc gccatcaagc accagcgtga ggtcggtgcc   1200
ggctacttcg acaccatcgc caccaccgtc gatcccaaca cctccacggc tgccctgaag   1260
ggctccaccg aggaaggcca gttccactag                                     1290

<210> SEQ ID NO 70
<211> LENGTH: 429
<212> TYPE: PRT
<213> ORGANISM: Rhodococcus jostii RHA1

<400> SEQUENCE: 70

Met Ser Thr Thr Gly Thr Pro Lys Thr Ala Ala Glu Ile Gln Gln Asp
1               5                   10                  15

Trp Asp Thr Asn Pro Arg Trp Lys Gly Val Thr Arg Asn Tyr Thr Ala
            20                  25                  30

Glu Gln Val Thr Lys Leu Gln Gly Thr Val Val Glu Glu Gln Thr Leu
        35                  40                  45

Ala Arg Arg Gly Ser Glu Ile Leu Trp Asp Leu Val Asn Asn Glu Asp
    50                  55                  60

Tyr Ile Asn Ser Leu Gly Ala Leu Thr Gly Asn Gln Ala Val Gln Gln
65                  70                  75                  80

Val Arg Ala Gly Leu Lys Ala Ile Tyr Leu Ser Gly Trp Gln Val Ala
                85                  90                  95

Gly Asp Ala Asn Leu Ser Gly His Thr Tyr Pro Asp Gln Ser Leu Tyr
            100                 105                 110

Pro Ala Asn Ser Val Pro Gln Val Val Arg Arg Ile Asn Asn Ala Leu
        115                 120                 125

Leu Arg Ala Asp Glu Ile Ala Lys Val Glu Gly Asp Thr Ser Val Asp
    130                 135                 140

Asn Trp Leu Ala Pro Ile Val Ala Asp Gly Glu Ala Gly Phe Gly Gly
145                 150                 155                 160

Ala Leu Asn Val Tyr Glu Leu Gln Lys Ala Met Ile Ala Ala Gly Val
                165                 170                 175
```

```
Ala Gly Ser His Trp Glu Asp Gln Leu Ala Ser Glu Lys Lys Cys Gly
            180                 185                 190

His Leu Gly Gly Lys Val Leu Val Pro Thr Gln His Ile Arg Thr
            195                 200                 205

Leu Thr Ser Ala Arg Leu Ala Ala Asp Val Ala Asp Val Pro Thr Val
210                 215                 220

Val Ile Ala Arg Thr Asp Ala Glu Ala Ala Thr Leu Ile Thr Ser Asp
225                 230                 235                 240

Val Asp Glu Arg Asp Gln Gln Phe Leu Asp Gly Thr Arg Thr Ala Glu
                245                 250                 255

Gly Phe Phe Gly Ile Lys Asn Gly Ile Glu Pro Cys Ile Ala Arg Ala
            260                 265                 270

Lys Ala Tyr Ala Pro Tyr Ala Asp Leu Ile Trp Met Glu Thr Gly Val
            275                 280                 285

Pro Asp Leu Glu Val Ala Lys Lys Phe Ala Glu Ser Val Arg Ser Glu
            290                 295                 300

Phe Pro Asp Gln Leu Leu Ala Tyr Asn Cys Ser Pro Ser Phe Asn Trp
305                 310                 315                 320

Lys Ala His Leu Asp Asp Ala Thr Ile Ala Lys Phe Gln Lys Glu Leu
                325                 330                 335

Gly Ala Met Gly Phe Lys Phe Gln Phe Ile Thr Leu Ala Gly Phe His
            340                 345                 350

Ser Leu Asn Tyr Gly Met Phe Asp Leu Ala His Gly Tyr Ala Arg Glu
            355                 360                 365

Gly Met Thr Ala Phe Val Asp Leu Gln Glu Arg Glu Phe Lys Ala Ala
            370                 375                 380

Glu Glu Arg Gly Phe Thr Ala Ile Lys His Gln Arg Glu Val Gly Ala
385                 390                 395                 400

Gly Tyr Phe Asp Ser Ile Ala Thr Thr Val Asp Pro Asn Thr Ser Thr
                405                 410                 415

Ala Ala Leu Lys Gly Ser Thr Glu Glu Gly Gln Phe His
            420                 425

<210> SEQ ID NO 71
<211> LENGTH: 1290
<212> TYPE: DNA
<213> ORGANISM: Rhodococcus jostii RHA1

<400> SEQUENCE: 71
atgtcgacca ccggcacccc gaagaccgca gctgaaatcc agcaggattg ggacaccaac      60
ccgcgctgga agggagtaac ccgcaactac acggcggagc aggtcaccaa gctccagggc     120
accgttgtcg aagagcagac cctcgcacgc cgtggttccg agatcctctg ggacctcgtg     180
aacaacgagg actacatcaa ctcgctgggc gcgctgaccg gcaaccaggc cgttcagcag     240
gtccgtgcag gcctcaaggc catctacctg tccggttggc aggtcgccgg tgacgcgaac     300
ctgtccggac ataccktaccc cgaccagagc ctctacccgg ccaactcggt cccgcaggtc     360
gtgcgccgca tcaacaatgc gctgctgcgt gccgacgaga tcgccaaggt cgagggcgac     420
acctccgtcg acaactggct cgccccgatc gtcgccgacg agaagcagg cttcggtggc     480 gcgctcaacg tctacgagct gcagaaggcc atgatcgcgg ccggcgtcgc cggttcgcac     540
tgggaagacc agctcgcgtc ggagaagaag tgtggccacc tcggtggcaa ggtcctcgtc     600
cccacgcagc agcacatccg caccctgacc tcggctcgcc tcgccgccga cgtcgcggac     660
```

```
gttcccaccg tggtcatcgc ccgcaccgat gccgaggccg cgaccctcat cacgtccgac    720
gtcgacgagc gcgaccagca gttcctggac ggaacccgca ccgccgaggg cttcttcggt    780
atcaagaacg gcatcgagcc ctgcatcgcg cgcgccaagg cctacgcccc gtacgccgac    840
ctcatctgga tggagaccgg cgtgccggac ctcgaggtcg ccaagaagtt cgccgagtcg    900
gttcgcagcg agttcccgga ccagctgctc gcgtacaact gctcgccgtc cttcaactgg    960
aaggcgcacc tggacgacgc caccatcgcg aagttccaga aggagctcgg cgcgatgggc   1020
ttcaagttcc agttcatcac cctggccggc ttccactcgc tcaactacgg catgttcgac   1080
ctggcgcacg gctacgcccg cgagggcatg accgccttcg tcgacctgca ggagcgcgag   1140
ttcaaggccg ccgaggagcg tggcttcacc gccatcaagc atcagcgtga ggtcggtgcc   1200
ggctacttcg acagcatcgc caccacggtc gaccccaaca cctcgacggc tgccctgaag   1260
ggctccaccg aagagggtca gttccactga                                   1290
```

<210> SEQ ID NO 72
<211> LENGTH: 57
<212> TYPE: PRT
<213> ORGANISM: Nicotiana tabacum

<400> SEQUENCE: 72

Met Ala Ser Ser Val Leu Ser Ser Ala Val Ala Thr Arg Ser Asn
1               5                   10                  15

Val Ala Gln Ala Asn Met Val Ala Pro Phe Thr Gly Leu Lys Ser Ala
            20                  25                  30

Ala Ser Phe Pro Val Ser Arg Lys Gln Asn Leu Asp Ile Thr Ser Ile
        35                  40                  45

Ala Ser Asn Gly Gly Arg Val Gln Cys
    50                  55

<210> SEQ ID NO 73
<211> LENGTH: 26
<212> TYPE: PRT
<213> ORGANISM: Arabidopsis thaliana

<400> SEQUENCE: 73

Met Arg Ile Leu Pro Lys Ser Gly Gly Gly Ala Leu Cys Leu Leu Phe
1               5                   10                  15

Val Phe Ala Leu Cys Ser Val Ala His Ser
            20                  25

<210> SEQ ID NO 74
<211> LENGTH: 9
<212> TYPE: PRT
<213> ORGANISM: Artificial
<220> FEATURE:
<223> OTHER INFORMATION: PTS-2 signal sequence
<220> FEATURE:
<221> NAME/KEY: misc_feature
<222> LOCATION: (3)..(7)
<223> OTHER INFORMATION: Xaa can be any naturally occurring amino acid

<400> SEQUENCE: 74

Arg Leu Xaa Xaa Xaa Xaa Xaa His Leu
1               5

<210> SEQ ID NO 75
<211> LENGTH: 10
<212> TYPE: PRT
<213> ORGANISM: Artificial
<220> FEATURE:

<223> OTHER INFORMATION: PTS-2 signal sequence

<400> SEQUENCE: 75

Met Arg Leu Ser Ile His Ala Glu His Leu
1               5                   10

<210> SEQ ID NO 76
<211> LENGTH: 85
<212> TYPE: PRT
<213> ORGANISM: Arabidopsis thaliana

<400> SEQUENCE: 76

Met Leu Arg Thr Val Ser Cys Leu Ala Ser Arg Ser Ser Ser Ser Leu
1               5                   10                  15

Phe Phe Arg Phe Phe Arg Gln Phe Pro Arg Ser Tyr Met Ser Leu Thr
                20                  25                  30

Ser Ser Thr Ala Ala Leu Arg Val Pro Ser Arg Asn Leu Arg Arg Ile
            35                  40                  45

Ser Ser Pro Ser Val Ala Gly Arg Arg Leu Leu Leu Arg Arg Gly Leu
        50                  55                  60

Arg Ile Pro Ser Ala Ala Val Arg Ser Val Asn Gly Gln Phe Ser Arg
65                  70                  75                  80

Leu Ser Val Arg Ala
                85

<210> SEQ ID NO 77
<211> LENGTH: 35
<212> TYPE: PRT
<213> ORGANISM: Chlamydomonas reinhardtii

<400> SEQUENCE: 77

Met Ala Leu Val Ala Arg Pro Val Leu Ser Ala Arg Val Ala Ala Ser
1               5                   10                  15

Arg Pro Arg Val Ala Ala Arg Lys Ala Val Arg Val Ser Ala Lys Tyr
                20                  25                  30

Gly Glu Asn
        35

<210> SEQ ID NO 78
<211> LENGTH: 29
<212> TYPE: PRT
<213> ORGANISM: Chlamydomonas reinhardtii

<400> SEQUENCE: 78

Met Gln Ala Leu Ser Ser Arg Val Asn Ile Ala Ala Lys Pro Gln Arg
1               5                   10                  15

Ala Gln Arg Leu Val Val Arg Ala Glu Glu Val Lys Ala
                20                  25

<210> SEQ ID NO 79
<211> LENGTH: 35
<212> TYPE: PRT
<213> ORGANISM: Chlamydomonas reinhardtii

<400> SEQUENCE: 79

Met Gln Thr Leu Ala Ser Arg Pro Ser Leu Arg Ala Ser Ala Arg Val
1               5                   10                  15

Ala Pro Arg Arg Ala Pro Arg Val Ala Val Thr Lys Ala Ala Leu
                20                  25                  30

Asp Pro Gln

<210> SEQ ID NO 80
<211> LENGTH: 31
<212> TYPE: PRT
<213> ORGANISM: Chlamydomonas reinhardtii

<400> SEQUENCE: 80

Met Gln Ala Leu Ala Thr Arg Pro Ser Ala Ile Arg Pro Thr Lys Ala
1               5                   10                  15

Ala Arg Arg Ser Ser Val Val Val Arg Ala Asp Gly Phe Ile Gly
            20                  25                  30

<210> SEQ ID NO 81
<211> LENGTH: 51
<212> TYPE: PRT
<213> ORGANISM: Chlamydomonas reinhardtii

<400> SEQUENCE: 81

Met Ala Phe Ala Leu Ala Ser Arg Lys Ala Leu Gln Val Thr Cys Lys
1               5                   10                  15

Ala Thr Gly Lys Lys Thr Ala Lys Ala Ala Ala Pro Lys Ser Ser
            20                  25                  30

Gly Val Glu Phe Tyr Gly Pro Asn Arg Ala Lys Trp Leu Gly Pro Tyr
        35                  40                  45

Ser Glu Asn
        50

<210> SEQ ID NO 82
<211> LENGTH: 50
<212> TYPE: PRT
<213> ORGANISM: Chlamydomonas reinhardtii

<400> SEQUENCE: 82

Met Ala Ala Val Ile Ala Lys Ser Ser Val Ser Ala Ala Val Ala Arg
1               5                   10                  15

Pro Ala Arg Ser Ser Val Arg Pro Met Ala Ala Leu Lys Pro Ala Val
            20                  25                  30

Lys Ala Ala Pro Val Ala Ala Pro Ala Gln Ala Asn Gln Met Met Val
        35                  40                  45

Trp Thr
    50

<210> SEQ ID NO 83
<211> LENGTH: 40
<212> TYPE: PRT
<213> ORGANISM: Chlamydomonas reinhardtii

<400> SEQUENCE: 83

Met Ala Ala Met Leu Ala Ser Lys Gln Gly Ala Phe Met Gly Arg Ser
1               5                   10                  15

Ser Phe Ala Pro Ala Pro Lys Gly Val Ala Ser Arg Gly Ser Leu Gln
            20                  25                  30

Val Val Ala Gly Leu Lys Glu Val
        35                  40

<210> SEQ ID NO 84
<211> LENGTH: 4
<212> TYPE: PRT
<213> ORGANISM: Arabidopsis thaliana

```
<400> SEQUENCE: 84

Cys Val Val Gln
1

<210> SEQ ID NO 85
<211> LENGTH: 9
<212> TYPE: PRT
<213> ORGANISM: Artificial
<220> FEATURE:
<223> OTHER INFORMATION: PTS-2 signal sequence

<400> SEQUENCE: 85

Arg Leu Ala Val Ala Val Ala His Leu
1               5
```

SYNTHETIC PATHWAY FOR BIOLOGICAL CARBON DIOXIDE SEQUESTRATION

STATEMENT OF PRIORITY

This application is a continuation-in-part of International Application No. PCT/US2016/043054, filed on Jul. 20, 2016, which claims the benefit, under 35 U.S.C. § 119 (e), of U.S. Provisional Application No. 62/194,446, filed on Jul. 20, 2015, the entire contents of which is incorporated by reference herein.

STATEMENT OF GOVERNMENT SUPPORT

This invention was made with government support under Grant No. DE-AR0000207 awarded by the United States Department of Energy (DOE). The United States government has certain rights in this invention.

STATEMENT REGARDING ELECTRONIC FILING OF A SEQUENCE LISTING

A Sequence Listing in ASCII text format, submitted under 37 C.F.R. § 1.821, entitled 5051-887_ST25.txt, 266,968 bytes in size, generated on Jul. 18, 2016 and filed via EFS-Web, is provided in lieu of a paper copy. This Sequence Listing is hereby incorporated herein by reference into the specification for its disclosures.

FIELD OF THE INVENTION

The present invention relates to methods for increasing carbon fixation and biomass production in plants.

BACKGROUND

All life depends on photosynthetic carbon fixation in which $CO_2$ is converted to organic compounds in the presence of water and light. However, this is an inefficient process, particularly in $C_3$ plants, because of a competing process called photorespiration. Photorespiration results in the release of about a quarter of the carbon that is fixed by photosynthesis. The inefficiency of $C_3$ photosynthesis is largely due to the enzyme ribulose-1,5-bisphosphate carboxylase oxygenase (Rubisco) that catalyzes two competing reactions, carboxylation and oxygenation. Carboxylation leads to net fixed carbon dioxide and oxygenation utilizes oxygen and results in a net loss of carbon. The relative concentrations of carbon dioxide and oxygen and the temperature as well as water availability determine which reaction occurs or dominates. Thus, $C_3$ plants do not grow efficiently in hot and/or dry areas because, as the temperature increases, Rubisco incorporates more oxygen. Some plants, such as $C_4$ and CAM (Crassulacean acid metabolism) plants, have developed mechanisms that reduce the effect of photorespiration by more efficiently delivering carbon dioxide to Rubisco, thereby outcompeting the oxygenase activity.

SUMMARY OF THE INVENTION

This invention is directed to methods for improving the efficiency of $CO_2$ fixation and increasing biomass production in plants.

Thus, in one aspect, the present invention provides a method for increasing carbon fixation and/or increasing biomass production in a plant, comprising: introducing into a plant, plant part, and/or plant cell a heterologous polynucleotide encoding a succinyl CoA synthetase polypeptide to produce a stably transformed plant, plant part, and/or plant, wherein the heterologous polynucleotide is from a bacterial or an archaeal species.

In another aspect, the present invention provides a method for increasing carbon fixation and/or increasing biomass production in a plant, comprising: introducing into a plant, plant part, and/or plant cell a heterologous polynucleotide encoding a 2-oxoglutarate:ferredoxin oxidoreductase polypeptide to produce a stably transformed plant, plant part, and/or plant, wherein the heterologous polynucleotide is from a bacterial or an archaeal species.

In still another aspect, a method for increasing carbon fixation and/or increasing biomass production in a plant is provided, comprising: introducing into a plant, plant part, and/or plant cell a heterologous polynucleotide encoding a 2-oxoglutarate carboxylase polypeptide to produce a stably transformed plant, plant part, and/or plant cell, wherein said heterologous polynucleotide is from a bacterial or an archaeal species.

In a further aspect, a method for increasing carbon fixation and/or increasing biomass production in a plant, comprising: introducing into a plant, plant part, and/or plant cell a heterologous polynucleotide encoding an oxalosuccinate reductase polypeptide to produce a stably transformed plant, plant part, and/or plant cell, wherein said heterologous polynucleotide is from a bacterial or an archaeal species.

In another aspect, the invention provides a method for increasing carbon fixation and/or increasing biomass production in a plant, comprising: introducing into a plant, plant part, and/or plant cell a heterologous polynucleotide encoding an isocitrate lyase polypeptide to produce a stably transformed plant, plant part, and/or plant cell, wherein said heterologous polynucleotide is from a bacterial or an archaeal species.

In an additional aspect of the invention, a method for increasing carbon fixation and/or increasing biomass production in a plant is provided, comprising: introducing into a plant, plant part, and/or plant cell a heterologous polynucleotide encoding a succinyl CoA synthetase polypeptide and a heterologous polynucleotide encoding a 2-oxoglutarate:ferredoxin oxidoreductase polypeptide to produce a stably transformed plant, plant part, and/or plant cell, wherein said heterologous polynucleotide encoding a succinyl CoA synthetase polypeptide and said heterologous polynucleotide encoding a 2-oxoglutarate:ferredoxin oxidoreductase polypeptide are from a bacterial or an archaeal species.

In a further aspect, a method for increasing carbon fixation and/or increasing biomass production in a plant is provided, comprising: introducing into a plant, plant part, and/or plant cell a heterologous polynucleotide encoding a 2-oxoglutarate carboxylase polypeptide and a heterologous polynucleotide encoding an oxalosuccinate reductase polypeptide to produce a stably transformed plant, plant part, and/or plant cell, wherein said heterologous polynucleotide encoding a 2-oxoglutarate carboxylase polypeptide and said heterologous polynucleotide encoding an oxalosuccinate reductase polypeptide are from a bacterial and/or an archaeal species. In a further aspect, the method optionally additionally comprises introducing into the plant, plant part, and/or plant cell a heterologous polynucleotide encoding an isocitrate lyase polypeptide, wherein said heterologous polynucleotide encoding isocitrate lyase is from a bacterial or archaeal species.

In a further aspect, the present invention provides stably transformed plants, plant parts and/or plant cells, seeds from said stably transformed plants, and crops comprising said stably transformed plants.

In additional aspects, the present invention provides products produced from the transformed plants, plant parts and/or plant cells, seeds and/or crops of this invention.

The foregoing and other objects and aspects of the present invention are explained in detail in the drawings and specification set forth below.

BRIEF DESCRIPTION OF THE DRAWINGS

FIG. 14 shows metabolites in both the synthetic pathway and the Krebs cycle (left panel) and metabolites exclusive to the Krebs cycle (right panel).

FIG. 18 provides a schematic showing the role of PEP carboxylase, PEP carboxy kinase, malic enzyme and pyruvate carboxylase (upper panel) and the pyruvate and oxaloacetate levels (left panel) and pyruvate and alanine levels in in WT and transgenic lines.

FIGS. 26A-26C shows respective protein levels (western blots) for each transgene; immunoblot developed with colorimetric staining (FIG. 26A) and immunoblot developed with ECL (FIG. 26B, FIG. 26C).

DETAILED DESCRIPTION

Figure 1:
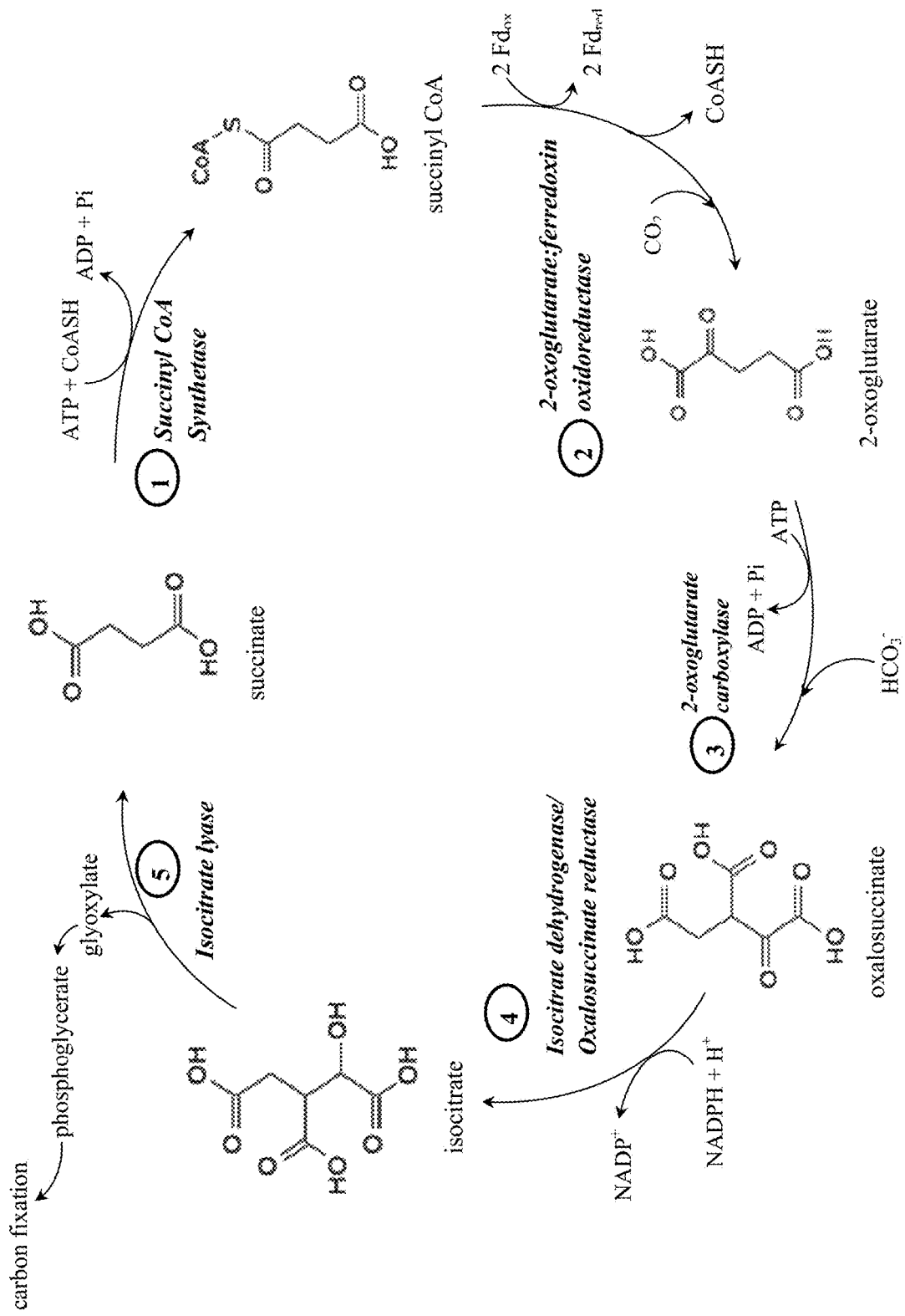
FIG. 1 shows a schematic for the condensed reverse tricarboxylic acid (crTCA) cycle.

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention.

Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, means variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The terms "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

"Complement" as used herein can mean 100% complementarity or identity with the comparator nucleotide sequence or it can mean less than 100% complementarity (e.g., about 80%, 81%, 82%, 83%, 84%, 85%, 86%, 87%, 88%, 89%, 90%, 91%, 92%, 93%, 94%, 95%, 96%, 97%, 98%, 99%, and the like, complementarity).

The terms "complementary" or "complementarity," as used herein, refer to the natural binding of polynucleotides under permissive salt and temperature conditions by base-pairing. For example, the sequence "5'-A-G-T-3" binds to the complementary sequence "3'-A-C-T-5'." Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

As used herein, the terms "express," "expresses," "expressed" or "expression," and the like, with respect to a nucleotide sequence (e.g., RNA or DNA) indicates that the nucleotide sequence is transcribed and, optionally, translated. Thus, a nucleotide sequence may express a polypeptide of interest or a functional untranslated RNA. A "functional" RNA includes any untranslated RNA that has a biological function in a cell, e.g., regulation of gene expression. Such functional RNAs include but are not limited to RNAi (e.g., siRNA, shRNA), miRNA, antisense RNA, ribozymes, RNA aptamers, and the like.

As used herein, the terms "fragment" when used in reference to a polynucleotide will be understood to mean a nucleic acid molecule or polynucleotide of reduced length relative to a reference nucleic acid molecule or polynucleotide and comprising, consisting essentially of and/or consisting of a nucleotide sequence of contiguous nucleotides identical or almost identical (e.g., 30%, 35%, 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleic acid or nucleotide sequence. Such a nucleic acid fragment according to the invention may be, where appropriate, included in a larger polynucleotide of which it is a constituent.

As used herein, a "functional" polypeptide or "functional fragment" is one that substantially retains at least one biological activity normally associated with that polypeptide. In particular embodiments, the "functional" polypeptide or "functional fragment" substantially retains all of the activities possessed by the unmodified peptide. By "substantially retains" biological activity, it is meant that the polypeptide retains at least about 50%, 55%, 60%, 65%, 70%, 75%, 80%, 85%, 90%, 91%, 92%, 93%, 94%, 95%, 96%, 97%, 98%, 99%, or more, of the biological activity of the native polypeptide (and can even have a higher level of activity than the native polypeptide). A "non-functional" polypeptide is one that exhibits little or essentially no detectable biological activity normally associated with the polypeptide (e.g., at most, only an insignificant amount, e.g., less than about 10% or even 5%).

As used herein, the term "gene" refers to a nucleic acid molecule capable of being used to produce mRNA, antisense RNA, miRNA, and the like. Genes may or may not be capable of being used to produce a functional protein. Genes can include both coding and non-coding regions (e.g., introns, regulatory elements, promoters, enhancers, termination sequences and 5' and 3' untranslated regions). A gene may be "isolated" by which is meant a nucleic acid molecule that is substantially or essentially free from components normally found in association with the nucleic acid molecule in its natural state. Such components include other cellular material, culture medium from recombinant production, and/or various chemicals used in chemically synthesizing the nucleic acid molecule.

"Genome" as used herein can refer to the nuclear genome, the chloroplast genome, the mitochondrial genome and/or a plasmid genome.

A "heterologous" or a "recombinant" nucleotide sequence is a nucleotide sequence not naturally associated with a host cell into which it is introduced, including non-naturally occurring multiple copies of a naturally occurring nucleotide sequence.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to said nucleotide sequence of the invention.

As used herein, hybridization, hybridize, hybridizing, and grammatical variations thereof, refer to the binding of two complementary nucleotide sequences or substantially complementary sequences in which some mismatched base pairs are present. The conditions for hybridization are well known in the art and vary based on the length of the nucleotide sequences and the degree of complementarity between the nucleotide sequences. In some embodiments, the conditions of hybridization can be high stringency, or they can be medium stringency or low stringency depending on the amount of complementarity and the length of the sequences to be hybridized. The conditions that constitute low, medium and high stringency for purposes of hybridization between nucleotide sequences are well known in the art (See, e.g., Gasiunas et al. (2012) *Proc. Natl. Acad. Sci.* 109:E2579-E2586; M. R. Green and J. Sambrook (2012) Molecular Cloning: A Laboratory Manual. 4th Ed., Cold Spring Harbor Laboratory Press, Cold Spring Harbor, N.Y.).

Two nucleotide sequences can also be considered to be substantially complementary when the two sequences hybridize to each other under stringent conditions. A non-limiting example of "stringent" hybridization conditions include conditions represented by a wash stringency of 50% formamide with 5×Denhardt's solution, 0.5% SDS and 1×SSPE at 42° C. "Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). In some representative embodiments, two nucleotide sequences considered to be substantially identical hybridize to each other under highly stringent conditions. Generally, highly stringent hybridization and wash conditions are selected to be about 5° C. lower than the thermal melting point ($T_m$) for the specific sequence at a defined ionic strength and pH.

An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). In some embodiments, "percent identity" can refer to the percentage of identical amino acids in an amino acid sequence.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

Optimal alignment of sequences for aligning a comparison window is well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BEST-FIT, FASTA, and TFASTA available as part of the GCG® Wisconsin Package® (Accelrys Inc., Burlington, Mass.). The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (Smith and Waterman, *Adv. Appl. Math.,* 2:482-489, 1981, Smith et al., *Nucleic Acids Res.* 11:2205-2220, 1983).

Useful methods for determining sequence identity are also disclosed in *Guide to Huge Computers* (Martin J. Bishop, ed., Academic Press, San Diego (1994)), and Carillo et al. (*Applied Math* 48:1073(1988)). More particularly, preferred computer programs for determining sequence identity include but are not limited to the Basic Local Alignment Search Tool (BLAST) programs which are publicly available from National Center Biotechnology Information (e.g., NCBI) at the National Library of Medicine, National Institute of Health, Bethesda, Md. 20894; see *BLAST Manual*, Altschul et al., e.g., NCBI, NLM, NIH; (Altschul et al., *J Mol. Biol.* 215:403-410 (1990)); version 2.0 or higher of BLAST programs allows the introduction of gaps (deletions and insertions) into alignments; for peptide sequence BLASTX can be used to determine sequence identity; and for polynucleotide sequence BLASTN can be used to determine sequence identity.

The terms "increase," "increasing," "increased," "enhance," "enhanced," "enhancing," and "enhancement" (and grammatical variations thereof), as used herein, describe an elevation in, for example, carbon fixation and/or biomass production, and/or an elevation in $CO_2$ uptake in a plant, plant part or plant cell, or in a photosynthetic bacterium. This increase can be observed by comparing the increase in the plant, plant part or plant cell, or photosynthetic bacterium transformed with, for example, a heterologous polynucleotide encoding a bacterial or archaeal succinyl CoA synthetase, 2-oxoglutarate:ferredoxin oxidoreductase, 2-oxoglutarate carboxylase, oxalosuccinate reductase or isocitrate lyase as compared to an appropriate control (e.g., the same organism (e.g., the same species of plant, plant part or plant cell, or photosynthetic bacterium) lacking (i.e., not transformed with) said heterologous polynucleotide(s)). Thus, as used herein, the terms "increase," "increasing," "increased," "enhance," "enhanced," "enhancing," and "enhancement" (and grammatical variations thereof), and similar terms indicate an elevation of at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more, or any range therein, as compared to a control (e.g., a plant, plant part and/or plant cell, or photosynthetic bacterium that does not comprise said heterologous polynucleotide).

"Increased biomass production" as used herein refers to a transformed plant or plant part having a greater dry weight over the entire plant or any organ of the plant (leaf, stem, roots, seeds, seed pods, flowers, etc), increased plant height, leaf number, and/or seed number or increased root volume compared to the native or wild type (e.g., a plant, plant part that is not transformed with the heterologous polynucleotides of the invention (e.g., heterologous polynucleotides encoding a succinyl CoA synthetase polypeptide, a 2-oxoglutarate:ferredoxin oxidoreductase polypeptide, a 2-oxoglutarate carboxylase polypeptide, an oxalosuccinate reductase polypeptide and/or an isocitrate lyase polypeptide). "Increased biomass production" can also refer to a greater dry weight of cells (e.g., tissue culture, cell suspension (e.g., algal culture, photosynthetic bacterial culture) and the like) as compared to cells not transformed with the heterologous polynucleotides of the invention.

"Increased carbon fixation" as used herein refers to a greater conversion of $CO_2$ to organic carbon compounds in a transgenic plant (e.g., a plant, plant part that is not transformed with the heterologous polynucleotides of the invention (e.g., heterologous polynucleotides encoding a succinyl CoA synthetase polypeptide, a 2-oxoglutarate: ferredoxin oxidoreductase polypeptide, a 2-oxoglutarate carboxylase polypeptide, an oxalosuccinate reductase polypeptide, and/or an isocitrate lyase polypeptide) when compared to the native or wild type (e.g., not transformed with said heterologous polynucleotides). "Increased carbon fixation" can be measured by analyzing $CO_2$ fixation rates using a Licor System or radiolabeled $^{14}CO_2$ or by quantifying dry biomass. Increased carbon fixation can also occur for transformed cells (e.g., tissue culture, cell suspension (e.g., algal culture, photosynthetic bacterial culture), and the like) as compared to cells not transformed with the heterologous polynucleotides of the invention.

In some embodiments, the recombinant nucleic acids molecules, nucleotide sequences and polypeptides of the invention are "isolated." An "isolated" nucleic acid molecule, an "isolated" nucleotide sequence or an "isolated" polypeptide is a nucleic acid molecule, nucleotide sequence or polypeptide that, by the hand of man, exists apart from its native environment and is therefore not a product of nature. An isolated nucleic acid molecule, nucleotide sequence or polypeptide may exist in a purified form that is at least partially separated from at least some of the other components of the naturally occurring organism or virus, for example, the cell or viral structural components or other polypeptides or nucleic acids commonly found associated with the polynucleotide. In representative embodiments, the isolated nucleic acid molecule, the isolated nucleotide sequence and/or the isolated polypeptide is at least about 1%, 5%, 10%, 20%, 30%, 40%, 50%, 60%, 70%, 80%, 90%, 95%, or more pure.

In other embodiments, an isolated nucleic acid molecule, polynucleotide or polypeptide may exist in a non-native environment such as, for example, a recombinant host cell. Thus, for example, with respect to nucleotide sequences, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the polynucleotides and their encoded polypeptides are "isolated" in that, by the hand of man, they exist apart from their native environment and therefore are not products of nature, however, in some embodiments, they can be introduced into and exist in a recombinant host cell.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "oligonucleotide" and "polynucleotide" are also used interchangeably herein to refer to a heteropolymer of nucleotides. Nucleic acid sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

By "operably linked" or "operably associated," it is meant that the indicated elements are functionally related to each other, and are also generally physically related. Thus, the term "operably linked" or "operably associated" as used herein, refers to nucleotide sequences on a single nucleic acid molecule that are functionally associated. Therefore, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a nucleotide sequence, and the promoter can still be considered "operably linked" to the nucleotide sequence.

Any plant (or groupings of plants, for example, into a genus or higher order classification) can be employed in practicing this invention including an angiosperm, a gymnosperm, a monocot, a dicot, a C3, C4, CAM plant, a microalgae, and/or a macroalgae. The methods of the present invention may additionally be practiced with photosynthetic bacteria.

The term "plant part," as used herein, includes but is not limited to reproductive tissues (e.g., petals, sepals, stamens, pistils, receptacles, anthers, pollen, flowers, fruits, flower bud, ovules, seeds, embryos, nuts, kernels, ears, cobs and husks); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomata, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts and callus.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ. In some embodiments, a plant cell can be an algal cell.

In some embodiments of this invention, a plant, plant part or plant cell can be from a genus including, but not limited to, the genus of *Camelina, Sorghum, Gossypium, Brassica, Allium, Armoracia, Poa, Agrostis, Lolium, Festuca, Calamogrostis, Deschampsia, Spinacia, Beta, Pisum, Chenopodium, Helianthus, Pastinaca, Daucus, Petroselium, Populus, Prunus, Castanea, Eucalyptus, Acer, Quercus, Salix, Juglans, Picea, Pinus, Abies, Lemna, Wolffia, Spirodela, Oryza* or *Gossypium*.

In other embodiments, a plant, plant part or plant cell can be from a species including, but not limited to, the species of *Camelina alyssum* (Mill.) Thell., *Camelina microcarpa* Andrz. ex DC., *Camelina rumelica* Velen., *Camelina sativa* (L.) Crantz, *Sorghum bicolor* (e.g., *Sorghum bicolor* L. Moench), *Gossypium hirsutum, Brassica oleracea, Brassica rapa, Brassica napus, Raphanus sativus, Armoracia rusticana, Allium sative, Allium cepa, Populus grandidentata, Populus tremula, Populus tremuloides, Prunus serotina, Prunus pensylvanica, Castanea dentate, Populus balsamifer, Populus deltoids, Acer Saccharum*, Acer *nigrum, Acer negundo, Acer rubrum, Acer saccharinum, Acer pseudoplatanus* or *Oryza sativa*. In additional embodiments, the plant, plant part or plant cell can be, but is not limited to, a plant of, or a plant part, or plant cell from wheat, barley, oats, turfgrass (bluegrass, bentgrass, ryegrass, fescue), feather reed grass, tufted hair grass, spinach, beets, chard, *quinoa*, sugar beets, lettuce, sunflower (*Helianthus annuus*), peas (*Pisum sativum*), parsnips (*Pastinaca sativa*), carrots (*Daucus carota*), parsley (*Petroselinum crispum*), duckweed, pine, spruce, fir, *eucalyptus*, oak, walnut, or willow. In particular embodiments, the plant, plant part and/or plant cell can be from *Camelina sativa*.

In further embodiments, a plant and/or plant cell can be an alga or alga cell from a class including, but not limited to, the class of Bacillariophyceae (diatoms), Haptophyceae, Phaeophyceae (brown algae), Rhodophyceae (red algae) or Glaucophyceae (red algae). In still other embodiments, a plant and/or plant cell can be an algae or algae cell from a genus including, but not limited to, the genus of *Achnanthidium, Actinella, Nitzschia, Nupela, Geissleria, Gomphonema, Planothidium, Halamphora, Psammothidium, Navicula, Eunotia, Stauroneis, Chlamydomonas, Dunaliella, Nannochloris, Nannochloropsis, Scenedesmus, Chlorella, Cyclotella, Amphora, Thalassiosira, Phaeodactylum, Chrysochromulina, Prymnesium, Thalassiosira, Phaeodactylum, Glaucocystis, Cyanophora, Galdieria*, or *Porphyridium*. Additional nonlimiting examples of genera and species of diatoms useful with this invention are provided by the US Geological Survey/Institute of Arctic and Alpine Research at westerndiatoms.colorado.edu/species.

In some embodiments, photosynthetic bacteria useful with this invention includes, but is not limited to, cyanobacteria, *Synechococcus* spp., *Synechocystis* spp., *Prochlorococcus* spp., purple bacteria including but not limited to Rhodospirillaceae or nitrogen-fixing cyanobacteria including but not limited to *Anabena* spp.

As used herein, the terms "reduce," "reduced," "reducing," "reduction," "diminish," "suppress," and "decrease" (and grammatical variations thereof) mean a decrease of at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100%, or any range therein, as compared to a control.

As used herein, the term "substantially identical" means that two nucleotide sequences have at least 70%, 75%, 80%, 85%, 90%, 91%, 92%, 93%, 94%, 95%, 96%, 97%, 98%, 99% or 100% sequence identity. Thus, for example, a homolog of a polynucleotide of the invention can have at least about 70%, 75%, 80%, 81%, 82%, 83%, 84%, 85%, 86%, 87%, 88%, 89%, 90%, 91%, 92%, 93%, 94%, 95%, 96%, 97%, 98%, 99% or more sequence identity to, for example, a polynucleotide encoding a succinyl CoA synthetase polypeptide, a 2-oxoglutarate:ferredoxin oxidoreductase polypeptide, a 2-oxoglutarate carboxylase polypeptide, a oxalosuccinate reductase polypeptide and/or a isocitrate lyase polypeptide.

As used herein, the terms "transformed" and "transgenic" refer to any plant, plant part, and/or plant cell that contains all or part of at least one recombinant (e.g., heterologous) polynucleotide. In some embodiments, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

The term "transgene" as used herein, refers to any nucleotide sequence used in the transformation of an organism. Thus, a transgene can be a coding sequence, a non-coding sequence, a cDNA, a gene or fragment or portion thereof, a genomic sequence, a regulatory element and the like. A "transgenic" organism, such as a transgenic plant, transgenic yeast, or transgenic bacterium, is an organism into which a transgene has been delivered or introduced and the transgene can be expressed in the transgenic organism to produce a product, the presence of which can impart an effect and/or a phenotype in the organism.

The term "transformation" as used herein refers to the introduction of a heterologous polynucleotide into a cell. Transformation of a plant, plant part, plant cell, yeast cell and/or bacterial cell may be stable or transient.

"Transient transformation" in the context of a polynucleotide means that a polynucleotide is introduced into the cell and does not integrate into the genome of the cell.

By "stably introducing" or "stably introduced" in the context of a polynucleotide introduced into a cell it is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein also includes the nuclear and the plastid genome, and therefore includes integration of the nucleic acid into, for example, the chloroplast genome. Stable transformation as used herein can also refer to a transgene that is maintained extrachromosomally, for example, as a minichromosome. The phrase "a stably transformed plant, plant part, and/or plant cell expressing said one or more polynucleotide sequences" and similar phrases used herein, means that the stably transformed plant, plant part, and/or plant cell comprises the one or more polynucleotide sequences and that said one or more polynucleotide sequences are functional in said stably transformed plant, plant part, and/or plant cell.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods. Transformation can also be detected by direct sequencing and/or hybridization protocols that are well known in the art.

Accordingly, the present invention is directed to compositions and methods for increasing carbon fixation and biomass production in a plant, plant cell and/or plant part, or in a photosynthetic bacterium by introducing in the plant, plant cell and/or plant part, or into the photosynthetic bacterium heterologous polynucleotides that encode polypeptides for the biological carbon sequestration/crTCA cycle enzymes as described herein.

Thus, in some embodiments, the present invention provides a method for increasing carbon fixation and/or increasing biomass production in a plant, comprising, consisting essentially of, or consisting of: introducing into a plant, plant part, and/or plant cell a heterologous polynucleotide encoding a succinyl CoA synthetase polypeptide to produce a stably transformed plant, plant part, and/or plant cell expressing said heterologous polynucleotide, thereby increasing carbon fixation and/or increasing biomass production in said stably transformed plant, plant part, and/or plant cell as compared to a control (e.g., a plant not comprising said heterologous polynucleotide), wherein the heterologous polynucleotide is from a bacterial and/or an archaeal species.

In another embodiment, a method for increasing carbon fixation and/or increasing biomass production in a plant is provided, comprising, consisting essentially of, or consisting of: introducing into a plant, plant part, and/or plant cell a heterologous polynucleotide encoding a 2-oxoglutarate:ferredoxin oxidoreductase polypeptide to produce a stably transformed plant, plant part, and/or plant cell expressing said heterologous polynucleotide, thereby increasing carbon fixation and/or increasing biomass production in said stably transformed plant, plant part, and/or plant cell as compared to a control, wherein the heterologous polynucleotide is from a bacterial and/or an archaeal species.

In additional embodiments, a method for increasing carbon fixation and/or increasing biomass production in a plant is provided, comprising, consisting essentially of, or consisting of: introducing into a plant, plant part, and/or plant cell a heterologous polynucleotide encoding a 2-oxoglutarate carboxylase polypeptide to produce a stably transformed plant, plant part, and/or plant cell expressing said heterologous polynucleotide, thereby increasing carbon fixation and/or increasing biomass production in said stably transformed plant, plant part, and/or plant cell as compared to a control, wherein the heterologous polynucleotide is from a bacterial and/or an archaeal species.

In some embodiments, a method for increasing carbon fixation and/or increasing biomass production in a plant is provided, comprising, consisting essentially of, or consisting of: introducing into a plant, plant part, and/or plant cell a heterologous polynucleotide encoding an isocitrate dehydrogenase/oxalosuccinate reductase polypeptide (both isocitrate dehydrogenase (ICDH) and oxalosuccinate reductase (OSR) are appropriate names for the enzyme catalyzing step four of the crTCA cycle) to produce a stably transformed plant, plant part, and/or plant cell expressing said heterologous polynucleotide, thereby increasing carbon fixation and/or increasing biomass production in said stably transformed plant, plant part, and/or plant cell as compared to a control, wherein the heterologous polynucleotide is from a bacterial and/or an archaeal species.

In further embodiments, a method for increasing carbon fixation and/or increasing biomass production in a plant is provided, comprising, consisting essentially of, or consisting of: introducing into a plant, plant part, and/or plant cell a heterologous polynucleotide encoding an isocitrate lyase polypeptide to produce a stably transformed plant, plant part, and/or plant cell expressing said heterologous polynucleotide, thereby increasing carbon fixation and/or increasing biomass production in said stably transformed plant as compared to a control, wherein the heterologous polynucleotide is from a bacterial and/or an archaeal species.

In still further embodiments, a method for increasing carbon fixation and/or increasing biomass production in a plant is provided, comprising, consisting essentially of, or consisting of: introducing into a plant, plant part, and/or plant cell a heterologous polynucleotide encoding a succinyl CoA synthetase polypeptide and a heterologous polynucleotide encoding a 2-oxoglutarate:ferredoxin oxidoreductase polypeptide to produce a stably transformed plant, plant part, and/or plant cell expressing said heterologous polynucleotides, thereby increasing carbon fixation and/or increasing biomass production in said stably transformed plant, plant part, and/or plant cell as compared to a control, wherein the heterologous polynucleotide encoding a succinyl CoA synthetase polypeptide and the heterologous polynucleotide encoding a 2-oxoglutarate:ferredoxin oxidoreductase polypeptide are from a bacterial and/or an archaeal species.

In some embodiments, a method for increasing carbon fixation and/or increasing biomass production in a plant is provided, comprising, consisting essentially of, or consisting of: introducing into a plant, plant part, and/or plant cell a heterologous polynucleotide encoding a 2-oxoglutarate carboxylase polypeptide and a heterologous polynucleotide encoding an oxalosuccinate reductase polypeptide to produce a stably transformed plant, plant part, and/or plant cell expressing said heterologous polynucleotides, thereby increasing carbon fixation and/or increasing biomass production in said stably transformed plant, plant part, and/or plant cell as compared to a control, wherein the heterologous polynucleotide encoding a 2-oxoglutarate carboxylase polypeptide and the heterologous polynucleotide encoding an oxalosuccinate reductase polypeptide are from a bacterial and/or an archaeal species.

In further embodiments, a method for increasing carbon fixation and/or increasing biomass production in a plant is provided, comprising, consisting essentially of, or consisting of: introducing into a plant, plant part, and/or plant cell a heterologous polynucleotide encoding a 2-oxoglutarate carboxylase polypeptide, a heterologous polynucleotide encoding an oxalosuccinate reductase polypeptide and a heterologous polynucleotide encoding an isocitrate lyase polypeptide to produce a stably transformed plant, plant part, and/or plant cell expressing said heterologous polynucleotides, thereby increasing carbon fixation and/or increasing biomass production in said stably transformed plant, plant part, and/or plant cell as compared to a control, wherein the heterologous polynucleotide encoding a 2-oxoglutarate carboxylase polypeptide, the heterologous polynucleotide encoding an oxalosuccinate reductase polypeptide and the heterologous polynucleotide encoding an isocitrate lyase polypeptide are from a bacterial and/or an archaeal species.

Thus, in some embodiments, the present invention provides a method for increasing carbon fixation and/or increasing biomass production in a photosynthetic bacterium, comprising, consisting essentially of, or consisting of: introducing into a photosynthetic bacterium a heterologous polynucleotide encoding a succinyl CoA synthetase polypeptide to produce a stably transformed photosynthetic bacterium expressing said heterologous polynucleotide, thereby increasing carbon fixation and/or increasing biomass production in said stably transformed photosynthetic bacterium as compared to a control (e.g., a photosynthetic bacterium not comprising said heterologous polynucleotide), wherein the heterologous polynucleotide is from a bacterial and/or an archaeal species.

In another embodiment, a method for increasing carbon fixation and/or increasing biomass production in a photosynthetic bacterium is provided, comprising, consisting essentially of, or consisting of: introducing into a photosynthetic bacterium a heterologous polynucleotide encoding a 2-oxoglutarate:ferredoxin oxidoreductase polypeptide to produce a stably transformed photosynthetic bacterium expressing said heterologous polynucleotide, thereby increasing carbon fixation and/or increasing biomass production in said stably transformed photosynthetic bacterium as compared to a control, wherein the heterologous polynucleotide is from a bacterial and/or an archaeal species.

In additional embodiments, a method for increasing carbon fixation and/or increasing biomass production in a photosynthetic bacterium is provided, comprising, consisting essentially of, or consisting of: introducing into a photosynthetic bacterium a heterologous polynucleotide encoding a 2-oxoglutarate carboxylase polypeptide to produce a stably transformed photosynthetic bacterium expressing said heterologous polynucleotide, thereby increasing carbon fixation and/or increasing biomass production in said stably transformed photosynthetic bacterium as compared to a control, wherein the heterologous polynucleotide is from a bacterial and/or an archaeal species.

In some embodiments, a method for increasing carbon fixation and/or increasing biomass production in a photosynthetic bacterium is provided, comprising, consisting essentially of, or consisting of: introducing into a photosynthetic bacterium a heterologous polynucleotide encoding an isocitrate dehydrogenase/oxalosuccinate reductase polypeptide (both isocitrate dehydrogenase (ICDH) and oxalosuccinate reductase (OSR) are appropriate names for the enzyme catalyzing step four of the crTCA cycle) to produce a stably transformed photosynthetic bacterium expressing said heterologous polynucleotide, thereby increasing carbon fixation and/or increasing biomass production in said stably transformed photosynthetic bacterium as compared to a control, wherein the heterologous polynucleotide is from a bacterial and/or an archaeal species.

In further embodiments, a method for increasing carbon fixation and/or increasing biomass production in a photosynthetic bacterium is provided, comprising, consisting essentially of, or consisting of: introducing into a photosynthetic bacterium a heterologous polynucleotide encoding an isocitrate lyase polypeptide to produce a stably transformed photosynthetic bacterium expressing said heterologous polynucleotide, thereby increasing carbon fixation and/or increasing biomass production in said stably transformed photosynthetic bacterium as compared to a control, wherein the heterologous polynucleotide is from a bacterial and/or an archaeal species.

In still further embodiments, a method for increasing carbon fixation and/or increasing biomass production in a photosynthetic bacterium is provided, comprising, consisting essentially of, or consisting of: introducing into a photosynthetic bacterium a heterologous polynucleotide encoding a succinyl CoA synthetase polypeptide and a heterologous polynucleotide encoding a 2-oxoglutarate:ferredoxin oxidoreductase polypeptide to produce a stably transformed photosynthetic bacterium expressing said heterologous polynucleotides, thereby increasing carbon fixation and/or increasing biomass production in said stably transformed photosynthetic bacterium as compared to a control, wherein the heterologous polynucleotide encoding a succinyl CoA synthetase polypeptide and the heterologous polynucleotide encoding a 2-oxoglutarate:ferredoxin oxidoreductase polypeptide are from a bacterial and/or an archaeal species.

In some embodiments, a method for increasing carbon fixation and/or increasing biomass production in a photosynthetic bacterium is provided, comprising, consisting essentially of, or consisting of: introducing into a photosynthetic bacterium a heterologous polynucleotide encoding a 2-oxoglutarate carboxylase polypeptide and a heterologous polynucleotide encoding an oxalosuccinate reductase polypeptide to produce a stably transformed photosynthetic bacterium expressing said heterologous polynucleotides, thereby increasing carbon fixation and/or increasing biomass production in said stably transformed photosynthetic bacterium as compared to a control, wherein the heterologous polynucleotide encoding a 2-oxoglutarate carboxylase polypeptide and the heterologous polynucleotide encoding an oxalosuccinate reductase polypeptide are from a bacterial and/or an archaeal species.

In further embodiments, a method for increasing carbon fixation and/or increasing biomass production in a photosynthetic bacterium is provided, comprising, consisting essentially of, or consisting of: introducing into a photosynthetic bacterium a heterologous polynucleotide encoding a 2-oxoglutarate carboxylase polypeptide, a heterologous polynucleotide encoding an oxalosuccinate reductase polypeptide and a heterologous polynucleotide encoding an isocitrate lyase polypeptide to produce a stably transformed photosynthetic bacterium expressing said heterologous polynucleotides, thereby increasing carbon fixation and/or increasing biomass production in said stably transformed photosynthetic bacterium as compared to a control, wherein the heterologous polynucleotide encoding a 2-oxoglutarate carboxylase polypeptide, the heterologous polynucleotide encoding an oxalosuccinate reductase polypeptide and the heterologous polynucleotide encoding an isocitrate lyase polypeptide are from a bacterial and/or an archaeal species.

In some aspects, the methods of the invention further comprise, consist essentially of, or consist of regenerating a stably transformed plant or plant part from the stably transformed plant cell, wherein expression of one or more of the heterologous polynucleotides in said regenerated and stably transformed plant or plant part results in the stably transformed plant and/or plant part having increased carbon fixation and/or increased biomass production as compared to a control (e.g., a plant or plant part not transformed with and stably expressing said heterologous polynucleotides).

Thus, in some embodiments, a method for producing a plant having increased carbon fixation and/or increased biomass production is provided, comprising, consisting essentially of, or consisting of: introducing into a plant, plant part, and/or plant cell a heterologous polynucleotide encoding a succinyl CoA synthetase polypeptide, a 2-oxoglutarate:ferredoxin oxidoreductase polypeptide, a 2-oxoglutarate carboxylase polypeptide, an oxalosuccinate reductase polypeptide or an isocitrate lyase polypeptide, thereby producing a stably transformed plant, plant part, and/or plant cell having increased carbon fixation and/or increased biomass production as compared to a control (e.g., a plant not comprising said heterologous polynucleotide), wherein the heterologous polynucleotide is from a bacterial and/or an archaeal species.

In other embodiments, a method for producing a plant having increased carbon fixation and/or increased biomass production is provided, comprising, consisting essentially of, or consisting of: introducing into a plant, plant part, and/or plant cell a heterologous polynucleotide encoding a succinyl CoA synthetase polypeptide and a heterologous polynucleotide encoding a 2-oxoglutarate:ferredoxin oxidoreductase polypeptide, thereby producing a stably transformed plant, plant part, and/or plant cell having increased carbon fixation and/or increased biomass production as compared to a control, wherein said heterologous polynucleotide encoding a succinyl CoA synthetase polypeptide and said heterologous polynucleotide encoding a 2-oxoglutarate:ferredoxin oxidoreductase polypeptide are from a bacterial and/or an archaeal species.

In further embodiments, a method for producing a plant having increased carbon fixation and/or increased biomass production is provided, comprising, consisting essentially of, or consisting of: introducing into a plant, plant part, and/or plant cell heterologous polynucleotide encoding a 2-oxoglutarate carboxylase polypeptide and a heterologous polynucleotide encoding an oxalosuccinate reductase polypeptide, thereby producing a stably transformed plant, plant part, and/or plant cell having increased carbon fixation and/or increased biomass production as compared to a control, wherein said heterologous polynucleotide encoding a 2-oxoglutarate carboxylase polypeptide and said heterologous polynucleotide encoding an oxalosuccinate reductase polypeptide are from a bacterial and/or an archaeal species.

In additional embodiments, a method for producing a plant having increased carbon fixation and/or increased biomass production is provided, comprising, consisting essentially of, or consisting of: introducing into a plant, plant part, and/or plant cell a heterologous polynucleotide encoding a 2-oxoglutarate carboxylase polypeptide, a heterologous polynucleotide encoding an oxalosuccinate reductase polypeptide and a heterologous polynucleotide encoding an isocitrate lyase polypeptide, thereby producing a stably transformed plant, plant part, and/or plant cell having increased carbon fixation and/or increased biomass production as compared to a control, wherein said heterologous polynucleotide encoding a 2-oxoglutarate carboxylase polypeptide, said heterologous polynucleotide encoding an oxalosuccinate reductase polypeptide and said heterologous polynucleotide encoding an isocitrate lyase polypeptide are from a bacterial and/or an archaeal species.

In additional embodiments, the preset invention provides methods for producing stably transformed photosynthetic bacteria having increased carbon fixation and/or increased biomass production Thus, in some embodiments, a method for producing a photosynthetic bacterium having is provided, comprising, consisting essentially of, or consisting of: introducing into a photosynthetic bacterium a heterologous polynucleotide encoding a succinyl CoA synthetase polypeptide, a 2-oxoglutarate:ferredoxin oxidoreductase polypeptide, a 2-oxoglutarate carboxylase polypeptide, an oxalosuccinate reductase polypeptide or an isocitrate lyase polypeptide, thereby producing a stably transformed photosynthetic bacterium having increased carbon fixation and/or increased biomass production as compared to a control (e.g., a photosynthetic bacterium not comprising said heterologous polynucleotide), wherein the heterologous polynucleotide is from a bacterial and/or an archaeal species.

In other embodiments, a method for producing photosynthetic bacterium having increased carbon fixation and/or increased biomass production is provided, comprising, consisting essentially of, or consisting of: introducing into a photosynthetic bacterium a heterologous polynucleotide encoding a succinyl CoA synthetase polypeptide and a heterologous polynucleotide encoding a 2-oxoglutarate:ferredoxin oxidoreductase polypeptide, thereby producing a stably transformed photosynthetic bacterium having increased carbon fixation and/or increased biomass production as compared to a control, wherein said heterologous polynucleotide encoding a succinyl CoA synthetase polypeptide and said heterologous polynucleotide encoding a 2-oxoglutarate:ferredoxin oxidoreductase polypeptide are from a bacterial and/or an archaeal species.

In further embodiments, a method for producing a photosynthetic bacterium having increased carbon fixation and/or increased biomass production is provided, comprising, consisting essentially of, or consisting of: introducing into a photosynthetic bacterium a heterologous polynucleotide encoding a 2-oxoglutarate carboxylase polypeptide and a heterologous polynucleotide encoding an oxalosuccinate reductase polypeptide, thereby producing a a stably transformed photosynthetic bacterium having increased carbon fixation and/or increased biomass production as compared to a control, wherein said heterologous polynucleotide encoding a 2-oxoglutarate carboxylase polypeptide and said heterologous polynucleotide encoding an oxalosuccinate reductase polypeptide are from a bacterial and/or an archaeal species.

In additional embodiments, a method for producing a photosynthetic bacterium having increased carbon fixation and/or increased biomass production is provided, comprising, consisting essentially of, or consisting of: introducing into a photosynthetic bacterium a heterologous polynucleotide encoding a 2-oxoglutarate carboxylase polypeptide, a heterologous polynucleotide encoding an oxalosuccinate reductase polypeptide and a heterologous polynucleotide encoding an isocitrate lyase polypeptide, thereby producing a stably transformed photosynthetic bacterium having increased carbon fixation and/or increased biomass production as compared to a control, wherein said heterologous polynucleotide encoding a 2-oxoglutarate carboxylase polypeptide, said heterologous polynucleotide encoding an oxalosuccinate reductase polypeptide and said heterologous polynucleotide encoding an isocitrate lyase polypeptide are from a bacterial and/or an archaeal species.

The polypeptides succinyl CoA synthetase, 2-oxoglutarate:ferredoxin oxidoreductase, 2-oxoglutarate carboxylase, oxalosuccinate reductase, and isocitrate lyase (i.e., the biological carbon sequestration/crTCA cycle polypeptides of the invention), and the polynucleotides that encode said polypeptides are known in the art and are produced by many different organisms. Thus, in some embodiments, a biological carbon sequestration polypeptide (crTCA cycle polypeptide) useful with this invention can be any archaeal or bacterial polypeptide useful for biological carbon sequestration and having the enzyme activity of succinyl CoA synthetase, 2-oxoglutarate:ferredoxin oxidoreductase, 2-oxoglutarate carboxylase, oxalosuccinate reductase, or isocitrate lyase. Selection of a particular polypeptide for use with this invention is based on a number of factors including, for example, the number of subunits in the enzyme (e.g., selecting those with the fewest number of subunits) and the kinetic properties of the individual polypeptides (e.g., a polypeptide with a high kcat value). Examples of organisms from which these polypeptides and polynucleotides can be derived include, but are not limited to, *Escherichia coli* (e.g., *E. coli* MG1655), *Azotobacter vinelandii* (e.g., *A. vinelandii* DJ), *Bradyrhizobium* sp. (e.g., *Bradyrhizobium* sp. BTAi1), *Azospirillum* sp (e.g., *Azospirillum* sp. B510), *Paenibacillus* sp. (e.g. *Paenibacillus* sp. JDR-2), *Halobacterium* sp. (e.g., *Halobacterium* sp NRC-1), *Hydrogenobacter thermophilus* (e.g., *H. thermophilus* TK-6), *Bacillus* sp (e.g., *Bacillus* sp M3-13), *Paenibacillus larvae* subsp. larvae (e.g., *Paenibacillus larvae* subsp. larvae B-3650), *Haladaptus paucihalophilus* (e.g., *H. paucihalophilus* DX253), *Magnetococcus* sp. (e.g., *Magnetococcus* sp. MC-1), *Candidatus Nitrospira defluvii* (e.g., *Candidatus Nitrospira defluvii* NIDE1204), *Thiocystis violascens* (e.g., *T. violascens* DSM198), *Mariprofundus ferroxydans* (e.g., *M. ferroxydans* PV-1), *Pseudomonas stutzeri* (e.g., *P. stutzeri* ATCC14405), *Acinetobacter baumannii* (e.g. *A. baumannii* ABT07, *A. baumannii* ACICU), *Chlorobium limicola* (e.g. *C. limicola* DSM 245), *Kosmotoga olearia* (e.g. *K. olearia* TBF 19.5.1), Marine gamma proteobacterium (e.g. Marine gamma proteobacterium HTCC2080), *Corynebacterium glutamicum* (e.g. *C. glutamicum* ATCC 13032), *Gordonia alkanivorans* (e.g. *G. alkanivorans* NBRC 16433), *Nocardia farcinica* (e.g. *N. farcinica* IFM 10152), *Rhodococcus pyridinivorans* (e.g. *R. pyridinivorans* AK37), *Rhodococcus jostii* (e.g. *R. jostii* RHA1) and *Clostridium ljungdahlii*.

Thus, in some embodiments, a polypeptide and/or polynucleotide encoding a polypeptide having the enzyme activity of succinyl CoA synthetase can be from *Escherichia coli, Azotobacter vinelandii, Bradyrhizobium* sp., *Azospirillum* sp., or any combination thereof. In some embodiments, the polypeptide having the enzyme activity of succinyl CoA synthetase can be a two subunit enzyme. In other embodiments, a polypeptide and/or polynucleotide encoding a polypeptide having the enzyme activity of 2-oxoglutarate:ferredoxin oxidoreductase can be from *Paenibacillus* sp., *Halobacterium* sp., *Hydrogenobacter thermophilus, Bacillus* sp, *Paenibacillus larvae* subsp. larvae, *Haladaptus paucihalophilus, Magnetococcus* sp., or any combination thereof. In further embodiments, the polypeptide having the enzyme activity of 2-oxoglutarate:ferredoxin oxidoreductase can be a two subunit enzyme. In still other embodiments, a polypeptide and/or polynucleotide encoding a polypeptide having the enzyme activity of 2-oxoglutarate carboxylase can be from *Candidatus Nitrospira defluvii, Hydrogenobacter thermophilus, Thiocystis violascens, Mariprofundus ferroxydans, Pseudomonas stutzeri*, or any combination thereof. In some embodiments, the polypeptide having the enzyme activity of 2-oxoglutarate carboxylase can be a two subunit enzyme. In additional embodiments, a polypeptide and/or polynucleotide encoding a polypeptide having the enzyme activity of oxalosuccinate reductase can be from *Acinetobacter baumannii, Chlorobium limicola, Kosmotoga olearia,* Marine gamma proteobacterium, or any combination thereof. In further embodiments, a polypeptide and/or polynucleotide encoding a polypeptide having the enzyme activity of isocitrate lyase can be from *Corynebacterium glutamicum, Gordonia alkanivorans, Nocardia farcinica, Rhodococcus pyridinivorans, Rhodococcus jostii,* or any combination thereof.

More particularly, in some embodiments, a polynucleotide encoding a succinyl CoA synthetase polypeptide useful with this invention includes, but is not limited to, a nucleotide sequence from *E. coli* strain K-12 substr. MG1655 (e.g., NCBI Accession Nos. NC_000913.2 (772,237 . . . 763,403), NC_000913.2 (763,403 . . . 764,272); see, e.g., SEQ ID NO:3); from *Azotobacter vinelandii* DJ (e.g., NCBI Accession Nos. NC_012560.1 (3,074,152 . . . 3,075,321), NC_012560.1 (3,073,268 . . . 3,074,155); see, e.g., SEQ ID NO:6); from *Bradyrhizobium* sp. BTAi1 (e.g., NCBI Accession Nos. NC_009485.1 (393,292 . . . 394,488), NC_009485.1 (394,545 . . . 395,429); see, e.g., SEQ ID NO:9); and/or from *Azospirillum* sp. B510 (e.g., NCBI Accession Nos. NC_013854.1 (2,941,010 . . . 2,942,206), NC_013854.1 (2,942,208 . . . 2,943,083); see, e.g., SEQ ID NO:12). In other embodiments, a succinyl CoA synthetase polypeptide can have an amino acid sequence that includes but is not limited to an amino acid sequence from *E. coli* strain K-12 substr. MG1655 (e.g., NCBI Accession Nos. NP_415256.1 and NP_415257.1); see, e.g., SEQ ID NO:1 and SEQ ID NO:2); from *Azotobacter vinelandii* DJ (e.g., NCBI Accession Nos. YP_002800115.1 and YP_002800114.1); see, e.g., SEQ ID NO:4 and SEQ ID NO:5); from *Bradyrhizobium* sp. BTAi1 (e.g., NCBI Accession Nos. YP_001236586.1 and YP_001236587.1); see, e.g., SEQ ID NO:7 and SEQ ID NO:8); and/or from *Azospirillum* sp. B510 (e.g., NCBI Accession Nos. YP_003449758.1 and YP_003449759.1); see, e.g., SEQ ID NO:10 and SEQ ID NO:11. In some embodiments, a heterologous polynucleotide encoding a succinyl CoA synthetase polypeptide can be from *E. coli* strain K-12 substr. MG1655. In some particular embodiments, a heterologous polynucleotide encoding a succinyl CoA synthetase from *E. coli* strain K-12 substr. MG1655 comprises, consists essentially of, or consists of the nucleotide sequence of SEQ ID NO:3.

In other embodiments, a polynucleotide encoding a 2-oxoglutarate:ferredoxin oxidoreductase polypeptide useful with this invention includes, but is not limited to, a nucleotide sequence from *Halobacterium* sp. NRC-1 (e.g., NCBI Accession Nos. NC_002607.1 (856,660 . . . 858,582), NC_002607.1 (855,719 . . . 856,657); see, e.g., SEQ ID NO:15); from *Hydrogenobacter thermophilus* TK-6 (e.g., NCBI Accession Nos. NC_013799.1 (997,525 . . . 999,348), NC_013799.1 (996,624 . . . 997,511); see, e.g., SEQ ID NO:18); from *Bacillus* sp. M3-13 (e.g., NCBI Accession Nos. NZ_ACPC01000013.1 (932 . . . 2,668), NZ_ACPC01000013.1 (65 . . . 931); see, e.g., SEQ ID NO:21); from *Paenibacillus larvae* subsp. *larvae* B-3650 (e.g., NCBI Accession Nos. NZ_ADZY02000226.1 (7,939 . . . 9,687), NZ_ADZY02000226.1 (7,085 . . . 7,951); see, e.g., SEQ ID NO:24); from *Haladaptatus paucihalophilus* DX253 (e.g., NCBI Accession Nos. NZ_AEMG01000009.1 (157,678 . . . 159,432), NZ_AEMG01000009.1 (156,818 . . . 157,681); see, e.g., SEQ ID NO:27); and/or from *Magnetococcus* sp. MC-1 (e.g., NCBI Accession Nos. NC_008576.1 (2,161,258 . . . 2,162,979), NC_008576.1 (2,162,976 . . . 2,163,854); see, e.g., SEQ ID NO:30). In other embodiments, a 2-oxoglutarate:ferredoxin oxidoreductase polypeptide can have an amino acid sequence that includes, but is not limited to, an amino acid sequence from *Halobacterium* sp. NRC-1 (e.g., NCBI Accession Nos. AAG19514.1, AAG19513.1, NP_280034.1 and NP_280033.1); see, e.g., SEQ ID NO:13 and SEQ ID NO:14); from *Hydrogenobacter thermophilus* TK-6 (e.g., NCBI Accession Nos. YP_003432752.1 and YP_003432751.1); see, e.g., SEQ ID NO:16 and SEQ ID NO:17); from *Bacillus* sp. M3-13 (e.g., NCBI Accession Nos. ZP_07708142.1 and ZP_07708141.1); see, e.g., SEQ ID NO:19 and SEQ ID NO:20); from *Paenibacillus larvae* subsp. *larvae* B-3650 (e.g., NCBI Accession Nos. ZP_09070120.1 and ZP_09070119.1); see, e.g., SEQ ID NO:22 and SEQ ID NO:23); from *Haladaptatus paucihalophilus* DX253 (e.g., NCBI Accession Nos. ZP_08044530.1 and ZP_08044529.1); see, e.g., SEQ ID NO:25 and SEQ ID NO:26); and/or from *Magnetococcus* sp. MC-1 (e.g., NCBI Accession Nos. YP_865663.1 and YP_865664.1); see, e.g., SEQ ID NO:28 and SEQ ID NO:29). In some embodiments, a heterologous polynucleotide encoding a 2-oxoglutarate:ferredoxin oxidoreductase polypeptide can be from *Paenibacillus* sp. subsp. *larvae* B-3650. In particular embodiments, a heterologous polynucleotide encoding a 2-oxoglutarate:ferredoxin oxidoreductase polypeptide from *Paenibacillus* sp. subsp. *larvae* B-3650 comprises, consists essentially of, or consists of the nucleotide sequence of SEQ ID NO:24.

In further embodiments, a polynucleotide encoding a 2-oxoglutarate carboxylase polypeptide useful with this invention includes, but is not limited to, a nucleotide sequence from *Hydrogenobacter thermophilus* TK-6 (e.g., NCBI Accession Nos. NC_013799.1 (1,271,487 . . . 1,273,445), NC_013799.1 (1,273,469 . . . 1,274,887); see, e.g., SEQ ID NO:33); from *Candidatus Nitrospira defluvii* (e.g., NCBI Accession Nos. NC_014355.1 (1,174,721 . . . 1,176,652), NC_014355.1 (1,176,781 . . . 1,178,199); see, e.g., SEQ ID NO:36); from *Hydrogenobacter thermophilus* TK-6 (e.g., NCBI Accession Nos. NC_013799.1 (1,271,487 . . . 1,273,445), NC_013799.1 (1,273,469 . . . 1,274,887); see, e.g., SEQ ID NO:39); from *Thiocystis violascens* DSM198 (e.g., NCBI Accession Nos. NZ_AGFC01000013.1 (61,879 . . . 63,297) and (63,889 . . . 65,718); see, e.g., SEQ ID NO:42); from Mariprofundus *ferrooxydans* PV-1 (e.g., NCBI Accession Nos. NZ_AATS01000007.1 (81,967 . . . 83,385) and (83,475 . . . 85,328); see, e.g., SEQ ID NO:45); and/or from *Pseudomonas stutzeri* ATCC14405 (AGSL01000085.1 (52,350 . . . 53,765) and (50,522 . . . 52,339); see, e.g., SEQ ID NO:48). In further embodiments, a 2-oxoglutarate carboxylase polypeptide can have an amino acid sequence that includes, but is not limited to, an amino acid sequence from *Hydrogenobacter thermophilus* TK-6 (e.g., NCBI Accession Nos. YP_003433044.1 and YP_003433045.1); see, e.g., SEQ ID NO:31 and SEQ ID NO:32); from *Candidatus Nitrospira defluvii* (e.g., NCBI Accession Nos. YP_003796887.1 and YP_003796888.1); see, e.g., SEQ ID NO:34 and SEQ ID NO:35); from *Hydrogenobacter thermophilus* TK-6 (e.g., NCBI Accession Nos. YP_003433044.1 and YP_003433045.1); see, e.g., SEQ ID NO:37 and SEQ ID NO:38); from *Thiocystis violascens* DSM198 (e.g., NCBI Accession Nos. ZP_08925050.1 and ZP_08925052.1); see, e.g., SEQ ID NO:40 and SEQ ID NO:41 and/or SEQ ID NO:43 and SEQ ID NO:44); from Mariprofundus *ferrooxydans* PV-1 (e.g., NCBI Accession Nos. ZP_01452577.1 and ZP_01452578.1); see, e.g., SEQ ID NO:46 and SEQ ID NO:47); and/or from *Pseudomonas stutzeri* ATCC14405 (e.g., NCBI Accession Nos. EHY78621.1 and EHY78620.1); see, e.g., SEQ ID NO:49 and SEQ ID NO:50). In some embodiments, a heterologous polynucleotide encoding a 2-oxoglutarate carboxylase polypeptide can be a 2-oxoglutarate carboxylase from *Candidatus Nitrospira defluvii*. In some particular embodiments, a heterologous polynucleotide encoding a 2-oxoglutarate carboxylase polypeptide from *Candidatus Nitrospira defluvii* comprises, consists essentially of, or consists of the nucleotide sequence of SEQ ID NO:36. In other embodiments, a heterologous polynucleotide encoding a 2-oxoglutarate carboxylase polypeptide can be a 2-oxoglutarate carboxylase polypeptide from *Hydrogenobacter thermophilus* TK-6. In some particular embodiments, a heterologous polynucleotide encoding a 2-oxoglutarate carboxylase polypeptide from *Hydrogenobacter thermophilus* TK-6 comprises, consists essentially of, or consists of the nucleotide sequence of SEQ ID NO:33, SEQ ID NO:39 and/or SEQ ID NO:42.

In still further embodiments, a polynucleotide encoding a oxalosuccinate reductase polypeptide useful with this invention includes, but is not limited to, a polynucleotide from *Chlorobium limicola* DSM 245 (e.g., NCBI Accession Nos. AB076021.1); see, e.g., SEQ ID NO:53); from Kosmotoga olearia TBF 19.5.1 (e.g., NCBI Accession Nos. NC_012785.1 (1,303,493 . . . 1,304,695); see, e.g., SEQ ID NO:55); from *Acinetobacter baumannii* ACICU (e.g., NCBI Accession Nos. NC_010611.1 (2,855,563 . . . 2,856,819); see, e.g., SEQ ID NO:57); from Marine gamma proteobacterium HTCC2080 (e.g., NCBI Accession Nos. NZ_AAVV01000002.1 (123,681 . . . 124,934); see, e.g., SEQ ID NO:59); and/or from *Nitrosococcus halophilus* Nc4 (e.g., NCBI Accession Nos. NC_013960.1 (2,610,547 . . . 2,611,815); see, e.g., SEQ ID NO:61). In other embodiments, an oxalosuccinate reductase polypeptide can have an amino acid sequence that includes, but is not limited to, an amino acid sequence from *Chlorobium limicola* DSM 245 (e.g., NCBI Accession Nos. BAC00856.1); see, e.g., SEQ ID NO:52); from Kosmotoga olearia TBF 19.5.1 (e.g., NCBI Accession Nos. YP_002940928.1); see, e.g., SEQ ID NO:54); from *Acinetobacter baumannii* ACICU (e.g., NCBI Accession Nos. YP_001847346.1); see, e.g., SEQ ID NO:56); from Marine gamma proteobacterium HTCC2080 (e.g., NCBI Accession Nos. ZP_01625318.1); see, e.g., SEQ ID NO:58); and/or from *Nitrosococcus halophilus* Nc4 (e.g., NCBI Accession Nos. YP_003528006.1); see, e.g., SEQ ID NO:60). In some embodiments, a heterologous polynucleotide encoding an oxalosuccinate reductase polypeptide can be from *Acinetobacter baumannii*. In some particular embodiments, a heterologous polynucleotide encoding an oxalosuccinate reductase polypeptide from *Acinetobacter baumannii* comprises, consists essentially of, or consists of nucleotide sequence of SEQ ID NO:57. In other embodiments, a heterologous polynucleotide encoding an oxalosuccinate reductase can be from *Chlorobium limicola*. In some particular embodiments, a heterologous polynucleotide encoding an oxalosuccinate reductase from *Chlorobium limicola* comprises, consists essentially of, or consists of nucleotide sequence of SEQ ID NO:53. In further embodiments, a heterologous polynucleotide encoding an oxalosuccinate reductase polypeptide can be from Kosmotoga olearia TBF 19.5.1. In some particular embodiments, a heterologous polynucleotide encoding an oxalosuccinate reductase polypeptide from Kosmotoga olearia TBF 19.5.1 comprises, consists essentially of, or consists of nucleotide sequence of SEQ ID NO:55. In still further embodiments, a heterologous polynucleotide encoding an oxalosuccinate reductase polypeptide can be from *Nitrosococcus halophilus* Nc4. In some particular embodiments, a heterologous polynucleotide encoding an oxalosuccinate reductase polypeptide from *Nitrosococcus halophilus* Nc4 comprises, consists essentially of, or consists of nucleotide sequence of SEQ ID NO:60.

In additional embodiments, a heterologous polynucleotide encoding an isocitrate lyase polypeptide useful with this invention includes, but is not limited to, a polynucleotide from *Corynebacterium glutamicum* ATCC 13032 (e.g., NCBI Accession Nos. NC_003450.3 (2,470,741 . . . 2,472,039); see, e.g., SEQ ID NO:63); from *Gordonia alkanivorans* NBRC 16433 (e.g., NCBI Accession Nos. NZ_BACI01000050.1 (37,665 . . . 38,960); see, e.g., SEQ ID NO:65); *Nocardia farcinica* IFM 10152 (e.g., NCBI Accession Nos. NC_006361.1 (5,525,226 . . . 5,526,515); see, e.g., SEQ ID NO:67); that from *Rhodococcus pyridinivorans* AK37 (e.g., NCBI Accession Nos. NZ_AHBW01000053.1 (20,169 . . . 21,458); see, e.g., SEQ ID NO:69); and/or from *Rhodococcus jostii* RHA1 (e.g., NCBI Accession Nos. NC_008268.1 (2,230,309 . . . 2,231,598); see, e.g., SEQ ID NO:71). In other embodiments, an isocitrate lyase polypeptide can have an amino acid sequence that includes, but is not limited to, an amino acid sequence from *Corynebacterium glutamicum* ATCC 13032 (e.g., NCBI Accession Nos. NP_601531.1); see, e.g., SEQ ID NO:62); from *Gordonia alkanivorans* NBRC 16433 (e.g., NCBI Accession Nos. ZP_08765259.1); see, e.g., SEQ ID NO:64); *Nocardia farcinica* IFM 10152 (e.g., NCBI Accession Nos. YP_121446.1); see, e.g., SEQ ID NO:66); that from *Rhodococcus pyridinivorans* AK37 (e.g., NCBI Accession Nos. ZP_09310682.1); see, e.g., SEQ ID NO:68); and that from *Rhodococcus jostii* RHA1 (e.g., NCBI Accession Nos. YP_702087.1); see, e.g., SEQ ID NO:70). In some embodiments, a heterologous polynucleotide encoding an isocitrate lyase polypeptide can be from *Corynebacterium glutamicum*. In some particular embodiments, a heterologous polynucleotide encoding an isocitrate lyase polypeptide from *Corynebacterium glutamicum* comprises, consists essentially of, or consists of nucleotide sequence of SEQ ID NO:63. In further embodiments, a heterologous polynucleotide encoding an isocitrate lyase polypeptide can be from *Rhodococcus pyridinivorans* AK37. In some particular embodiments, a heterologous polynucleotide encoding an isocitrate lyase polypeptide from *Rhodococcus pyridinivorans* AK37 comprises, consists essentially of, or consists of nucleotide sequence of SEQ ID NO:68.

In further embodiments, polypeptides and the polynucleotides encoding said polypeptides can be modified for use with this invention. For example, a native or wild type intergenic spacer sequence in a selected polynucleotide can be substituted with another known spacer or a synthetic spacer sequence. Thus, for example, the intergenic spacer sequence in the 2-oxoglutarate carboxylase polynucleotide sequence from *Candidatus Nitrospira defluvii* and/or *Thiocystis violascens* DSM198 can be substituted with the 26 base pair spacer from the 2-oxoglutarate carboxylase *Hydrogenobacter thermophilus* polynucleotide sequence (see, e.g., the spacer sequence in SEQ ID NO:33) resulting in a 2-oxoglutarate carboxylase polypeptide having the nucleotide sequence of SEQ ID NO: 36 or SEQ ID NO:45, respectively.

Other polypeptide modifications useful with this invention include amino acid substitutions (and the corresponding base pair changes in the respective polynucleotide encoding said polypeptide). Thus, in some embodiments, a polypeptide and/or polynucleotide sequence of the invention can be a conservatively modified variant. As used herein, "conservatively modified variant" refers to polypeptide and polynucleotide sequences containing individual substitutions, deletions or additions that alter, add or delete a single amino acid or nucleotide or a small percentage of amino acids or nucleotides in the sequence, where the alteration results in the substitution of an amino acid with a chemically similar amino acid. Conservative substitution tables providing functionally similar amino acids are well known in the art.

As used herein, a conservatively modified variant of a polypeptide is biologically active and therefore possesses the desired activity of the reference polypeptide (e.g., succinyl CoA synthetase, 2-oxoglutarate:ferredoxin oxidoreductase, 2-oxoglutarate carboxylase, oxalosuccinate reductase, isocitrate lyase) as described herein. The variant can result from, for example, a genetic polymorphism or human manipulation. A biologically active variant of the reference polypeptide can have at least about 30%, 35%, 40%, 45%, 50%, 55%, 60%, 65%, 70%, 75%, 80%, 85%, 90%, 91%, 92%, 93%, 94%, 95%, 96%, 97%, 98%, 99%, or more sequence identity (e.g., about 30% to about 99% or more sequence identity and any range therein) to the amino acid sequence for the reference polypeptide as determined by sequence alignment programs and parameters described elsewhere herein. An active variant can differ from the reference polypeptide sequence by as few as 1-15 amino acid residues, as few as 1-10, such as 6-10, as few as 5, as few as 4, 3, 2, or even 1 amino acid residue.

Naturally occurring variants may exist within a population. Such variants can be identified by using well-known molecular biology techniques, such as the polymerase chain reaction (PCR), and hybridization as described below. Synthetically derived nucleotide sequences, for example, sequences generated by site-directed mutagenesis or PCR-mediated mutagenesis which still encode a polypeptide of the invention, are also included as variants. One or more nucleotide or amino acid substitutions, additions, or deletions can be introduced into a nucleotide or amino acid sequence disclosed herein, such that the substitutions, additions, or deletions are introduced into the encoded protein. The additions (insertions) or deletions (truncations) may be made at the N-terminal or C-terminal end of the native protein, or at one or more sites in the native protein. Similarly, a substitution of one or more nucleotides or amino acids may be made at one or more sites in the native protein.

For example, conservative amino acid substitutions may be made at one or more predicted, preferably nonessential amino acid residues. A "nonessential" amino acid residue is a residue that can be altered from the wild-type sequence of a protein without altering the biological activity, whereas an "essential" amino acid is required for biological activity. A "conservative amino acid substitution" is one in which the amino acid residue is replaced with an amino acid residue with a similar side chain. Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues, or for amino acid residues residing within a conserved motif, where such residues are essential for protein activity.

In some embodiments, amino acid changes can be made to alter the catalytic activity of an enzyme. For example, amino acid substitutions can be made to a thermoactive enzyme that has little activity at room temperature (e.g., about 20° C. to about 50° C.) so as to increase activity at these temperatures. A comparison can be made between the thermoactive enzyme and a mesophilic homologue having activity at the desired temperatures. This can provide discrete differences in amino acids that can then be the focus of amino acid substitutions.

Thus, in some embodiments, amino acid sequence variants of a reference polypeptide can be prepared by mutating the nucleotide sequence encoding the enzyme. The resulting mutants can be expressed recombinantly in plants, and screened for those that retain biological activity by assaying for the enzyme activity (e.g., succinyl CoA synthetase activity, 2-oxoglutarate:ferredoxin oxidoreductase activity, 2-oxoglutarate carboxylase activity, oxalosuccinate reductase activity, isocitrate lyase activity) using standard assay techniques as described herein. Methods for mutagenesis and nucleotide sequence alterations are known in the art. See, e.g., Kunkel (1985) *Proc. Natl. Acad. Sci. USA* 82:488-492; Kunkel et al. (1987) *Methods in Enzymol.* 154:367-382; and *Techniques in Molecular Biology* (Walker & Gaastra eds., MacMillan Publishing Co. 1983) and the references cited therein; as well as U.S. Pat. No. 4,873,192. Clearly, the mutations made in the DNA encoding the variant must not disrupt the reading frame and preferably will not create complementary regions that could produce secondary mRNA structure. See, EP Patent Application Publication No. 75,444. Guidance as to appropriate amino acid substitutions that do not affect biological activity of the protein of interest may be found in the model of Dayhoff et al. (1978) *Atlas of Protein Sequence and Structure* (National Biomedical Research Foundation, Washington, D.C.).

In a representative embodiment, the large subunit from the 2-oxoglutarate carboxylase polypeptide (cfiA) from *Hydrogenobacter thermophilus* TK-6 can be modified at residue 203 to be alanine (A) instead of methionine (M), at residue 205 to be valine (V) instead of phenylalanine (F), at residue 234 to be methionine (M) instead of threonine (T), at residue 236 to be isoleucine (I) instead of threonine (T), at residue 240 to be leucine (L) instead of methionine (M), at residue 274 to be arginine (R) instead of glutamic acid (E) and/or at residue 288 to be glutamine (Q) instead of aspartic acid (D) as shown, for example, in the amino acid sequences of SEQ ID NO:38 and SEQ ID NO:41 and the corresponding codon changes as shown, for example, in the nucleotide sequences of SEQ ID NO:39 or SEQ ID NO:42. Such changes result in a thermophilic 2-oxoglutarate carboxylase that can function at lower temperatures than the native *H. themophilus* TK-6 2-oxoglutarate carboxylase. The amino acids targeted for substitution were identified by comparing the *H. themophilus* TK-6 2-oxoglutarate carboxylase with its nearest mesophilic homolog from *Candidatus Nitrospira defluvii*.

The deletions, insertions and substitutions in the polypeptides described herein are not expected to produce radical changes in the characteristics of the polypeptide (e.g., the temperature at which the polypeptide is active). However, when it is difficult to predict the exact effect of the substitution, deletion or insertion in advance of doing so, one of skill in the art will appreciate that the effect can be evaluated by routine screening assays for the particular polypeptide activities of interest (e.g., succinyl CoA synthetase, 2-oxoglutarate:ferredoxin oxidoreductase, 2-oxoglutarate carboxylase, oxalosuccinate reductase, isocitrate lyase) as described herein.

In some embodiments, the compositions of the invention can comprise functional fragments of the polypeptide. As used herein, "functional fragment" means a portion of the reference polypeptide that retains the polypeptide activity of, for example, succinyl CoA synthetase, 2-oxoglutarate: ferredoxin oxidoreductase, 2-oxoglutarate carboxylase, oxalosuccinate reductase, or isocitrate lyase. A fragment also means a portion of a nucleic acid molecule encoding the reference polypeptide. An active fragment of the polypeptide can be prepared, for example, by isolating a portion of a polypeptide-encoding nucleic acid molecule that expresses an encoded fragment of the polypeptide (e.g., by recombinant expression in vitro), and assessing the activity of the fragment. Nucleic acid molecules encoding such fragments can be at least about 150, 200, 250, 300, 350, 400, 450, 500, 550, 600, 650, 700, 800, 900, 1,000, 1,100, 1,200, 1,300, 1,400, 1,500, 1,600, 1,700, 1,800, 1,900, or 2000 contiguous nucleotides, or up to the number of nucleotides present in a full-length polypeptide-encoding nucleic acid molecule. As such, polypeptide fragments can be at least about 50, 60, 70, 80, 90, 100, 125, 150, 175, 200, 225, 250, 275, 300, 325, 350, 375, 400, 425, 450, 475, 500, 525, 550, 575, 600, 625, 650, 675, or 700 contiguous amino acid residues, or up to the total number of amino acid residues present in the full-length polypeptide.

Methods for assaying the activities of the crTCA cycle enzymes of the invention (e.g., succinyl CoA synthetase, 2-oxoglutarate:ferredoxin oxidoreductase, 2-oxoglutarate carboxylase, oxalosuccinate reductase and isocitrate lyase) are known in the art. Exemplary activity assays for these enzymes are set forth below.

Succinyl CoA Synthetase.

The succinyl CoA synthetase assay is a spectrophotometric method that measures the increase of absorbance at 232 nm in response to thioester formation. The standard reaction solution consists of 10 mM sodium succinate, 10 mM $MgCl_2$, 0.1 mM CoA, 0.1 mM DTT, 0.4 mM nucleotide (ATP or GTP) and 0.1 M KCl in 50 mM Tris-HCl (pH 7.4). The reaction is started with the addition of purified succinyl CoA synthetase or crude extract containing SCS. The reaction is monitored in a spectrophotometer set at 232 nm at 25° C. (See, e.g., Bailey et al. A dimeric form of *Escherichia coli* succinyl-CoA synthetase produced by site-directed mutagenesis. *J. Mol. Biol.* 285:1655-1666 (1999); Bridger et al. Succinyl coenzyme A synthetase from *Escherichia coli. Methods Enzymol.* 13:70-75 (1969)).

For the LC/MS method of detection of succinyl CoA produced (LC-ESI-IT), the enzyme reactions are stopped by the addition of 30 μL of 15% (wt/vol) trifluoroacetic acid. A Nucleosil RP C18 (5 μm, 100-Å pores; Knauer GmbH, Berlin, Germany) reverse-phased column serves to separate the CoA esters at 30° C. A 50 mM concentration of ammonium acetate (pH 5.0) adjusted with acetic acid (eluent A) and 100% (vol/vol) methanol (eluent B) serves as eluents. Elution occurs at a flow rate of 0.3 ml/min. Ramping is performed as follows: equilibration with 90% eluent A for 2 min before injection and 90 to 45% eluent A for 20 min, followed by holding for 2 min, and then a return to 90% eluent A within 5 min after injection. Detection of CoA esters occurs at 259 nm with a photodiode array detector. The instrument is tuned by direct infusion of a solution of 0.4 mM CoA at a flow rate of 10 μL/min into the ion source of the mass spectrometer to optimize the ESI-MS system for maximum generation of protonated molecular ions (parents) of CoA derivatives. The following tuning parameters are retained for optimum detection of CoA esters: capillary temperature, 300° C.; sheet gas flow, 12 liters/h; auxiliary gas flow, 6 liters/h; and sweep gas flow, 1 liter/h. The mass range is set to m/z 50 to 1,000 Da when running in the scan mode. The collision energy in the MS mode is set to 30 V. See, e.g., Schurmann et al. Novel Reaction of Succinyl Coenzyme A (Succinyl-CoA) Synthetase: Activation of 3-Sulfinopropionate to 3-Sulfinopropionyl-CoA in *Advenella mimigardefordensis* Strain DPN7T during Degradation of 3,3-Dithiodipropionic Acid. *J Bacteriol.* 193(12):3078 (2011).

Figure 2:
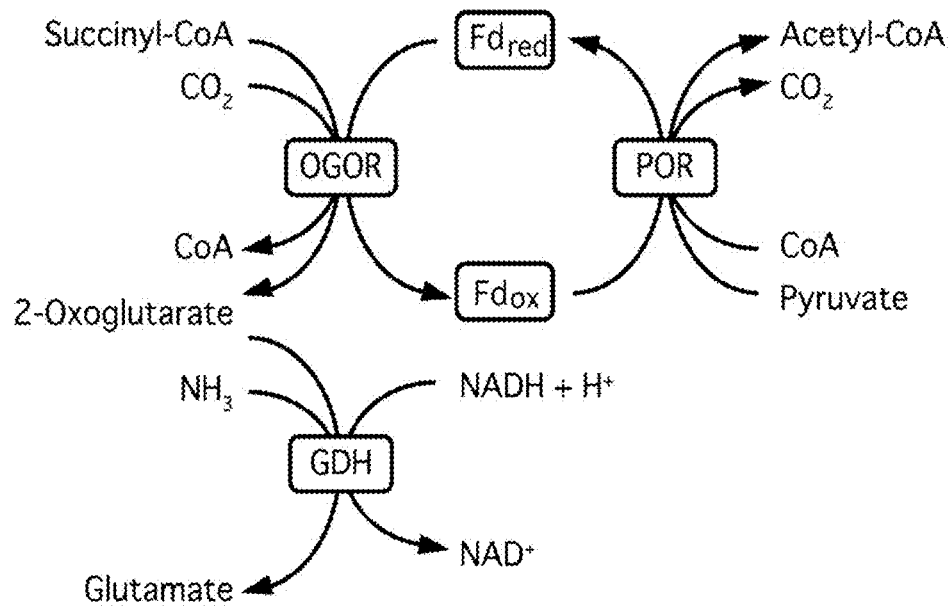
FIG. 2 shows a schematic view of 2-oxoglutarate:ferredoxin oxidoreductase (OGOR) enzyme assay.

2-Oxoglutarate:ferredoxin oxidoreductase. The assay for the forward reaction for 2-oxoglutarate:ferredoxin oxidoreductase (OGOR) is a coupled spectrophotometric assay based in the changes of NADH levels, which are measured at 340 nm. As shown in FIG. 2, the OGOR enzyme reaction is coupled with GDH catalyzed conversion of 2-oxoglutarate to glutamate, consuming NADH to NAD+. The pyruvate oxoreductase (POR) reaction reproduces reduced form of ferredoxin (Yamamoto et al. Carboxylation reaction catalyzed by 2-oxoglutarate:ferredoxin oxidoreductases from *Hydrogenobacter thermophilus. Extremophiles.* 14:79-85 (2010)). In some aspects, the transgenic plants of this invention additionally comprise heterologous/recombinant ferredoxin from, for example, *Hydrogenobacter thermophilus* TK-6 and/or from *Clostridium ljungdahlii*, to assist OGOR in catalyzing the conversion of succinyl-CoA to 2-oxoglutarate as described herein. In other embodiments, the plant's endogenous levels of ferredoxin are sufficient to assist OGOR in catalyzing the conversion of succinyl-CoA to 2-oxoglutarate and thus, introduction of a heterologous ferredoxin is unnecessary.

For the reverse reaction for OGOR, enzymatic activity of recombinant OGOR in the cell-free extract is determined by 2-oxoglutarate dependent reduction of methyl viologen at 578 nm. The standard assay mixture contains 10 mM MOPS (pH 6.8), 1 mM $MgCl_2$, 1 mM DTT, 20 mM NaHCO3, 5 mM $NH_4Cl$, 0.25 mM CoA, 0.26 mM NADH, 100 mM pyruvate, 1 mM succinyl-CoA, and proteins (OGOR, POR, ferredoxin, and GDH). The gas phase in the quartz cell is replaced with argon. The reaction is initiated by addition of succinyl-CoA. The change in A340 (representing a decrease in the consumption of NADH) is measured using a spectrophotometer. The measurement is taken 30 s following succinyl-CoA addition. The reaction mixtures contain 50 mM Tris/HCl, pH 7.5.5 mM sodium 2-oxoglutarate, 1 mM $MgCl_2$, 2.5 mM DTT, 0.1 mM CoA, 50 uM TPP, and 1 mM methyl viologen in a final volume of 2 ml. The reduction of methyl viologen is monitored at 578 nm. (See, e.g., Yun et al. *Biochem. Biophys. Res. Comm.* 282: 589-594 (2001); Wahl et al. *J Biol Chem.* 262: 10489-10496 (1987).

For the GC/MS method for the measurement of targeted metabolites including succinate, 2-oxoglutarate, glyoxylate, and citrate (GC-EI), the enzyme reactions are stopped by the addition of 30 μL of 15% (wt/vol) trifluoroacetic acid. GC/GC/MS experiments are performed using a LECO Pegasus III time-of-flight mass spectrometer with the 4D upgrade (LECO Corp., St. Joseph, Mich., USA). Column 1 is a 20m Rtx-5 capillary column with an internal diameter of 250 μm and a film thickness of 0.5 μm and column 2 was a 2m Rtx-200 (Restek, Bellefonte, Pa., USA) with a 180 μm internal diameter and 0.2 μm film thickness. The two columns are joined by a cryogenic modulator with a modulation period of 1.5 s with a hot pulse time of 0.40 s. Ultra high purity helium is used as the carrier gas at constant flow mode of 1 mL/min. 1 μL of a given sample is injected in triplicate in split-less mode via an Agilent 7683 autosampler. The inlet temperature is set at 280° C. The temperature program used for column 1 begins at 60° C. with a hold time of 0.25 min, then increased at 8° C./min to 280° C. with a hold time at 280° C. for 10 min. Column 2 is held in a separate oven which is initially set at 70° C. and followed the same temperature program as column 1. The ion source temperature is set to 250° C. Mass spectra are collected from m/z 40 to 600 at 100 spectra/s with a 5 min solvent delay (Yang et al. *Journal of Chromatography A*, 1216:3280-3289 (2009)).

2-Oxoglutarate Carboxylase.

Figure 3:
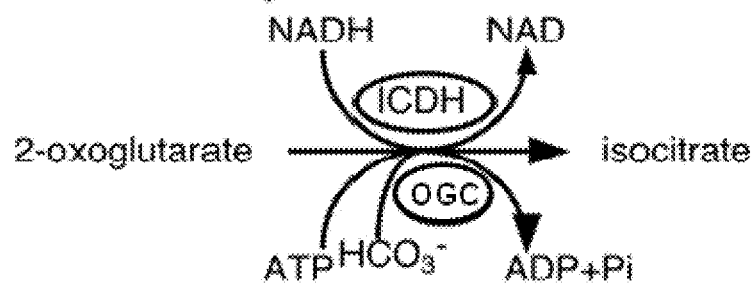
FIG. 3 shows a schematic view of reductive carboxylation catalyzed by 2-oxoglutarate carboxylase/isocitrate dehydrogenase (OGC/ICDH) (adapted from Aoshima et al. *Mol. Microbiol.* 62:748-759 (2006)).

The assay for 2-oxoglutarate carboxylase is a spectrophotometric assay in which the reductive carboxylation of 2-oxoglutarate to isocitrate is monitored indirectly at 340 nm (measuring NADH oxidation). See FIG. 3. Note that this assay is actually measuring the combined reactions of crTCA Cycle Reaction #3 and #4 (OGC and oxalosuccinate reductase). The reaction mixture for this assay (total volume of 250 µl) is composed of 100 mM Bicine-KOH (prepared from 1 M stock solution of pH 8.5, adjusted at room temperature), 50 mM NaHCO$_3$, 10 mM 2-oxoglutarate, 10 mM Mg-ATP, 0.25 mM NADH, 3.6 mg of ICDH (from *H. thermophilus*, recombinant) and OGC. The reaction is started by the addition of NADH and OGC. NADH oxidation is monitored at 340 nm (e=6.3 mM-1cm-1) for 1 min. One unit of activity is defined as 1 mmol of NADH oxidized per min (Aoshima et al. *Mol. Microbiol.* 62:748-759 (2006)). The GC/MS method for OGC is the same as that set forth for crTCA cycle reaction #2 above.

Oxalosuccinate Reductase.

The assay provided herein for crTCA cycle reaction #3 (see, e.g., (Aoshima et al. *Mol. Microbiol.* 62:748-759 (2006)). For the LC/MS method for the detection of isocitrate produced (LC-ESI), chromatographic separation is carried out using a 250×4.6 mm (5 µm) Allure Organic Acids column (Restek Corp., Bellefonte, Pa.) fitted with a 10×4.6 mm (5 µm) guard column at 30° C. Mobile phase is water/methanol (85:15) containing 0.5% formic acid, delivered at 0.7 mL/min. The column effluent is split in a ratio of 1:1 before the ionization source. The injection volume is 10 µL. Two multiple reaction monitoring (MRM) transitions in the negative ion mode are used. The dwell time, interchannel delay, and interscan delay are 0.1, 0.02, and 0.1 s, respectively. Other operating parameters are as follows: capillary voltage, 3 kV; source and desolvation temperature, 120 and 350° C.; desolvation and cone gas flow rates, 900 and 50 L/h, respectively; cone voltage, 20 V; collision energy, 20 eV. (See, e.g., Ehling et al. *J. Agric. Food Chem.* 59:2229-2234(2011)).

Isocitrate lyase.

This is a continuous spectrophotometric rate determination in which isocitrate lyase (ICL) converts isocitrate to succinate and glyoxylate. The glyoxylate is chemically converted to glyoxylate phenylhydrazone in the presence of phenylhydrazine. The glyoxylate phenylhydrazone is measured at 324 nm. The reaction mixture contains 30 mM imidazole (pH 6.8), 5 mM MgCl$_2$, 1 mM EDTA, 4 mM phenylhydrazine and 10 mM isocitrate. The reaction was performed at room temperature. After adding ICL, the reaction was continuously monitored at 324 nm (See, e.g., Chell et al. *Biochemical Journal* 173:165-177 (1978)).

These assays can be performed on protein extracts from plants, plant parts (e.g., leaf, stem, seed, and the like) and plant cells (e.g., cell cultures comprising tissue culture, a suspension of plant cells such as algal cells, protoplasts and the like) or protein extracts from cells and/or cell cultures of photosynthetic bacteria.

In some embodiments, a heterologous polynucleotide encoding a succinyl CoA synthetase polypeptide, a 2-oxoglutarate:ferredoxin oxidoreductase polypeptide, a 2-oxoglutarate carboxylase, oxalosuccinate reductase polypeptide and/or a isocitrate lyase polypeptide (e.g., the polynucleotides encoding the biological carbon sequestration/crTCA cycle enzymes) as well as any other heterologous polynucleotide encoding a polypeptide or functional nucleic acid of interest can be comprised within an expression cassette. As used herein, "expression cassette" means a recombinant nucleic acid molecule comprising at least one polynucleotide sequence of interest (e.g., a heterologous polynucleotide encoding a biological carbon sequestration polypeptide, and the like), wherein said recombinant nucleic acid molecule is operably associated with at least one control sequence (e.g., a promoter). Thus, some embodiments of the invention provide expression cassettes designed to express a recombinant nucleic acid molecule/heterologous polynucleotide encoding polypeptides having the enzyme activity of succinyl CoA synthetase, 2-oxoglutarate:ferredoxin oxidoreductase, 2-oxoglutarate carboxylase, oxalosuccinate reductase, and/or isocitrate lyase.

An expression cassette comprising a recombinant nucleic acid molecule may be chimeric, meaning that at least one of its components is heterologous with respect to at least one of its other components. An expression cassette may also be one that is naturally occurring but has been obtained in a recombinant form useful for heterologous expression.

In some embodiments, heterologous polynucleotides encoding a succinyl CoA synthetase polypeptide, a 2-oxoglutarate:ferredoxin oxidoreductase polypeptide, a 2-oxoglutarate carboxylase polypeptide, an oxalosuccinate reductase polypeptide and/or an isocitrate lyase polypeptide can be comprised in a single expression cassette. In some embodiments, the single expression cassette can further comprise a heterologous polynucleotide encoding any other polypeptide or functional nucleic acid of interest. The expression cassette can be operably linked to a promoter that drives expression of all of the polynucleotides comprised in the expression cassette and/or the expression cassette can comprise one or more promoters operably linked to one or more of the heterologous polynucleotides for driving the expression of said heterologous polynucleotides individually or in combination. In other embodiments, the heterologous polynucleotides encoding a succinyl CoA synthetase polypeptide, a 2-oxoglutarate:ferredoxin oxidoreductase polypeptide, a 2-oxoglutarate carboxylase polypeptide, an oxalosuccinate reductase polypeptide and/or an isocitrate lyase polypeptide (and/or any other polypeptide or functional nucleic acid of interest) can be comprised in more than one expression cassette.

When the heterologous polynucleotides are comprised within more than one expression cassette, said heterologous polynucleotides encoding the crTCA cycle polypeptides of this invention can be introduced into plants singly or more than one at a time using co-transformation methods as known in the art. In addition to transformation technology, traditional breeding methods as known in the art can be used to assist in introducing into a single plant each of the polynucleotides encoding the crTCA cycle enzymes alone or in combination as described herein and/or any additional polynucleotides of interest to produce a plant, plant part, and/or plant cell comprising and expressing each of the desired heterologous polynucleotides of interest.

Any promoter useful for initiation of transcription in a cell of a plant can be used in the expression cassettes of the present invention. A "promoter," as used herein, is a nucleotide sequence that controls or regulates the transcription of a nucleotide sequence (i.e., a coding sequence) that is operably associated with the promoter. The coding sequence may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. The promoter region may comprise other elements that act as regulators of gene expression. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in Genetic Engineering of Plants, T. Kosuge, C. Meredith and A. Hollaender (eds.), Plenum Press, pp. 211-227).

Promoters can include, for example, constitutive, inducible, temporally regulated, developmentally regulated, chemically regulated, tissue-preferred and/or tissue-specific promoters for use in the preparation of recombinant nucleic acid molecules, i.e., "chimeric genes" or "chimeric polynucleotides." A promoter can be identified in and isolated from the organism to be transformed and then inserted into the nucleic acid construct to be used in transformation of the organism.

The choice of promoter will vary depending on the temporal and spatial requirements for expression, and also depending on the host cell to be transformed. Thus, for example, expression of the heterologous polynucleotide encoding the polypeptides of the crTCA cycle as described herein can be in any plant, plant part, (e.g., in leaves, in stalks or stems, in ears, in inflorescences (e.g. spikes, panicles, cobs, etc.), in roots, seeds and/or seedlings, and the like), or plant cells (including algae cells). For example, in the case of a multicellular organism such as a plant where expression in a specific tissue or organ is desired, a tissue-specific or tissue preferred promoter can be used (e.g., a root specific/preferred promoter). In contrast, where expression in response to a stimulus is desired a promoter inducible by stimuli or chemicals can be used. Where continuous expression at a relatively constant level is desired throughout the cells or tissues of an organism a constitutive promoter can be chosen.

Thus, promoters useful with the invention include, but are not limited to, those that drive expression of a nucleotide sequence constitutively, those that drive expression when induced, and those that drive expression in a tissue- or developmentally-specific manner. These various types of promoters are known in the art. Promoters can be identified in and isolated from the plant to be transformed and then inserted into the expression cassette to be used in transformation of the plant.

Non-limiting examples of a promoter include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdcal) (See, Walker et al. *Plant Cell Rep.* 23:727-735 (2005); Li et al. *Gene* 403:132-142 (2007); Li et al. *Mol Biol. Rep.* 37:1143-1154 (2010)). PrbcS1 and Pactin are constitutive promoters and Pnr and Pdcal are inducible promoters. Pnr is induced by nitrate and repressed by ammonium (Li et al. *Gene* 403:132-142 (2007)) and Pdcal is induced by salt (Li et al. *Mol Biol. Rep.* 37:1143-1154 (2010)).

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and *arabidopsis* (Norris et al. 1993. *Plant Molec. Biol.* 21:895-906). The maize ubiquitin promoter (UbiP) has been developed in transgenic monocot systems and its sequence and vectors constructed for monocot transformation are disclosed in the patent publication EP 0 342 926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231: 150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, and flower specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, herein incorporated by reference in its entirety. Other non-limiting examples of tissue specific or tissue preferred promoters useful with the invention the cotton rubisco promoter disclosed in U.S. Pat. No. 6,040,504; the rice sucrose synthase promoter disclosed in U.S. Pat. No. 5,604,121; the root specific promoter described by de Framond (FEBS 290:103-106 (1991); EP 0 452 269 to Ciba-Geigy); the stem specific promoter described in U.S. Pat. No. 5,625,136 (to Ciba-Geigy) and which drives expression of the maize trpA gene; and the cestrum yellow leaf curling virus promoter disclosed in WO 01/73087.

Additional examples of plant tissue-specific/tissue preferred promoters include, but are not limited to, the root hair-specific cis-elements (RHEs) (Kim et al. *The Plant Cell*

18:2958-2970 (2006)), the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology*, 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986) *Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), *petunia* chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J.* 10:2605-2612).

Particularly useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from *Arabidopsis* (Gan et al. (1995) *Science* 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

In some embodiments of the invention, inducible promoters can be used. Thus, for example, chemical-regulated promoters can be used to modulate the expression of a gene in an organism through the application of an exogenous chemical regulator. Regulation of the expression of nucleotide sequences of the invention via promoters that are chemically regulated enables the polypeptides of the invention to be synthesized only when, for example, a crop of plants are treated with the inducing chemicals. Depending upon the objective, the promoter may be a chemical-inducible promoter, where application of a chemical induces gene expression, or a chemical-repressible promoter, where application of the chemical represses gene expression.

Chemical inducible promoters useful with plants are known in the art and include, but are not limited to, the maize Int-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid (e.g., the PR1a system), steroid-responsive promoters (see, e.g., the glucocorticoid-inducible promoter in Schena et al. (1991) *Proc. Natl. Acad. Sci. USA* 88, 10421-10425 and McNellis et al. (1998) *Plant J.* 14, 247-257) and tetracycline-inducible and tetracycline-repressible promoters (see, e.g., Gatz et al. (1991) *Mol. Gen. Genet.* 227, 229-237, and U.S. Pat. Nos. 5,814,618 and 5,789,156, Lac repressor system promoters, copper-inducible system promoters, salicylate-inducible system promoters (e.g., the PR1a system), glucocorticoid-inducible promoters (Aoyama et al. (1997) *Plant J.* 11:605-612), and ecdysone-inducible system promoters.

Other non-limiting examples of inducible promoters include ABA- and turgor-inducible promoters, the auxin-binding protein gene promoter (Schwob et al. (1993) *Plant J.* 4:423-432), the UDP glucose flavonoid glycosyl-transferase promoter (Ralston et al. (1988) *Genetics* 119:185-197), the MPI proteinase inhibitor promoter (Cordero et al. (1994) *Plant J.* 6:141-150), and the glyceraldehyde-3-phosphate dehydrogenase promoter (Kohler et al. (1995) *Plant Mol. Biol.* 29:1293-1298; Martinez et al. (1989) *J. Mol. Biol.* 208:551-565; and Quigley et al. (1989) *J. Mol. Evol.* 29:412-421). Also included are the benzene sulphonamide-inducible (U.S. Pat. No. 5,364,780) and alcohol-inducible (Int'l Patent Application Publication Nos. WO 97/06269 and WO 97/06268) systems and glutathione S-transferase promoters. Likewise, one can use any of the inducible promoters described in Gatz (1996) *Current Opinion Biotechnol.* 7:168-172 and Gatz (1997) *Annu. Rev. Plant Physiol. Plant Mol. Biol.* 48:89-108. Other chemically inducible promoters useful for directing the expression of the nucleotide sequences of this invention in plants are disclosed in U.S. Pat. No. 5,614,395 herein incorporated by reference in its entirety. Chemical induction of gene expression is also detailed in the published application EP 0 332 104 (to Ciba-Geigy) and U.S. Pat. No. 5,614,395. In some embodiments, a promoter for chemical induction can be the tobacco PR-1a promoter.

In particular embodiments, promoters useful with algae include, but are not limited to, the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdcal) (See, Walker et al. *Plant Cell Rep.* 23:727-735 (2005); Li et al. *Gene* 403:132-142 (2007); Li et al. *Mol Biol. Rep.* 37:1143-1154 (2010)), the promoter of the $\sigma^{70}$-type plastid rRNA gene (Prrn), the promoter of the psbA gene (encoding the photosystem-II reaction center protein D1) (PpsbA), the promoter of the psbD gene (encoding the photosystem-II reaction center protein D2) (PpsbD), the promoter of the psaA gene (encoding an apoprotein of photosystem I) (PpsaA), the promoter of the ATPase alpha subunit gene (PatpA), and promoter of the RuBisCo large subunit gene (PrbcL), and any combination thereof (See, e.g., De Cosa et al. *Nat. Biotechnol.* 19:71-74 (2001); Daniell et al. *BMC Biotechnol.* 9:33 (2009); Muto et al. *BMC Biotechnol.* 9:26 (2009); Surzycki et al. *Biologicals* 37:133-138 (2009)).

In some embodiments, the heterologous polynucleotides of the invention (e.g., the biological carbon sequestration/ crTCA cycle polypeptides described herein) can be transformed into the nucleus or into, for example, the chloroplast using standard techniques known in the art of plant transformation.

Thus, in some embodiments, heterologous polynucleotides encoding (1) a succinyl CoA synthetase polypeptide, (2) a 2-oxoglutarate:ferredoxin oxidoreductase polypeptide, (3) a 2-oxoglutarate carboxylase polypeptide, (4) an oxalosuccinate reductase polypeptide, or (5) an isocitrate lyase polypeptide, or (6) a succinyl CoA synthetase polypeptide and a 2-oxoglutarate:ferredoxin oxidoreductase polypeptide, (7) a 2-oxoglutarate carboxylase polypeptide and an oxalosuccinate reductase polypeptide, or (8) a 2-oxoglutarate carboxylase polypeptide, an oxalosuccinate reductase polypeptide and an isocitrate lyase polypeptide can be transformed into and expressed in the nucleus and the polypeptides produced remain in the cytosol. In other embodiments, heterologous polynucleotides encoding (1) a succinyl CoA synthetase polypeptide, (2) a 2-oxoglutarate:ferredoxin oxidoreductase polypeptide, (3) a 2-oxoglutarate carboxylase polypeptide, (4) an oxalosuccinate reductase polypeptide, or (5) an isocitrate lyase polypeptide, or (6) a succinyl CoA synthetase polypeptide and a 2-oxoglutarate:ferredoxin oxidoreductase polypeptide, (7) a 2-oxoglutarate carboxylase polypeptide and an oxalosuccinate reductase polypeptide, or (8) a 2-oxoglutarate carboxylase polypeptide, an oxalosuccinate reductase polypeptide and an isocitrate lyase polypeptide can be transformed into and expressed in the nucleus, wherein one or more of the polypeptides can be targeted to the chloroplast. Thus, in particular embodiments, the one or more heterologous polynucleotides encoding (1) a succinyl CoA synthetase polypeptide, (2) a 2-oxoglutarate:ferredoxin oxidoreductase polypeptide, (3) a 2-oxoglutarate carboxylase polypeptide, (4) an oxalosuccinate reductase polypeptide, or (5) an isocitrate lyase polypeptide, or (6) a succinyl CoA synthetase polypeptide and a 2-oxoglutarate:ferredoxin oxidoreductase polypeptide, (7) a 2-oxoglutarate carboxylase polypeptide and an oxalosuccinate reductase polypeptide, or (8) a 2-oxoglutarate carboxylase polypeptide, an oxalosuccinate reductase polypeptide and an isocitrate lyase polypeptide can be operably associated with at least one targeting nucleotide sequence encoding a signal peptide that targets the polypeptides to the chloroplast.

A signal sequence may be operably linked at the N- or C-terminus of a heterologous nucleotide sequence or nucleic acid molecule. Signal peptides (and the targeting nucleotide sequences encoding them) are well known in the art and can be found in public databases such as the "Signal Peptide Website: An Information Platform for Signal Sequences and Signal Peptides." (www.signalpeptide.de); the "Signal Peptide Database" (proline.bic.nus.edu.sg/spdb/index.html) (Choo et al., BMC Bioinformatics 6:249 (2005)(available on www.biomedcentral.com/1471-2105/6/249/abstract); ChloroP (www.cbs.dtu.dk/services/ChloroP/; predicts the presence of chloroplast transit peptides (cTP) in protein sequences and the location of potential cTP cleavage sites); LipoP (www.cbs.dtu.dk/services/LipoP/; predicts lipoproteins and signal peptides in Gram negative bacteria); MITO-PROT (ihg2.helmholtz-muenchen.de/ihg/mitoprot.html; predicts mitochondrial targeting sequences); PlasMit (gecco.org.chemie.uni-frankfurt.de/plasmit/index.html; predicts mitochondrial transit peptides in Plasmodium falciparum); Predotar (urgi.versailles.inra.fr/predotar/predotar.html; predicts mitochondrial and plastid targeting sequences); PTS1 (mendel.imp.ac.at/mendeljsp/sat/pts1/PTS1predictorjsp; predicts peroxisomal targeting signal 1 containing proteins); SignalP (www.cbs.dtu.dk/services/SignalP/; predicts the presence and location of signal peptide cleavage sites in amino acid sequences from different organisms: Gram-positive prokaryotes, Gram-negative prokaryotes, and eukaryotes). The SignalP method incorporates a prediction of cleavage sites and a signal peptide/non-signal peptide prediction based on a combination of several artificial neural networks and hidden Markov models; and TargetP (www-.cbs.dtu.dk/services/TargetP/); predicts the subcellular location of eukaryotic proteins—the location assignment is based on the predicted presence of any of the N-terminal presequences: chloroplast transit peptide (cTP), mitochondrial targeting peptide (mTP) or secretory pathway signal peptide (SP)). (See also, von Heijne, G., Eur J Biochem 133 (1) 17-21 (1983); Martoglio et al. Trends Cell Biol 8 (10):410-5 (1998); Hegde et al. Trends Biochem Sci 31(10): 563-71 (2006); Dultz et al. J Biol Chem 283(15):9966-76 (2008); Emanuelsson et al. Nature Protocols 2(4) 953-971 (2007); Zuegge et al. 280(1-2):19-26 (2001); Neuberger et al. J Mol Biol. 328(3):567-79 (2003); and Neuberger et al. J Mol Biol. 328(3):581-92 (2003)).

Exemplary signal peptides include, but are not limited to those provided in Table 1.

TABLE 1

Amino acid sequences of representative signal peptides.

| Source | Sequence | Target |
|---|---|---|
| Rubisco small subunit (tobacco) | MASSVLSSAAVATRSNVAQANMVAPFTGLKSAASF PVSRKQNLDITSIASNGGRVQC (SEQ ID NO: 72) | chloroplast |
| Arabidopsis proline-rich protein 2 (AT2G21140) | MRILPKSGGGALCLLFVPALCSVAHS (SEQ ID NO: 73) | cell wall/secretory pathway |
| PTS-2 (conserved in eukaryotes) | RLX$_5$HL (SEQ ID NO: 74) MRLSIHAEHL (SEQ ID NO: 75) SKL | peroxisome |
| Arabidopsis presequence protease1 (AT3G19170) | MLRTVSCLASRSSSSLFFRFFRQFPRSYMSLTSSTAAL RVPSRNLRRISSPSVAGRRLLLRRGLRIPSAAVRSVN GQFSRLSVRA (SEQ ID NO: 76) | mitochondria and chloroplast |

TABLE 1-continued

Amino acid sequences of representative signal peptides.

| Source | Sequence | Target |
|---|---|---|
| *Chlamydomonas reinhardtii*-(Stroma-targeting cTPs: photosystem I (PSI) subunits P28, P30, P35 and P37, respectively) | MALVARPVLSARVAASRPRVAARKAVRVSAKYGEN (SEQ ID NO: 77)<br>MQALSSRVNIAAKPQRAQRLVVRAEEVKA (SEQ ID NO: 78)<br>MQTLASRPSLRASARVAPRRAPRVAVVTKAALDPQ (SEQ ID NO: 79)<br>MQALATRPSAIRPTKAARRSSVVVRADGFIG (SEQ ID NO: 80) | chloroplast |
| *C. reinhardtii* - chlorophyll a/b protein (cabII-1) | MAFALASRKALQVTCKATGKKTAAKAAAPKSSGVE FYGPNRAKWLGPYSEN (SEQ ID NO: 81) | chloroplast |
| *C. reinhardtii* - Rubisco small subunit | MAAVIAKSSVSAAVARPARSSVRPMAALKPAVKAA PVAAPAQANQMMVWT (SEQ ID NO: 82) | chloroplast |
| *C. reinhardtii* - ATPase-γ | MAAMLASKQGAFMGRSSFAPAPKGVASRGSLQVVA GLKEV (SEQ ID NO: 83) | chloroplast |
| *Arabidopsis thaliana* abscisic acid receptor PYL 10 | CVVQ (SEQ ID NO: 84) | membrane |

X$_5$ means any five amino acids can be present in the sequence to target the protein to the peroxisome (e.g. RLAVAVAHL, SEQ ID NO: 85).

Thus, in representative embodiments of the invention, a heterologous polynucleotide encoding (a) succinyl CoA synthetase, (b) 2-oxoglutarate:ferredoxin oxidoreductase, (c) 2-oxoglutarate carboxylase, (d) oxalosuccinate reductase, and/or (e) isocitrate lyase to be expressed in a plant, plant cell, plant part can be operably linked to a chloroplast targeting sequence encoding a chloroplast signal peptide, optionally wherein said chloroplast signal peptide is encoded by an amino acid sequence that includes, but is not limited to, the amino acid sequence of SEQ ID NO:72, SEQ ID NO:76, SEQ ID NO:77, SEQ ID NO:78, SEQ ID NO:79, SEQ ID NO:80, SEQ ID NO:82,or SEQ ID NO:83.

Targeting to a membrane is similar to targeting to an organelle. Thus, specific sequences on a protein (targeting sequences or motifs) can be recognized by a transporter, which then imports the protein into an organelle or in the case of membrane association, the transporter can guide the protein to and associate it with a membrane. Thus, for example, a specific cysteine residue on a C-terminal motif of a protein can be modified posttranslation where an enzyme (prenyltransferases) then attaches a hydrophobic molecule (geranylgeranyl or farnesyl) (See, e.g., Running et al. *Proc Natl Acad Sci USA* 101: 7815-7820 (2004); Maurer-Stroh et al. *Genome Biology* 4:212 (2003)). This hydrophobic addition guides and associates the protein to a membrane (in case of the cytosol, the membrane would be the plasma membrane or the cytosolic site of the nuclear membrane (Polychronidou et al. *Molecular Biology of the Cell* 21: 3409-3420 (2010)). More specifically, in representative embodiments, a protein prenyltransferase can catalyze the covalent attachment of a 15-carbon farnesyl or 20-carbon geranylgeranyl isoprenoid to C-terminal cysteines of selected proteins carrying a CaaX motif where C=cysteine; a=aliphatic amino acid; x=any amino acid. For plants, this motif most often is CVVQ (SEQ ID NO:84). The addition of prenyl groups facilitates membrane association and protein—protein interactions of the prenylated proteins.

In still other embodiments of the invention, a signal peptide can direct a polypeptide of the invention to more than one organelle (e.g., dual targeting). Thus, in some embodiments, a signal peptide that can target a polypeptide of the invention to more than one organelle is encoded by an amino acid sequence that includes, but is not limited to, the amino acid sequence of SEQ ID NO:76.

In addition to promoters operably linked to a heterologous polynucleotide of the invention, an expression cassette also can include other regulatory sequences. As used herein, "regulatory sequences" means nucleotide sequences located upstream (5' non-coding sequences), within or downstream (3' non-coding sequences) of a coding sequence, and which influence the transcription, RNA processing or stability, or translation of the associated coding sequence. Regulatory sequences include, but are not limited to, enhancers, introns, translation leader sequences, translation termination sequences, and polyadenylation signal sequences, as described herein.

Thus, in some embodiments of the present invention, the expression cassettes can include at least one intron. An intron useful with this invention can be an intron identified in and isolated from a plant to be transformed and then inserted into the expression cassette to be used in transformation of the plant. As would be understood by those of skill in the art, the introns as used herein comprise the sequences required for self excision and are incorporated into the nucleic acid constructs in frame. An intron can be used either as a spacer to separate multiple protein-coding sequences in one nucleic acid construct, or an intron can be used inside one protein-coding sequence to stabilize the mRNA. If they are used within a protein-coding sequence, they are inserted "in-frame" with the excision sites included.

Non-limiting examples of introns useful with the present invention can be introns from the RuBisCO small subunit (rbcS) gene, the RuBisCO large subunit (rbcL) gene, the actin gene, the nitrate reductase gene (nr), the duplicated carbonic anhydrase gene 1 (Tdca1), the psbA gene, the atpA gene, or any combination thereof.

In some embodiments of the invention, an expression cassette can comprise an enhancer sequence. Enhancer sequences can be derived from, for example, any intron from any highly expressed gene. In particular embodiments, an enhancer sequence usable with this invention includes, but is not limited to, the nucleotide sequence of ggagg (e.g., ribosome binding site).

An expression cassette also can optionally include a transcriptional and/or translational termination region (i.e., a termination region) that is functional in plants, yeast or bacteria. A variety of transcriptional terminators are available for use in expression cassettes and are responsible for the termination of transcription beyond the heterologous polynucleotide of interest and correct mRNA polyadenylation. The termination region may be native to the transcriptional initiation region, may be native to the operably linked nucleotide sequence of interest, may be native to the host cell, or may be derived from another source (i.e., foreign or heterologous to the promoter, the nucleotide sequence of interest, the host cell, or any combination thereof). Non-limiting examples of transcriptional terminators useful for plants can be a CAMV 35S terminator, a tml terminator, a nopaline synthase terminator and/or a pea rbcs E9 terminator, a RubisCo small subunit gene 1 (TrbcS1) terminator, an actin gene (Tactin) terminator, a nitrate reductase gene (Tnr) terminator, and/or aa duplicated carbonic anhydrase gene 1 (Tdca1) terminator.

Further non-limiting examples of terminators useful with this invention for expression of the heterologous polynucleotides of the invention or other heterologous polynucleotides of interest in algae include a terminator of the psbA gene (TpsbA), a terminator of the psaA gene (encoding an apoprotein of photosystem I) (TpsaA), a terminator of the psbD gene (TpsbD), a RuBisCo large subunit terminator (TrbcL), a terminator of the $\sigma^{70}$-type plastid rRNA gene (Trrn), and/or a terminator of the ATPase alpha subunit gene (TatpA).

An expression cassette of the invention also can include a nucleotide sequence for a selectable marker, which can be used to select a transformed plant, plant part and/or plant cell. As used herein, "selectable marker" means a nucleotide sequence that when expressed imparts a distinct phenotype to a plant, plant part and/or plant cell expressing the marker and thus allows such a transformed plant, plant part, and/or plant cell to be distinguished from that which does not have the marker. Such a nucleotide sequence may encode either a selectable or screenable marker, depending on whether the marker confers a trait that can be selected for by chemical means, such as by using a selective agent (e.g., an antibiotic, herbicide, or the like), or whether the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a nucleotide sequence encoding aadA (i.e., spectinomycin and streptomycin resistance), a nucleotide sequence encoding neo (i.e., kanamycin resistance), a nucleotide sequence encoding aphA6 (i.e., kanamycin resistance), a nucleotide sequence encoding nptII (i.e., kanamycin resistance), a nucleotide sequence encoding bar (i.e., phosphinothricin resistance), a nucleotide sequence encoding cat (i.e., chloramphenicol resistance), a nucleotide sequence encoding badh (i.e., betaine aldehyde resistance), a nucleotide sequence encoding egfp, (i.e., enhanced green fluorescence protein), a nucleotide sequence encoding gfp, (i.e., green fluorescent protein), a nucleotide sequence encoding luc (i.e., luciferase), a nucleotide sequence encoding ble (bleomycin resistance), a nucleotide sequence encoding ereA (erythromycin resistance), and any combination thereof.

Further examples of selectable markers useful with the invention include, but are not limited to, a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella ozaenae* that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hph that confers resistance to hygromycin.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac" 263-282 In: *Chromosome Structure and Function: Impact of New Concepts,* 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) *Proc. Natl. Acad. Sci. USA* 75:3737-3741); a nucleotide sequence encoding xylE that encodes a catechol dioxygenase (Zukowsky et al. (1983) *Proc. Natl. Acad. Sci. USA* 80:1101-1105); a nucleotide sequence encoding tyrosinase, an enzyme capable of oxidizing tyrosine to DOPA and dopaquinone, which in turn condenses to form melanin (Katz et al. (1983) *J. Gen. Microbiol.* 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) *Science* 234:856-859); a nucleotide sequence encoding Bla that confers ampicillin resistance; or a nucleotide sequence encoding aequorin which may be employed in calcium-sensitive bioluminescence detection (Prasher et al. (1985) *Biochem. Biophys. Res. Comm.* 126:1259-1268), and/or any combination thereof. One of skill in the art is capable of choosing a suitable selectable marker for use in an expression cassette of this invention.

An expression cassette comprising a heterologous polynucleotide of the invention (e.g., polynucleotide(s) encoding biological carbon sequestration polypeptides of the invention), also can optionally include additional polynucleotides that encode other desired traits. Such desired traits can be, for example, polynucleotides which confer high light tolerance, increased drought tolerance, increased flooding tolerance, increased tolerance to soil contaminants, increased yield, modified fatty acid composition of the lipids, increased oil production in seed, increased and modified starch production in seeds, increased and modified protein production in seeds, modified tolerance to herbicides and pesticides, production of terpenes, increased seed number, and/or other desirable traits for agriculture or biotechnology.

Such polynucleotides can be stacked with any combination of nucleotide sequences to create plants, plant parts and/or plant cells having the desired phenotype. Stacked combinations can be created by any method including, but not limited to, any conventional methodology (e.g., cross breeding for plants), or by genetic transformation. If stacked by genetic transformation, nucleotide sequences encoding additional desired traits can be combined at any time and in any order. For example, a transgenic plant comprising one or more desired traits can be used as the target to introduce further traits by subsequent transformation. The additional nucleotide sequences can be introduced simultaneously in a co-transformation protocol with a nucleotide sequence, nucleic acid molecule, nucleic acid construct, and/or other composition of the invention, provided by any combination of expression cassettes. For example, if two nucleotide sequences will be introduced, they can be incorporated in separate cassettes (trans) or can be incorporated on the same cassette (cis). Expression of the nucleotide sequences can be driven by the same promoter or by different promoters. It is further recognized that nucleotide sequences can be stacked at a desired genomic location using a site-specific recombination system. See, e.g., International Patent Application Publication Nos. WO 99/25821; WO 99/25854; WO 99/25840; WO 99/25855 and WO 99/25853.

Any nucleotide sequence to be transformed into a plant, plant part and/or plant cell can be modified for codon usage bias using species specific codon usage tables. The codon usage tables are generated based on a sequence analysis of the most highly expressed genes for the species of interest. When the nucleotide sequences are to be expressed in the nucleus, the codon usage tables are generated based on a sequence analysis of highly expressed nuclear genes for the species of interest. The modifications for the nucleotide sequences for selection are determined by comparing the species specific codon usage table with the codons present in the native polynucleotide sequences. In those embodiments in which each of codons in native polynucleotide sequence for selection are sufficiently used, then no modifications are needed (e.g., a frequency of more than 30% for a codon used for a specific amino acid in that species would indicate no need for modification). In other embodiments, wherein up to 3 nucleotides have to be modified in the polynucleotide sequence, site-directed mutagenesis can be used according to methods known in the art (Zheng et al. *Nucleic Acids Res.* 32:e115 (2004); Dammai, *Meth. Mol. Biol* 634:111-126 (2010); Davis and Vierstra. *Plant Mol. Biol.* 36(4): 521-528 (1998)). In still other embodiments, wherein more than three nucleotide changes are necessary, a synthetic nucleotide sequence can be generated using the same codon usage as the highly expressed genes that were used to develop the codon usage table.

A heterologous polynucleotide encoding (a) a succinyl CoA synthetase polypeptide, (b) an 2-oxoglutarate:ferredoxin oxidoreductase polypeptide, (c) a 2-oxoglutarate carboxylase polypeptide, (d) an oxalosuccinate reductase polypeptide, and/or (e) an isocitrate lyase polypeptide as described herein; and/or functional fragments thereof (e.g., a functional fragment of the nucleotide sequences of SEQ ID NOs:3, 6, 9, 12, 15, 18, 21, 24, 27, 30, 33, 36, 39, 42, 45, 48, 51, 53, 55, 57, 59, 61, 63, 65, 67, 69, 71, and/or any combination thereof or the amino acid sequences of SEQ ID NOs:1, 2, 4, 5, 7, 8, 10, 11, 13, 14, 16, 17, 19, 20, 22, 23, 25, 26, 28, 29, 31, 32, 34, 35, 37, 38, 40, 41, 43, 44, 46, 47, 49, 50, 52, 54, 56, 58, 60, 62, 64, 66, 68, 70, and/or any combination thereof) can be introduced into a cell of a plant by any method known to those of skill in the art. In some embodiments of the invention, transformation of a cell comprises nuclear transformation. In other embodiments, transformation of a cell comprises plastid transformation (e.g., chloroplast transformation).

Procedures for transforming plants are well known and routine in the art and are described throughout the literature. Non-limiting examples of transformation methods include transformation via bacterial-mediated nucleic acid delivery (e.g., via Agrobacteria), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)). General guides to the transformation of yeast include Guthrie and Fink (1991) (Guide to yeast genetics and molecular biology. In *Methods in Enzymology*, (Academic Press, San Diego) 194:1-932) and guides to methods related to the transformation of bacteria include Aune and Aachmann (*Appl. Microbiol Biotechnol* 85:1301-1313 (2010)).

A polynucleotide therefore can be introduced into a plant, plant part, plant cell in any number of ways that are well known in the art. The methods of the invention do not depend on a particular method for introducing one or more nucleotide sequences into a plant, only that they gain access to the interior the cell. Where more than polynucleotide is to be introduced, they can be assembled as part of a single nucleic acid construct, or as separate nucleic acid constructs, and can be located on the same or different nucleic acid constructs. Accordingly, the polynucleotide can be introduced into the cell of interest in a single transformation event, or in separate transformation events, or, alternatively, a polynucleotide can be incorporated into a plant as part of a breeding protocol.

In some embodiments, when a plant part or plant cell is stably transformed, it can then be used to regenerate a stably transformed plant comprising a heterologous polynucleotide encoding (1) a succinyl CoA synthetase polypeptide, (2) a 2-oxoglutarate:ferredoxin oxidoreductase polypeptide, (3) a 2-oxoglutarate carboxylase polypeptide, (4) an oxalosuccinate reductase polypeptide, or (5) an isocitrate lyase polypeptide, or (6) a succinyl CoA synthetase polypeptide and a 2-oxoglutarate:ferredoxin oxidoreductase polypeptide, (7) a 2-oxoglutarate carboxylase polypeptide and an oxalosuccinate reductase polypeptide, or (8) a 2-oxoglutarate carboxylase polypeptide, an oxalosuccinate reductase polypeptide and an isocitrate lyase polypeptide as described herein. Means for regeneration can vary from plant species to plant species, but generally a suspension of transformed protoplasts or a petri plate containing transformed explants is first provided. Callus tissue is formed and shoots may be induced from callus and subsequently root. Alternatively, somatic embryo formation can be induced in the callus tissue. These somatic embryos germinate as natural embryos to form plants. The culture media will generally contain various amino acids and plant hormones, such as auxin and cytokinins. It may also be advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

The regenerated plants are transferred to standard soil conditions and cultivated in a conventional manner. The plants are grown and harvested using conventional procedures.

The particular conditions for transformation, selection and regeneration of a plant can be optimized by those of skill in the art. Factors that affect the efficiency of transformation include the species of plant, the target tissue or cell, composition of the culture media, selectable marker genes, kinds of vectors, and light/dark conditions. Therefore, these and other factors may be varied to determine an optimal transformation protocol for any particular plant species. It is recognized that not every species will react in the same manner to the transformation conditions and may require a slightly different modification of the protocols disclosed herein. However, by altering each of the variables, an optimum protocol can be derived for any plant species.

Further, the genetic properties engineered into the transgenic seeds and plants, plant parts, and/or plant cells of the present invention described herein can be passed on by sexual reproduction or vegetative growth and therefore can be maintained and propagated in progeny plants. Generally, maintenance and propagation make use of known agricultural methods developed to fit specific purposes such as harvesting, sowing or tilling.

Accordingly, in some aspects of the invention, a stably transformed plant, plant part and/or plant cell, or a stably transformed photosynthetic bacterium is provided, which comprises in its genome one or more recombinant nucleic acid molecules/heterologous polynucleotides of the invention and has increased carbon fixation and/or increased biomass production. Thus, in some embodiments, the invention provides a stably transformed plant, plant part and/or plant cell, or a stably transformed photosynthetic bacterium comprising in its genome at least one heterologous polynucleotide encoding (1) a succinyl CoA synthetase polypeptide, (2) a 2-oxoglutarate:ferredoxin oxidoreductase polypeptide, (3) a 2-oxoglutarate carboxylase polypeptide, (4) an oxalosuccinate reductase polypeptide, or (5) an isocitrate lyase polypeptide, or (6) a succinyl CoA synthetase polypeptide and a 2-oxoglutarate:ferredoxin oxidoreductase polypeptide, (7) a 2-oxoglutarate carboxylase polypeptide and an oxalosuccinate reductase polypeptide, or (8) a 2-oxoglutarate carboxylase polypeptide, an oxalosuccinate reductase polypeptide and an isocitrate lyase polypeptide, which when expressed results in the stably transformed plant, plant part or plant cell, or the stably transformed photosynthetic bacterium having increased carbon fixation and/or increased biomass production. In representative embodiments, the at least one heterologous polynucleotide encoding (1) a succinyl CoA synthetase polypeptide, (2) a 2-oxoglutarate: ferredoxin oxidoreductase polypeptide, (3) a 2-oxoglutarate carboxylase polypeptide, (4) an oxalosuccinate reductase polypeptide, or (5) an isocitrate lyase polypeptide, or (6) a succinyl CoA synthetase polypeptide and a 2-oxoglutarate: ferredoxin oxidoreductase polypeptide, (7) a 2-oxoglutarate carboxylase polypeptide and an oxalosuccinate reductase polypeptide, or (8) a 2-oxoglutarate carboxylase polypeptide, an oxalosuccinate reductase polypeptide and an isocitrate lyase polypeptide when expressed in a plant, plant part, and/or plant cell may be expressed in the nucleus and targeted to the chloroplast and/or may be expressed in the chloroplast.

Additionally provided herein are seeds produced from the stably transformed plants of the invention, wherein said seeds comprise in their genome (1) a heterologous polynucleotide encoding a succinyl CoA synthetase polypeptide, (2) a heterologous polynucleotide encoding a 2-oxoglutarate:ferredoxin oxidoreductase polypeptide, (3) a heterologous polynucleotide encoding a 2-oxoglutarate carboxylase polypeptide, (4) a heterologous polynucleotide encoding an oxalosuccinate reductase polypeptide, or (5) a heterologous polynucleotide encoding an isocitrate lyase polypeptide, or (6) a heterologous polynucleotide encoding a succinyl CoA synthetase polypeptide and a heterologous polynucleotide encoding a 2-oxoglutarate:ferredoxin oxidoreductase polypeptide, (7) a heterologous polynucleotide encoding a 2-oxoglutarate carboxylase polypeptide and a heterologous polynucleotide encoding an oxalosuccinate reductase polypeptide, or (8) a heterologous polynucleotide encoding a 2-oxoglutarate carboxylase polypeptide, a heterologous polynucleotide encoding an oxalosuccinate reductase polypeptide and a heterologous polynucleotide encoding an isocitrate lyase polypeptide, wherein said heterologous polynucleotides are from a bacterial or archaeal species.

The present invention further provides products produced from the stably transformed plant, plant cell or plant part of the invention. In some embodiments, the product produced can include but is not limited to biofuel, food, drink, animal feed, fiber, and/or pharmaceuticals.

The following examples are not intended to be a detailed catalog of all the different ways in which the present invention may be implemented or of all the features that may be added to the present invention. Persons skilled in the art will appreciate that numerous variations and additions to the various embodiments may be made without departing from the present invention. Hence, the following descriptions are intended to illustrate some particular embodiments of the invention, and not to exhaustively specify all permutations, combinations and variations thereof.

EXAMPLES

Example 1. The Synthetic crTCA Pathway Enzymes

Increasing the productivity of a $C_3$ plant such as *camelina* to levels seen for $C_4$ plants (e.g. corn) requires improving photosynthetic carbon fixation. One limiting factor is the oxygenase activity of the $CO_2$-fixing Ribulose 1,5 bisphosphate Carboxylase/Oxygenase (RUBISCO) that reduces the photosynthetic productivity by up to 30%. The present invention provides methods and compositions for improving carbon fixation in plants by introducing a synthetic carbon fixation pathway that is independent of RUBISCO but works in concert with the existing Calvin Benson cycle.

Specifically, this invention provides a "condensed reverse TCA (crTCA) cycle," that employs a (1) succinyl-CoA synthetase for catalyzing the conversion of succinate to succinyl-CoA, (2) a 2-oxoglutarate:ferredoxin oxidoreductase for converting succinyl-CoA to 2-oxoglutarate (i.e., 2-ketoglutarate), (3) a 2-oxoglutarate carboxylase for converting 2-oxoglutarate to oxalosuccinate, (4) an oxalosuccinate reductase for converting oxalosuccinate to isocitrate, and (5) an isocitrate lyase for cleaving isocitrate into succinate and glyoxylate (FIG. 1).

For generation of the synthetic crTCA cycle, specific enzymes were chosen from source bacteria based on the following criteria: (1) experimentally determined function of the enzyme, (2) target enzymes having the fewest subunits, and (3) in cases in which enzyme activity is unavailable, enzyme choice based on highest homology levels to characterized enzymes having the desired activity.

Candidate Enzymes

For the succinyl CoA synthetase enzyme activity, the characterized *Escherichia coli* version of this enzyme can be used (e.g., SucC and SucD, NCBI Accession Nos: NC_000913.2 (762,237 . . . 763,403), NC_000913.2 (763, 403 . . . 764,272),NP_415256.1 and NP_415257.1) (Buck et al. *J Gen Microbiol* 132:1753-62 (1986)). Additional succinyl CoA synthetase versions that can also be used include those from *Azotobacter vinelandii* DJ, (NCBI Accession Nos. NC_012560.1 (3,074,152 . . . 3,075,321), NC_012560.1 (3,073,268 . . . 3,074,155, YP_002800115.1 and YP_002800114.1; *Bradyrhizobium* sp. BTAi1, (NCBI Accession Nos. NC_009485.1 (393,292 . . . 394,488), NC_009485.1 (394,545 . . . 395,429),YP_001236586.1 and YP_001236587.1); and/or *Azospirillum* sp. B510, (NCBI Accession Nos. NC_013854.1 (2,941,010 . . . 2,942,206), NC_013854.1 (2,942,208 . . . 2,943,083), YP_003449758.1 and YP_003449759.1) (See, e.g., the nucleotide sequences of SEQ ID NOs:3, 6, 9 and/or 12; the amino acid sequences of SEQ ID NOs:1, 2, 4, 5, 7, 8, 10 and/or 11).

Oxoglutarate:ferredoxin oxidoreductase (OOR) enables the crTCA cycle to function in the reverse direction (Buchanan and Arnon *Photosynth Res* 24:47-53 (1990). There are two types of OORs, a two subunit version expressed in the anaerobic phototrophic bacterium *Chlorobium limicola* (Buchanan and Arnon *Photosynth Res* 24:47-53 (1990)) and the aerobic halophile *Halobacterium salinarum* (Kerscher and Oesterhelt *Eur J Biochem* 116:587-94(1981)) and a four subunit version expressed in anaerobic sulfur reducing bacteria such as *Sulfurimonas denitrificans* (Hugler et al. *J. Bacteriol* 187:3020-7 (2005)). Because the crTCA cycle is meant to function in plants using oxygenic photosynthesis and limiting enzyme subunits can simplify the generation of the transgenic plant lines, the two subunit version of OOR from an aerobic bacterium can be used. Based on homology to the biochemically characterized *H. salinarum* OOR, a two subunit OOR was selected with good identity from the aerobic bacterium *Paenibacillus larvae* subsp. larvae B-3650 ((NCBI Accession Nos. PlarlB_020100012680 and PlarlB_020100012675, NZ_ADZY02000226.1 (7,939 . . . 9,687), NZ_ADZY02000226.1 (7,085 . . . 7,951), ZP_09070120.1 and ZP_09070119.1). Additional versions of OOR that could be used include the following: *Halobacterium* sp. NRC-1 korA, korB, (NCBI Accession Nos. NC_002607.1 (856,660 . . . 858,582), NC_002607.1 (855, 719 . . . 856,657), AAG19514.1 and AAG19513.1, NP_280034.1 and NP_280033.1); *Hydrogenobacter thermophilus* TK-6 korA, korB, ((NCBI Accession Nos. NC_013799.1 (997,525 . . . 999,348), NC_013799.1 (996, 624 . . . 997,511), YP_003432752.1 and YP_003432751.1; *Bacillus* sp. M3-13 Bm3-1 010100005806, Bm3-1_010100005801, NZ_ACPC01000013.1 (932Dz,668), NZ_ACPC01000013.1 (65 . . . 931), ZP_07708142.1 and ZP_07708141.1); *Haladaptatus paucihalophilus* DX253 (NCBI Accession Nos. ZOD2009_10775, ZOD2009-10770, contig00009, whole genome shotgun sequence NZ_AEMG01000009.1 (157,678DZ59,432), NZ_AEMG01000009.1 (156,818 . . . 157,681), ZP_08044530.1 and ZP_08044529.1); and/or *Magnetococcus* sp. (NCBI Accession Nos. MC-1 Mmc1_1749, Mmc1_1750, NC_008576.1 (2,161,258 . . . 2,162,979), NC_008576.1 (2,162,976 . . . 2,163,854), YP_865663.1 and YP_865664.1). (See, e.g., the nucleotide sequences of SEQ ID NOs:15, 18, 21, 24, 27 and/or 30; or the amino acid sequences of SEQ ID NOs: 13, 14, 16, 17, 19, 20, 22, 23, 25, 26, 28 and/or 29).

A 2-oxoglutarate carboxylase characterized from the thermophilic chemoautotrophic bacterium *Hydrogenobacter thermophilus* TK-6, optimally functions at 80° C. (Aoshima and Igarashi *Mol Microbiol* 62:748-59(2006)). Homology analysis using the *H. thermophilus* korA; and korB subunit sequences identified subunits from a nitrite-oxidizing bacterium *Candidatus Nitrospira defluvii* having high identity (pycA, and pycB; NCBI Accession Nos. NC_014355.1 (1,174,721DZ,176,652), NC_014355.1 (1,176,781DZ,178, 199), YP_003796887.1 and YP_003796888.1). These genes are identified as subunits of pyruvate carboxylase in the *N. defluvii* genome; however, protein modeling analysis determined that the *N. defluvii* carboxylase has high specificity for oxoglutarate. Additional versions of 2-oxoglutarate carboxylase that could be used include, for example, *Hydrogenobacter thermophilus* TK-6 cfiA, cfiB, (NCBI Accession Nos. NC_013799.1 (1,271,487 . . . 1,273,445), NC_013799.1 (1,273,469DZ,274,887), YP_003433044.1 and YP_003433045.1 and its modified version (see, e.g., SEQ ID NOs:37-42)); *Thiocystis violascens* DSM198 (NCBI Accession Nos. ThiviDRAFT_1483, ThiviDRAFT_1486, whole genome shotgun sequence, ctg263, NZ_AGFC01000013.1 (61,879 . . . 63,297) and (63,889 . . . 65,718), ZP_08925050.1 and ZP_08925052.1); *Mariprofundus ferrooxydans* PV-1 (NCBI Accession Nos. SPV1_07811, SPV1_07816, NZ_AATS01000007.1 whole genome shotgun sequence, 1099921033908 (81,967 . . . 83,385) and (83,475 . . . 85,328), ZP_01452577.1 AND ZP_01452578.1); and/or *Pseudomonas stutzeri* ATCC14405 (NCBI Accession Nos. PstZobell_14412 and PstZobell_14407, CCUG 16156 contig00098, whole genome shotgun sequence AGSL01000085.1 (52,350 . . . 53,765) and (50,522 . . . 52,339), EHY78621.1 and EHY78620.1). (See, e.g., the nucleotide sequences of SEQ ID NOs: 33, 36, 39, 42, 45, 48 and/or 51; or the amino acid sequences of SEQ ID NOs: 31, 32, 34, 35, 37, 38, 40, 41, 43, 44, 46, 47, 49 and/or 50).

An oxalosuccinate reductase has also been characterized from *H. thermophilus* (Aoshima and Igarashi *Mol Microbiol* 62:748-59(2006)). We identified a further oxalosuccinate reductase from the soil bacterium *Acinetobacter baumannii* (NCBI Accession Nos. ACICU_02687, NC_010611.1 (2,855,563 . . . 2,856,819) YP_001847346.1), which has high homology to oxalosuccinate reductase from *H. thermophilus*. Additional versions of oxalosuccinate reductase that also could be used include the following: *Chlorobium limicola* DSM 245 Cl-idh, (NCBI Accession Nos. AB076021.1, BAC00856.1); *Kosmotoga olearia* TBF 19.5.1 (NCBI Accession Nos. Kole_1227, NC_012785.1 (1,303,493DZ,304,695), YP_002940928.1); Marine gamma proteobacterium HTCC2080 (NCBI Accession Nos. MGP2080_11238, 1100755000543, whole genome shotgun sequence NZ_AAVV01000002.1 (123,681 . . . 124,934), ZP_01625318.1); and/or *Nitrosococcus halophilus* Nc4 (NCBI Accession Nos. NhaI_2539, NC_013960.1 (2,610, 547Dz,611,815), YP_003528006.1). (See, e.g., the nucleotide sequences of SEQ ID NOs: 53, 55, 57, 59 and/or 61; or the amino acid sequences of SEQ ID NOs: 52, 54, 56, 58 and/or 60).

For isocitrate lyase, the biochemically characterized version from *Corynebacterium glutamicum* ((NCBI Accession Nos. NCgl2248, NC_003450.3 (2,470,741 . . . 2,472,039) NP_601531.1) can be used (Reinscheid et al. *J Bacteriol* 176:474-83 (1994)). Additional versions of isocitrate lyase that could be used include the following: *Gordonia alkanivorans* NBRC 16433 aceA (locus tag=GOALK_050_00390), contig: GOALK050, whole genome shotgun sequence (NCBI Accession Nos. NZ_BACI01000050.1 (37,665 . . . 38,960), ZP_08765259.1); *Nocardia farcinica* IFM 10152 aceA (locus tag=nfa52300), NC_006361.1 (5,525,226 . . . 5,526,515) YP_121446.1; *Rhodococcus pyridinivorans* AK37 (NCBI Accession Nos. AK37_18248, contig53, whole genome shotgun sequence NZ_AHBW01000053.1 (20,169 . . . 21,458), ZP_09310682.1); and/or *Rhodococcus jostii* RHA1 (NCBI Accession Nos. RHA1_ro02122, NC_008268.1 (2,230,309Dz,231,598), YP_702087.1). (See, e.g., the nucleotide sequences of SEQ ID NOs: 63, 65, 67, 69 and/or 71; or the amino acid sequences of SEQ ID NOs: 62, 64, 66, 68 and/or 70).

Example 2. In Vitro Function of the Individual crTCA Cycle Enzymes and Demonstration of the Full Cycle Function Using LC-MS Analysis $C_3$ plants do not grow efficiently in hot and/or dry areas because, as the temperature increases, Rubisco incorporates more oxygen. To help overcome this limitation, two sets of bacterial enzymes with carbon fixing activities have been cloned into plant expression constructs for use in the $C_3$ oilseed producing plant *Camelina sativa*. The first carbon fixing construct known as C1 contains sequences for: (1) a 2-oxoglutarate carboxylase that converts 2-oxoglutarate to oxalosuccinate, (2) a oxalosuccinate reductase (ICDH/OSR) that converts oxalosuccinate to isocitrate, and (3) a isocitrate lyase that cleaves isocitrate into succinate and glyoxylate. The second carbon fixing construct known as C2 contains sequences for: (1) succinyl-CoA synthetase that catalyzes the conversion of succinate to succinyl-CoA and (2) a 2-oxoglutarate:ferredoxin oxidoreductase that converts succinyl-CoA to 2-oxoglutarate (a.k.a 2-ketoglutarate). A 2-oxoglutarate carboxylase utilizes ATP to catalyze the carboxylation of 2-oxoglutarate into oxalosuccinate. Transformed into the chloroplast, this reaction can provide additional carbon assimilation for the formation of substrate for nitrogen assimilation or incorporation in other biomass. Bacterial oxalosuccinate reductase catalyzes the NAD-dependent conversion of oxalosuccinate to isocitrate which can further be exported from the chloroplast into the mitochondria for further energy production or conversion into amino acids or other components. Individually expressed in chloroplasts, this enzyme can provide a bypass for feedback inhibition of carbon assimilation. Thus, these bacterial enzymes will scavenge carbon dioxide and bicarbonate from the chloroplast and generate metabolites that can feed into existing pathways present in chloroplasts, thereby enhancing the ability of plant cells to fix carbon, which can increase plant productivity.

Further carbon fixing constructs include those designed to express (1) a heterologous polynucleotide encoding a succinyl CoA synthetase polypeptide; (2) a heterologous polynucleotide encoding a 2-oxoglutarate:ferredoxin oxidoreductase polypeptide; (3) a heterologous polynucleotide encoding a 2-oxoglutarate carboxylase; (4) a heterologous polynucleotide encoding an oxalosuccinate reductase polypeptide; (5) a heterologous polynucleotide encoding an isocitrate lyase polypeptide; or (6) a heterologous polynucleotide encoding a 2-oxoglutarate carboxylase and a heterologous polynucleotide encoding an oxalosuccinate reductase polypeptide.

The present invention demonstrates in vitro function of the complete crTCA cycle using a $^{13}C$-labeled biocarbonate containing reaction and LC-MS analysis.

Purified crTCA cycle enzymes were evaluated individually using appropriate spectrophotometric-based activity assays and their specific activities determined. To demonstrate the in vitro function of the crTCA cycle, we conducted triplicate LC-MS experiments, and followed the production of crTCA cycle intermediates using $^{13}C$-labeled bicarbonate. The LC-MS reaction samples including all of the five crTCA cycle enzymes (see Table 1 for quantities and identity of enzymes used). In addition to the crTCA cycle enzymes, the reaction mixtures contained 50 mM Tris-HCl, pH 8.0, 4 mM NADH, 5 mM ATP, 5 mM MgCl2, 20 mM NaH13CO3, 0.5 mM CoA, 100 μM succinyl-CoA, 1 mM 2-oxoglutarate, and 70 μg HyTh ferredoxin, in a 700 μL volume. The reactions were initiated by addition of succinyl CoA and incubated for 0, 15, 30, 60, 90, and 120 minutes at 30° C. and were stopped by adding 50 μL of methanol. The $^{13}C$-labeled crTCA cycle intermediates were analyzed by LC-MS, and quantification of the different labeled species of the crTCA cycle intermediates was performed using standards analyzed alongside the experimental samples.

TABLE 2 crTCA Cycle Enzymes Used for LC-MS Analysis

| Cycle Enzyme | Source Organism | Amount of Enzyme Used |
|---|---|---|
| (1) Succinyl CoA Synthetase (SCS) | *Bradyrhizobium* sp.BTAi1 | 6 μg |
| (2) 2-Oxoglutarate:ferredoxin oxidoreductase (KOR) | *Hydrogenobacter thermophilus* TK-6 | 9.6 μg |
| (3) 2-Oxoglutarate carboxylase (OGC) | *Mariprofundus ferrooxydans* PV-1 | 66 μg |
| (4) Oxalosuccinate reductase (OSR, ICDH) | *Nitrosococcus halophilus* Nc4 | 9.6 μg |
| (5) Isocitrate lyase (ICL) | *Nocardia farcinica* IFM 10152 | 9.2 μg |

Figure 6:
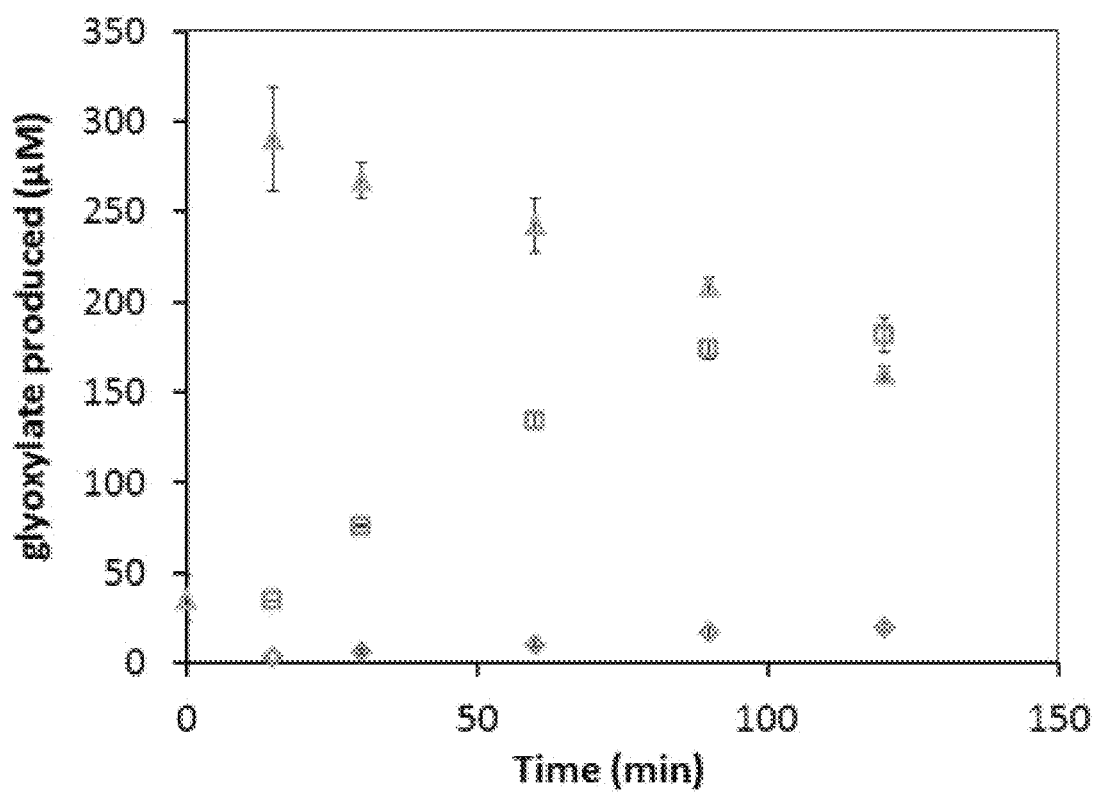
FIG. 6 shows the amount of glyoxylate detected by LC-MS over time for the full crTCA cycle reaction conducted under anaerobic conditions (diamonds, unlabeled glyoxylate; squares, 1-$^{13}$C-glyoxylate; and triangles, 2-$^{13}$C-glyoxylate). The results were corrected based on the natural abundance of the $^{13}$C glyoxylate.

In FIG. 6, the averaged amounts of glyoxylate from three separate reaction replicates (unlabeled, 1-$^{13}C$-glyoxylate and 2-$^{13}C$-glyoxylate) are shown in response to incubation time. As seen in FIG. 6, 1-C and 2-C $^{13}C$-glyoxylate species are reproducibly observed, which indicates that the crTCA cycle successfully functioned in replicate reactions as a cycle under the conditions tested.

Figure 7:
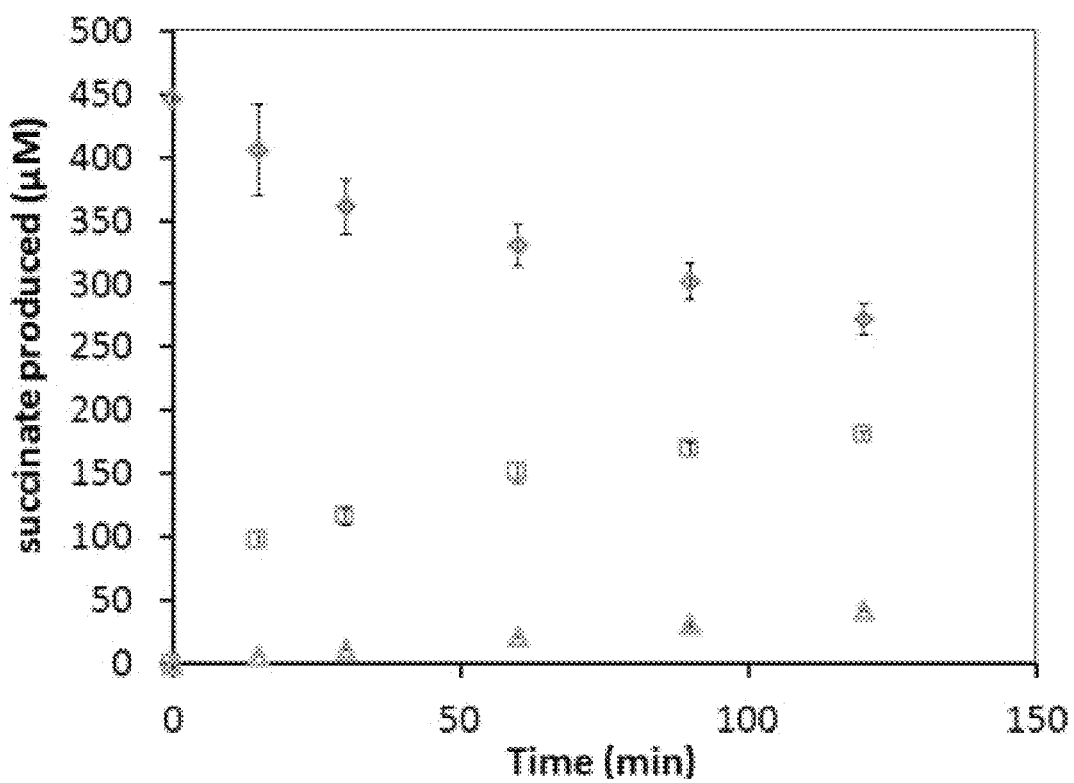
FIG. 7 shows the amount of succinate detected by LC-MS over time for the full crTCA cycle reaction conducted under anaerobic conditions (diamonds, unlabeled succinate; squares, 1-$^{13}$C-succinate; and triangles, 2-$^{13}$C-succinate). The results were corrected based on the natural abundance of the $^{13}$C succinate.
Figure 8:
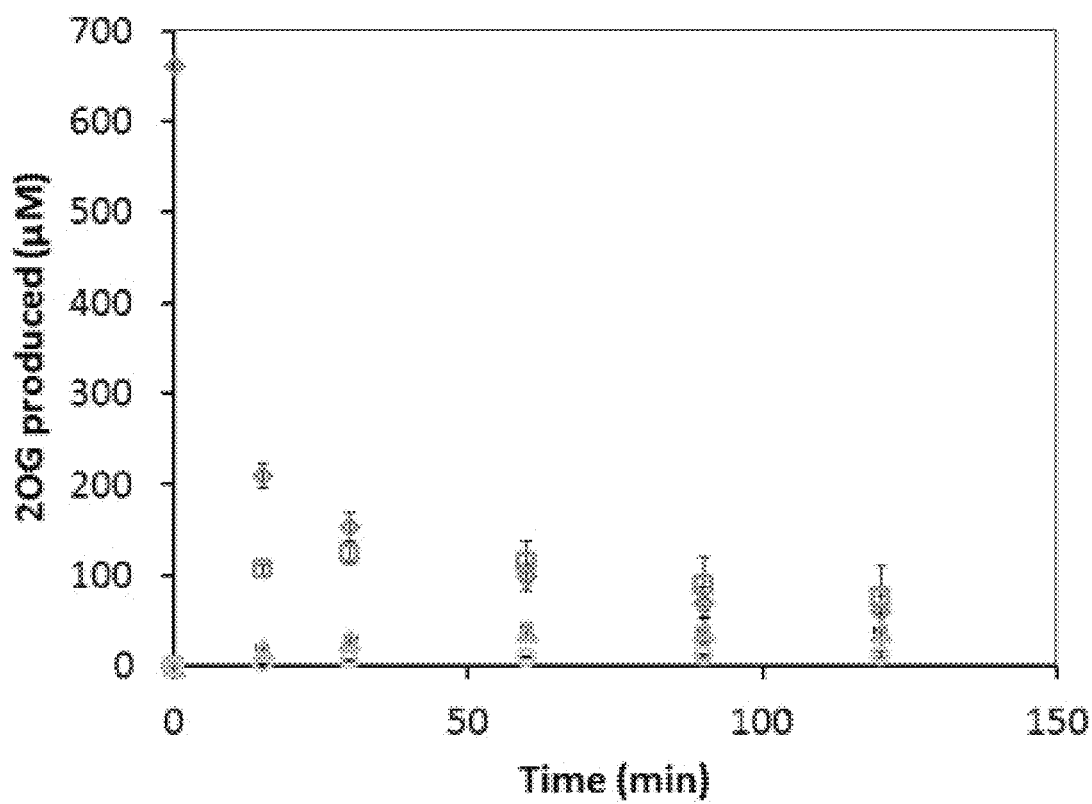
FIG. 8 shows the amount of 2-oxoglutarate detected by LC-MS over time for the full crTCA cycle reaction conducted under anaerobic conditions (diamonds, unlabeled 2-oxoglutarate; squares, 1-$^{13}$C-2-oxoglutarate; and triangles, 2-$^{13}$C-2-oxoglutarate). The results were corrected based on the natural abundance of the $^{13}$C 2-oxoglutarate.

Quantitation of the $^{13}C$-labeled succinate and 2-oxoglutarate was also completed and the results are shown in FIG. 7 and FIG. 8, respectively.

The averages of the highest observed quantities for crTCA cycle intermediates for the three reaction replicates (including all unlabeled and labeled species detected) for the reactions conducted at 30° C. under anaerobic conditions are presented in Table 3.

TABLE 3

LC-MS Quantitation of crTCA Cycle Metabolites

| Glyoxylate | non-labeled | 0 | 290 ± 30 |
|---|---|---|---|
| | one $^{13}C$ labeled | 0 | 182 ± 10 |
| | two $^{13}C$ labeled | 0 | 21 ± 4 |

TABLE 3-continued

| LC-MS Quantitation of crTCA Cycle Metabolites | | | |
|---|---|---|---|
| Succinate and succinyl-CoA | non-labeled | 100 | N/A |
| | one $^{13}$C labeled | 0 | 180 ± 4 |
| | two $^{13}$C labeled | 0 | 43 ± 1 |
| 2-Oxoglutarate | non-labeled | 1000 | N/A |
| | one $^{13}$C labeled | 0 | 120 ± 10 |
| | two $^{13}$C labeled | 0 | 40 ± 10 |
| | three $^{13}$C labeled | 0 | 12 ± 3 |

The step 3 intermediate, oxalosuccinate, could not be detected by LC-MS because of its lability, and the step 4 intermediate, isocitrate, was not detected in quantifiable amounts, most likely because the isocitrate lyase step (enzyme step 5) is so efficient in converting isocitrate to succinate and glyoxylate that detectable pools of isocitrate do not accumulate. From the quantification of the crTCA cycle intermediates it is clear that the cycle is functional as the glyoxylate produced in the reaction (493 µM total) is approximately 49% of the starting concentration of 2-oxoglutarate (1 mM).

Example 3. Western Analysis and Activity for Transient Expression of crTCA Cycle Enzymes in Tobacco Each of the cycle genes was used to transform tobacco for transient expression. A strategy similar to the one used for *Camelina* transformation was used to design these constructs. The synthesized crTCA cycle nucleotide sequences also include a chloroplast localization (ctp from tobacco) sequence and a 6×-his tag to aid in confirmation of expression and affinity-purification for activity assays. Synthesized elements were cloned into pCAMBIA2300_EGFP_BAR (containing the eGFP fluorescent marker and a Basta resistance gene) using HindIII and BamHI restriction sites. Each crTCA nucleotide sequence includes its own 35S promoter and NOS terminator. We have obtained RT-PCR, Western blot and enzymatic assay data for the transient expression for four of the five crTCA cycle enzymes (SCS, KOR, OSR, and ICL) in tobacco. However, we have not yet confirmed the expression of the *M. ferrooxydans* OGC (MaFe OGC) in tobacco by Western analysis.

Example 4. Western Blot Analysis Demonstrating crTCA Cycle Enzyme Expression in *Camelina* Transformed with Either crTCA Cycle Construct #1 or #2

Figure 4:
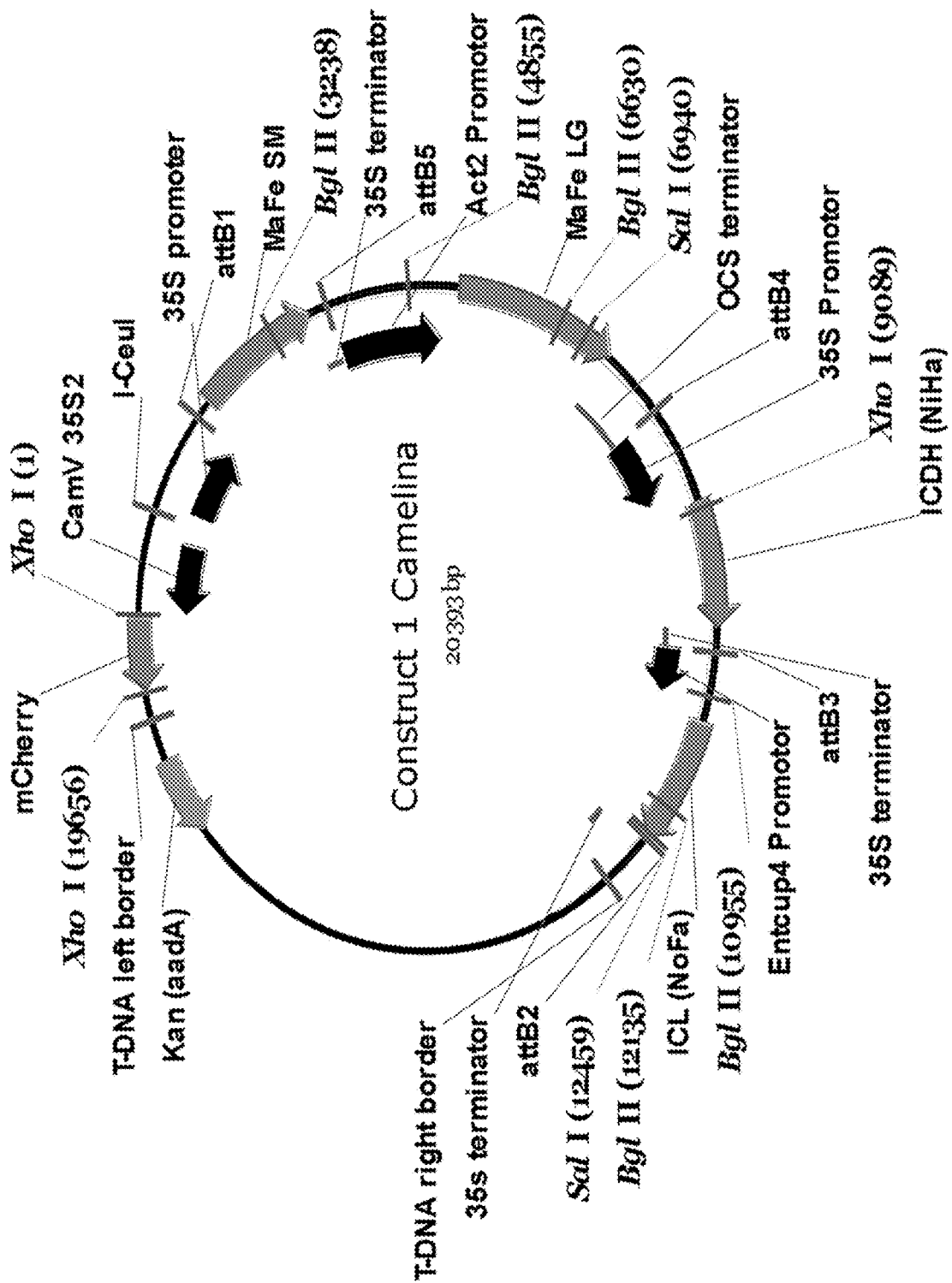
FIG. 4 shows construct 1 comprising the elements for cloning, selection and expression of chloroplast targeted isocitrate dehydrogenase/oxalosuccinate reductase (ICDH/OSR), isocitrate lyase (ICL) and the chloroplast targeted two subunits of OGC.
Figure 5:
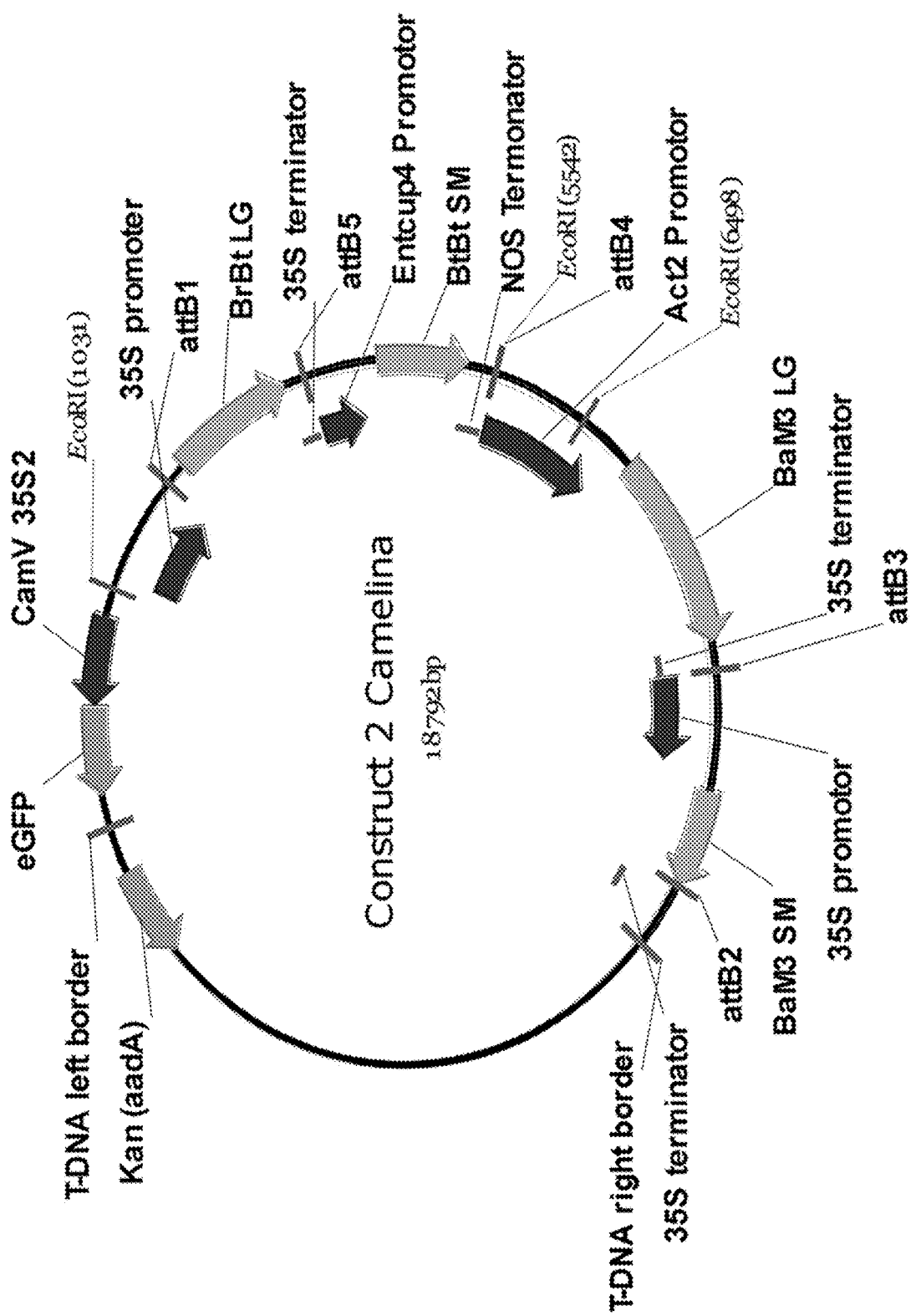
FIG. 5 shows construct 2 comprising the elements for cloning, selection and expression of chloroplast targeted two subunits each of succinyl CoA synthetase (SCS) and 2-oxoglutarate:ferredoxin oxidoreductase (KOR).

*Camelina* plants transformed with either Construct 1 (OGC/OSR (or ICDH)/ICL; FIG. 4) or Construct 2 (SCS/KOR; FIG. 5) were evaluated by western blot analysis to detect expression of crTCA cycle enzymes. Leaf samples used for the western analysis came from plants which were confirmed for gene expression by RT-PCR analysis. The membrane was probed with peptide antibodies designed to detect crTCA cycle enzymes. Probing with peptide antibodies designed to detect crTCA cycle enzymes #1 or #2, peptide antibodies designed to detect crTCA cycle enzymes #3 or #4 and with peptide antibodies designed to detect crTCA cycle enzyme #5, isocitrate lyase showed that each of enzymes was produced (see, Table 4). The WT sample was used as a control in a western blot analysis of *Camelina* transformed with Construct #1 and verified by RT-PCR analysis to express crTCA cycle enzyme #5 (ICL).

Example 5. crTCA Expressing *Camelina* Plants

Transgene-positive T1 plants for C1 (OCG+OSR (ICDH)+ICL) or C2 (SCS+KOR) have yielded T2 plants that were confirmed by genotyping and analyzed for expression. Crosses between C1 and C2 T2 plants were made in November and December 2014. F1 seeds were harvested and analyzed for mCherry and eGFP fluorescence. 71 mCherry-positive F1 seeds were harvested from 11 crosses with a C2 female parent. This suggests that the integration of both constructs was complete following those crosses. Another 373 mCherry-positive F1 seeds were harvested from C1 female parents. Observation of eGFP fluorescence in those seedlings confirmed the presence of the C2 construct in F1 tissue.

Figure 9:
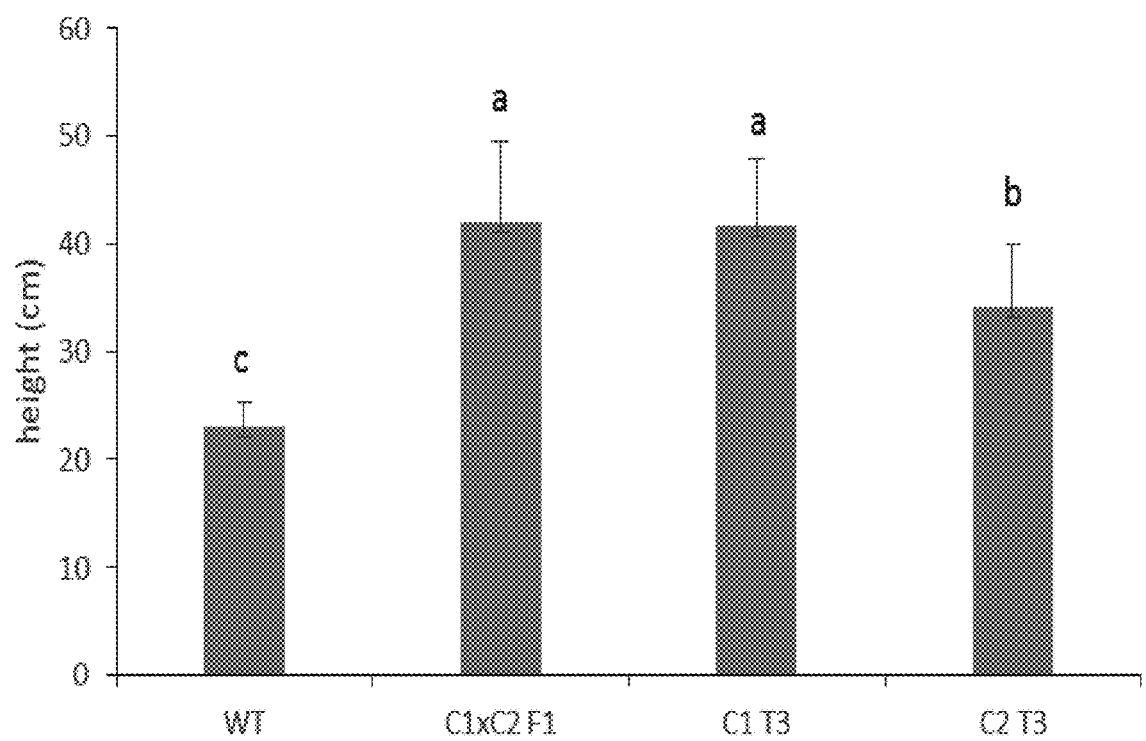
FIG. 9 shows plant heights at 30 DAP. C1×C2 F1 plants are significantly taller than wild type and C2 T3 but not significantly taller than C1 T3. Values labeled with the same letter are not significantly different according to Fisher's LSD test (p=0.05). C2 plants were transformed with Construct 2 and C1 plants were transformed with Construct 1.
Figure 10:
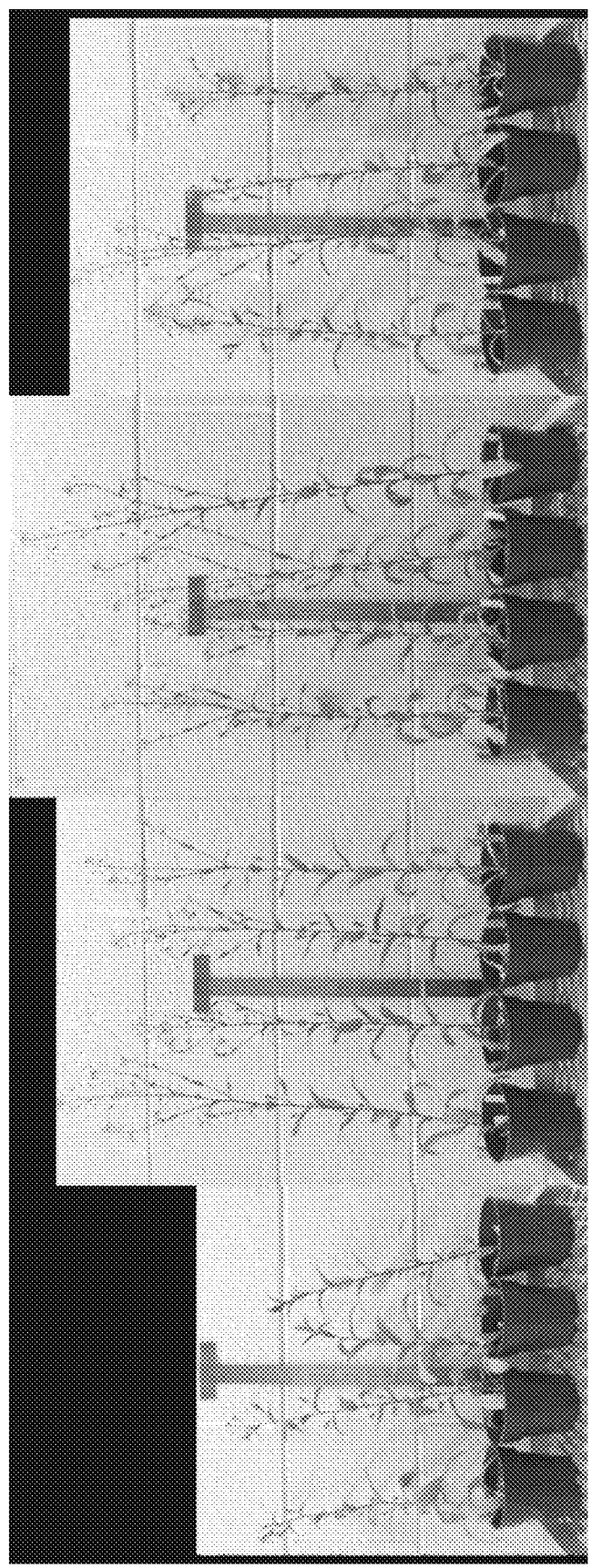
FIG. 10 shows *C. sativa* plants at 36 days after planting (DAP). Panel A: Wild-type, Panel B; C1×C2 F1 plants, Panel C; C1 T3 plants, and Panel D: C2 T3 plants. Both parental lines, C1 and C2 and the F1 of their cross exhibit a significant increase in plant height over wild type plants.

Forty-eight F1 plants showing mCherry and eGFP fluorescence were genotyped and those confirmed by genotyping to contain C1 and C2 constructs were planted in soil. At 30 days after planting (DAP), the F1 plants (FIG. 9 and FIG. 10, panel B) had an average height of 42 cm, compared to 23 cm for the wild-type (FIG. 9 and FIG. 10, panel A). The

TABLE 4

Summary of Western Analysis and Activity for Transient Expression of crTCA Cycle Enzymes in Tobacco

Figure 11:
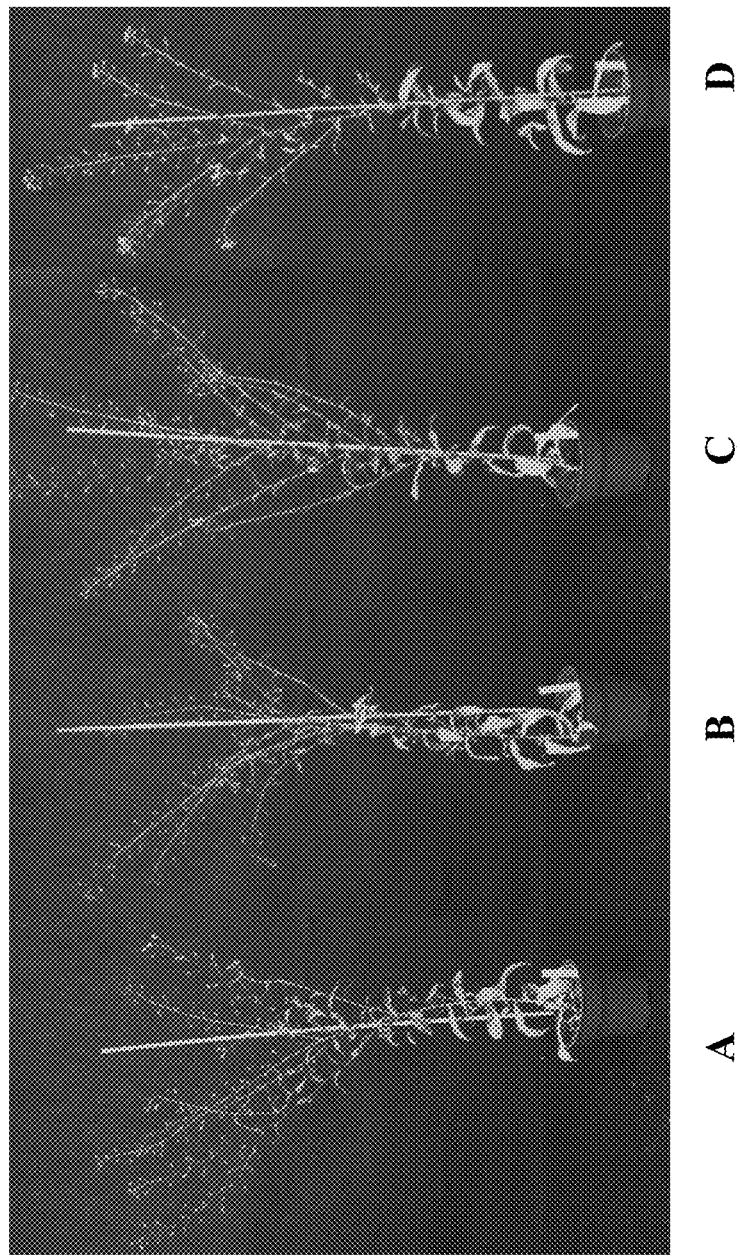
FIG. 11 shows *C. sativa* plants at 48 DAP. Panel A: C1 T3 plants; Panel B: C2 T3 plants; Panel C: C1×C2 F1 plants; and Panel D: Wild-type.

| Construct Name | crTCA cycle enzyme | Gene variant and Source Organism | Detection by Western Analysis | Enzyme Activity (nmole/min/mg) |
|---|---|---|---|---|
| Tob1-SCS-BrBT-C | #1 - Succinyl CoA Synthetase | BrBT *Bradyrhizobium* sp.BTAi1 | Yes | 133 ± 7.2 (EV) 170 ± 5 (BrBt-C) |
| Tob2-KOR-BaM3-C | #2 - 2-Oxoglutarate: ferredoxin Oxidoreductase | BaM3 *Bacillus* sp. M3-13 | Yes | 0.44 ± 0.26 (EV) 3.67 ± 0.6 (BaM3-C) |
| Tob3-OGC-MaFe-N | #3 - 2-Oxoglutarate Carboxylase | MaFe *Mariprofundus ferrooxydans* PV-1 | Not confirmed | 15 ± 9 (EV) 20 ± 10 (MaFe-N) |
| Tob4-ICDH-NiHa-N | #4 - Oxalosuccinate Reductase/ICDH | NiHa *Nitrosococcus halophilus* Nc4 | Yes | 2.7 ± 0.45 (EV) 8.95 ± 0.44 (NiHa-N) |
| Tob5-ICL-NoFa-N | #5 - Isocitrate Lyase | NoFa *Nocardia farcinica* IFM 10152 | Yes | 1.94 ± 0.3 (EV) 4.66 ± 0.25 (NoFa-N) | parental C1 and C2 (T3) were planted at the same time to perform phenotypic analysis and comparison of the F1 crosses and the parental lines. All the C1 and C2 T3 plants carried all the elements of their corresponding construct. At 30 DAP, the C1 and C2 T3 plants (FIG. 9, FIG. 10, panel C and panel D) had an average height of 41.6 cm and 34 cm, respectively. Additionally, on Mar. 5, 2015, 24 C1 T3 seedlings, 24 C2 T3 seedlings and 48 C1×C2 F1 seedlings were transplanted and genotyped. The differences in development and height continued as shown in FIG. 11.

Example 6

C1, C2 and C3 are contained in three different pCambia 2300 plasmids.

Figure 12:
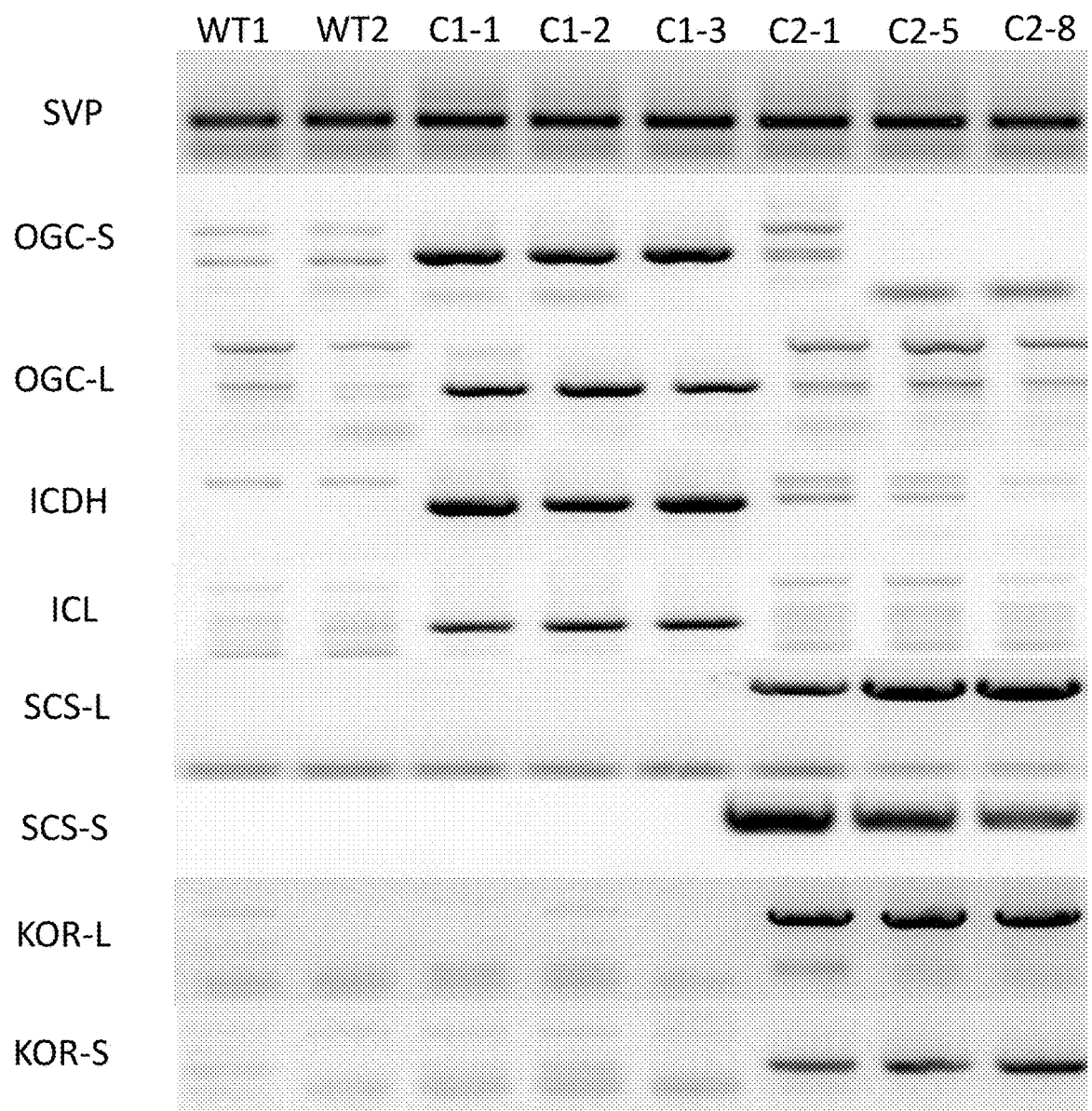
FIG. 12 shows expression of transgenes in the respective transgenic *Camelina* lines (C1-1, C1-2, C1-3, C2-1, C2-5, C2-8) as compared to wild type (WT1, WT2).

C1 carries the genes coding for the OGC small and large subunits, ICDH and ICL, C2 carries the genes coding for the small and large subunits of SCS and KOR, and C3 carries sequences coding for a biotin ligase and a ferredoxin which will support crTCA function. A modified version of the C2 construct holding different versions of the KOR elements was also introduced. C1 and C2 plasmids hold the sequences for a different fluorescent selectable marker while C3 carries the Bar gene sequence. crTCA Expression in Camelina was confirmed by RT-PCR and Western Blot for all crTCA enzymes (FIG. 12).

C1 T3, C2 T3 and C1×C2 F1 plants sets have been growing in the greenhouse or Phytotron and are being or have been harvested (T4 and F2 seeds). C3 (C1 background) T1, C2-mod (C1 background) T1 as well as C2-mod (w-t background) T2 seeds have been harvested. Those seeds have been plated on selection medium and have generated T1/T2 seedlings, which are now growing in the greenhouse (aged 14 to 21 DAP). Finally, a set of C3 (C1, C2 and w-t background) T1 plants is at the maturing stage. These lines were crossed and are currently grown out for evaluation. Data showing the number filling pods per total crosses in parent lines containing the F1 generation of the crossed lines is provided in Table 5 below.

TABLE 5

Number filling pods/total crosses in parent lines.

| Female | Male | # pods/total crosses |
|---|---|---|
| C2MT3 | C3C1T2 | 53/72 |
| C3C1T2 | C2MT3 | 48/75 |
| C2MC1T2 | C3T2 | 16/28 |
| C3T2 | C2MC1T2 | 16/27 |

Analysis of Metabolites in the Generated Camelina Lines.

Figure 13:
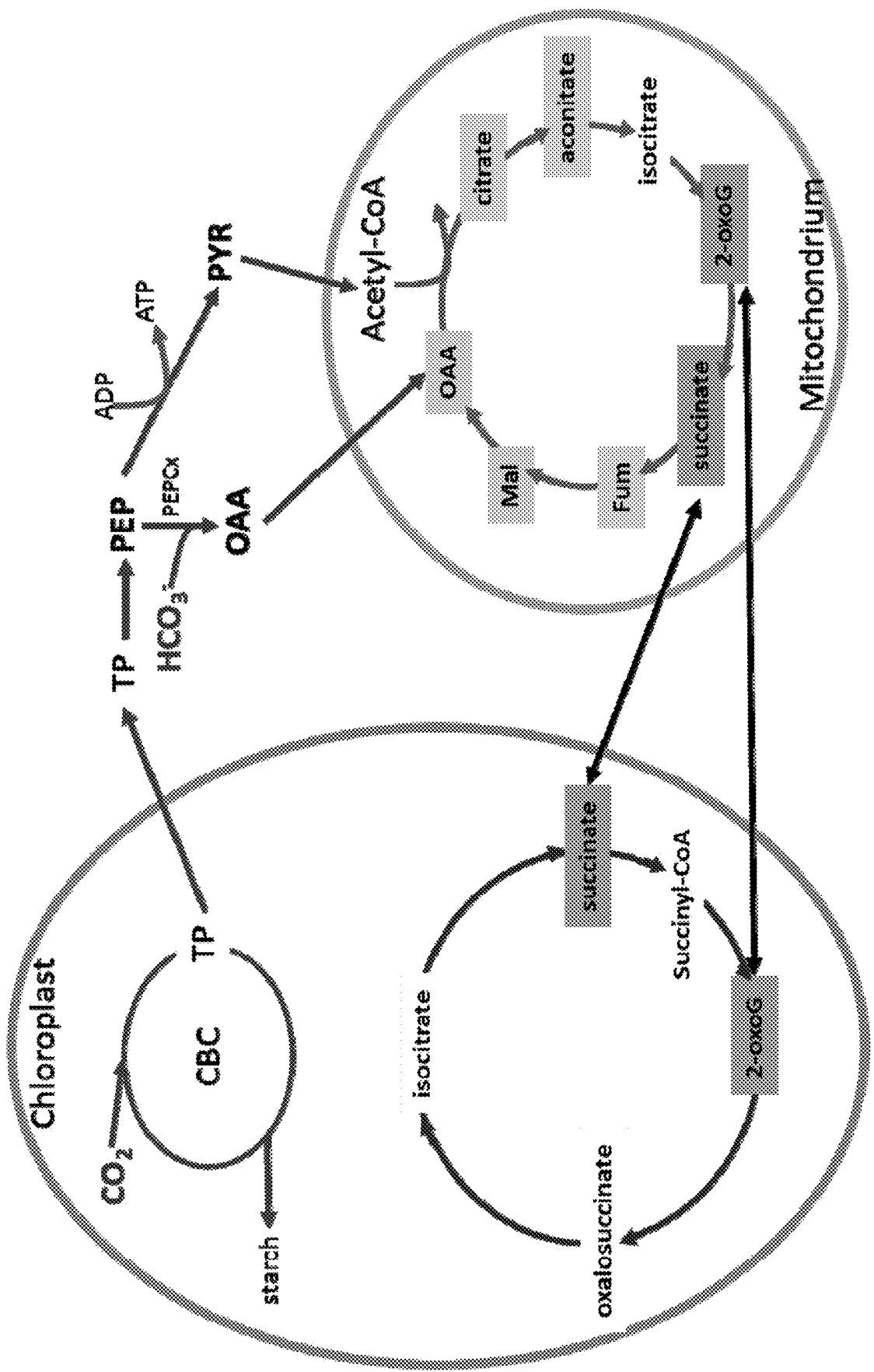
FIG. 13 provides a schematic of potential partial pathways function in shifting plant metabolism in the partial crTCA expressing lines.
Figure 15:
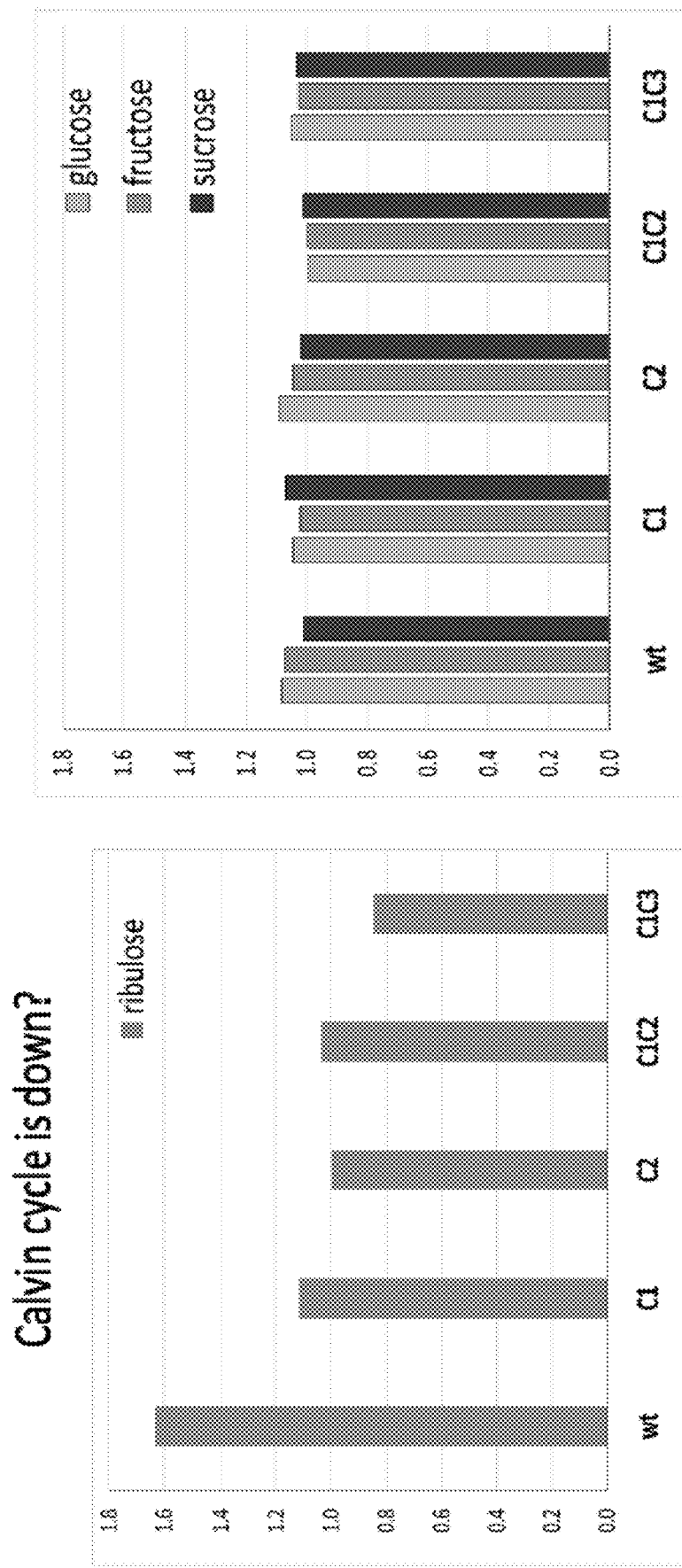
FIG. 15 shows steady-state levels of the Benson Calvin cycle (left panel) and sugar levels (right panel) in WT and transgenic lines.

Leaf tissue was collected from plants that were about 4 week-old, ground in liquid nitrogen and lyophilized for analysis. The results show an increase in metabolites associated with respiration. Potential partial pathways function in shifting plant metabolism in the partial crTCA expressing lines (FIG. 13). Compared to WT tissue, transgenic lines showed quantitative differences in the steady-state levels of several metabolites involved in the crTCA cycle or in the Krebs cycle (FIG. 14). Compared to WT tissue, transgenic lines showed quantitative differences in the steady-state levels of the Benson Calvin cycle, but there were no statistically significant differences in sugar levels (FIG. 15).

Figure 16:
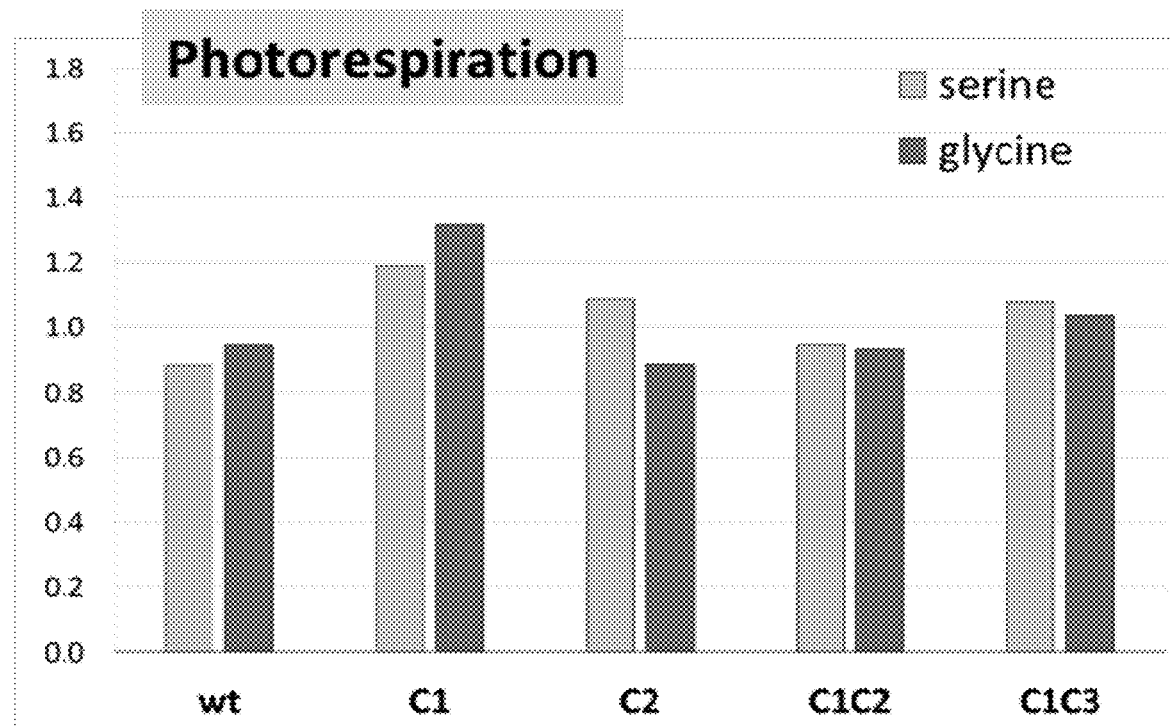
FIG. 16 shows serine and glycine levels for WT and transgenic lines.
Figure 17:
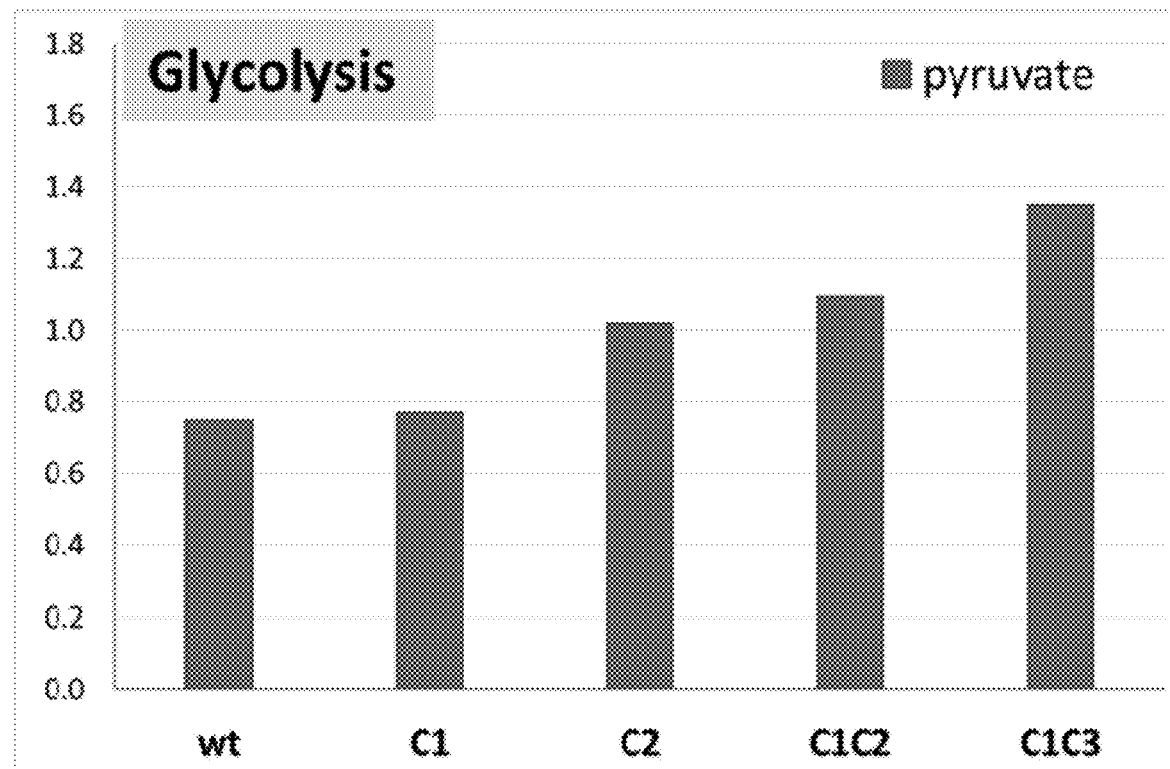
FIG. 17 shows pyruvate levels for WT and transgenic lines.

The ratio of serine/glycine indicates shifts in photorespiration when CO2 fixation is limiting. We did not observe any significant shift in the ser/gly ratio (FIG. 16) and an accumulation of pyruvate could indicate that flux through glycosysis for pyruvate synthesis is faster than metabolic reactions (or transport) that require pyruvate or other downstream metabolites as substrates as shown in FIG. 17. See also, FIG. 18.

Figure 19:
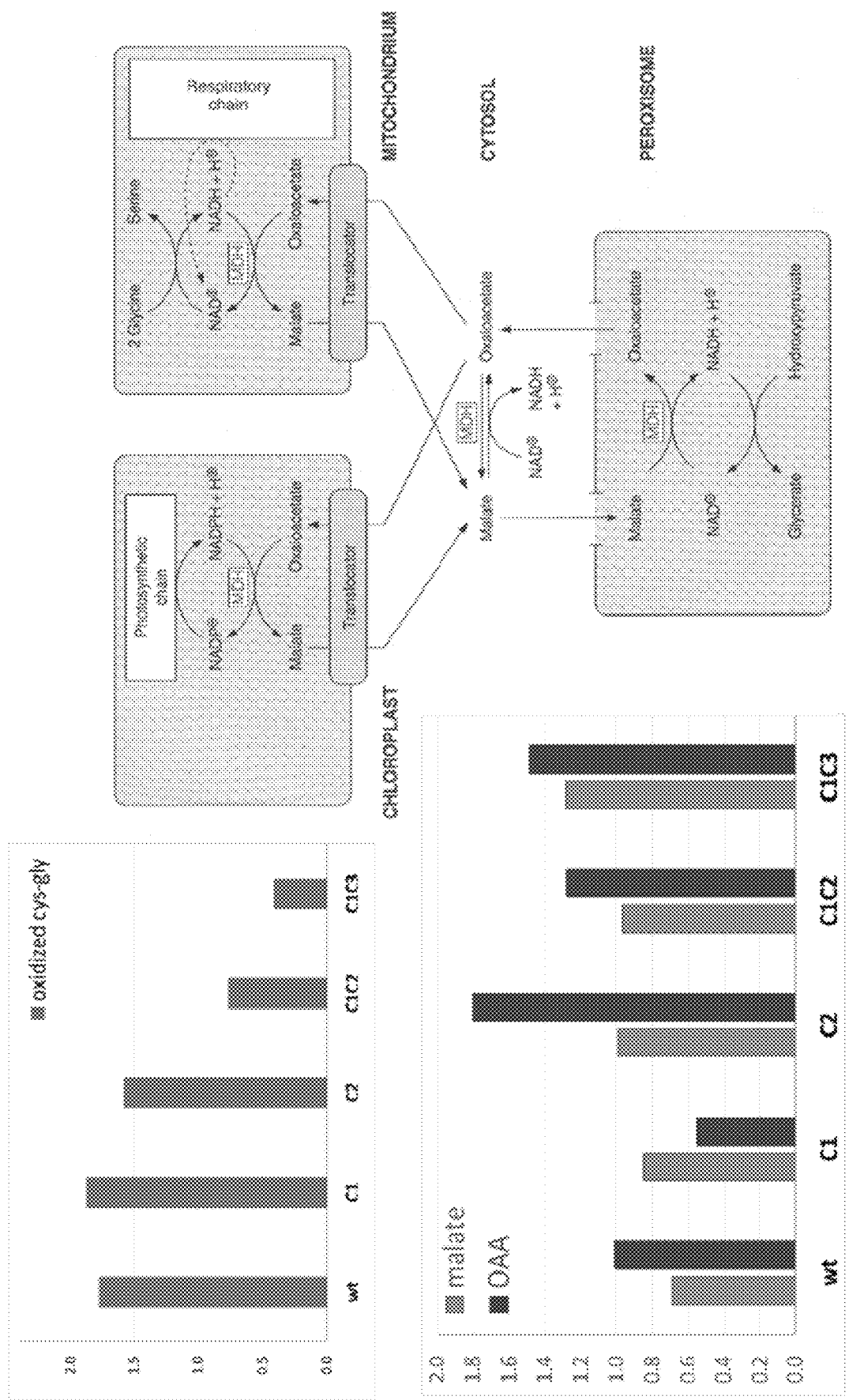
FIG. 19 shows the effect of the synthetic cycle on redox balance.

The data in FIG. 19 suggest that the activity of the synthetic cycle enzymes is affected by light and availability of $CO_2$. Thus, it may be that field growth would provide higher light intensities.

Example 7

This example presents data for the fully integrated Synthetic CO2 fixation cycle genes. All genes are present. The plants were generated by crossing homozygeous partial cycle plants (C1, C2+C3) as parents and are therefore, heterozygeous for all transgenes. independent crosses (X13, X32, X36, x50) were generated and analyzed plants for their physiology, genomics and agronomic traits.

Figure 20:
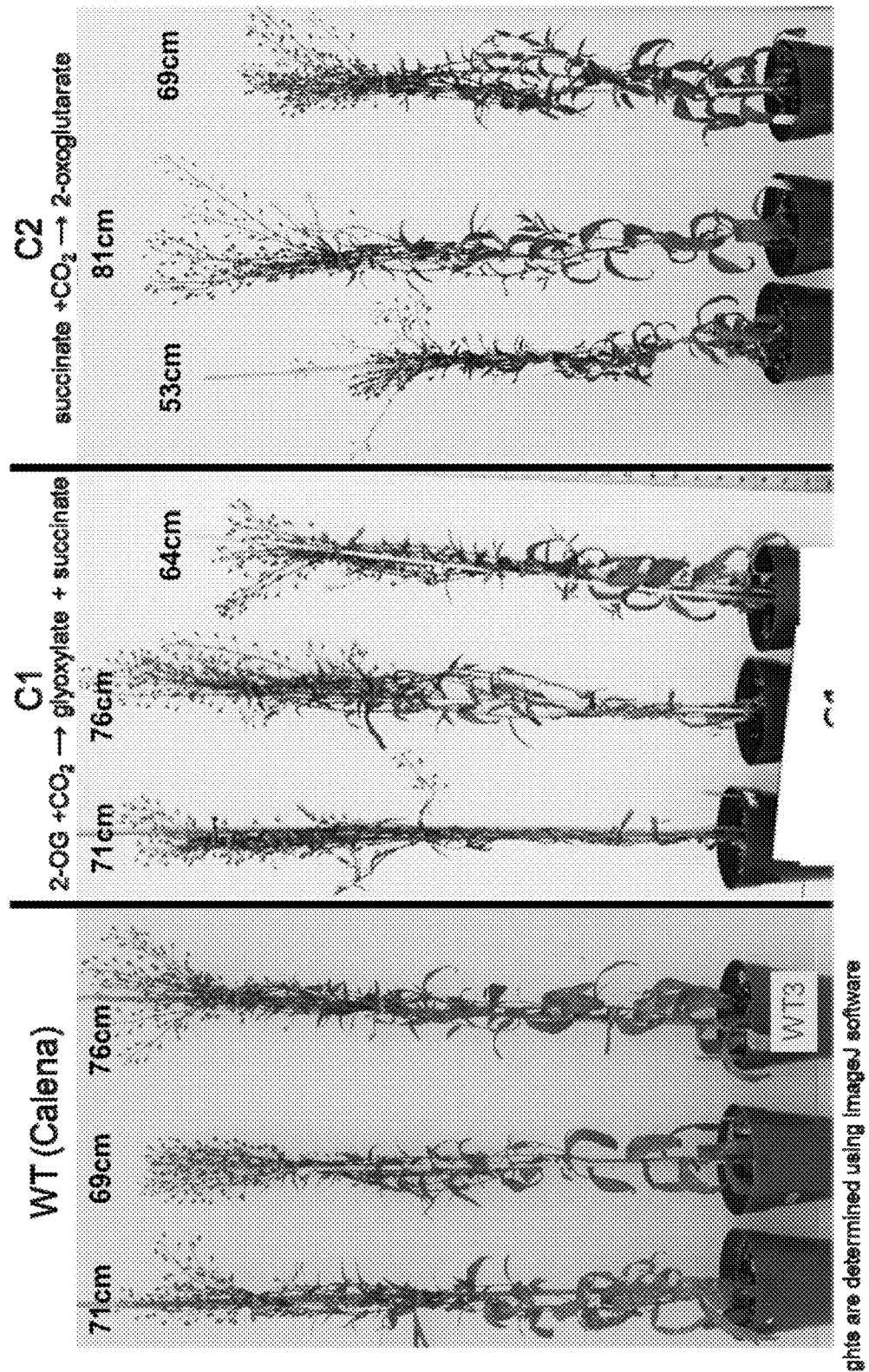
FIG. 20 shows the growth phenotype and height of *Camelina* wild type (wt) plants and C1 and C2 parent plants. While there is variation in the height of the parent plants, the wt plants are fairly uniform. We chose the tallest wt plant (WT3) as a visual comparison in the images with the integrated crosses (FIG. 21).

The growth phenotype and height of Camelina wild type (wt) plants and C1 and C2 parent plants are shown in FIG. 20. The constructs are as follows C1:
2-Oxoglutarate carboxylase: OGC (small/large subunits)
Isocitrate Dehydrogenase=Oxalosuccinate reductase ICDH
Isocitrate Lyase ICL
mCherry C2:
Succinyl-CoA Synthase SCS (large/small subunits)
2-Oxoglutarate:ferredoxin oxidoreductase=Ketoglutarate Oxidoreductase KOR (large/small subunits)
eGFP C3:
Biotin ligase (BirA): Coenzyme for OGC
Ferredoxin (Fdx)
BAR While variation in the height of the parent plants was observed, the wt plants are fairly uniform. The tallest wt plant (WT3) was chosen as a visual comparison in the images with the integrated crosses (FIG. 21A-21C).

Figure 21A:
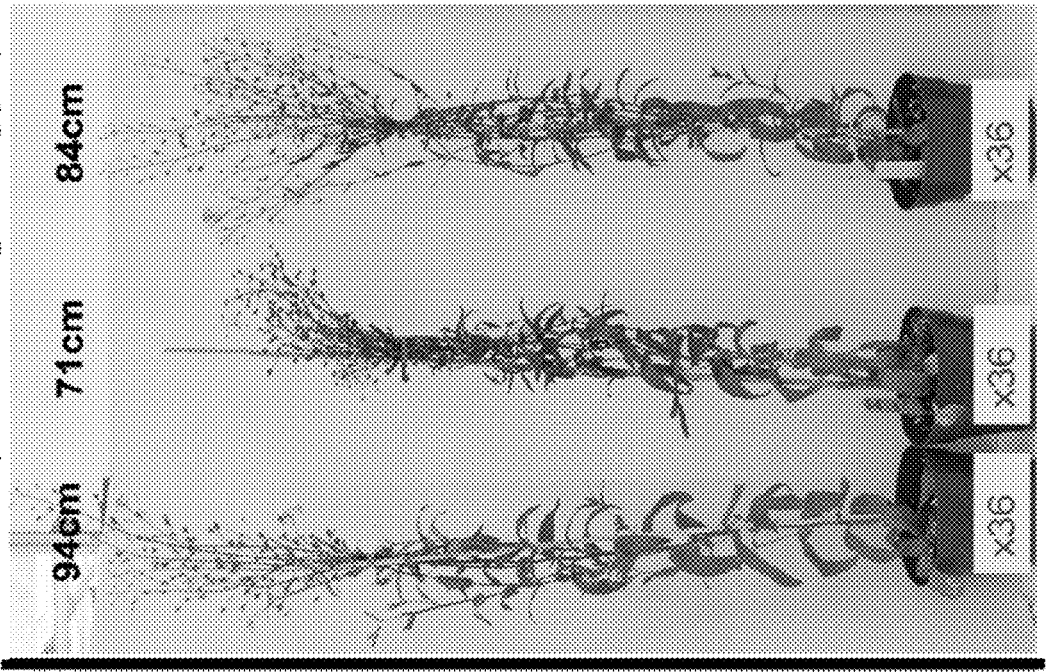
FIGS. 21A-21C shows the growth phenotype of full cycle for three integrated lines: C1 (FIG. 21A), C2 (FIG. 21B), C3 (FIG. 21C). For comparison, the tallest wt plant, WT3, was included in the images.
Figure 21B:
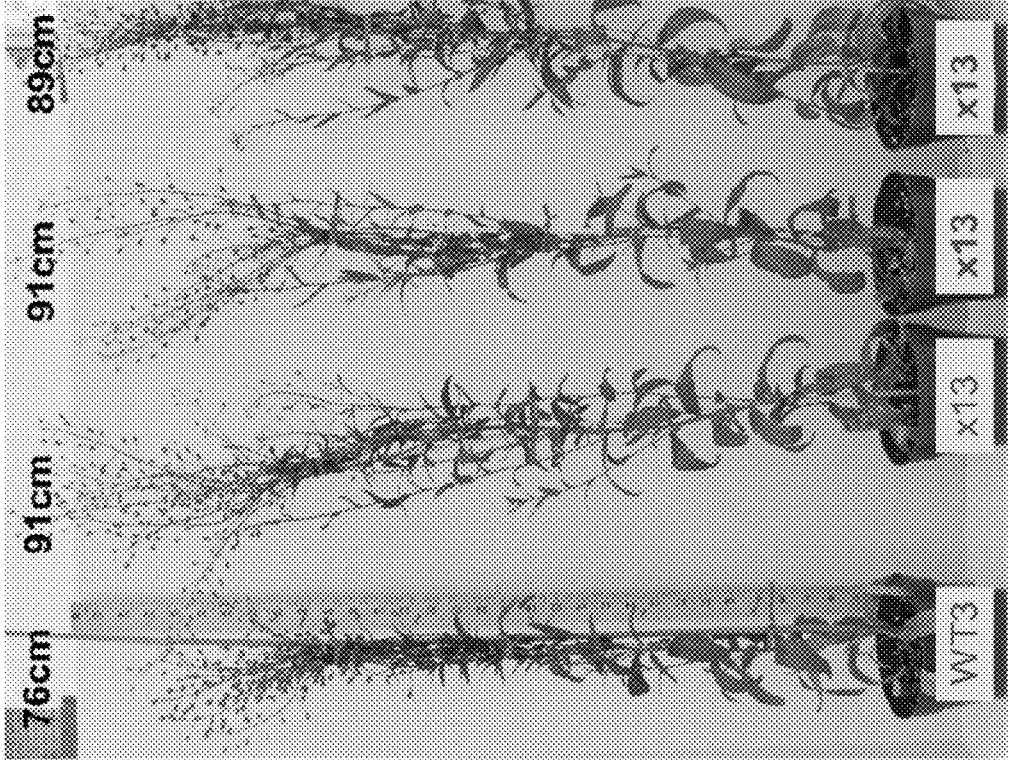
Figure 21C:
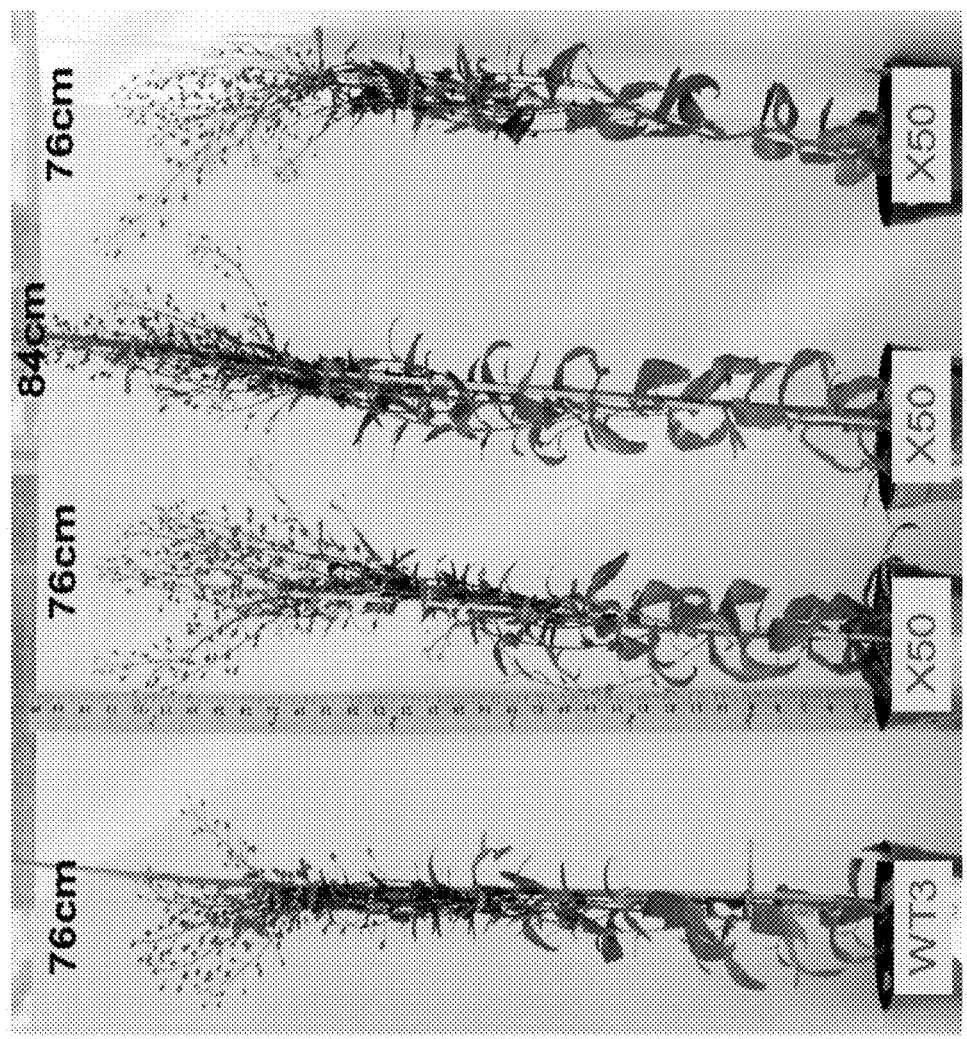

FIGS. 21A-21C shows the growth phenotype of full cycle (C1, C2, C3) integrated lines The x13 plants were clearly taller when compared with wt, while 2 of the 3 x36 crosses were taller than wt. All of the x50 crosses were the same height or taller than wt.

A functional CO2 fixation cycle would be expected to show increased $CO_2$ fixation rates during photosynthesis. Photosynthetic $CO_2$ fixation rates were measured at either 10 am in the morning or 10 pm at night from 3 independent leaves from 3 independent plants per genotype at either ambient (400 ppm) (FIG. 22A) or elevated (1600 ppm) (FIG. 22B) CO2 atmosphere.

Figure 22A:
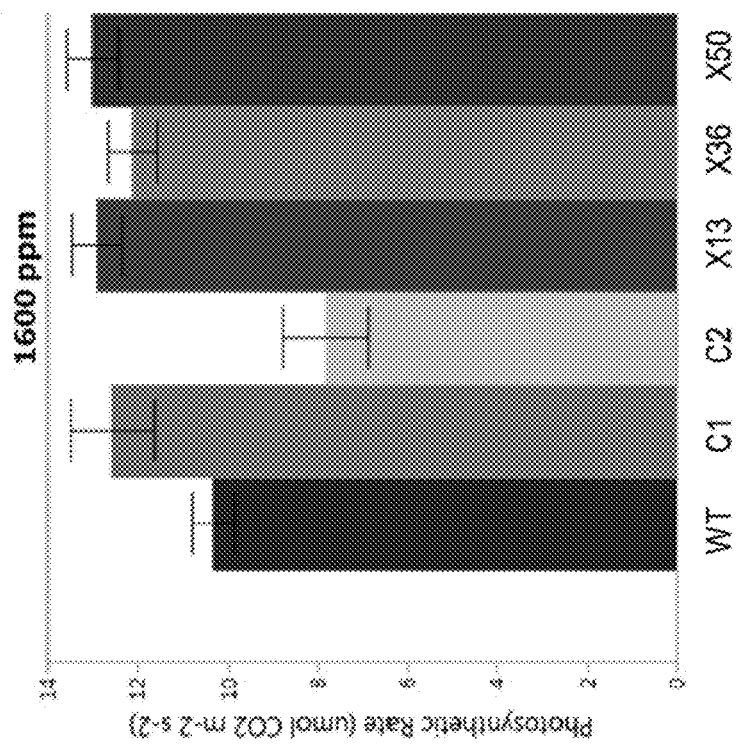
FIGS. 22A-22C shows photosynthetic $CO_2$ fixation rates (FIG. 22A-22B) and dark respiration (FIG. 22C) in the integrated crosses (X13, X36, X50) compared to wt or parent lines when measured under ambient $CO_2$ (400 ppm) (FIG. 22A) or under elevated $CO_2$ (1600 ppm) (FIG. 22B).
Figure 22B:
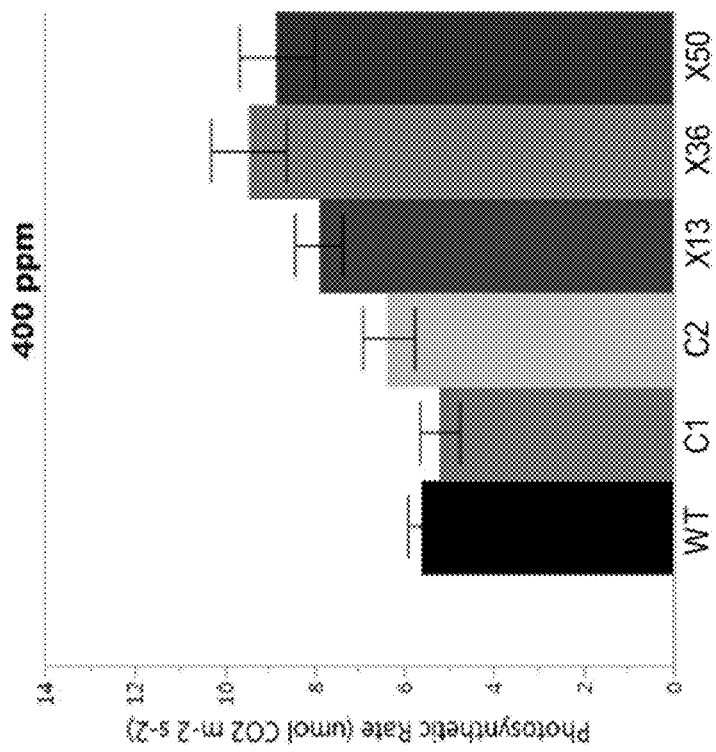
Figure 22C:
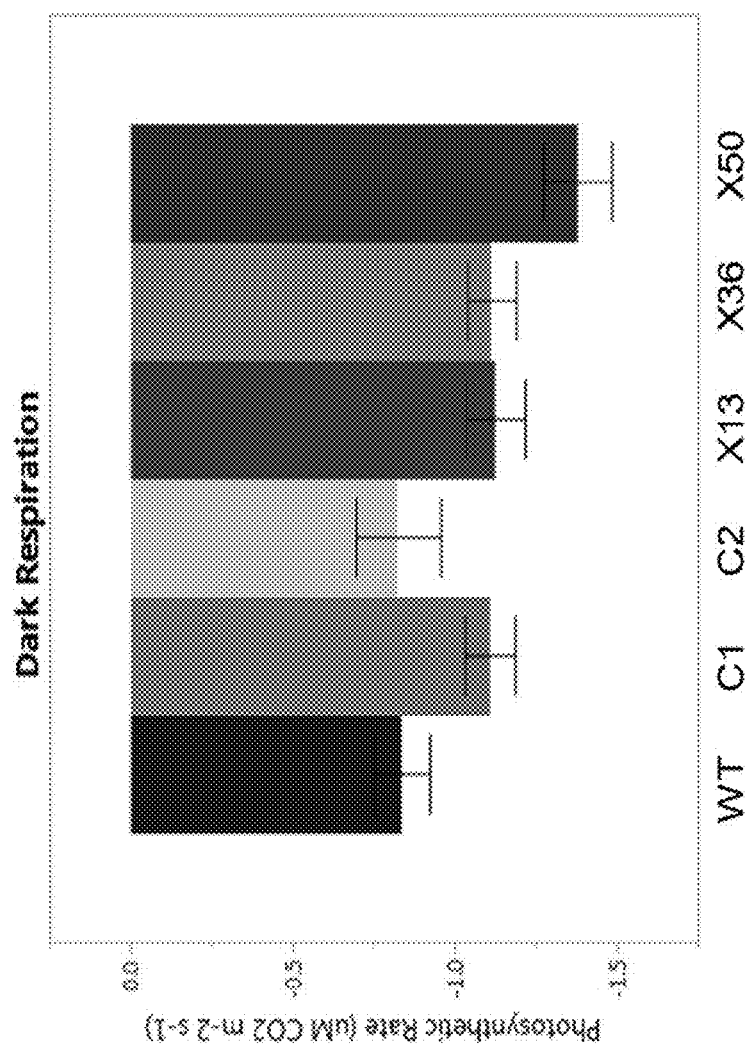

As shown in FIGS. 22A-22C, photosynthetic CO2 fixation rates were significantly higher in the integrated crosses (x13, x36, x50) compared to wt or parent lines when measured under ambient CO2 (400 ppm) (FIG. 22A). When the CO2 fixation rates were measured under elevated CO2 (1600 ppm) (FIG. 22B), the rates were significantly elevated in all genotypes with exception of C2. Interestingly, the transgenic lines only containing construct C1 were performing better under elevated CO2 compared to wt, and similar to the integrated crosses. Dark respiration (FIG. 22C) was significantly higher in C1 and integrated crosses compared to wt and C2. This suggests that the elevated CO2 fixation rate resulted in increased carbon storage (e.g. starch or sucrose or lipids) in the leaf during the day which enabled increased respiration and therefore growth (see FIG. 20 and FIGS. 21A-21C) during the night.

TABLE 6

The ratio of photosynthetic (light) CO2 assimilation rates at elevated CO2 (1600 ppm) to ambient CO2 (400 ppm)

|  | WT | C1 | C2 | ×13 | ×36 | ×50 |
|---|---|---|---|---|---|---|
| ΔPSR (1600-400 ppm) | 4.7 | 6.5 | 1.3 | 4.5 | 2.3 | 5.2 |

To evaluate the actual expression levels of the transgenes in the parent lines and crosses, transcript (qRT-PCR) and protein levels were measured.

Figure 23:
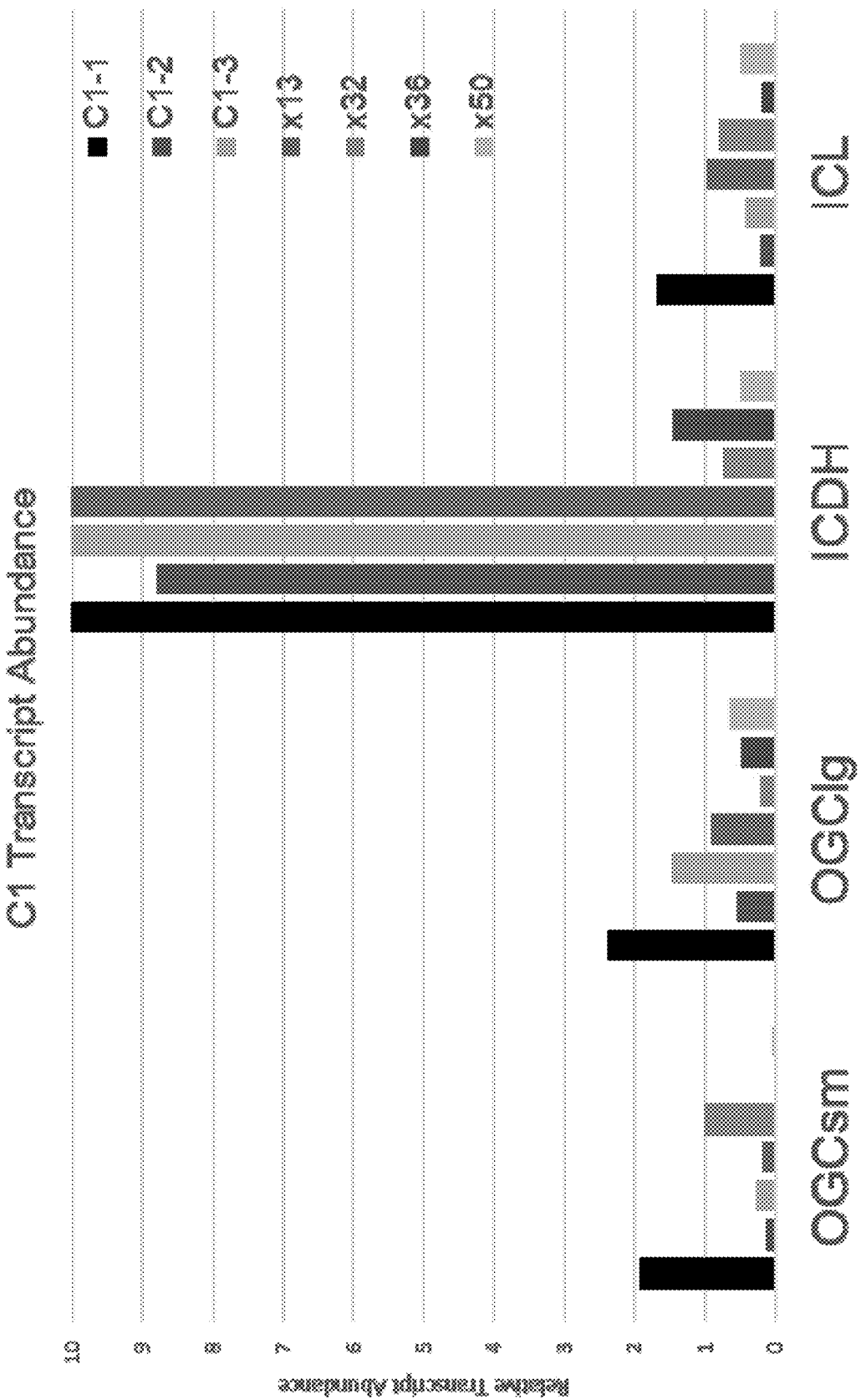
FIG. 23 shows transcript abundance of C1 transgenes in the C1 parent lines and the integrated crosses.

FIG. 23 shows transcript abundance of C1 transgenes in the C1 parent lines and the integrated crosses. Transgene specific primers were used and expression was normalized to standard endogenous genes. While we were able to detect transcript for all transgenes in all genotypes, the relative abundance levels varied dramatically. Our analysis showed that the transcript abundances were not due to the different promoters used in the constructs.

Figure 24:
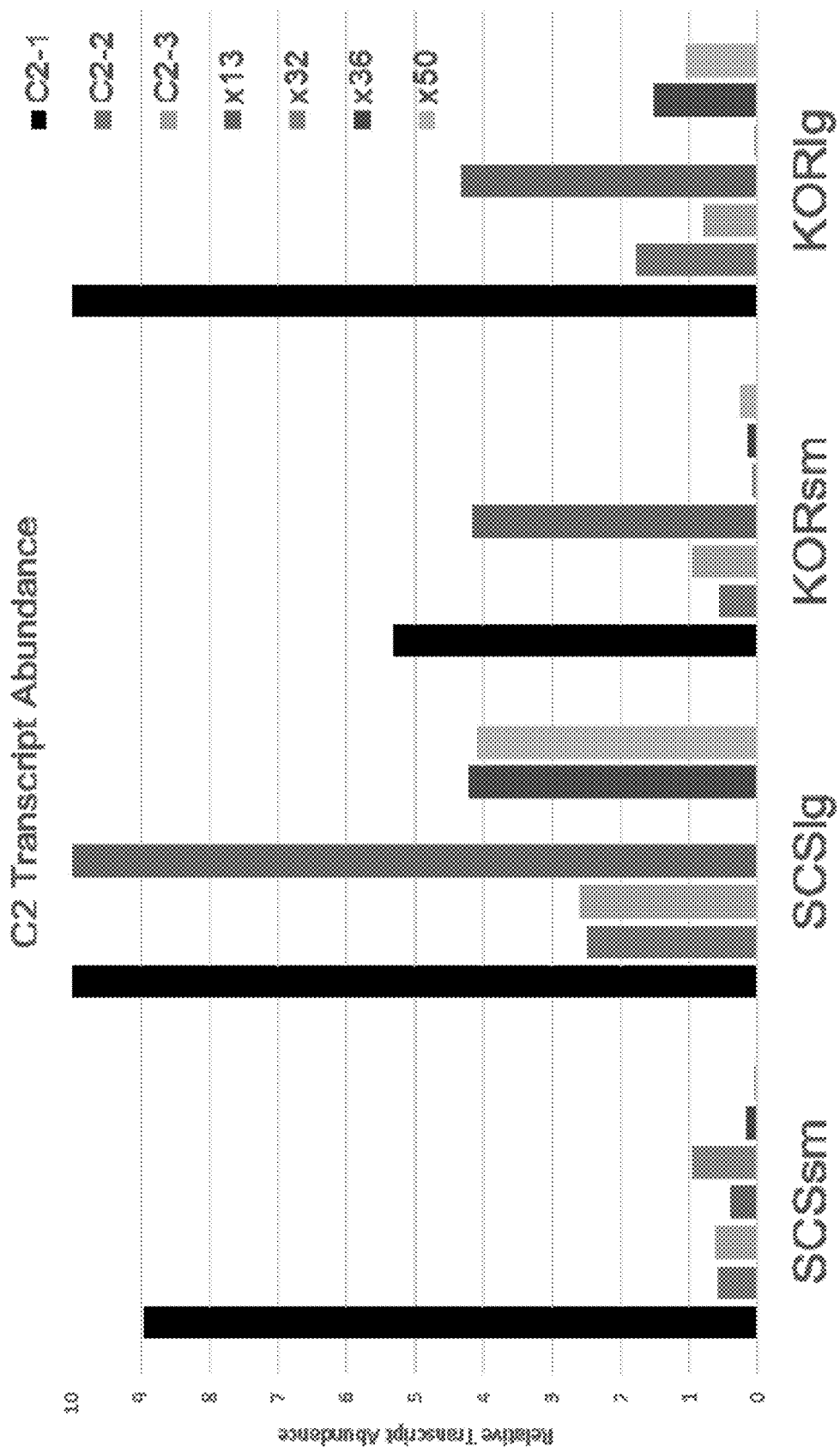
FIG. 24 shows transcript abundance of C2 transgenes in the C2 parent lines and the integrated crosses.

FIG. 24 shows transcript abundance of C2 transgenes in the C2 parent lines and the integrated crosses. Transgene specific primers were used and expression was normalized to standard endogenous genes. While we were able to detect transcript for all transgenes in all genotypes, the relative abundance levels varied dramatically. Our analysis showed that the transcript abundances were not due to the different promoters used in the constructs.

Figure 25:
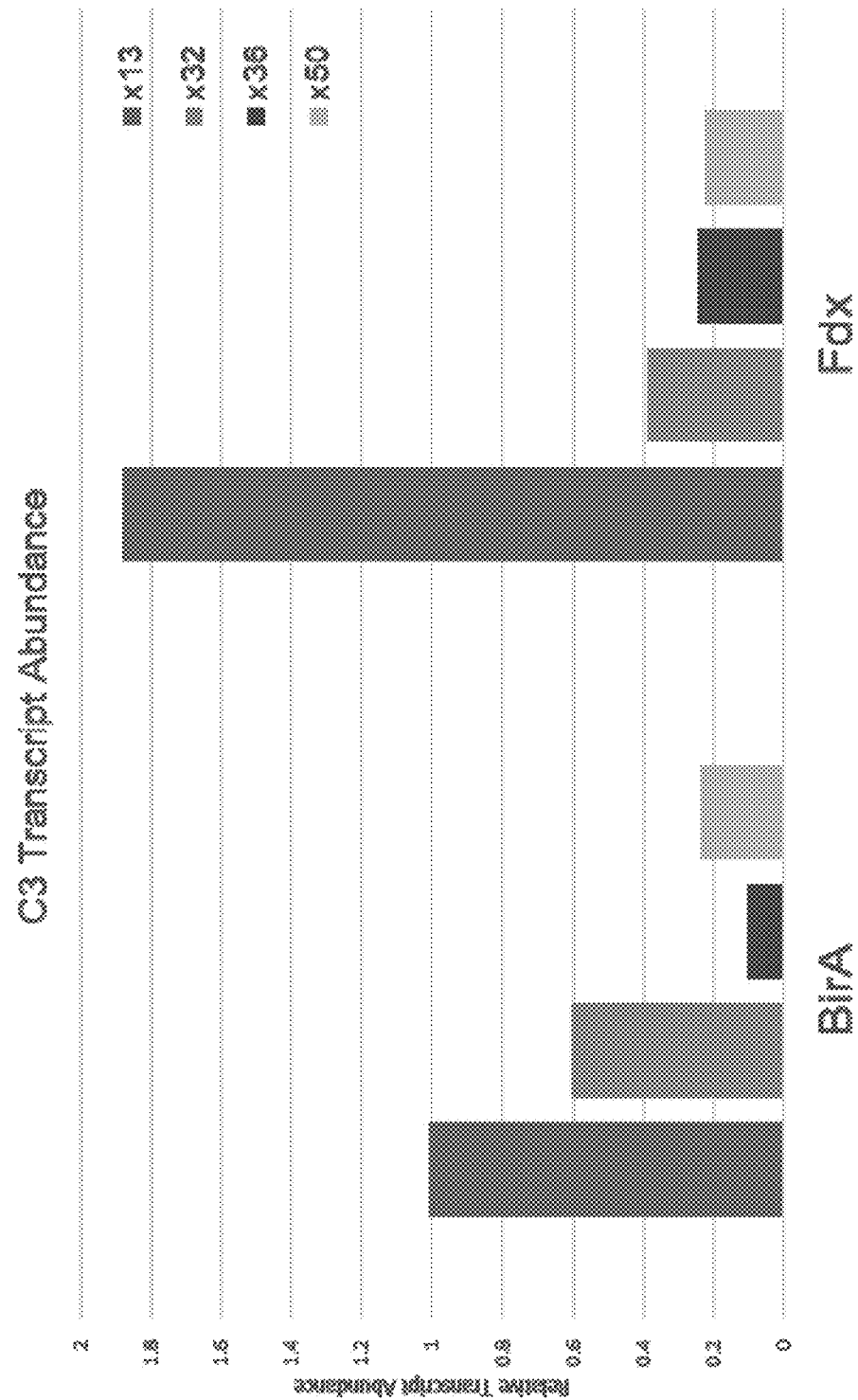
FIG. 25 shows transcript abundance of C3 transgenes in the integrated crosses.

FIG. 25 shows transcript abundance of C3 transgenes in the integrated crosses. Transgene specific primers were used and expression was normalized to standard endogenous genes. While we were able to detect transcript for all transgenes in all genotypes, the relative abundance levels varied dramatically. Our analysis showed that the transcript abundances were not due to the different promoters used in the constructs.

Despite the large differences in the transcript abundances (FIGS. 23-25), the respective protein levels (western blots) (FIGS. 26A-26C) did not show the same variation. Instead, fairly similar quantities of transgenic proteins were observed that did not correlate with transcript abundance differences. Without being bound by theory, this may suggest that the proteins were more stable than the transcripts and post-transcriptional regulation may be responsible for the discrepancy between transcript and protein levels for each transgene.

Figure 27A:
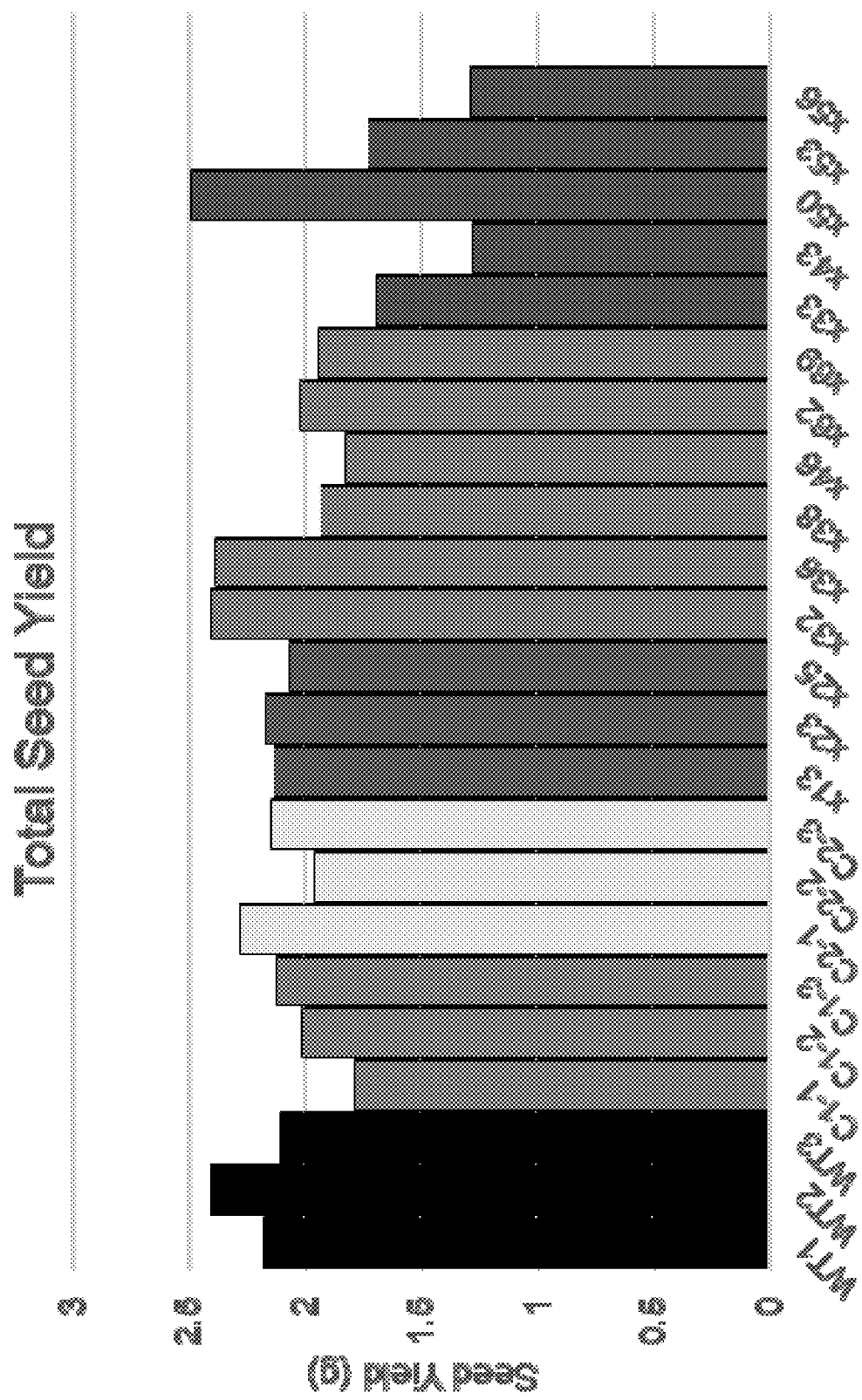
FIGS. 27A-27B shows seed yield (g seed/plant) (FIG. 27A) and seed weight (FIG. 27B) of wt, parent and integrated, crossed lines.
Figure 27B:
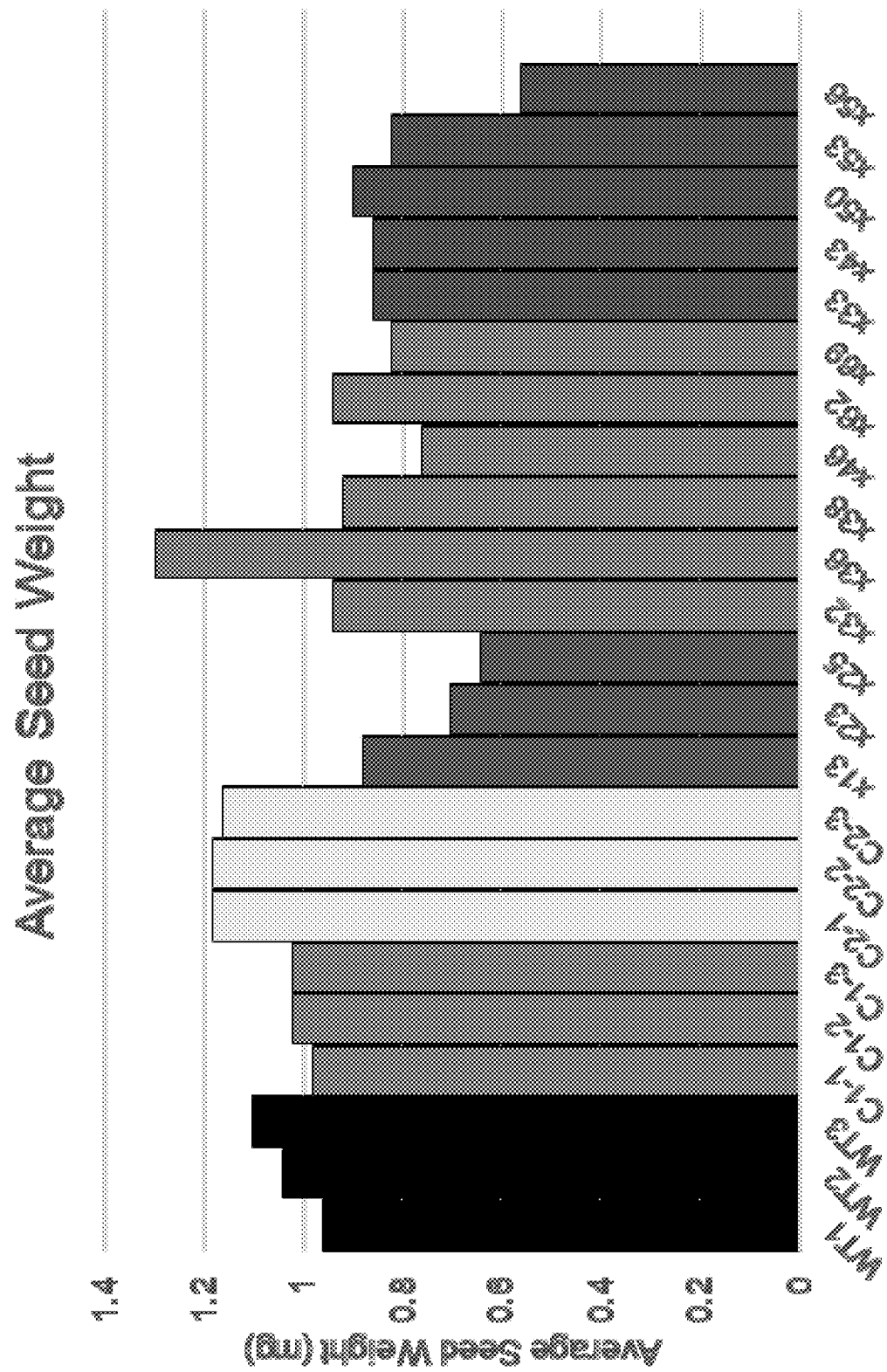

Further, despite the increases in CO2 fixation, seed yield did not correlate with height increases or CO2 fixation rates. As shown in FIGS. 27A-27B, seed yield (g seed/plant) was not significantly different between wt, parent and integrated, crossed lines. Further, average seed weight was lower in the integrated lines compared to parent and wt plants. This indicates that the parent and wt plants made relatively fewer but heavier seeds per plant compared to the integrated crosses which may make more seeds having lower per seed weight. The statistical significance here is relatively low due to the low number of plants for each line. Experiments with larger plant numbers are currently under way and field trials planned for fully homozygous integrated lines.

The above examples clearly illustrate the advantages of the invention. Although the present invention has been described with reference to specific details of certain embodiments thereof, it is not intended that such details should be regarded as limitations upon the scope of the invention except as and to the extent that they are included in the accompanying claims.

That which is claimed:

1. A method for increasing carbon fixation and/or increasing biomass production in a plant, comprising:
 introducing into a plant, plant part, and/or plant cell a heterologous polynucleotide encoding a succinyl CoA synthetase polypeptide, a heterologous polynucleotide encoding a 2-oxoglutarate:ferredoxin oxidoreductase polypeptide, a heterologous polynucleotide encoding a 2-oxoglutarate carboxylase polypeptide, a heterologous polynucleotide encoding an oxalosuccinate reductase polypeptide, and/or a heterologous polynucleotide encoding an isocitrate lyase polypeptide to produce a stably transformed plant, plant part, and/or plant cell, wherein the heterologous polynucleotide encoding a succinyl CoA synthetase polypeptide, the heterologous polynucleotide encoding a 2-oxoglutarate:ferredoxin oxidoreductase polypeptide, the heterologous polynucleotide encoding a 2-oxoglutarate carboxylase polypeptide, the heterologous polynucleotide encoding an oxalosuccinate reductase polypeptide, and the heterologous polynucleotide encoding an isocitrate lyase polypeptide are from a bacterial and/or an archaeal species.

2. The method of claim 1, comprising:
 introducing into a plant, plant part, and/or plant cell a heterologous polynucleotide encoding a succinyl CoA synthetase polypeptide and a heterologous polynucleotide encoding a 2-oxoglutarate:ferredoxin oxidoreductase polypeptide to produce a stably transformed plant, plant part, and/or plant cell, wherein the heterologous polynucleotide encoding a succinyl CoA synthetase polypeptide and the heterologous polynucleotide encoding a 2-oxoglutarate:ferredoxin oxidoreductase polypeptide are from a bacterial and/or an archaeal species.

3. A method for producing a plant having increased carbon fixation and/or increased biomass production, comprising:
 introducing into a plant, plant part, and/or plant cell a heterologous polynucleotide encoding a 2-oxoglutarate carboxylase (OGC) polypeptide, a heterologous polynucleotide encoding an oxalosuccinate reductase (ICDH/OSR) polypeptide, and a heterologous polynucleotide encoding an isocitrate lyase (ICL) polypeptide to produce a stably transformed plant, plant part, and/or plant cell, wherein the heterologous polynucleotide encoding a 2-oxoglutarate carboxylase polypeptide, the heterologous polynucleotide encoding an oxalosuccinate reductase polypeptide, and the heterologous polynucleotide encoding an isocitrate ylase polypeptide, are from a bacterial and/or an archaeal species.

4. The method for producing a plant of claim 3, comprising:
 introducing into a plant, plant part, and/or plant cell a heterologous polynucleotide encoding a succinyl CoA synthetase polypeptide and a heterologous polynucleotide encoding a 2-oxoglutarate:ferredoxin oxidoreductase polypeptide to produce a stably transformed plant, plant part, and/or plant cell, wherein the heterologous polynucleotide encoding a succinyl CoA synthetase polypeptide, and the heterologous polynucleotide encoding a 2-oxoglutarate:ferredoxin oxidoreductase polypeptide are from a bacterial and/or an archaeal species.

5. The method of claim 1, wherein the heterologous polynucleotide encoding a 2-oxoglutarate carboxylase polypeptide, the heterologous polynucleotide encoding an oxalosuccinate reductase polypeptide and/or the heterologous polynucleotide encoding an isocitrate lyase polypeptide is/are operably linked to a promoter.

6. The method of claim 2, wherein the heterologous polynucleotide encoding a succinyl CoA synthetase polypeptide and the heterologous polynucleotide encoding a 2-oxoglutarate:ferredoxin oxidoreductase polypeptide are operably linked to a promoter.

7. The method of claim 3, wherein the heterologous polynucleotide encoding a succinyl CoA synthetase polypeptide and the heterologous polynucleotide encoding a 2-oxoglutarate:ferredoxin oxidoreductase polypeptide are operably linked to a promoter.

8. The method of claim 4, wherein the heterologous polynucleotide encoding a succinyl CoA synthetase polypeptide and the heterologous polynucleotide encoding a 2-oxoglutarate:ferredoxin oxidoreductase polypeptide are operably linked to a promoter.

9. The method of claim 1, wherein the heterologous polynucleotide encoding a heterologous polynucleotide encoding a succinyl CoA synthetase polypeptide and the heterologous polynucleotide encoding a 2-oxoglutarate:ferredoxin oxidoreductase polypeptide are introduced into a nucleus and/or a chloroplast of said plant, plant part, and/or plant cell.

10. The method of claim 1, wherein the heterologous polynucleotide encoding a 2-oxoglutarate carboxylase polypeptide, the heterologous polynucleotide encoding an isocitrate lyase polypeptide are introduced into a nucleus of said plant, plant part, and/or plant cell and are operably linked to an polynucleotide encoding an amino acid sequence that targets said polypeptides to the chloroplast.

11. The method of claim 1, wherein the heterologous polynucleotide encoding the 2-oxoglutarate carboxylase polypeptide is from *Candidatus Nitrospira defluvii, Hydrogenobacter thermophilus, Thiocystis violascens, Mariprofundus ferroxydans,* or *Pseudomonas stutzeri,* the heterologous polynucleotide encoding the oxalosuccinate reductase polypeptide is from *Acinetobacter baumannii, Chlorobium limicola, Kosmotoga olearia, Nitrosococcus halophilus* or Marine gamma proteobacterium and the heterologous polynucleotide encoding the isocitrate lyase is from *Corynebacterium glutamicum, Gordonia alkanivorans, Nocardia farcinica, Rhodococcus pyridinivorans, Rhodococcus jostii.*

12. The method of claim 2, wherein-the heterologous polynucleotide encoding the succinyl CoA synthetase polypeptide is from *Escherichia coli, Azotobacter vinelandii, Bradyrhizobium* sp., or *Azospirillum* sp., and the heterologous polynucleotide encoding the 2-oxoglutarate:ferredoxin oxidoreductase polypeptide is from *Paenibacillus* sp., *Halobacterium* sp., *Hydrogenobacter thermophilus, Bacillus* sp, *Paenibacillus larvae* subsp. larvae, *Haladaptus paucihalophilus, Magnetococcus* sp.

13. The method of claim 3, wherein the heterologous polynucleotide encoding the 2-oxoglutarate carboxylase polypeptide is from *Candidatus Nitrospira defluvii, Hydrogenobacter thermophilus, Thiocystis violascens, Mariprofundus ferroxydans,* or *Pseudomonas stutzeri,* the heterologous polynucleotide encoding the oxalosuccinate reductase polypeptide is from *Acinetobacter baumannii, Chlorobium limicola, Kosmotoga olearia, Nitrosococcus halophilus* or Marine gamma proteobacterium, and the heterologous polynucleotide encoding the isocitrate lyase is from *Corynebacterium glutamicum, Gordonia alkanivorans, Nocardia farcinica, Rhodococcus pyridinivorans, Rhodococcus jostii.*

14. The method of claim 4, wherein-the heterologous polynucleotide encoding the succinyl CoA synthetase polypeptide is from *Escherichia coli, Azotobacter vinelandii, Bradyrhizobium* sp., *Azospirillum* sp., and the heterologous polynucleotide encoding the 2-oxoglutarate:ferredoxin oxidoreductase polypeptide is from *Paenibacillus* sp *Halobacterium* sp., *Hydrogenobacter thermophilus, Bacillus* sp, *Paenibacillus larvae* subsp. larvae, *Haladaptus paucihalophilus,* or *Magnetococcus* sp.

15. The method of claim 1, wherein the 2-oxoglutarate carboxylase is from *Mariprofundus ferrooxydans,* the heterologous polynucleotide encoding the oxalosuccinate reductase polypeptide is from *Nitrosococcus halophilus,* and the heterologous polynucleotide encoding the isocitrate lyase is from *Nocardia farcinica.*

16. The method of claim 2, wherein the heterologous polynucleotide encoding the succinyl CoA synthetase polypeptide is from *Bradyrhizobium* sp. and the heterologous polynucleotide encoding the 2-oxoglutarate:ferredoxin oxidoreductase polypeptide is from *Hydrogenobacter thermophilus.*

17. The method of claim 3, wherein the 2-oxoglutarate carboxylase is from *mariprofundus ferrooxydans,* the heterologous poloynucleotide encoding the oxalosuccinate reductase polypeptide is from *Nitrosococcus halophilus,* and the heterologous olynucleotide encoding the isocitrate lyase is from *Nocardia farcinica.*

18. The method of claim 4, wherein the heterologous polynucleotide encoding the succinyl CoA synthetase polypeptide is from *Bradyrhizobium* sp. and the heterologous polynucleotide encoding the 2-oxoglutarate:ferredoxin oxidoreductase polypeptide is from *Hydrogenobacter thermophilus.*

* * * * *

UNITED STATES PATENT AND TRADEMARK OFFICE
CERTIFICATE OF CORRECTION

PATENT NO. : 10,752,911 B2
APPLICATION NO. : 15/875313
DATED : August 25, 2020
INVENTOR(S) : Grunden et al.

It is certified that error appears in the above-identified patent and that said Letters Patent is hereby corrected as shown below:

In the Specification

Column 6, Line 4: Please correct ""5'-A-G-T-3"" to read -- "5'-A-G-T-3" --

Column 9, Line 10: Please correct "(BLAST)" to read -- (BLAST®) --

Column 9, Line 13: Please correct "*BLAST*" to read -- *BLAST®* --

Column 9, Line 16: Please correct "BLAST" to read -- BLAST® --

Column 28, Line 47: Please correct "7.5.5 mM" to read -- 7.5, 5 mM --

Column 34, Line 3: Please correct "Int-2" to read -- In2-2 --

Column 47, Line 14: Please correct "AK37 18248" to read -- AK37_18248 --

In the Claims

Column 225, Lines 20-41, Claim 1: Please delete and replace with the following:
1. A method for increasing carbon fixation and/or increasing biomass production in a plant, the method comprising:
    introducing into a plant, plant part, and/or plant cell a heterologous polynucleotide encoding a 2-oxoglutarate carboxylase (OGC) polypeptide, a heterologous polynucleotide encoding an oxalosuccinate reductase (ICDH/OSR) polypeptide, and a heterologous polynucleotide encoding an isocitrate lyase (ICL) polypeptide to produce a stably transformed plant, plant part, and/or plant cell, wherein the heterologous polynucleotide encoding a 2-oxoglutarate carboxylase polypeptide, the heterologous polynucleotide encoding an oxalosuccinate reductase polypeptide, and the heterologous polynucleotide encoding an isocitrate lyase polypeptide are from a bacterial and/or an archaeal species.

Signed and Sealed this
Ninth Day of February, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,752,911 B2

Column 225, Line 43, Claim 2: Please correct "a plant" to read -- the plant --

Column 225, Lines 55-56, Claim 3: Please correct "production, comprising:" to read -- production, the method comprising: --

Column 226, Line 19, Claim 3: Please correct "ylase" to read -- lyase --

Column 226, Line 20, Claim 3: Please correct "peptide, are" to read -- peptide are --

Column 226, Lines 65-66, Claim 10: Please correct "an isocitrate" to read -- an oxalosuccinate reductase polypeptide and the heterologous polynucleotide encoding an isocitrate --

Column 227, Line 15, Claim 12: Please correct "wherein-the" to read -- wherein the --

Column 227, Line 23, Claim 12: Please correct "*paucihalophilus, Magnetococcus*" to read -- *paucihalophilus,* or *Magnetococcus* --

Column 228, Line 1, Claim 14: Please correct "wherein-the" to read -- wherein the --

Column 228, Line 4, Claim 14: Please correct "*Azospirillum* sp.," to read -- *Azospirillum* sp. --

Column 228, Line 6, Claim 14: Please correct "*Paenibacillus* sp" to read -- *Paenibacillus* sp., --

Column 228, Line 23, Claim 17: Please correct "*mariprofundus*" to read -- *Mariprofundus* --

Column 228, Line 26, Claim 17: Please correct "olynucleotide" to read -- polynucleotide --